United States Patent
Ogrunc et al.

(10) Patent No.: US 11,723,926 B2
(45) Date of Patent: Aug. 15, 2023

(54) SENESCENT CELL-ASSOCIATED ANTIGEN-BINDING DOMAINS, ANTIBODIES AND CHIMERIC ANTIGEN RECEPTORS COMPRISING THE SAME, AND USES THEREOF

(71) Applicant: StarkAge Therapeutics, Lille (FR)

(72) Inventors: Müge Ogrunc, Paris (FR); Thierry Mathieu, Brussels (BE)

(73) Assignee: StarkAge Therapeutics, Lille (FR)

( * ) Notice: Subject to any disclaimer, the term of this patent is extended or adjusted under 35 U.S.C. 154(b) by 0 days.

(21) Appl. No.: 17/032,510

(22) Filed: Sep. 25, 2020

(65) Prior Publication Data

US 2022/0193130 A1    Jun. 23, 2022

Related U.S. Application Data

(63) Continuation-in-part of application No. 16/585,256, filed on Sep. 27, 2019, now abandoned.

(30) Foreign Application Priority Data

Sep. 27, 2019   (EP) ..................................... 19200182

(51) Int. Cl.
    *A61K 35/17*      (2015.01)
    *C07K 16/28*      (2006.01)
    *C12N 5/0783*     (2010.01)

(52) U.S. Cl.
    CPC .......... *A61K 35/17* (2013.01); *C07K 16/2896* (2013.01); *C12N 5/0636* (2013.01); *C07K 2317/24* (2013.01); *C07K 2317/31* (2013.01)

(58) Field of Classification Search
    CPC ................ A61K 35/17; C07K 16/2896; C07K 2317/24; C07K 2317/31; C12N 5/0636
    See application file for complete search history.

(56) References Cited

FOREIGN PATENT DOCUMENTS

| EP | 3029069 A1 | 6/2016 |
|----|------------|--------|
| WO | 2001064750 A2 | 9/2001 |
| WO | 2002092127 A1 | 11/2002 |
| WO | 2005118643 A2 | 12/2005 |
| WO | 2007014169 A2 | 2/2007 |
| WO | 2018002358 A1 | 1/2018 |
| WO | 2018027197 A1 | 2/2018 |
| WO | 2018160768 A1 | 9/2018 |
| WO | 2020160518 A1 | 8/2020 |

OTHER PUBLICATIONS

Althubiti et al., "Characterization of novel markers of senescence and their prognostic potential in cancer". Cell Death Dis. Nov. 20, 2014;5(11):e1528.
Baar et al., "Targeted Apoptosis of Senescent Cells Restores Tissue Homeostasis in Response to Chemotoxicity and Aging". Cell. Mar. 23, 2017;169(1):132-147.e16.
Chang et al., "Clearance of senescent cells by ABT263 rejuvenates aged hematopoietic stem cells in mice". Nat Med. Jan. 2016;22(1):78-83.
Guedan et al., "Engineering and Design of Chimeric Antigen Receptors". Mol Ther Methods Clin Dev. Dec. 31, 2018;12:145-156.
Hashimoto et al., "Elimination of p19ARF-expressing cells enhances pulmonary function in mice". JCI Insight. Aug. 4, 2016;1(12):e87732.
Kim et al., "Identification of senescent cell surface targetable protein DPP4". Genes Dev. Aug. 1, 2017;31(15):1529-1534.
Kral et al., "Sustained PI3K Activation exacerbates BLM-induced Lung Fibrosis via activation of pro-inflammatory anti pro-fibrotic pathways". Sci Rep. Mar. 14, 2016;6:23034.
Lehmann et al., "Senolytic drugs target alveolar epithelial cell function and attenuate experimental lung fibrosis ex vivo". Eur Respir J. Aug. 3, 2017;50(2).pii:1602367.
Muñoz-Espin et al., "Cellular senescence: from physiology to pathology". Nat Rev Mol Cell Biol. Jul. 2014;15(7):482-96.
Myrianthopoulos et al., "Senescence and senotherapeutics: a new field in cancer therapy". Pharmacol Ther. Jan. 2019;193:31-49.
Nho et al., "IPF fibroblasts are desensitized to type I collagen matrix-induced cell death by suppressing low autophagy via aberrant Akt/mTOR kinases". PLoS One. Apr. 11, 2014;9(4):e94616.
Schafer et al., "Cellular senescence mediates fibrotic pulmonary disease". Nat Commun. Feb. 23, 2017;8:14532.
Senis et al., "Targeting receptor-type protein tyrosine phosphatases with biotherapeutics: is outside-in better than inside-out?". Molecules. Mar. 2, 2018;23(3):569.
Soare et al., "Dipeptidylpeptidase 4 as a marker of activated fibroblasts and a potential target for the treatment of fibrosis in systemic sclerosis". Arthritis Rheumatol. Jan. 2020;72(1):137-149.
Takahashi et al., "A monoclonal antibody against CD148, a receptor-like tyrosine phosphatase, inhibits endothelial-cell growth and angiogenesis". Blood. Aug. 15, 2006;108(4):1234-42.
Tangye et al., "CD148: a receptor-type protein tyrosine phosphatase involved in the regulation of human T cell activation". J Immunol. Oct. 1, 1998;161(7):3249-55.
Tsuboi et al., "The tyrosine phosphatase CD148 interacts with the p85 regulatory subunit of phosphoinositide 3-kinase". Biochem J. Jul. 1, 2008;413(1):193-200.
Yosef et al., "Directed elimination of senescent cells by inhibition of BCL-W and BCL-XL". Nat Commun. Apr. 6, 2016;7:11190.
Cartellier et al., "Chimeric Antigen Receptor-Engineered T Cells for Immunotherapy of Cancer," Journal of Biomedicine and Biotechnology, vol. 2010, Article ID 956304, (2010).
Chicaybam et al., "Chimeric Antigen Receptors in Cancer Immuno-Gene Therapy: Current Status and Future Directions," International Reviews of Immunology, 30:5-6, 294-311 (2011).
He et al., "Senescence in Health and Disease," Cell. Jun. 1, 2017; 169(6): 1000-1011 (2017).

*Primary Examiner* — Amy E Juedes
*Assistant Examiner* — Peter Johansen
(74) *Attorney, Agent, or Firm* — Panitch Schwarze Belisario & Nadel LLP; Erin M. Dunston

(57) ABSTRACT

The invention relates to DPP4-binding domains, as well as antibodies and chimeric antigen receptors (CAR) comprising the same. Also disclosed are methods for treating, preventing or alleviating senescence-related diseases or disorders, or for depleting and/or killing senescent cells.

15 Claims, 8 Drawing Sheets
Specification includes a Sequence Listing.

SENESCENT CELL-ASSOCIATED ANTIGEN-BINDING DOMAINS, ANTIBODIES AND CHIMERIC ANTIGEN RECEPTORS COMPRISING THE SAME, AND USES THEREOF

FIELD OF INVENTION

The invention relates to DPP4-binding domains, as well as antibodies and chimeric antigen receptors (CAR) comprising the same. Also disclosed are methods for treating, preventing or alleviating senescence-related diseases or disorders, or for depleting and/or killing senescent cells.

BACKGROUND OF INVENTION

Cellular senescence is an evolutionarily conserved state of stable replicative arrest induced by several pro-ageing stressors, including telomere attrition, oxidative stress, DNA damage and oncogene activation. Cellular senescence is associated with apoptosis resistance, and results in secretion of a broad repertoire of cytokines, chemokines, growth factors, matrix remodeling proteases: the so-called senescence-associated secretory phenotype (SASP). This cellular state also promotes proliferation and tissue deterioration.

Conversely, senescence is also anti-proliferative, and may be requisite for optimal cutaneous wound healing. Therefore, cellular senescence is an example of antagonistic pleiotropy in which natural selection favors processes that are beneficial early in life, even if they cause harmful effects later in post-reproduction life.

Since its discovery, senescence, once defined as the limited replicative capacity of primary human fibroblasts, now serves as a key player driving organismal aging via exhaustion of tissue repair capacity. Several human pathologies have been associated with detrimental effects of senescence such as lung fibrosis, type 2 diabetes, obesity, osteoarthritis, ocular diseases, Alzheimer's and Parkinson's disease (Munoz-Espin and Serrano, 2014. Nat Rev Mol Cell Biol. 2014 July; 15(7):482-96). Therapeutic strategies so far to balance these pathologies related to accumulation of senescent cells are dependent on direct elimination of senescent cells based on their intrinsic properties (e.g., their apoptotic resistance or P53 dependence) (Yosef et al., 2016. Nat Commun. 7:11190; Chang et al., 2016. Nat Med. 22(1):78-83; Baar et al., 2017. Cell. 169(1):132-147). Although these first-generation senolytic approaches serve as a proof-of-principle for drug discovery targeting senescence, they are limited by their observed toxic side effects.

While the role of senescence and the contribution of senescent cells are increasingly recognized in the context of aging and a variety of disease states, relatively little is known regarding the influences of senescent cells in normal lung growth and aging per se, or in the induction or progression of lung diseases across the age spectrum, such as bronchopulmonary dysplasia, asthma, chronic obstructive pulmonary disease, or pulmonary fibrosis. However, crucial evidences have been recently provided by several groups that cellular senescence contributes to lung ageing (Hashimoto et al., 2016. JCI Insight. 1(12):e87732; Lehmann et al., 2017. Eur Respir J. 50(2):1602367; Schafer et al., 2017. Nat Commun. 8:14532).

Among lung diseases, idiopathic pulmonary fibrosis (IPF) is a typical example of an ageing disease characterized by a progressive destruction of lung parenchyma and interstitial remodeling, leading to IPF symptoms (i.e., chronic shortness of breath, cough, fatigue and weight loss) and resulting in dramatic truncation of healthspan and lifespan.

The potential to blunt lung disease by targeting senescent cells using a novel class of drugs called "senolytics" is currently discussed. Indeed, two studies by Lehmann et al. and Schafer et al. suggest that cellular senescence is a salient feature of lung fibrosis, and that targeting/elimination of these cells could be beneficial. In particular, they show that cellular senescence markers such as SAβG, P21, P16INK4a and DNA damage response are detectable within IPF patients, as well as in experimental models of lung fibrosis. They further demonstrate that senescent cell elimination rejuvenates pulmonary health in aged mice. However, it is unclear whether and how senescent cells regulate IPF in humans or if their removal may be an efficacious intervention strategy.

Although promising, it cannot be excluded that senolytic drugs could be detrimental in IPF patients. Indeed, senolytic drug treatment may result in massive epithelial cell depletion by apoptosis, which could trigger diffuse alveolar damage and acute exacerbation, since the regenerative capacity of epithelial cells in IPF patients is impaired.

There remains thus a need for alternative strategies for depleting senescent cells and improving health and lung functions of IPF patients.

The Inventors have developed such alternative strategy, by potentiating an immune response against senescent cells in a way that would lead to their clearance from lung tissue. They provide herein a new association of two cell surface markers, DPP4 and DEP1, which are targeted to detect and deplete senescent cells in the lung. Senescent cells are immunogenic in nature and are subject to immune surveillance mechanisms.

Dipeptidyl peptidase 4 (DPP4, also named CD26) is a cell surface protease with a wide range of biological functions. As a serine-type protease, DPP4 preferentially cleaves off substrates with proline and alanine at the penultimate position. Expression of DPP4 is widespread throughout the body. Interestingly, DPP4 has been identified as a senescent cell surface targetable protein, functionally required for fibroblast activation and tissue fibrosis (Kyoung et al., 2017. Genes Dev. 31(15):1529-1534).

Density Enhanced Protein Tyrosine Phosphatase (DEP1, also named CD148, HPTP-eta, or PTP receptor type J (PTPRJ)) is an enzyme that removes phosphate groups covalently attached to tyrosine residues in proteins. DEP1 is highly expressed on both hematopoietic and nonhematopoietic cells, including lung cells. It has been shown that DEP1 can directly interact with and dephosphorylate the regulatory subunit of PI3K (p85) (Tsuboi et al., 2008. Biochem J. 413(1):193-200) and that hyperactivation of PI3K/Akt plays an important role in the profibrotic phenotype of IPF-derived lung fibroblasts by promoting cell proliferation and migration and myofibroblast differentiation (Kral et al., 2016. Sci Rep. 6:23034; Nho et al., 2014. PLoS One. 9(4):e94616).

The Inventors herein provide antibodies, bispecific antibodies, chimeric antigen receptors (CARs) and bispecific CARs, including immune cell populations expressing said CARs directed specifically against senescent cells for treatment and prophylaxis of age-related diseases and disorders, and other diseases and disorders associated or exacerbated by the presence of senescent cells, such as, for example, pulmonary fibrosis. The antibodies and CARs described herein are specific for at least one senescent cell-associated antigen (e.g., DEP1 and/or DPP4), and induce the clearance (i.e., removal, elimination, destruction) of senescent cells. Said clearance may, for example, be mediated by antibody-dependent cell cytotoxicity (ADCC) or complement dependent cytotoxicity (CDC) or both.

SUMMARY

The present invention relates to a DPP4-binding domain, comprising a combination of three heavy chain variable region (HCVR)'s complementary-determining regions (CDRs) and three light chain variable region (LCVR)'s CDRs, said combination being as defined in Table 3.

In one embodiment, the DPP4-binding domain comprises:
a) a HCVR which comprises the following three CDRs:
   $V_H$-CDR1 selected from the group consisting of SEQ ID NO: 109 and 108;
   $V_H$-CDR2 selected from the group consisting of SEQ ID NO: 122 and 127;
   $V_H$-CDR3 selected from the group consisting of SEQ ID NO: 139 and 138;
b) a LCVR which comprises the following three CDRs:
   $V_L$-CDR1 selected from the group consisting of SEQ ID NO: 148 and 147;
   $V_L$-CDR2 selected from the group consisting of SEQ ID NO: 160 and 159;
   $V_L$-CDR3 selected from the group consisting of SEQ ID NO: 172 and 171.

In one embodiment, the DPP4-binding domain is selected from the group consisting of:
i. a DPP4-binding domain comprising a $V_H$-CDR1 with SEQ ID NO: 109, a $V_H$-CDR2 with SEQ ID NO: 122, a $V_H$-CDR3 with SEQ ID NO: 139, a $V_L$-CDR1 with SEQ ID NO: 148, a $V_L$-CDR2 with SEQ ID NO: 160 and a $V_L$-CDR3 with SEQ ID NO: 172; and ii. a DPP4-binding domain comprising a $V_H$-CDR1 with SEQ ID NO: 108, a $V_H$-CDR2 with SEQ ID NO: 127, a $V_H$-CDR3 with SEQ ID NO: 138, a $V_L$-CDR1 with SEQ ID NO: 147, a $V_L$-CDR2 with SEQ ID NO: 159 and a $V_L$-CDR3 with SEQ ID NO: 171.

In one embodiment, the DPP4-binding domain is selected from the group consisting of:

i. a DPP4-binding domain comprising a HCVR with a sequence sharing at least 80% of sequence identity with the non-CDR regions of SEQ ID NO: 185 and a LCVR with a sequence sharing at least 80% of sequence identity with the non-CDR regions of SEQ ID NO: 213; and ii. a DPP4-binding domain comprising a HCVR with a sequence sharing at least 80% of sequence identity with the non-CDR regions of SEQ ID NO: 197 and a LCVR with a sequence sharing at least 80% of sequence identity with the non-CDR regions of SEQ ID NO: 212.

The present invention also relates to a DEP1-binding domain, comprising a combination of three heavy chain variable region (HCVR)'s complementary-determining regions (CDRs) and three light chain variable region (LCVR)'s CDRs, said combination being as defined in Table 1.

In one embodiment, the DEP1-binding domain comprises:

a) a HCVR which comprises the following three CDRs:
   - $V_H$-CDR1 selected from the group consisting of SEQ ID NO: 10, 11 and 5;
   - $V_H$-CDR2 selected from the group consisting of SEQ ID NO: 21, 25 and 12;
   - $V_H$-CDR3 selected from the group consisting of SEQ ID NO: 30, 32 and 29;

b) a LCVR which comprises the following three CDRs:
   - $V_L$-CDR1 selected from the group consisting of SEQ ID NO: 37, 38 and 33;
   - $V_L$-CDR2 selected from the group consisting of SEQ ID NO: 44, 46 and 40;
   - $V_L$-CDR3 selected from the group consisting of SEQ ID NO: 53, 52 and 49.

In one embodiment, the DEP1-binding domain is selected from the group consisting of:

i. a DEP1-binding domain comprising a $V_H$-CDR1 with SEQ ID NO: 10, a $V_H$-CDR2 with SEQ ID NO: 21, a $V_H$-CDR3 with SEQ ID NO: 30, a $V_L$-CDR1 with SEQ ID NO: 37, a $V_L$-CDR2 with SEQ ID NO: 44 and a $V_L$-CDR3 with SEQ ID NO: 53;

ii. a DEP1-binding domain comprising a $V_H$-CDR1 with SEQ ID NO: 11, a $V_H$-CDR2 with SEQ ID NO: 25, a $V_H$-CDR3 with SEQ ID NO: 32, a $V_L$-CDR1 with SEQ ID NO: 38, a $V_L$-CDR2 with SEQ ID NO: 46 and a $V_L$-CDR3 with SEQ ID NO: 52; and iii. a DEP1-binding domain comprising a $V_H$-CDR1 with SEQ ID NO: 5, a $V_H$-CDR2 with SEQ ID NO: 12, a $V_H$-CDR3 with SEQ ID NO: 29, a $V_L$-CDR1 with SEQ ID NO: 33, a $V_L$-CDR2 with SEQ ID NO: 40 and a $V_L$-CDR3 with SEQ ID NO: 49.

In one embodiment, the DEP1-binding domain is selected from the group consisting of:

i. a DEP1-binding domain comprising a HCVR with a sequence sharing at least 80% of sequence identity with the non-CDR regions of SEQ ID NO: 68 and a LCVR with a sequence sharing at least 80% of sequence identity with the non-CDR regions of SEQ ID NO: 89;

ii. a DEP1-binding domain comprising a HCVR with a sequence sharing at least 80% of sequence identity with the non-CDR regions of SEQ ID NO: 72 and a LCVR with a sequence sharing at least 80% of sequence identity with the non-CDR regions of SEQ ID NO: 93; and iii. a DEP1-binding domain comprising a HCVR with a sequence sharing at least 80% of sequence identity with the non-CDR regions of SEQ ID NO: 58 and a LCVR with a sequence sharing at least 80% of sequence identity with the non-CDR regions of SEQ ID NO: 78.

The present invention also relates to an isolated antibody or antigen-binding fragment thereof comprising the DPP4-binding domain or the DEP1-binding domain of the invention.

In one embodiment, the isolated antibody or antigen-binding fragment thereof is a bispecific antibody comprising the DPP4-binding domain and the DEP1-binding domain of the invention.

The present invention also relates to a chimeric antigen receptor (CAR) comprising:

a. at least one extracellular binding domain, comprising at least one DPP4-binding domain and/or at least one DEP1-binding domain of the invention,
b. an extracellular spacer domain,
c. a transmembrane domain,
d. optionally, at least one costimulatory domain, and
e. at least one intracellular signaling domain.

The present invention also relates to an immune cell engineered to express the CAR of the invention at its surface.

The present invention also relates to a population of immune cells, comprising a plurality of immune cells of the invention.

In one embodiment, the population of immune cells of the invention comprises:

a) a plurality of immune cells of the invention, engineered to express a CAR comprising at least one DPP4-binding domain of the invention at its surface; and a plurality of immune cells of the invention, engineered to express a CAR comprising at least one DEP1-binding domain of the invention at its surface; or b) a plurality of immune cells of the invention, engineered to express a CAR comprising at least one DPP4-binding domain of the invention and a CAR comprising at least one DEP1-binding domain of the invention, at its surface; or c) a plurality of immune cells of the invention, engineered to express a CAR comprising at least one DPP4-binding domain of the invention and at least one DEP1-binding domain of the invention at its surface.

The present invention also relates to a composition comprising:

the isolated antibody or antigen-binding fragment thereof of the invention,
the immune cell of the invention, and/or
the population of immune cells of the invention.

In one embodiment, the composition of the invention is a pharmaceutical composition and further comprising at least one pharmaceutically acceptable excipient.

In one embodiment, the composition of the invention is for use as a drug.

In one embodiment, the composition of the invention is for use in treating, preventing or alleviating a senescence-related disease or disorder, preferably selected from the group consisting of fibrotic diseases, premalignant disorders, inflammatory diseases and cancers.

In one embodiment, the senescence-related disease or disorder is a fibrotic disease, preferably a pulmonary fibrotic disease.

In one embodiment, the composition of the invention is for use in depleting and/or killing senescent cells.

Definitions

"A", "an" and "the" are intended to include both singular and plural forms, unless the context clearly indicates otherwise.

"About", preceding a figure encompasses plus or minus 10%, or less, of the value of said figure. It is to be understood that the value to which the term "about" refers is itself also specifically, and preferably, disclosed.

"Antibody-dependent cell-mediated cytotoxicity" or "ADCC" refers to a cell-mediated cytotoxicity induced in an antibody-dependent manner when the Fc region of said antibody bound to its antigen binds to the Fc receptor on effector cells such as natural killer cells, macrophages, neutrophils, eosinophils and mononuclear cells (e.g., peripheral blood mononuclear cells), thereby leading to lysis of the target cell. ADCC can be measured using assays that are known and available in the art (e.g., Clynes et al., 1998. *Proc Natl Acad Sci USA*. 95(2):652-6).

"Antibody-dependent cell-mediated phagocytosis" or "ADCP" or "opsonisation" refers to a cell-mediated reaction in which nonspecific cytotoxic cells (e.g., phagocytes, macrophages) that express Fc receptors (FcRs) recognize antibody bound on a target cell and induce phagocytosis of the target cell. ADCP can be measured using assays that are known and available in the art (e.g., Clynes et al., 1998. *Proc Natl Acad Sci USA*. 95(2):652-6).

"Adnectins", also known as monobodies, is well known in the art and refer to proteins designed to bind with high affinity and specificity to antigens. They belong to the class of molecules collectively called "antibody mimetics".

"Allogeneic" refers to a graft derived from a different animal of the same species.

"Alphabody" that may also be referred to as Cell-Penetrating Alphabodies, refer to a type of antibody mimetics consisting of small 10 kDa proteins engineered to bind to a variety of antigens. Alphabodies are able to reach and bind to intracellular protein targets.

"Affibodies" are well-known in the art and refer to affinity proteins based on a 58 amino acid residue protein domain, derived from one of the IgG binding domain of staphylococcal protein A (Frejd & Kim, 2017. *Exp Mol Med.* 49(3):e306; U.S. Pat. No. 5,831,012).

"Affilins" are well known in the art and refer to artificial proteins designed to selectively bind antigens. They resemble antibodies in their affinity and specificity to antigens but not in structure which makes them a type of antibody mimetic "Affinity" and "avidity" are well-known in the art and are used to defined the strength of an antibody-antigen complex. Affinity measures the strength of interaction between an epitope and an antigen binding site on an antibody. It may be expressed by an affinity constant KA or by a dissociation constant KD. Avidity (or functional affinity) gives a measure of the overall strength of an antibody-antigen complex. It may depend on different parameters, including in particular the affinity of the antibody or antigen-binding fragment thereof for an epitope, (ii) the valency of both the antibody and the antigen and (iii) structural arrangement of the parts that interact. Affinities of antibodies or antigen-binding fragment thereof can be readily determined using conventional techniques, for example, those described by Scatchard, 1949. *Ann NY Acad Sci.* 51:660-672. Binding properties of an antibody or antigen-binding fragment thereof to antigens, cells or tissues may generally be determined and assessed using immunodetection methods including, for example, ELISA, immunofluorescence-based assays, such as immuno-histochemistry (IHC) and/or fluorescence-activated cell sorting (FACS) or by surface plasmon resonance (SPR, e.g., using BIAcore®).

"Antibody" and "immunoglobulin" may be used interchangeably and refer to a protein having a combination of two heavy and two light chains whether or not it possesses any relevant specific immunoreactivity. "Antibodies" refers to such assemblies which have significant known specific immunoreactive activity to an antigen of interest (e.g., human DEP1 and/or DPP4). The term "anti-DEP1 antibodies or anti-DPP4 antibodies" is used herein to refer to antibodies which exhibit immunological specificity for human DEP1 antigen or human DPP4 antigens, respectively. As explained elsewhere herein, "specificity" for human DEP1 does not exclude cross-reaction with species homologues of human DEP1, such as, for example, with simian DEP1, and "specificity" for human DPP4 does not exclude cross-reaction with species homologues of human DPP4 such as, for example, with simian DPP4.

Antibodies and immunoglobulins comprise light and heavy chains, with or without an interchain covalent linkage between them. Basic immunoglobulin structures in vertebrate systems are relatively well understood. The generic term "immunoglobulin" comprises five distinct classes of antibody that can be distinguished biochemically. Although the following discussion will generally be directed to the IgG class of immunoglobulin molecules, all five classes of antibodies are within the scope of the present invention. With regard to IgG, immunoglobulins comprise two identical light polypeptide chains of molecular weight of about 23 kDa, and two identical heavy chains of molecular weight of about 53-70 kDa. The four chains are joined by disulfide bonds in a "Y" configuration wherein the light chains bracket the heavy chains starting at the mouth of the "Y" and continuing through the variable region. The light chains of an antibody are classified as either kappa (κ) or lambda (λ). Each heavy chain class may be bonded with either a κ or λ light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma (γ), mu (μ), alpha (α), delta (δ) or epsilon (ε) with some subclasses among them (e.g., γ1-γ4). It is the nature of this chain that determines the "class" of the antibody as IgG, IgM, IgA IgD or IgE, respectively. The immunoglobulin subclasses or "isotypes" (e.g., IgG1, IgG2, IgG3, IgG4, IgA1, etc.) are well characterized and are known to confer functional specialization. Modified versions of each of these classes and isotypes are readily discernable to the skilled artisan in view of the instant disclosure and, accordingly, are within the scope of the present invention. As indicated above, the variable region of an antibody allows the antibody to selectively recognize and specifically bind epitopes on antigens. That is, the light chain variable domain (VL domain) and heavy chain variable domain (VH domain) of an antibody combine to form the variable region that defines a three-dimensional antigen binding site. This quaternary antibody structure forms the antigen binding site presents at the end of each arm of the "Y". More specifically, the antigen binding site is defined by three complementarity determining regions (CDRs) on each of the VH and VL chains.

"Anticalins" are well known in the art and refer to an antibody mimetic technology, wherein the binding specificity is derived from lipocalins. Anticalins may also be formatted as dual targeting protein, called Duocalins.

"Antigen" refers any substance that is capable of stimulating an immune response, specifically activating immunes cells. In general, two main divisions of antigens are recognized: foreign antigens (or heteroantigens) and autoantigens (or self-antigens).

Antigen molecules possess by definition, at least one epitope (or antigenic sites) which produce corresponding antibodies.

"Antigen-binding fragment", as used herein, refers to a part or region of an antibody or chimeric antigen receptor (CAR), which comprises fewer amino acid residues than the whole antibody or CAR. An "antigen-binding fragment" binds to an antigen and/or competes with the whole antibody and/or CAR from which it was derived for antigen binding (e.g., specific binding to human senescent associated-cell antigen). Antigen-binding fragments encompasses, without any limitation, single chain antibodies, Fv, Fab, Fab', Fab'-SH, F(ab)'2, Fd, defucosylated antibodies, diabodies, triabodies and tetrabodies.

"Armadillo repeat protein-based scaffold", as used herein, refers to a type of antibody mimetics corresponding to artificial peptide binding scaffolds based on armadillo repeat proteins. Armadillo repeat proteins are characterized by an armadillo domain, composed of tandem armadillo repeats of approximately 42 amino acids, which mediates interactions with peptides or proteins.

"Atrimers" are well known in the art and refers to binding molecules for target protein that trimerize as a perquisite for their biological activity. They are relatively large compared to other antibody mimetic scaffolds.

"Autologous" is meant to refer to any material derived from the same individual to which it is later to be re-introduced into the individual.

"Avimers" are well known in the art and refer to an antibody mimetic technology.

"Complement-dependent cytotoxicity" or "CDC" refers to the induction of the lysis of antigen-expressing cells recognized by an antibody or antigen-binding fragment thereof of the invention in the presence of complement. The complement activation pathway is initiated by the binding of the first component of the complement system (C1q) to a molecule (e.g., an antibody) complexed with a cognate antigen. CDC can be measured using assays that are known and available in the art (e.g., Clynes et al., 1998. *Proc Natl Acad Sci USA.* 95(2):652-6; Gazzano-Santaro et al., 1997. *J Immunol Methods.* 202(2): 163-71).

"CDR" or "complementarity determining region" means the non-contiguous antigen combining sites found within the variable region of both heavy and light chain polypeptides. The precise amino acid sequence boundaries of a given CDR can be determined using any of a number of well-known schemes, including those described by Kabat et al. (1991), "Sequences of Proteins of Immunological Interest" 5th Ed. Public Health Service, National Institutes of Health, Bethesda, Md. ("Kabat" numbering scheme), Al-Lazikani et al., 1997. *J Mol Biol.* 273(4):927-48 ("Chothia" numbering scheme), or a combination thereof. More recently, a universal numbering system has been developed and widely adopted, ImMunoGeneTics (IMGT) Information System® (Lefranc et al., 1999. *Nucleic Acids Res.* 27(4209-12). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues may be readily identified. This information can be used in grafting and replacement of CDR residues from immunoglobulins of one species into an acceptor framework from, typically, a human antibody. Correspondence between the Kabat numbering and the IMGT unique numbering system is also well known to one skilled in the art (e.g., Lefranc et al., supra). Thus, in one embodiment, by CDR regions or CDR, it is intended to indicate the hypervariable regions of the heavy and light chains of the immunoglobulins as defined by IMGT® numbering system (e.g. Lefranc et al., supra).

| Heavy chain variable region (HCVR or $V_H$) | | | |
|---|---|---|---|
| | $V_H$-CDR1 | $V_H$-CDR2 | $V_H$-CDR3 |
| Start | Approx, at residue 26 (always 4 after a Cys) according to | Always 15 residues after the end of $V_H$-CDR1 according to Kabat/AbM's | Always 33 residues after end of $V_H$-CDR2 Always 2 residues after a |

|  | Chothia/AbM's definition Kabat's definition starts 5 residues later | definition | Cys |
|---|---|---|---|
| Residue before | Always Cys-Xaa-Xaa-Xaa, with Xaa being any amino acid according to Chothia/AbM's definition | Typically, Leu-Glu-Trp-Ile-Gly, but a number of variations | Always Cys-Xaa-Xaa, with Xaa being any amino acid Typically, Cys-Ala-Arg |
| Residue after | Always Trp Typically, Trp-Val, but also, Trp-Ile or Trp-Ala | Lys/Arg-Leu/Ile/Val/Phe/Thr/Ala-Thr/Ser/Ile/Ala | Always Trp-Gly-Xaa-Gly, with Xaa being any amino acid |
| Length | 10 to 12 residues according to AbM's definition Chothia's definition excludes the last 4 residues 5 to 7 residues according to Kabat's definition | 16 to 19 residues according to Kabat's definition AbM's definition ends 7 residues earlier | 3 to 25 residues |

| Light chain variable region (LCVR or $V_L$) | | |
|---|---|---|
| $V_L$-CDR1 | $V_L$-CDR2 | $V_L$-CDR3 |
| Start Approx, at residue 24 | Always 16 residues after the end of $V_L$-CDR1 | Always 33 residues after end of $V_L$-CDR2 (except NEW (PDB ID: 7FAB) which has the deletion at the end of CDR-L2*) |
| Residue before Always Cys | Generally, Ile-Tyr, but also, Val-Tyr, Ile-Lys or Ile-Phe | Always Cys |
| Residue after Always Trp Typically, Trp-Tyr-Gln, but also, Trp-Leu-Gln, Trp-Phe-Gln or Trp-Tyr-Leu | | Always Phe-Gly-Xaa-Gly, with Xaa being any amino acid |
| Length 10 to 17 residues | Always 7 residues (except NEW (PDB ID: 7FAB) which has a deletion in this region*) | 7 to 11 residues |

\* Saul & Poljak, 1992. *Proteins*. 14(3):363-71

"Cell", "cell line" and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid "Chimeric antigen receptor" or "CAR refers to engineered receptors, which graft an antigen specificity onto cells with intracellular signal generation (such as, for example, T cells or phagocytic cells). CARs are also known as artificial T cell receptors, chimeric T cell receptors or chimeric immunoreceptors.

"Co-stimulatory domain" or "CSD", when used in a relationship with a chimeric antigen receptor (CAR), refers to the portion of the CAR which enhances the proliferation, survival and/or development of memory cells. The CARs of the invention may comprise one or more co-stimulatory domains. Co-stimulatory domains are apparent to those of skill in the art and may be used in connection with alternate embodiments of the invention.

"DARPins" or "Designed Ankyrin Repeat Proteins" are well known in the art and refer to an antibody mimetic DRP (designed repeat protein) technology developed to exploit the binding abilities of non-antibody polypeptides.

"DEP1", also known as PTPRJ, SCC1, CD148, HPTPeta or R-PTP-ETA, refers to a protein encoded by a gene which is a member of the protein tyrosine phosphatase (PTP) family. PTPs are known to be signaling molecules that regulate a variety of cellular processes, including cell growth, differentiation, mitotic cycle, and oncogenic transformation. This PTP possesses an extracellular region containing five fibronectin type III repeats, a single transmembrane region, and a single intracytoplasmic catalytic domain, and thus represents a receptor-type PTP. This protein is present in all hematopoietic lineages, and was shown to negatively regulate T cell receptor signaling possibly through interfering with the phosphorylation of Phospholipase C Gamma 1 and Linker for Activation of T Cells. This protein can also dephosphorylate the PDGF beta receptor, and may be involved in UV-induced signal transduction. In human, multiple transcript variants encoding different isoforms have been found for this gene. In the sense of the present invention, human DEP1 (or hDEP1) is a protein with an amino acid sequence SEQ ID NO: 1.

SEQ ID NO: 1
MKPAAREARLPPRSPGLRWALPLLLLLLRLGQILCAGGTPSPIPDPSVAT

VATGENGITQISSTAESFHKQNGTGTPQVETNTSEDGESSGANDSLRTPE

-continued

QGSNGTDGASQKTPSSTGPSPVFDIKAVSISPTNVILTWKSNDTAASEYK

YVVKHKMENEKTITVVHQPWCNITGLRPATSYVFSITPGIGNETWGDPRV

IKVITEPIPVSDLRVALTGVRKAALSWSNGNGTASCRVLLESIGSHEELT

QDSRLQVNISGLKPGVQYNINPYLLQSNKTKGDPLGTEGGLDASNTERSR

AGSPTAPVHDESLVGPVDPSSGQQSRDTEVLLVGLEPGTRYNATVYSQAA

NGTEGQPQAIEFRTNAIQVFDVTAVNISATSLTLIWKVSDNESSSNYTYK

IHVAGETDSSNLNVSEPRAVIPGLRSSTFYNITVCPVLGDIEGTPGFLQV

HTPPVPVSDFRVTVVSTTEIGLAWSSHDAESFQMHITQEGAGNSRVEITT

NQSIIIGGLFPGTKYCFEIVPKGPNGTEGASRTVCNRTVPSAVFDIHVVY

VTTTEMWLDWKSPDGASEYVYHLVIESKHGSNHTSTYDKAITLQGLIPGT

LYNITISPEVDHVWGDPNSTAQYTRPSNVSNIDVSTNTTAATLSWQNFDD

ASPTYSYCLLIEKAGNSSNATQVVTDIGITDATVTELIPGSSYTVEIFAQ

VGDGIKSLEPGRKSFCTDPASMASFDCEVVPKEPALVLKWTCPPGANAGF

ELEVSSGAWNNATHLESCSSENGTEYRTEVTYLNFSTSYNISITTVSCGK

MAAPTRNTCTTGITDPPPPDGSPNITSVSHNSVKVKFSGFEASHGPIKAY

AVILTTGEAGHPSADVLKYTYEDFKKGASDTYVTYLIRTEEKGRSQSLSE

VLKYEIDVGNESTTLGYYNGKLEPLGSYRACVAGFTNITFHPQNKGLIDG

AESYVSFSRYSDAVSLPQDPGVICGAVFGCIFGALVIVTVGGFIFWRKKR

KDAKNNEVSFSQIKPKKSKLIRVENFEAYFKKQQADSNCGFAEEYEDLKL

VGISQPKYAAELAENRGKNRYNNVLPYDISRVKLSVQTHSTDDYINANYM

PGYHSKKDFIATQGPLPNTLKDFWRMVWEKNVYAIIMLTKCVEQGRTKCE

EYWPSKQAQDYGDITVAMTSEIVLPEWTIRDFTVKNIQTSESHPLRQFHF

TSWPDHGVPDTTDLLINFRYLVRDYMKQSPPESPILVHCSAGVGRTGTFI

AIDRLIYQIENENTVDVYGIVYDLRMHRPLMVQTEDQYVFLNQCVLDIVR

SQKDSKVDLIYQNTTAMTIYENLAPVTTFGKTNGYIA hDEP1 is composed of several domains, as follows:
- a signal peptide, comprising or consisting of amino acid residues 1-35 of SEQ ID NO: 1;
- an extracellular domain, comprising or consisting of amino acid residues 36-975 of SEQ ID NO: 1, itself comprising:
  - a fibronectin type-III domain 1, comprising or consisting of amino acid residues 121-209 of SEQ ID NO: 1;
  - a fibronectin type-III domain 2, comprising or consisting of amino acid residues 207-291 of SEQ ID NO: 1;
  - a fibronectin type-III domain 3, comprising or consisting of amino acid residues 271-364 of SEQ ID NO: 1;
  - a fibronectin type-III domain 4, comprising or consisting of amino acid residues 368-456 of SEQ ID NO: 1;
  - a fibronectin type-III domain 5, comprising or consisting of amino acid residues 457-541 of SEQ ID NO: 1;
  - a fibronectin type-III domain 6, comprising or consisting of amino acid residues 542-623 of SEQ ID NO: 1;
  - a fibronectin type-III domain 7, comprising or consisting of amino acid residues 625-720 of SEQ ID NO: 1;
  - a fibronectin type-III domain 8, comprising or consisting of amino acid residues 721-817 of SEQ ID NO: 1; and
  - a fibronectin type-III domain 9, comprising or consisting of amino acid residues 816-902 of SEQ ID NO: 1;
- a transmembrane domain, comprising or consisting of amino acid residues 976-996 of SEQ ID NO: 1; and
- a cytoplasmic domain, comprising or consisting of amino acid residues 997-1337 of SEQ ID NO: 1.

"Diabodies", as used herein, refers to small antibody fragments prepared by constructing scFv fragments with short linkers (about 5-10 residues) between the HCVR and LCVR such that inter-chain but not intra-chain pairing of the variable domains is achieved, resulting in a bivalent fragment, i.e., fragment having two antigen-binding sites. Bispecific diabodies are heterodimers of two "crossover" scFv fragments in which the HCVR and LCVR of the two antibodies are present on different polypeptide chains. Diabodies are described more fully in European patent EP0404097, International patent application WO1993011161; and in Holliger et al., 1993. *Proc Natl Acad Sci USA*. 90(14):6444-8.

"Domain antibodies" are well-known in the art and refer to the smallest functional binding units of antibodies, corresponding to the variable regions of either the heavy or light chains of antibodies.

"Domain kunitz peptide" refer to a type of antibody mimetics, and is based on the active domains of proteins inhibiting the function of proteases.

"DPP4" (also known as ADABP, adenosine deaminase complexing protein 2, ADCP-2, dipeptidyl peptidase IV, DPP IV, CD26, or TP103) refers to an intrinsic membrane glycoprotein and a serine exopeptidase that cleaves X-proline dipeptides from the N-terminus of polypeptides.

In the sense of the present invention, human DPP4 (or hDPP4) is a protein with an amino acid sequence SEQ ID NO: 101.

SEQ ID NO: 101
MKTPWKVLLGLLGAAALVTIITVPVVLLNKGTDDATADSRKTYTLTDYLK

NTYRLKLYSLRWISDHEYLYKQENNILVFNAEYGNSSVFLENSTFDEFGH

SINDYSISPDGQFILLEYNYVKQWRHSYTASYDIYDLNKRQLITEERIPN

NTQWVTWSPVGHKLAYVWNNDIYVKIEPNLPSYRITWTGKEDIIYNGITD

WVYEEEVFSAYSALWWSPNGTFLAYAQFNDTEVPLIEYSFYSDESLQYPK

TVRVPYPKAGAVNPTVKFFVVNTDSLSSVTNATSIQITAPASMLIGDHYL

CDVTWATQERISLQWLRRIQNYSVMDICDYDESSGRWNCLVARQHIEMST

TGWVGRFRPSEPHFTLDGNSFYKIISNEEGYRHICYFQIDKKDCTFITKG

TWEVIGIEALTSDYLYYISNEYKGMPGGRNLYKIQLSDYTKVTCLSCELN

PERCQYYSVSFSKEAKYYQLRCSGPGLPLYTLHSSVNDKGLRVLEDNSAL

DKMLQNVQMPSKKLDFIILNETKFWYQMILPPHFDKSKKYPLLLDVYAGP

CSQKADTVFRLNWATYLASTENIIVASFDGRGSGYQGDKIMHAINRRLGT

FEVEDQIEAARQFSKMGFVDNKRIAIWGWSYGGYVTSMVLGSGSGVFKCG

IAVAPVSRWEYYDSVYTERYMGLPTPEDNLDHYRNSTVMSRAENFKQVEY

-continued

LLIHGTADDNVHFQQSAQISKALVDVGVDFQAMWYTDEDHGIASSTAHQH

IYTHMSHFIKQCFSLP hDPP4 is composed of several domains, as follows:
a cytoplasmic domain, comprising or consisting of amino acid residues 1-6 of SEQ ID NO: 101;
a transmembrane domain, comprising or consisting of amino acid residues 7-28 of SEQ ID NO: 101; and
an extracellular domain, comprising or consisting of amino acid residues 29-766 of SEQ ID NO: 101.

"Epitope", also known as "antigenic determinant", refers to a specific arrangement of amino acids located on a protein or proteins (or antigen(s)) to which an antibody or antigen-binding fragment thereof or chimeric antigen receptor (CAR) binds. Epitopes often consist of a chemically active surface grouping of molecules such as amino acids or sugar side chains, and have specific three-dimensional structural characteristics as well as specific charge characteristics. Epitopes can be linear (or sequential) or conformational, i.e., involving two or more sequences of amino acids in various regions of the antigen that may not necessarily be contiguous.

"Evasins" are well known in the art and refer to a class of chemokine-binding proteins.

"Extracellular spacer domain" or "ESD" or "hinge domain", when used in a relationship with a chimeric antigen receptor (CAR), refers to the hydrophilic region which is between the antigen-specific targeting region and the transmembrane domain. The extracellular spacer domains are apparent to those of skill in the art and may be used in connection with alternate embodiments of the invention.

"Framework region" or "FR region" includes the amino acid residues that are part of the variable region, but are not part of the CDRs (e.g., using the IMGT® numbering definition of CDRs). The framework regions for the light chain are similarly separated by each of the LCVR's CDRs. In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainders of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Fc domain" "Fc portion" and "Fc region" refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and μ for human antibodies), or a naturally occurring allotype thereof.

"Fynomers" are well known in the art and refer to proteins that belong to the class of antibody mimetic. They are attractive binding molecules due to their high thermal stability and reduced immunogenicity.

"Fv", as used herein, refers to the minimum antibody fragment that contains a complete antigen-recognition and -binding site. This fragment consists of a dimer of one HCVR and one LCVR in tight, non-covalent association. From the folding of these two domains emanate six hypervariable loops (three loops each from the heavy and light chain) that contribute to antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Heavy chain region" includes amino acid sequences derived from the constant domains of an immunoglobulin heavy chain. A protein comprising a heavy chain region comprises at least one of a $C_H 1$ domain, a hinge (e.g., upper, middle, and/or lower hinge region) domain, a $C_H 2$ domain, a $C_H 3$ domain, or a variant or fragment thereof. In an embodiment, the antibody or antigen-binding fragment thereof according to the present invention may comprise the Fc region of an immunoglobulin heavy chain (e.g., a hinge portion, a $C_H 2$ domain, and a $C_H 3$ domain). In another embodiment, the antibody or antigen-binding fragment thereof according to the present invention lacks at least a region of a constant domain (e.g., all or part of a $C_H 2$ domain). In certain embodiments, at least one, and preferably all, of the constant domains are derived from a human immunoglobulin heavy chain. For example, in one preferred embodiment, the heavy chain region comprises a fully human hinge region. In other preferred embodiments, the heavy chain region comprising a fully human Fc region (e.g., hinge, $C_H 2$ and $C_H 3$ domain sequences from a human immunoglobulin). In certain embodiments, the constituent constant domains of the heavy chain region are from different immunoglobulin molecules. For example, a heavy chain region of a protein may comprise a $C_H 2$ domain derived from an IgG1 molecule and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. As set forth above, it will be understood by one of ordinary skill in the art that the constant domains of the heavy chain region may be modified such that they vary in amino acid sequence from the naturally occurring (wild-type) immunoglobulin molecule. That is, the antibody or antigen-binding fragment thereof according to the present invention may comprise alterations or modifications to one or more of the heavy chain constant domains ($C_H 1$, hinge, $C_H 2$ or $C_H 3$) and/or to the light chain constant domain ($C_L$). Exemplary modifications include additions, deletions or substitutions of one or more amino acids in one or more domains.

"Hinge region", when used in a relationship with an antibody, includes the region of a heavy chain molecule that joins the $C_H 1$ domain to the $C_H 2$ domain in an antibody. This hinge region comprises approximately 25 residues and is flexible, thus allowing the two N-terminal antigen binding regions to move independently. Hinge regions can be subdivided into three distinct domains: upper, middle, and lower domains (Roux et al., 1998. *J Immunol.* 161(8):4083-90).

"Hypervariable loop" is not strictly synonymous to complementarity determining region (CDR), since the hypervariable loops (HVs) are defined on the basis of structure, whereas CDRs are defined based on sequence variability (Kabat et al., 1991. *Sequences of proteins of immunological interest* (5th ed.). Bethesda, Md.: U.S. Dep. of Health and Human Services) and the limits of the HVs and the CDRs may be different in some $V_H$ and $V_L$ domains. The CDRs of the $V_L$ and $V_H$ domains can typically be defined by the Kabat/Chothia definition as already explained hereinabove.

"Identity" or "identical", when used in a relationship between the sequences of two or more amino acid sequences, or of two or more nucleic acid sequences, refers to the degree of sequence relatedness between amino acid sequences or nucleic acid sequences, as determined by the number of matches between strings of two or more amino acid residues or nucleic acid residues. "Identity" measures the percent of identical matches between the smaller of two or more sequences with gap alignments (if any) addressed by a particular mathematical model or computer program (i.e., "algorithms"). Identity of related amino acid sequences or nucleic acid sequences can be readily calculated by known methods. Such methods include, but are not limited to, those described in Lesk A. M. (1988). *Computational molecular biology: Sources and methods for sequence analysis*. New York, N.Y.: Oxford University Press; Smith D. W. (1993). *Biocomputing: Informatics and genome projects*. San Diego, Calif.: Academic Press; Griffin A. M. & Griffin H. G. (1994). *Computer analysis of sequence data, Part 1*. Totowa, N.J.: Humana Press; von Heijne G. (1987). *Sequence analysis in molecular biology: treasure trove or trivial pursuit*. San Diego, Calif.: Academic press; Gribskov M. R. & Devereux J. (1991). *Sequence analysis primer*. New York, N.Y.: Stockton Press; Carillo et al., 1988. *SIAM J Appl Math*. 48(5):1073-82. Preferred methods for determining identity are designed to give the largest match between the sequences tested. Methods of determining identity are described in publicly available computer programs. Preferred computer program methods for determining identity between two sequences include the GCG program package, including GAP (Genetics Computer Group, University of Wisconsin, Madison, Wis.; Devereux et al., 1984. *Nucleic Acids Res*. 12(1 Pt 1):387-95), BLASTP, BLASTN, and FASTA (Altschul et al., 1990. *J Mol Biol*. 215(3):403-10). The BLASTX program is publicly available from the National Center for Biotechnology Information (NCBI) and other sources (BLAST Manual, Altschul et al. NCB/NLM/NIH Bethesda, Md. 20894). The well-known Smith Waterman algorithm may also be used to determine identity.

"Intracellular signaling domain" or "ISD" or "cytoplasmic domain", when used in a relationship with a chimeric antigen receptor (CAR), refers to the portion of the CAR which transduces the effector function signal and directs the cell to perform its specialized function. Intracellular signaling domains are be apparent to those of skill in the art and may be used in connection with alternate embodiments of the invention.

"Isolated" means altered or removed from the natural state. For example, a nucleic acid or a peptide naturally present in a living animal is not "isolated" but the same nucleic acid or peptide partially or completely separated from the coexisting materials of its natural state is "isolated". An isolated nucleic acid or protein can exist in substantially purified form, or can exist in a non-native environment such as, for example, a host cell.

"Knottin" or "inhibitor cystine knot" refer to an antibody mimetic comprising a protein structural motif containing three disulfide bridges.

"Monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies or antigen-binding fragment thereof according to the present invention may be prepared by the hybridoma methodology first described by Kohler et al., 1975. *Nature*. 256(5517):495-7, or may be made using recombinant DNA methods in bacterial, eukaryotic animal or plant cells (U.S. Pat. No. 4,816,567). The "monoclonal antibodies" may also be isolated from phage antibody libraries using the techniques described in Clackson et al., 1991. *Nature*. 352(6336):624-8 and Marks et al., 1991. *J Mol Biol*. 222(3):581-97, for example.

"Linker", when used in a relationship with a chimeric antigen receptor (CAR), refers to an oligo- or polypeptide region from about 1 to 100 amino acids in length, which links together any of the domains/regions of the CAR of the invention. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Linkers are apparent to those of skill in the art and may be used in connection with alternate embodiments of the invention.

"Nanobodies" are well-known in the art and refer to antibody-derived therapeutic proteins that contain the unique structural and functional properties of naturally-occurring heavy chain antibodies (Muyldermans, 2013. *Annu Rev Biochem*. 82:775-97). These heavy chain antibodies may contain a single variable domain (VHH) and two constant domains ($C_H2$ and $C_H3$).

"Prevent", "preventing" and "prevention" refer to prophylactic and preventative measures, wherein the object is to reduce the chances that a subject will develop the pathologic condition or disorder over a given period of time. Such a reduction may be reflected, e.g., in a delayed onset of at least one symptom of the pathologic condition or disorder in the subject.

"Proliferating cell" refers to a cell that is undergoing cell division.

"Promoter" is used to define a control sequence, that is a region of a vector at which initiation and rate of transcription are controlled. It may contain genetic elements to which regulatory proteins and molecules may bind, such as RNA polymerase and other transcription factors, to initiate the specific transcription a nucleic acid sequence. The phrases "operatively positioned" "operatively linked" "under control" and "under transcriptional control" mean that a promoter is in a correct functional location and/or orientation in relation to a nucleic acid to control transcriptional initiation and/or expression of that nucleic acid.

A promoter typically comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer", which refers to a cis-acting regulatory sequence involved in the transcriptional activation of a nucleic acid sequence. A promoter may be one naturally associated with a nucleic acid, as may be obtained by isolating the 5' non-coding sequences located upstream of the coding segment and/or exon. Such a promoter can be referred to as "endogenous". Similarly, an enhancer may be one naturally associated with a nucleic acid, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring", i.e., containing different elements of different transcriptional regulatory regions, and/or mutations that alter expression. For example, promoters that are most commonly used in recombinant DNA construction include the lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906). Furthermore, it is contemplated the control sequences that direct transcription and/or expression of sequences within non-nuclear organelles such as mitochondria, chloroplasts, and the like, can be employed as well. Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989). The promoters employed may be constitutive, tissue-specific, inducible, and/or useful under the appropriate conditions to direct high-level expression of the introduced DNA segment, such as is advantageous in the large-scale production of recombinant proteins and/or peptides. The promoter may be heterologous or endogenous.

Additionally, any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize a specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

"Recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g., a mouse) which is transgenic due to human immunoglobulin genes; or antibodies which are produced, expressed, generated or isolated in any other way in which particular immunoglobulin gene sequences (such as human immunoglobulin gene sequences) are assembled with other DNA sequences. Recombinant antibodies include, for example, chimeric and humanized antibodies.

"Senescent cells" refers to cells that are in cell cycle arrest, generally during the G1 transition of the cell cycle or in few cases in G2, elicited by replicative exhaustion due to telomere attrition or in response to stresses such as DNA damage, chemotherapeutic drugs, or aberrant expression of oncogenes. According to one embodiment, the senescent cells are generally characterized by at least one or more of the following characteristics: activation of the p53/p21CIP1 and/or pRb/p16INK4A tumor suppressor pathways, cells whose proliferation is irreversibly arrested, shortening of telomere size, expression of senescent-associated beta-galactosidase activity, specific chromatin modification, specific secretome, increase in reactive oxygen species and altered overall mitochondrial activity. Senescent cells and senescent cell-associated antigens can be detected by techniques and procedures described in the art.

"Single chain antibody", as used herein, refers to any antibody or fragment thereof that is a protein having a primary structure comprising or consisting of one uninterrupted sequence of contiguous amino acid residues, including without limitation (1) single-chain Fv molecules (scFv); (2) single chain proteins containing only one light chain variable domain, or a fragment thereof that contains the three CDRs of the light chain variable domain, without an associated heavy chain moiety; and (3) single chain proteins containing only one heavy chain variable region, or a fragment thereof containing the three CDRs of the heavy chain variable region, without an associated light chain moiety.

"Single-chain Fv", also abbreviated as "sFv" or "scFv", refers to antibody fragments that comprise the $V_H$ and $V_L$ antibody domains connected into a single amino acid chain. Preferably, the scFv amino acid sequence further comprises a flexible peptidic linker between the $V_H$ and $V_L$ domains that enables the scFv to form the desired structure for antigen binding (Plückthun, 1994. "Antibodies from

*Escherichia coli*". In Rosenberg & Moore (Eds.), *The pharmacology of monoclonal antibodies*. Handbook of Experimental Pharmacology, 113:269-315. Springer: Berlin, Heidelberg). Flexible peptidic linkers are generally composed of small, non-polar (e.g., glycine, Gly, G) or polar (e.g., serine, Ser, S; or threonine, Thr, T) amino acids, as suggested by Argos (1990. *J Mol Biol.* 211(4):943-958). The small size of these amino acids provides flexibility, and allows for mobility of the connecting functional domains, such as the $V_H$ and $V_L$ domains. In one embodiment, the flexible peptidic linker may be a short oligo- or polypeptide, preferably having a length ranging from 2 to 30 amino acids. In one embodiment, the flexible peptidic linker comprises glycine-serine repeats. In one embodiment, the flexible peptidic linker comprises one, or several repeats of, such as 2, 3, 4, 5 or more repeats of, GS linker(s) (i.e., a sequence of one Gly and one Ser), $G_2S$ linker(s) (i.e., a sequence of two Gly and one Ser), $G_3S$ linker(s) (i.e., a sequence of three Gly and one Ser), $G_4S$ linker(s) (i.e., a sequence of four Gly and one Ser), or $G_5S$ linker(s) (i.e., a sequence of five Gly and one Ser).

"Subject" refers to a mammal, preferably a human. In one embodiment, a subject may be a "patient", i.e., a warm-blooded animal, more preferably a human, who/which is awaiting the receipt of, or is receiving medical care or was/is/will be the object of a medical procedure, or is monitored for the development of a disease. The term "mammal" refers here to any mammal, including humans, domestic and farm animals, and zoo, sports, or pet animals, such as dogs, cats, cattle, horses, sheep, pigs, goats, rabbits, etc. Preferably, the mammal is a primate, more preferably a human.

"Therapeutically effective amount" refers to the level or amount of an antibody as described herein that is aimed at, without causing significant negative or adverse side effects to the target, (1) delaying or preventing the onset of a disease, disorder, or condition; (2) slowing down or stopping the progression, aggravation, or deterioration of one or more symptoms of the disease, disorder, or condition; (3) bringing about ameliorations of the symptoms of the disease, disorder, or condition; (4) reducing the severity or incidence of the disease, disorder, or condition; or (5) curing the disease, disorder, or condition. A therapeutically effective amount may be administered prior to the onset of the disease, disorder, or condition, for a prophylactic or preventive action. Alternatively or additionally, the therapeutically effective amount may be administered after initiation of the disease, disorder, or condition, for a therapeutic action.

"Transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid.

"Transmembrane domain" or "TMD", when used in a relationship with a chimeric antigen receptor (CAR), refers to the region of the CAR which crosses the plasma membrane. The transmembrane domain of the CAR of the invention is the transmembrane region of a transmembrane protein (for example Type I transmembrane proteins), an artificial hydrophobic sequence or a combination thereof. Other transmembrane domains are apparent to those of skill in the art and may be used in connection with alternate embodiments of the invention.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a cancer or an infection if, after receiving a therapeutic amount of an antibody according to the methods of the present invention, the patient shows observable and/or measurable reduction in or absence of one or more of the following: reduction in the number of cancer cells (or tumor size), or pathogenic cells; reduction in the percent of total cells that are cancerous or pathogenic; and/or relief to some extent, one or more of the symptoms associated with the specific disease or condition; reduced morbidity and mortality, and improvement in quality of life issues. The above parameters for assessing successful treatment and improvement in the disease are readily measurable by routine procedures familiar to a physician.

"Unibodies" are well known in the art and refer to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

"Variable" refers to the fact that certain regions of the variable domains $V_H$ and $V_L$ differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the $V_L$ domain and the $V_H$ domain which form part of the antigen binding site. The first, second and third hypervariable loops of the Vλ light chain domain are referred to herein as L1 (λ), L2 (λ) and L3 (λ) and may be defined as comprising residues 24-33 (L1(λ), consisting of 9, 10 or 11 amino acid residues), 49-53 L2 (λ), consisting of 3 residues) and 90-96 (L3(λ), consisting of 6 residues) in the $V_L$ domain (Morea et al., 2000. *Methods.* 20(3):267-79). The first, second and third hypervariable loops of the Vκ light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the $V_L$ domain (Morea et al., 2000. *Methods.* 20(3):267-79). The first, second and third hypervariable loops of the $V_H$ domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., 2000. *Methods.* 20(3):267-79). Unless otherwise indicated, the terms L1, L2 and L3 respectively refer to the first, second and third hypervariable loops of a VL domain, and encompass hypervariable loops obtained from both Vκ and Vλ isotypes. The terms H1, H2 and H3 respectively refer to the first, second and third hypervariable loops of the $V_H$ domain, and encompass hypervariable loops obtained from any of the known heavy chain isotypes, including gamma (γ), mu (μ), alpha (α), delta (δ) or epsilon (ε). The hypervariable loops L1, L2, L3, H1, H2 and H3 may each comprise part of a "complementarity determining region" or "CDR", as defined hereinabove.

"Vector" is used to refer to a carrier nucleic acid molecule into which a nucleic acid sequence can be inserted, for introduction into a cell where it can be replicated. A nucleic acid sequence can be "exogenous", which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One skilled in the art would be well equipped to construct a vector through standard recombinant techniques (see, e.g., Maniatis et al., 1988 and Ausubel et al., 1994).

In one embodiment, the vector can be an "expression vector". This term refers to any type of genetic construct comprising a nucleic acid coding for an RNA capable of being transcribed. In some cases, RNA molecules are then translated into a protein, polypeptide, or peptide. In other cases, these sequences are not translated, e.g., in the production of antisense molecules or ribozymes. Expression vectors can contain a variety of control sequences, which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described herein. In particular, expression vectors can contain one or several promoter(s), enhancer(s), internal ribosome entry site(s) (IRES), multiple cloning site(s) (MCS), splicing site(s), termination signal(s), origin(s) of replication, and/or selectable marker(s).

The vector may be a "plasmid vector". In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 hours, the cells are collected by centrifugation and washed to remove residual media.

The vector may be a "viral vector". The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells).

In one embodiment, the viral vector may be an adenoviral vector. Although adenoviral vectors are known to have a low capacity for integration into genomic DNA, this feature is counterbalanced by the high efficiency of gene transfer afforded by these vectors.

In one embodiment, the viral vector may be an adeno-associated viral (AAV) vector. Increased transfection efficiencies have been reported in cell systems using adenovirus coupled systems (Kelleher & Vos, 1994. Biotechniques. 17(6):1110-7; Cotten et al., 1992. Proc Natl Acad Sci USA. 89(13):6094-8; Curiel, 1994. Nat Immun. 13(2-3):141-64). AAV is an attractive vector system as it has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368.

In one embodiment, the viral vector may be a retroviral vector. Retroviruses are useful as delivery vectors because of their ability to integrate their genes into the host genome, transferring a large amount of foreign genetic material, infecting a broad spectrum of species and cell types and of being packaged in special cell lines. In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed. When a recombinant plasmid containing a cDNA, together with the retroviral LTR and packaging sequences is introduced into a special cell line (e.g., by calcium phosphate precipitation), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells. Lentiviruses are complex retroviruses, which, in addition to the common retroviral genes gag, pol, and env, contain other genes with regulatory or structural function. Lentiviral vectors are well known in the art (see, e.g., U.S. Pat. Nos. 6,013,516 and 5,994,136). Some examples of lentivirus include the human immunodeficiency viruses HIV-1 and HIV-2, and the simian immunodeficiency virus SIV. Lentiviral vectors have been generated by attenuating the HIV virulence genes, for example, the genes env, vif, vpr, vpu and nef are deleted making the vector biologically safe. Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other viral vectors may also be employed in the present invention. Vectors derived from viruses such as vaccinia virus, sindbis virus, cytomegalovirus and herpes simplex virus may be employed. They offer several attractive features for various mammalian cells.

"Versabodies" are well known in the art and refer to another antibody mimetic technology. They are small proteins of 3-5 kDa with >15% cysteines, which form a high disulfide density scaffold, replacing the hydrophobic core the typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T cell epitopes, because the residues that contribute most to MHC presentation are hydrophobic. All four of these properties are well-known to affect immunogenicity, and together they are expected to cause a large decrease in immunogenicity.

"Xenogeneic" refers to a graft derived from an animal of a different species.

DETAILED DESCRIPTION

A first object of the present invention is an antigen-binding domain directed to a senescent cell-associated antigen.

In one embodiment, the antigen-binding domain of the invention recognizes and is capable of binding to a senescent cell-associated antigen.

The presence of senescent cells can be determined by detection of senescent cell-associated molecules include growth factors, proteases, cytokines (e.g., inflammatory cytokines), chemokines, cell-related metabolites, reactive oxygen species (e.g., $H_2O_2$), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP, i.e., which includes secreted factors which may make up the pro-inflammatory phenotype of a senescent cell), senescent-messaging secretome, and DNA damage secretory program (DDSP). For example, the presence of senescent cells in tissues can be analyzed by histochemistry or immunohistochemistry techniques that detect the senescence marker, SA-beta gal (SA-Bgal) (see, for example, Dimri et al., 1995. *Proc Natl Acad Sci USA*. 92(20):9363-7).

Senescent cell-associated antigens include molecules that are overexpressed in senescent cells compared to their quiescent or non-senescent counterparts. Certain senescent cell-associated antigens are tissue specific while others are ubiquitously overexpressed in senescent cells. In particular embodiments of the immunogenic compositions described herein, a senescent cell-associated antigen is an antigen present on the cell surface of a senescent cell (e.g., receptor proteins, channel forming proteins, proteins that facilitate diffusion or active transport of molecules and ion across the membrane, cell recognition proteins, and enzymes). These antigens may be present on the cell surface of a cell exclusively or at a greater level on senescent cells compared with non-senescent cells and are therefore useful as immunogens for evoking a specific immune response. Examples of senescent cell-associated antigens include polypeptides and proteins (including glycoproteins), lipids, glycolipids, and carbohydrate molecules that contribute to or are markers of a senescence cell.

In one embodiment, the senescent cell according to the present invention expresses a senescent cell-associated antigen or a combination of senescent cell-associated antigens that are characteristic of senescence. Such senescent cell-associated antigens include, but are not limited to, actin cytoplasmic 1 (ACTB), A disintegrin and metalloproteinase with thrombospondin motifs 7 (ADAMTS7), amyloid-like protein 2 (APLP2), armadillo repeat-containing X-linked protein 3 (ARMCX-3), ATP synthase subunit alpha mitochondrial (ATP5F1A), V-type proton ATPase subunit d 2 (ATP6V0D2), beta-2-microglobulin (B2MG), cholinesterase (BCHE), uncharacterized protein C11orf87 (C11orf87), membrane cofactor protein (CD46), CD57, cyclin-dependent kinase inhibitor 2A "p16INK4a" (CDKN2A), cathepsin B (CTSB), neuferricin (CYB5D2), dipeptidyl peptidase 4 "DPP4" (DPP4), electron transfer flavoprotein beta subunit lysine methyltransferase (ETFB), F-box/LRR-repeat protein 7 (FBXL 7), integral membrane protein GPR137B (GPR137B), interferon alpha-inducible protein 27-like protein 1 (IFI27L1), interleukin-15 receptor subunit alpha (IL15RA), killer cell lectin-like receptor subfamily G member 1 (KLRG1), lysosome-associated membrane glycoprotein 2 (LAMP2), glutathione S-transferase LANCL1 (LANCL1), major vault protein (MVP), unconventional myosin-X (MYO10), sialidase-1 (NEU1), NHS-like protein 2 (NHSL2), neurogenic locus notch homolog protein 3 (NOTCH3), neuronal PAS domain-containing protein 2 (NPAS2), olfactory receptor 1F1 (OR1F1), prolyl 4-hydroxylase beta subunit precursor (P4HB), protein disulfide isomerase (PDI), astrocytic phosphoprotein PEA-15 (PEA15), phospholipase D3 (PLD3), receptor-type tyrosine-protein phosphatase C isoform RA "CD45RA" (PTPRC), receptor-type tyrosine-protein phosphatase eta "DEP1" (PTPRJ), Ras-related protein Rab-23 (RAB23), retinoic acid receptor beta (RARB), RNA-binding region-containing protein 3 (RNPC3), protein adenylyltransferase SelO mitochondrial (SELO), thioredoxin reductase-like selenoprotein T (SELT), semaphorin-5B (SEMA5B), stress-associated endoplasmic reticulum protein 1 (SERP1), plasminogen activator inhibitor 1 (SERPINE1), sodium/hydrogen exchanger 7 (SLC9A7), sorting nexin-3 (SNX3), syntaxin-4 (STX4), TBC1 domain family member 1 (TBC1D1), transforming growth factor beta regulator 1 (TBRG1), transcription elongation factor A N-terminal and central domain-containing protein (TCEANC), tissue factor pathway inhibitor (TFPI), BTB/POZ domain-containing adapter for CUL3-mediated RhoA degradation protein 2 (TNFAIP1), tumor necrosis factor receptor superfamily member 10D "DCR2" (TNFRSF10D), tubulin gamma-2 chain (TUBG2), Ubl carboxyl-terminal hydrolase 18 (USP18), vesicle-associated membrane protein 3 (VAMP3), vacuolar protein sorting-associated protein 26A (VPS26A), and zinc finger protein 419 (ZNF419).

In one embodiment, the senescent cell-associated antigen is selected from the group comprising or consisting of DEP1 and DPP4.

In one embodiment, the senescent cell according to the present invention expresses the DEP1 and/or DPP4 antigen.

The presence of the senescent cell-associated antigens, in particular of DEP1 and/or DPP4, can be determined by any one of numerous immunochemistry methods practiced in the art, such as immunoblotting analysis.

In one embodiment, the senescent cell-associated antigen is DEP1, such as, e.g., human DEP1, or orthologs thereof, including murine and rat DEP1. In one embodiment, the senescent cell-associated antigen is human DEP1 (hDEP1) with SEQ ID NO: 1.

In one embodiment, the antigen-binding domain of the invention recognizes and is capable of binding to DEP1, such as, e.g., to human DEP1, or orthologs thereof, including murine and rat DEP1. Hence, the antigen-binding domain of the invention is a "DEP1-binding domain".

In one embodiment, the DEP1-binding domain of the invention recognizes and is capable of binding to human DEP1 (hDEP1) with SEQ ID NO: 1.

In one embodiment, the DEP1-binding domain of the invention recognizes and is capable of binding to the extracellular domain of human DEP1 (hDEP1) comprising or consisting of amino acid residues 36-975 of SEQ ID NO: 1.

The binding between the DEP1-binding domain of the invention and DEP1 implies that said DEP1-binding domain exhibits appreciable affinity for DEP1. In other words, the DEP1-binding domain of the invention is specific for, or is immunospecific for, or specifically bind to, DEP1.

The affinity between the DEP1-binding domain of the invention and DEP1 can be determined by various methods well known from the one skilled in the art. These methods include, but are not limited to, biosensor analysis (including, e.g., Biacore analysis), Blitz analysis and Scatchard plot.

Alternatively or additionally, whether the DEP1-binding domain of the invention binds to DEP1 can be tested readily by, inter alia, comparing the reaction of said DEP1-binding domain with DEP1 or a fragment thereof (in particular, a fragment comprising or consisting of an epitope of DEP1) with the reaction of said DEP1-binding domain with proteins or antigens other than DEP1 or a fragment thereof.

In one embodiment, the DEP1-binding domain of the invention recognizes and is capable of binding to DEP1 with a $K_D$-affinity constant less than or equal to $10^{-6}$ M, preferably less than or equal to $10^{-7}$ M, $5 \cdot 10^{-8}$ M, $10^{-8}$ M, $5 \cdot 10^{-9}$ M, $10^{-9}$ M or less; as may be determined, e.g., by biosensor analysis, particularly by Biacore Analysis.

In one embodiment, the DEP1-binding domain of the invention comprises a heavy chain variable region (abbreviated herein as HCVR or $V_H$) which comprises at least one, preferably at least two, more preferably the following three complementary-determining regions (CDRs):

| | |
|---|---|
| $V_H$-CDR1: | any one of SEQ ID NO: 5 to 11; |
| $V_H$-CDR2: | any one of SEQ ID NO: 12 to 25; |
| $V_H$-CDR3: | any one of SEQ ID NO: 26 to 32. |

| SEQ ID NO | SEQUENCE |
|---|---|
| 5 | SYYIS |
| 6 | NIAMY |
| 7 | NYTIS |
| 8 | SDSIS |
| 9 | NYSIS |
| 10 | DYNMA |
| 11 | NYYMA |
| 12 | YINTGSGGTNYNEKFKG |
| 13 | HIRTKPHNFATYYANSVKG |
| 14 | YIYAGTGDTNYNEKFKG |
| 15 | HIRTKPHNYATYYADSVKG |
| 16 | YIHPGSGVTNYNEKFKG |
| 17 | YIHPGSGVTNYNEKFRG |
| 18 | YIYPGSGDTNYNEKFKG |
| 19 | TISYDDSRTYYRDSVKG |
| 20 | YITNSFGSAYYRDSVKG |
| 21 | TISYDDYRTYYRDSVKG |
| 22 | YITNSLGSAYYRDSVKG |
| 23 | YITNSFGSTYYRDSVKG |
| 24 | YITNGYGSTYYRDSVKG |
| 25 | YITNGFGSTYYRDSVKG |
| 26 | YFDY |
| 27 | GFGDY |
| 28 | YFDH |
| 29 | DKWVD |
| 30 | QGGIIRGVWFPY |
| 31 | VPLGAFVY |
| 32 | VPLGAFVS |

In one embodiment, the DEP1-binding domain of the invention comprises aHCVR which comprises at least one, preferably at least two, more preferably the following three complementary-determining regions (CDRs):
$V_H$-CDR1: SEQ ID NO: 5;
$V_H$-CDR2: SEQ ID NO: 12;
$V_H$-CDR3: SEQ ID NO: 26.

In one embodiment, the DEP1-binding domain of the invention comprises aHCVR which comprises at least one, preferably at least two, more preferably the following three complementary-determining regions (CDRs):
$V_H$-CDR1: SEQ ID NO: 6;
$V_H$-CDR2: SEQ ID NO: 13;
$V_H$-CDR3: SEQ ID NO: 27.

In one embodiment, the DEP1-binding domain of the invention comprises aHCVR which comprises at least one, preferably at least two, more preferably the following three complementary-determining regions (CDRs):
$V_H$-CDR1: SEQ ID NO: 7;
$V_H$-CDR2: SEQ ID NO: 14;
$V_H$-CDR3: SEQ ID NO: 28.

In one embodiment, the DEP1-binding domain of the invention comprises aHCVR which comprises at least one, preferably at least two, more preferably the following three complementary-determining regions (CDRs):
$V_H$-CDR1: SEQ ID NO: 5;
$V_H$-CDR2: SEQ ID NO: 12;
$V_H$-CDR3: SEQ ID NO: 29.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 6;
  $V_H$-CDR2: SEQ ID NO: 15;
  $V_H$-CDR3: SEQ ID NO: 27.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 5;
  $V_H$-CDR2: SEQ ID NO: 16;
  $V_H$-CDR3: SEQ ID NO: 26.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 8;
  $V_H$-CDR2: SEQ ID NO: 16;
  $V_H$-CDR3: SEQ ID NO: 26.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 5;
  $V_H$-CDR2: SEQ ID NO: 16;
  $V_H$-CDR3: SEQ ID NO: 26.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 8;
  $V_H$-CDR2: SEQ ID NO: 17;
  $V_H$-CDR3: SEQ ID NO: 26.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 9;
  $V_H$-CDR2: SEQ ID NO: 18;
  $V_H$-CDR3: SEQ ID NO: 28.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 10;
  $V_H$-CDR2: SEQ ID NO: 19;
  $V_H$-CDR3: SEQ ID NO: 30.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 11;
  $V_H$-CDR2: SEQ ID NO: 20;
  $V_H$-CDR3: SEQ ID NO: 31.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 10;
  $V_H$-CDR2: SEQ ID NO: 21;
  $V_H$-CDR3: SEQ ID NO: 30.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 11;
  $V_H$-CDR2: SEQ ID NO: 22;
  $V_H$-CDR3: SEQ ID NO: 31.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 11;
  $V_H$-CDR2: SEQ ID NO: 23;
  $V_H$-CDR3: SEQ ID NO: 31.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 11;
  $V_H$-CDR2: SEQ ID NO: 24;
  $V_H$-CDR3: SEQ ID NO: 31.

In one embodiment, the DEP1-binding domain of the invention comprises aHCVR which comprises at least one, preferably at least two, more preferably the following three complementary-determining regions (CDRs):
  $V_H$-CDR1: SEQ ID NO: 11;
  $V_H$-CDR2: SEQ ID NO: 25;
  $V_H$-CDR3: SEQ ID NO: 32.

In one embodiment, the DEP1-binding domain of the invention comprises a light chain variable region (abbreviated herein as LCVR or $V_L$) which comprises at least one, preferably at least two, more preferably the following three complementary-determining regions (CDRs):

$V_L$-CDR1: any one of SEQ ID NO: 33 to 39;
$V_L$-CDR2: any one of SEQ ID NO: 40 to 46;
$V_L$-CDR3: any one of SEQ ID NO: 47 to 54.

| SEQ ID NO | SEQUENCE |
|---|---|
| 33 | RASQDVGIYVN |
| 34 | KSSQSLKHSDGKTYLN |
| 35 | QASQDIGNNLI |
| 36 | RSSQSLKHSDGKTYLN |
| 37 | QASQDIGNWLA |
| 38 | LASEGISNYLA |
| 39 | LASEDIYSYLA |
| 40 | RATNLAD |
| 41 | QVSKLDS |
| 42 | YATNLAN |
| 43 | RATTLAD |
| 44 | GATTLAD |
| 45 | HANPLHD |
| 46 | YANPLHD |
| 47 | LQYDEFPPT |
| 48 | CQGSYSPYT |
| 49 | LQYDEWPYT |
| 50 | LQYDEYPPT |
| 51 | QQTSSTPWT |
| 52 | QQGYKFPYT |

-continued

| SEQ ID NO | SEQUENCE |
|---|---|
| V$_L$-CDR1: | any one of SEQ ID NO: 33 to 39; |
| V$_L$-CDR2: | any one of SEQ ID NO: 40 to 46; |
| V$_L$-CDR3: | any one of SEQ ID NO: 47 to 54. |
| 53 | QQASSAPWT |
| 54 | QQGYKFPYS |

In one embodiment, the DEP1-binding domain of the invention comprises a LCVR which comprises at least one, preferably at least two, more preferably the following three complementary-determining regions (CDRs):
 V$_L$-CDR1: SEQ ID NO: 33;
 V$_L$-CDR2: SEQ ID NO: 40;
 V$_L$-CDR3: SEQ ID NO: 47.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 34;
 V$_L$-CDR2: SEQ ID NO: 41;
 V$_L$-CDR3: SEQ ID NO: 48.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 35;
 V$_L$-CDR2: SEQ ID NO: 42;
 V$_L$-CDR3: SEQ ID NO: 47.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 33;
 V$_L$-CDR2: SEQ ID NO: 40;
 V$_L$-CDR3: SEQ ID NO: 49.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 36;
 V$_L$-CDR2: SEQ ID NO: 41;
 V$_L$-CDR3: SEQ ID NO: 48.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 33;
 V$_L$-CDR2: SEQ ID NO: 40;
 V$_L$-CDR3: SEQ ID NO: 50.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 33;
 V$_L$-CDR2: SEQ ID NO: 43;
 V$_L$-CDR3: SEQ ID NO: 50.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 37;
 V$_L$-CDR2: SEQ ID NO: 44;
 V$_L$-CDR3: SEQ ID NO: 51.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 38;
 V$_L$-CDR2: SEQ ID NO: 45;
 V$_L$-CDR3: SEQ ID NO: 52.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 37;
 V$_L$-CDR2: SEQ ID NO: 44;
 V$_L$-CDR3: SEQ ID NO: 53.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 38;
 V$_L$-CDR2: SEQ ID NO: 45;
 V$_L$-CDR3: SEQ ID NO: 54.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 39;
 V$_L$-CDR2: SEQ ID NO: 45;
 V$_L$-CDR3: SEQ ID NO: 52.

In one embodiment, the DEP1-binding domain of the invention comprises a LCVR which comprises at least one, preferably at least two, more preferably the following three complementary-determining regions (CDRs):
 V$_L$-CDR1: SEQ ID NO: 38;
 V$_L$-CDR2: SEQ ID NO: 46;
 V$_L$-CDR3: SEQ ID NO: 52.

In one embodiment, the DEP1-binding domain of the invention comprises a combination of (i) at least one, preferably at least two, more preferably three HCVR's CDRs and (ii) at least one, preferably at least two, more preferably three LCVR's CDRs, said combination being as defined in Table 1.

In one embodiment, the DEP1-binding domain of the invention comprises a combination of (i) three HCVR's CDRs and (ii) three LCVR's CDRs, said combination being as defined in Table 1.

TABLE 1

Preferred combinations of HCVR's and LCVRs CDRs. The CDRs are defined by their SEQ ID NOs. First column indicates the clone's name.

| Clone's name | V$_H$-CDR1 | V$_H$-CDR2 | V$_H$-CDR3 | V$_L$-CDR1 | V$_L$-CDR2 | V$_L$-CDR3 |
|---|---|---|---|---|---|---|
| 5738-10-R3A-B2 | 5 | 12 | 26 | 33 | 40 | 47 |
| 5738-10-R3A-C6 | 6 | 13 | 27 | 34 | 41 | 48 |
| 5738-10-R3A-D1 | 7 | 14 | 28 | 35 | 42 | 47 |
| 5738-10-R3A-D5 | 5 | 12 | 29 | 33 | 40 | 49 |
| 5738-10-R3A-D8 | 6 | 15 | 27 | 36 | 41 | 48 |
| 5738-10-R3A-D11 | 5 | 16 | 26 | 33 | 40 | 47 |
| 5738-10-R4A-E7 | 8 | 16 | 26 | 33 | 40 | 47 |
| 5738-10-R4A-E9 | 5 | 16 | 26 | 33 | 40 | 50 |
| 5738-10-R4A-F12 | 8 | 16 | 26 | 33 | 40 | 50 |
| 5738-10-R4A-G4 | 8 | 17 | 26 | 33 | 40 | 47 |
| 5738-10-R4A-G11 | 9 | 18 | 28 | 33 | 43 | 50 |
| 5738-10-R4A-G12 | 8 | 16 | 26 | 33 | 40 | 50 |

TABLE 1-continued

Preferred combinations of HCVR's and LCVRs CDRs. The CDRs are defined by their SEQ ID NOs. First column indicates the clone's name.

| Clone's name | $V_H$-CDR1 | $V_H$-CDR2 | $V_H$-CDR3 | $V_L$-CDR1 | $V_L$-CDR2 | $V_L$-CDR3 |
|---|---|---|---|---|---|---|
| 5738-13-R2A-C1 | 10 | 19 | 30 | 37 | 44 | 51 |
| 5738-13-R2A-D3 | 11 | 20 | 31 | 38 | 45 | 52 |
| 5738-13-R4A-D11 | 10 | 21 | 30 | 37 | 44 | 53 |
| 5738-13-R3A-F5 | 11 | 22 | 31 | 38 | 45 | 54 |
| 5738-13-R4A-F11 | 11 | 23 | 31 | 39 | 45 | 52 |
| 5738-13-R2A-H3 | 11 | 24 | 31 | 38 | 45 | 52 |
| 5738-13-R2A-H4 | 11 | 25 | 32 | 38 | 46 | 52 |
| 5738-13-R4A-H9 | 11 | 25 | 32 | 38 | 45 | 52 |
| 5738-13-R4A-H11 | 11 | 25 | 32 | 38 | 45 | 52 |

In one embodiment, the DEP1-binding domain of the invention comprises a combination of (i) three HCVR's CDRs and (ii) three LCVR's CDRs, said combination being that of any one of the following clones as defined in Table 1: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the DEP1-binding domain of the invention comprises a combination of (i) three HCVR's CDRs and (ii) three LCVR's CDRs, said combination being that of any one of the following clones as defined in Table 1: 5738-10-R3A-C6, 5738-10-R3A-D5, 5738-10-R4A-G12, 5738-13-R4A-D11, and 5738-13-R2A-H4.

In one embodiment, the DEP1-binding domain of the invention comprises a combination of (i) three HCVR's CDRs and (ii) three LCVR's CDRs, said combination being that of any one of the following clones as defined in Table 1: 5738-10-R4A-G12, 5738-13-R4A-D11, and 5738-13-R2A-H4.

In one embodiment, the DEP1-binding domain of the invention comprises a combination of (i) three HCVR's CDRs and (ii) three LCVR's CDRs, said combination being that of any one of the following clones as defined in Table 1: 5738-13-R4A-D11, and 5738-13-R2A-H4.

In one embodiment, the DEP1-binding domain of the invention comprises a combination of (i) three HCVR's CDRs and (ii) three LCVR's CDRs, said combination being that of clone 5738-13-R2A-C1 as defined in Table 1. In one embodiment, the DEP1-binding domain of the invention comprises a combination of (i) three HCVR's CDRs and (ii) three LCVR's CDRs, said combination being that of clone 5738-13-R2A-D3 as defined in Table 1. In one embodiment, the DEP1-binding domain of the invention comprises a combination of (i) three HCVR's CDRs and (ii) three LCVR's CDRs, said combination being that of clone 5738-13-R4A-D11 as defined in Table 1. In one embodiment, the DEP1-binding domain of the invention comprises a combination of (i) three HCVR's CDRs and (ii) three LCVR's CDRs, said combination being that of clone 5738-13-R3A-F5 as defined in Table 1. In one embodiment, the DEP1-binding domain of the invention comprises a combination of (i) three HCVR's CDRs and (ii) three LCVR's CDRs, said combination being that of clone 5738-13-R4A-F11 as defined in Table 1. In one embodiment, the DEP1-binding domain of the invention comprises a combination of (i) three HCVR's CDRs and (ii) three LCVR's CDRs, said combination being that of clone 5738-13-R2A-H3 as defined in Table 1. In one embodiment, the DEP1-binding domain of the invention comprises a combination of (i) three HCVR's CDRs and (ii) three LCVR's CDRs, said combination being that of clone 5738-13-R2A-H4 as defined in Table 1. 5738-13-R4A-H9 as defined in Table 1. In one embodiment, the DEP1-binding domain of the invention comprises a combination of (i) three HCVR's CDRs and (ii) three LCVR's CDRs, said combination being that of clone 5738-13-R4A-H11 as defined in Table 1.

In one embodiment, the DEP1-binding domain of the invention comprises a HCVR comprising or consisting of the sequence SEQ ID NO: 55; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 55.

```
                                              SEQ ID NO: 55
QVQLKQSGAELAKPGSSVKISCKASGYTFTSYYISWIKQTTGQGLEYIGY

INTGSGGTNYNEKFKGKATLTVDKSSSTAFMQLSSLTPDDSAVYYCARYF

DYWGQGVMVTVSS
```

In one embodiment, the DEP1-binding domain of the invention comprises a HCVR comprising or consisting of the sequence SEQ ID NO: 56; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 56.

```
                                              SEQ ID NO: 56
EVKLVESGGGLVQPKESLKISCAASGFTFSNIAMYWVRQAPGKGLEWVAH

IRTKPHNFATYYANSVKGRFTISRDDSKNMVYLQMDNLKPEDTAMYYCSV

GFGDYWGQGVMVTVSS
```

In one embodiment, the DEP1-binding domain of the invention comprises a HCVR comprising or consisting of the sequence SEQ ID NO: 57; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 57.

```
                                              SEQ ID NO: 57
EVQLQQSGAELAKPGSSVKISCKASGYTFTNYTISWIKQTTGQGLEYIGY

IYAGTGDTNYNEKFKGKATLTVDKSSNTAFMQLSSLTPDDSAVYYCARYF

DHWGQGVMVTVSS
```

In one embodiment, the DEP1-binding domain of the invention comprises a HCVR comprising or consisting of the sequence SEQ ID NO: 58; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 58.

```
                                              SEQ ID NO: 58
EVQLQQSGAELAKPGSSVKISCKASGYTFTSYYISWIKQTTGQGLEYIGY

INTGSGGTNYNEKFKGKATLTVDKSSSTAFMQLSSLTPDDSAVYYCARDK

WVDWGQGVMVTVSS
```

In one embodiment, the DEP1-binding domain of the invention comprises a HCVR comprising or consisting of the sequence SEQ ID NO: 59; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 59.

SEQ ID NO: 59
EVQLEESGGGLVQPKESLKISCAVSGFTFSNIAMYWVRQAPGKGLEWVGH

IRTKPHNYATYYADSVKGRFTISRDDSNNMVYLEMDNLKPEDTAMYYCSV

GFGDYWGQGVMVTVSS

In one embodiment, the DEP1-binding domain of the invention comprises a HCVR comprising or consisting of the sequence SEQ ID NO: 60; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 60.

SEQ ID NO: 60
QVQLKQSGAELAKPGSSVKISCKASGYTFTSYYISWIKQTTGQGLEYIGY

IHPGSGVTNYNEKFKGKATLTVDKSSSTAFMQLSSLTPDDSAIYYCARYF

DYWGQGVMVTVSS

In one embodiment, the DEP1-binding domain of the invention comprises a HCVR comprising or consisting of the sequence SEQ ID NO: 61; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 61.

SEQ ID NO: 61
QVQLKQSGVELAKPGSSVKISCKASGYTFTSDSISWIKQTTGQGLEYIGYI

HPGSGVTNYNEKFKGKATLTVDKSSSTAFMQLSSLTPDDSAIYYCARYFDY

WGQGVMVTVSS

In one embodiment, the DEP1-binding domain of the invention comprises a HCVR comprising or consisting of the sequence SEQ ID NO: 62; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 62.

SEQ ID NO: 62
EVQLQQSGVELAKPGSSVKISCKASGYTFTSDSISWIKQTTGQGLEYIGYI

HPGSGVTNYNEKFKGKATLTVDKSSSTAFMQLSSLTPDDSAIYYCARYFDY

WGQGVMVTVSS

In one embodiment, the DEP1-binding domain of the invention comprises a HCVR comprising or consisting of the sequence SEQ ID NO: 63; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 63.

SEQ ID NO: 63
EVQLQQSGVELAKPGSSVKISCKASGYTFTSDSISWIKQTTGQGLEYIGYI

HPGSGVTNYNEKFRGKATLTVDKSSSTAFMQLSSLTPDDSAIYYCARYFDY

WGQGVMVTVSS

In one embodiment, the DEP1-binding domain of the invention comprises a HCVR comprising or consisting of the sequence SEQ ID NO: 64; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 64.

SEQ ID NO: 64
QVQLQQPRAELAKPGSSVKISCKASGYTFTNYSISWIKQTTGQGLEYIGYI

YPGSGDTNYNEKFKGKATLTVDKSSSTAFMQLSSLTPDDSAVYYCARYFDH

WGQGTLVTVSS

In one embodiment, the DEP1-binding domain of the invention comprises a HCVR comprising or consisting of the sequence SEQ ID NO: 65; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 65.

SEQ ID NO: 65
QVQLKESGAELAKPGSSVKISCKASGYTFTSDSISWIKQTTGQGLEYIGYI

HPGSGVTNYNEKFKGKATLTVDKSSSTAFMQLSSLTPDDSAIYYCARYFDY

WGQGVMVTVSS

In one embodiment, the DEP1-binding domain of the invention comprises a HCVR comprising or consisting of the sequence SEQ ID NO: 66; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 66.

SEQ ID NO: 66
QVQLKESGGGLVQPGRSLKLSCAASGFTFSDYNMAWVRQAPKKGLEWVATI

SYDDSRTYYRDSVKGRFAISRDDAKGTLNLQMDSLRSEDTATYYCARQGGI

IRGVWFPYWGQGTLVTVSS

In one embodiment, the DEP1-binding domain of the invention comprises a HCVR comprising or consisting of the sequence SEQ ID NO: 67; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 67.

SEQ ID NO: 67
EVKLVESGGGLVQPGGSLKLSCAASGFTFSNYYMAWVRQAPTKGLEWVAYI

TNSFGSAYYRDSVKGRFTISRDNAKSTLYLQMDSLRSEDTATYYCSTVPLG

AFVYWGQGTLVTVSS

In one embodiment, the DEP1-binding domain of the invention comprises a HCVR comprising or consisting of the sequence SEQ ID NO: 68; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 68.

SEQ ID NO: 68
QVQLKESGGGLVQPGRSLKLSCAASGFSFGDYNMAWVRQAPKKGLEWVATI

SYDDYRTYYRDSVKGRFTISRDDAKATLYLQMDSLRSEDTATYYCARQGGI

IRGVWFPYWGQGTLVTVSS

In one embodiment, the DEP1-binding domain of the invention comprises a HCVR comprising or consisting of the sequence SEQ ID NO: 69; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 69.

SEQ ID NO: 69
EVKLVESGGGLVQPGGSLKLSCAASGFTFSNYYMAWVRQAPTKGLEWVAYI

TNSLGSAYYRDSVKGRFTISRDNAKSTLYLQMDSLRSEDTATYYCSTVPLG

AFVYWGQGTLVTVSS

In one embodiment, the DEP1-binding domain of the invention comprises a HCVR comprising or consisting of the sequence SEQ ID NO: 70; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 70.

SEQ ID NO: 70
EVKLVESGGGLVQPGGSLKLSCAASGFTFSNYYMAWVRQAPTKGLEWVAYI

TNSFGSTYYRDSVKGRFTISRDNAKSTLYLQMDSLRSEDTATYYCSTVPLG

AFVYWGQGTLVTVSS

In one embodiment, the DEP1-binding domain of the invention comprises a HCVR comprising or consisting of the sequence SEQ ID NO: 71; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 71.

SEQ ID NO: 71
EVKLVESGGGLVQPGRSLKLSCAASGFTFSNYYMAWVRQAPTKGLEWVAYI

TNGYGSTYYRDSVKGRFTISRDNAKSTLYLQMDSLRSEDTATYYCSTVPLG

AFVYWGQGTLVTVSS

In one embodiment, the DEP1-binding domain of the invention comprises a HCVR comprising or consisting of the sequence SEQ ID NO: 72; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 72.

SEQ ID NO: 72
EVKLVESGGGLVQPGRSLKLSCAASGFTFSNYYMAWVRQAPTKGLEWVAYI

TNGFGSTYYRDSVKGRFTISRDNAKSTLYLQMDSLRSEDTATYYCSTVPLG

AFVSWGQGTLVTVSS

In one embodiment, the DEP1-binding domain of the invention comprises a HCVR comprising or consisting of the sequence SEQ ID NO: 73; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 73.

SEQ ID NO: 73
EVKLVESGGGLVQPGRSLKLSCAASGFTFSNYYMAWVRQAPTKGLEWVAYI

TNGFGSTYYRDSVKGRFTISRDNAKSTLYLQMDSLRSEDAATYYCSTVPLG

AFVSWGQGTLVTVSS

In one embodiment, the DEP1-binding domain of the invention comprises a HCVR comprising or consisting of the sequence SEQ ID NO: 74; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 74.

SEQ ID NO: 74
EVKLVESGGGLVQPGGSLKLSCAASGFTFSNYYMAWVRQAPTKGLEWVAYI

TNGFGSTYYRDSVKGRFTISRDNAKSTLYLQMDSLRSEDTATYYCSTVPLG

AFVSWGQGTLVTVSS

In one embodiment, the DEP1-binding domain of the invention comprises a LCVR comprising or consisting of the sequence SEQ ID NO: 75; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 75.

SEQ ID NO: 75
DIVMTQSPSSMSVSLGDTVTITCRASQDVGIYVNWFQQKPGKPPRRMIYRA

TNLADGVPSRFSGTRSGSDYSLTISSLESEDVADYHCLQYDEFPPTFGSGT

KLDIK

In one embodiment, the DEP1-binding domain of the invention comprises a LCVR comprising or consisting of the sequence SEQ ID NO: 76; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 76.

SEQ ID NO: 76
DIVMTQAPLSLSVAIGQSASISCKSSQSLKHSDGKTYLNWIFQSPGQSPKR

LIYQVSKLDSGVPDRFSGTGSETDFTLKISRVEAEDLGVYYCCQGSYSPYT

FGAGTKLELK

In one embodiment, the DEP1-binding domain of the invention comprises a LCVR comprising or consisting of the sequence SEQ ID NO: 77; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 77.

SEQ ID NO: 77
DILMTQSPSSMSASLGDRVTITCQASQDIGNNLIWFQQKPGKSPRRMIYYA

TNLANGVPSRFSGSRSGSDYSLSISSLESEDVADYHCLQYDEFPPTFGSGT

KLEIK

In one embodiment, the DEP1-binding domain of the invention comprises a LCVR comprising or consisting of the sequence SEQ ID NO: 78; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 78.

SEQ ID NO: 78
DILMTQSPSSMSVSLGDTVTITCRASQDVGIYVNWFQQKPGKPPRRMIYRA

TNLADGVPSRFSGSRSGSNYSLTIRSLESEDVADYHCLQYDEWPYTFGAGT

KLELK

In one embodiment, the DEP1-binding domain of the invention comprises a LCVR comprising or consisting of the sequence SEQ ID NO: 79; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 79.

SEQ ID NO: 79
DIVMTQAPLSLSVDIGQSASISCRSSQSLKHSDGKTYLNWVFQSPGQSPKR

LIYQVSKLDSGVPDRFSGSGSEADFTLKISRVEAEDLGVYYCCQGSYSPYT

FGAGTKLELK

In one embodiment, the DEP1-binding domain of the invention comprises a LCVR comprising or consisting of the sequence SEQ ID NO: 80; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 80.

SEQ ID NO: 80
DIQLTQSPSSMSVSQGDTVTITCRASQDVGIYVNWFQQKPGKSPRRMIYRA

TNLADGVPSRFSGSRSGSDYSLTIASLESEDVADYHCLQYDEFPPTFGSGT

NLEIK

In one embodiment, the DEP1-binding domain of the invention comprises a LCVR comprising or consisting of the sequence SEQ ID NO: 81; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 81.

SEQ ID NO: 81
DILMTQSPSSMSVSLGDTVTITCRASQDVGIYVNWFQQIPGKSPRRLIYRA

TNLADGVPSRFSGSRSGSDYSLTIASLESEDVADYHCLQYDEFPPTFGSGT

KLEIK

In one embodiment, the DEP1-binding domain of the invention comprises a LCVR comprising or consisting of the sequence SEQ ID NO: 82; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 82.

SEQ ID NO: 82
DILMTQSPSSMSVSQGDTVTITCRASQDVGIYVNWFQQKPGKSPRRMIHRA

TNLADGVPSRFSGSRSGSDYSLTITSLESEDVADYHCLQYDEYPPTFGSGT

NLEIK

In one embodiment, the DEP1-binding domain of the invention comprises a LCVR comprising or consisting of the sequence SEQ ID NO: 83; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 83.

SEQ ID NO: 83
DILMTQSPSSMSVSLGDTVTITCRASQDVGIYVNWFQQKPGKSPRRMIHRA

TNLADGVPSRFSGSRSGSDYSLTISSLESEDVADYHCLQYDEYPPTFGSGT

KLEIK

In one embodiment, the DEP1-binding domain of the invention comprises a LCVR comprising or consisting of the sequence SEQ ID NO: 84; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 84.

SEQ ID NO: 84
DIVMTQSPSSMSVSLGDTVTITCRASQDVGIYVNWFQQKPGKSPRRMIYRA

TNLADGVPSRFSGSRSGSDYSLTIASLESEDVADYHCLQYDEFPPTFGSGT

KLEIK

In one embodiment, the DEP1-binding domain of the invention comprises a LCVR comprising or consisting of the sequence SEQ ID NO: 85; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 85.

SEQ ID NO: 85
DILMTQSPSSMSVSLGDTVTITCRASQDVGIYVNWFQQKPGKSPRRMIYRA

TTLADGVPSRFSGSRSGSDYSLTISSLESEDVADYHCLQYDEYPPTFGSGT

KLEIK

In one embodiment, the DEP1-binding domain of the invention comprises a LCVR comprising or consisting of the sequence SEQ ID NO: 86; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 86.

SEQ ID NO: 86
DILMTQSPSSMSVSLGDTVTITCRASQDVGIYVNWFQQKPGKSPRRMIYRA

TNLADGVPSRFSGSRSGSDYSLTISSLESEDVADYHCLQYDEYPPTFGGGT

KLELK

In one embodiment, the DEP1-binding domain of the invention comprises a LCVR comprising or consisting of the sequence SEQ ID NO: 87; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 87.

SEQ ID NO: 87
DIQLTQSPASLSASLEEIVTITCQASQDIGNWLAWYQQKPGKSPHLLIYGA

TTLADGVPSRSGSRSGTQYSLKISRLQVEDVGMYYCQQTSSTPWTFGGGTK

LELK

In one embodiment, the DEP1-binding domain of the invention comprises a LCVR comprising or consisting of the sequence SEQ ID NO: 88; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 88.

SEQ ID NO: 88
DIQMTQTPHSLSASLGETVSIECLASEGISNYLAWYQQKPGKSPQLLISHA

NPLHDGVPSRFSGDGSGTQYSLKIRNMQPEDEGVYYCQQGYKFPYTFGAGT

KLELK

In one embodiment, the DEP1-binding domain of the invention comprises a LCVR comprising or consisting of the sequence SEQ ID NO: 89; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 89.

SEQ ID NO: 89
DIQMTQTPASLSASLEEIVTITCQASQDIGNWLAWYQQKPGKSPHLLIYGA

TTLADGVPSRFSGSRSGTQYSLKISRLQAEDIGIYYCQQASSAPWTFGGGT

KLELK

In one embodiment, the DEP1-binding domain of the invention comprises a LCVR comprising or consisting of the sequence SEQ ID NO: 90; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 90.

SEQ ID NO: 90
DIQMTQTPHSLSASLGETVSIECLASEGISNYLAWYQQKPGKSPQLLISHA

NPLHDGVPSRFSGSGSGTQYSLKIRNMQPEDEGVYYCQQGYKFPYSFGAGT

KLELK

In one embodiment, the DEP1-binding domain of the invention comprises a LCVR comprising or consisting of the sequence SEQ ID NO: 91; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 91.

SEQ ID NO: 91
DIQLTQSPASLSASLGETVSIECLASEDIYSYLAWYQQKPGKSPQLLISHA

NPLHDGVPSRFSGSGSGTQYSLKIRNMQPEDEGVYYCQQGYKFPYTFGAGT

KLELK

In one embodiment, the DEP1-binding domain of the invention comprises a LCVR comprising or consisting of the sequence SEQ ID NO: 92; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 92.

SEQ ID NO: 92
DIQMTQTPHSLSASLGETVSIECLASEGISNYLAWYQQKPGKSPQLLISHA

NPLHDGVPSRFSGSGSGTQYSLKIRNMQPEDEGVYYCQQGYKFPYTFGAGT

KLELK

In one embodiment, the DEP1-binding domain of the invention comprises a LCVR comprising or consisting of the sequence SEQ ID NO: 93; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 93.

SEQ ID NO: 93
DIQMTQTPHSLSASLGETVSIECLASEGISNYLAWYQQKPGKSPQLLISYA

NPLHDGVPSRFSGSGSGTQFSLKIRNMQPEDEGVYYCQQGYKFPYTFGAGT

KLELT

In one embodiment, the DEP1-binding domain of the invention comprises a LCVR comprising or consisting of the sequence SEQ ID NO: 94; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 94.

SEQ ID NO: 94
DIQMTQTPHSLSASLGETVSIECLASEGISNYLAWYQQKPGKSPQLLISHA

NPLHDGVPSRFSGSGSGTQFSLKIRNMQPEDEGVYYCQQGYKFPYTFGAGT

KLELK

In one embodiment, the DEP1-binding domain of the invention comprises a combination of (i) a HCVR and (ii) a LCVR, said combination being as defined in Table 2.

TABLE 2

Preferred combinations of HCVR and LCVR. The HCVR and LCVR are defined by their SEQ ID NOs. First column indicates the clone's name.

| Clone's name | HCVR | LCVR |
|---|---|---|
| 5738-10-R3A-B2 | 55 | 75 |
| 5738-10-R3A-C6 | 56 | 76 |
| 5738-10-R3A-D1 | 57 | 77 |
| 5738-10-R3A-D5 | 58 | 78 |
| 5738-10-R3A-D8 | 59 | 79 |
| 5738-10-R3A-D11 | 60 | 80 |
| 5738-10-R4A-E7 | 61 | 81 |
| 5738-10-R4A-E9 | 60 | 82 |
| 5738-10-R4A-F12 | 62 | 83 |
| 5738-10-R4A-G4 | 63 | 84 |
| 5738-10-R4A-G11 | 64 | 85 |
| 5738-10-R4A-G12 | 65 | 86 |
| 5738-13-R2A-C1 | 66 | 87 |
| 5738-13-R2A-D3 | 67 | 88 |
| 5738-13-R4A-D11 | 68 | 89 |
| 5738-13-R3A-F5 | 69 | 90 |
| 5738-13-R4A-F11 | 70 | 91 |
| 5738-13-R2A-H3 | 71 | 92 |
| 5738-13-R2A-H4 | 72 | 93 |
| 5738-13-R4A-H9 | 73 | 94 |
| 5738-13-R4A-H11 | 74 | 94 |

In one embodiment, the DEP1-binding domain of the invention comprises a combination of (i) a HCVR and (ii) a LCVR, combination being that of any one of the following clones as defined in Table 2: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the DEP1-binding domain of the invention comprises a combination of (i) a HCVR and (ii) a LCVR, combination being that of any one of the following clones as defined in Table 2: 5738-10-R3A-C6, 5738-10-R3A-D5, 5738-10-R4A-G12, 5738-13-R4A-D11, and 5738-13-R2A-H4.

In one embodiment, the DEP1-binding domain of the invention comprises a combination of (i) a HCVR and (ii) a LCVR, combination being that of any one of the following clones as defined in Table 2: 5738-10-R4A-G12, 5738-13-R4A-D11, and 5738-13-R2A-H4.

In one embodiment, the DEP1-binding domain of the invention comprises a combination of (i) a HCVR and (ii) a LCVR, combination being that of any one of the following clones as defined in Table 2: 5738-13-R4A-D11, and 5738-13-R2A-H4.

In one embodiment, the DEP1-binding domain of the invention comprises a combination of (i) a HCVR and (ii) a LCVR, combination being that of clone 5738-13-R2A-C1 as defined in Table 2. In one embodiment, the DEP1-binding domain of the invention comprises a combination of (i) a HCVR and (ii) a LCVR, combination being that of clone 5738-13-R2A-D3 as defined in Table 2. In one embodiment, the DEP1-binding domain of the invention comprises a combination of (i) a HCVR and (ii) a LCVR, combination being that of clone 5738-13-R4A-D11 as defined in Table 2. In one embodiment, the DEP1-binding domain of the invention comprises a combination of (i) a HCVR and (ii) a LCVR, combination being that of clone 5738-13-R3A-F5 as defined in Table 2. In one embodiment, the DEP1-binding domain of the invention comprises a combination of (i) a HCVR and (ii) a LCVR, combination being that of clone 5738-13-R4A-F11 as defined in Table 2. In one embodiment, the DEP1-binding domain of the invention comprises a combination of (i) a HCVR and (ii) a LCVR, combination being that of clone 5738-13-R2A-H3 as defined in Table 2. In one embodiment, the DEP1-binding domain of the invention comprises a combination of (i) a HCVR and (ii) a LCVR, combination being that of clone 5738-13-R2A-H4 as defined in Table 2. In one embodiment, the DEP1-binding domain of the invention comprises a combination of (i) a HCVR and (ii) a LCVR, combination being that of clone 5738-13-R4A-H9 as defined in Table 2. 5738-13-R4A-H11 as defined in Table 2.

In one embodiment, the senescent cell-associated antigen is DPP4, such as, e.g., human DPP4 or orthologs thereof, including murine and rat DPP4. In one embodiment, the senescent cell-associated antigen is human DPP4 (hDPP4) with SEQ ID NO: 101.

In one embodiment, the antigen-binding domain of the invention recognizes and is capable of binding to DPP4, such as, e.g., to human DPP4, or orthologs thereof, including murine and rat DPP4. Hence, the antigen-binding domain of the invention is a "DPP4-binding domain".

In one embodiment, the DPP4-binding domain of the invention recognizes and is capable of binding to human DPP4 (hDPP4) with SEQ ID NO: 101.

In one embodiment, the DPP4-binding domain of the invention recognizes and is capable of binding to the extracellular domain of human DPP4 (hDPP4) comprising or consisting of amino acid residues 29-766 of SEQ ID NO: 101.

The binding between the DPP4-binding domain of the invention and DPP4 implies that said DPP4-binding domain exhibits appreciable affinity for DPP4. In other words, the DPP4-binding domain of the invention is specific for, or is immunospecific for, or specifically bind to, DPP4.

The affinity between the DPP4-binding domain of the invention and DPP4 can be determined by various methods well known from the one skilled in the art. These methods include, but are not limited to, biosensor analysis (including, e.g., Biacore analysis), Blitz analysis and Scatchard plot.

Alternatively or additionally, whether the DPP4-binding domain of the invention binds to DPP4 can be tested readily by, inter alia, comparing the reaction of said DPP4-binding domain with DPP4 or a fragment thereof (in particular, a fragment comprising or consisting of an epitope of DPP4) with the reaction of said DPP4-binding domain with proteins or antigens other than DPP4 or a fragment thereof.

In one embodiment, the DPP4-binding domain of the invention recognizes and is capable of binding to DPP4 with a KD-affinity constant less than or equal to $10^{-6}$ M, preferably less than or equal to $10^{-7}$ M, $5 \cdot 10^{-8}$ M, $10^{-8}$ M, $5 \cdot 10^{-9}$ M, $10^{-9}$ M or less; as may be determined, e.g., by biosensor analysis, particularly by Biacore Analysis.

In one embodiment, the DPP4-binding domain of the invention comprises a heavy chain variable region (abbreviated herein as HCVR or $V_H$) which comprises at least one, preferably at least two, more preferably the following three complementary-determining regions (CDRs):

$V_H$-CDR1: any one of SEQ ID NO: 104 to 112;
$V_H$-CDR2: any one of SEQ ID NO: 113 to 129;
$V_H$-CDR3: any one of SEQ ID NO: 130 to 142.

| SEQ ID NO | SEQUENCE | SEQ ID NO | SEQUENCE |
|---|---|---|---|
| 104 | NYGMA | 124 | YINPGGGIGYNEKFKG |
| 105 | TSDRCVS | 125 | QISHSGSTSYNPSLKS |

-continued

V_H-CDR1: any one of SEQ ID NO: 104 to 112;
V_H-CDR2: any one of SEQ ID NO: 113 to 129;
V_H-CDR3: any one of SEQ ID NO: 130 to 142.

| SEQ ID NO | SEQUENCE | SEQ ID NO | SEQUENCE |
|---|---|---|---|
| 106 | NFGMA | 126 | SINPGSGGIGYNEKFKG |
| 107 | DNYWG | 127 | SINPGGGGTGYNEKFKG |
| 108 | TYDIG | 128 | QISHSGSTSYNPSLIS |
| 109 | GNYLA | 129 | QISHTGSSTYNPSLKS |
| 110 | SNYWG | 130 | HRLIYTTDYYYEVMDV |
| 111 | TYDRG | 131 | HRLIYTTDYYYEVMDA |
| 112 | GNYWG | 132 | NSGDGRFAY |
| 113 | TISYDGNDTYYRDSVKG | 133 | HKLIYTTDYYYEVMDA |
| 114 | TTSYDGNDTYYRDSVKG | 134 | HRLMYTTDYYYEVMDD |
| 115 | TICWDDSKGYNPSLKN | 135 | HRLIYTTDYYYEVLDA |
| 116 | TINYDGRNTYYRDSVKG | 136 | HKLIYTTDYYYEVMDV |
| 117 | TINYDGSNTYYRDSVKG | 137 | YGAGASFDY |
| 118 | TINYDGRDTYYRDSVKG | 138 | PLRRVLDY |
| 119 | HISHSGSSTYNPSLKS | 139 | HGHYVMDV |
| 120 | YINPGSGGIGYNEKFKG | 140 | YGAGSSFDY |
| 121 | SINPGSGGIAYSEKFKG | 141 | PLRRVLDN |
| 122 | HIKSSGTTTYNPSLKS | 142 | PLRVLDY |
| 123 | SINPGSGGIGYNERFKG | | |

In one embodiment, the DPP4-binding domain of the invention comprises a HCVR which comprises at least one, preferably at least two, more preferably the following three complementary-determining regions (CDRs):
V_H-CDR1: SEQ ID NO: 104;
V_H-CDR2: SEQ ID NO: 113;
V_H-CDR3: SEQ ID NO: 130.

In one embodiment, the DPP4-binding domain of the invention comprises a HCVR which comprises at least one, preferably at least two, more preferably the following three complementary-determining regions (CDRs):
V_H-CDR1: SEQ ID NO: 104;
V_H-CDR2: SEQ ID NO: 114;
V_H-CDR3: SEQ ID NO: 131.

In one embodiment, the DPP4-binding domain of the invention comprises a HCVR which comprises at least one, preferably at least two, more preferably the following three complementary-determining regions (CDRs):
V_H-CDR1: SEQ ID NO: 105;
V_H-CDR2: SEQ ID NO: 115;
V_H-CDR3: SEQ ID NO: 132.

In one embodiment, the DPP4-binding domain of the invention comprises a HCVR which comprises at least one, preferably at least two, more preferably the following three complementary-determining regions (CDRs):
V_H-CDR1: SEQ ID NO: 104;
V_H-CDR2: SEQ ID NO: 116;
V_H-CDR3: SEQ ID NO: 133.

In one embodiment, the DPP4-binding domain of the invention comprises a HCVR which comprises at least one, preferably at least two, more preferably the following three complementary-determining regions (CDRs):
V_H-CDR1: SEQ ID NO: 104;
V_H-CDR2: SEQ ID NO: 117;
V_H-CDR3: SEQ ID NO: 134.

In one embodiment, the DPP4-binding domain of the invention comprises a HCVR which comprises at least one, preferably at least two, more preferably the following three complementary-determining regions (CDRs):
V_H-CDR1: SEQ ID NO: 104;
V_H-CDR2: SEQ ID NO: 113;
V_H-CDR3: SEQ ID NO: 135.

In one embodiment, the DPP4-binding domain of the invention comprises a HCVR which comprises at least one, preferably at least two, more preferably the following three complementary-determining regions (CDRs):
V_H-CDR1: SEQ ID NO: 104;
V_H-CDR2: SEQ ID NO: 116;
V_H-CDR3: SEQ ID NO: 136.

In one embodiment, the DPP4-binding domain of the invention comprises a HCVR which comprises at least one, preferably at least two, more preferably the following three complementary-determining regions (CDRs):
V_H-CDR1: SEQ ID NO: 106;
V_H-CDR2: SEQ ID NO: 118;
V_H-CDR3: SEQ ID NO: 131.

In one embodiment, the DPP4-binding domain of the invention comprises a HCVR which comprises at least one, preferably at least two, more preferably the following three complementary-determining regions (CDRs):
V_H-CDR1: SEQ ID NO: 107;
V_H-CDR2: SEQ ID NO: 119;
V_H-CDR3: SEQ ID NO: 137.

In one embodiment, the DPP4-binding domain of the invention comprises a HCVR which comprises at least one, preferably at least two, more preferably the following three complementary-determining regions (CDRs):
V_H-CDR1: SEQ ID NO: 108;
V_H-CDR2: SEQ ID NO: 120;
V_H-CDR3: SEQ ID NO: 138.

In one embodiment, the DPP4-binding domain of the invention comprises a HCVR which comprises at least one, preferably at least two, more preferably the following three complementary-determining regions (CDRs):
V_H-CDR1: SEQ ID NO: 108;
V_H-CDR2: SEQ ID NO: 121;
V_H-CDR3: SEQ ID NO: 138.

In one embodiment, the DPP4-binding domain of the invention comprises a HCVR which comprises at least one, preferably at least two, more preferably the following three complementary-determining regions (CDRs):
V_H-CDR1: SEQ ID NO: 109;
V_H-CDR2: SEQ ID NO: 122;
V_H-CDR3: SEQ ID NO: 139.

In one embodiment, the DPP4-binding domain of the invention comprises a HCVR which comprises at least one, preferably at least two, more preferably the following three complementary-determining regions (CDRs):
V_H-CDR1: SEQ ID NO: 108;
V_H-CDR2: SEQ ID NO: 123;
V_H-CDR3: SEQ ID NO: 138.

In one embodiment, the DPP4-binding domain of the invention comprises a HCVR which comprises at least one, preferably at least two, more preferably the following three complementary-determining regions (CDRs):

V_H-CDR1: SEQ ID NO: 108;
V_H-CDR2: SEQ ID NO: 124;
V_H-CDR3: SEQ ID NO: 138.

In one embodiment, the DPP4-binding domain of the invention comprises a HCVR which comprises at least one, preferably at least two, more preferably the following three complementary-determining regions (CDRs):
V_H-CDR1: SEQ ID NO: 110;
V_H-CDR2: SEQ ID NO: 125;
V_H-CDR3: SEQ ID NO: 140.

In one embodiment, the DPP4-binding domain of the invention comprises a HCVR which comprises at least one, preferably at least two, more preferably the following three complementary-determining regions (CDRs):
V_H-CDR1: SEQ ID NO: 108;
V_H-CDR2: SEQ ID NO: 126;
V_H-CDR3: SEQ ID NO: 141.

In one embodiment, the DPP4-binding domain of the invention comprises a HCVR which comprises at least one, preferably at least two, more preferably the following three complementary-determining regions (CDRs):
V_H-CDR1: SEQ ID NO: 108;
V_H-CDR2: SEQ ID NO: 126;
V_H-CDR3: SEQ ID NO: 138.

In one embodiment, the DPP4-binding domain of the invention comprises a HCVR which comprises at least one, preferably at least two, more preferably the following three complementary-determining regions (CDRs):
V_H-CDR1: SEQ ID NO: 111;
V_H-CDR2: SEQ ID NO: 127;
V_H-CDR3: SEQ ID NO: 138.

In one embodiment, the DPP4-binding domain of the invention comprises a HCVR which comprises at least one, preferably at least two, more preferably the following three complementary-determining regions (CDRs):
V_H-CDR1: SEQ ID NO: 110;
V_H-CDR2: SEQ ID NO: 128;
V_H-CDR3: SEQ ID NO: 140.

In one embodiment, the DPP4-binding domain of the invention comprises a HCVR which comprises at least one, preferably at least two, more preferably the following three complementary-determining regions (CDRs):
V_H-CDR1: SEQ ID NO: 112;
V_H-CDR2: SEQ ID NO: 125;
V_H-CDR3: SEQ ID NO: 140.

In one embodiment, the DPP4-binding domain of the invention comprises a HCVR which comprises at least one, preferably at least two, more preferably the following three complementary-determining regions (CDRs):
V_H-CDR1: SEQ ID NO: 108;
V_H-CDR2: SEQ ID NO: 127;
V_H-CDR3: SEQ ID NO: 138.

In one embodiment, the DPP4-binding domain of the invention comprises a HCVR which comprises at least one, preferably at least two, more preferably the following three complementary-determining regions (CDRs):
V_H-CDR1: SEQ ID NO: 108;
V_H-CDR2: SEQ ID NO: 127;
V_H-CDR3: SEQ ID NO: 142.

In one embodiment, the DPP4-binding domain of the invention comprises a light chain variable region (abbreviated herein as LCVR or VL) which comprises at least one, preferably at least two, more preferably the following three complementary-determining regions (CDRs):

| V_L-CDR1: any one of SEQ ID NO: 143 to 151; |
| V_L-CDR2: any one of SEQ ID NO: 152 to 163; |
| V_L-CDR3: any one of SEQ ID NO: 164 to 173. |

| SEQ ID NO | SEQUENCE | SEQ ID NO | SEQUENCE |
|---|---|---|---|
| 143 | KSSQSLLYNENKKNYLA | 159 | YTSNLQS |
| 144 | KSSQSLLHSNGNTYLN | 160 | DASHLAS |
| 145 | RSSQSLLHSNGNTYLN | 161 | YTSSFQD |
| 146 | LASEGISNYLA | 162 | YTISLQD |
| 147 | RASQGISNKLN | 163 | YASSLQD |
| 148 | RASQSVSTSTYNFMH | 164 | QEYYKFPWT |
| 149 | RASQGIGNKLN | 165 | QDYYHFPWT |
| 150 | RASQGISKKLN | 166 | MQATHAPFT |
| 151 | GASQGIGNKVN | 167 | QQYYKFPWP |
| 152 | WASTRES | 168 | QQYYKFPWT |
| 153 | SVSKLES | 169 | QQYYKFPYT |
| 154 | WASTREA | 170 | QQGYKYPWT |
| 155 | WASTRKS | 171 | QQDASFPPT |
| 156 | SVSNLES | 172 | QQSRELPLT |
| 157 | YTSSLQD | 173 | QQDTSFPPT |
| 158 | YTSRLQS | | |

In one embodiment, the DPP4-binding domain of the invention comprises a LCVR which comprises at least one, preferably at least two, more preferably the following three complementary-determining regions (CDRs):
V_L-CDR1: SEQ ID NO: 143;
V_L-CDR2: SEQ ID NO: 152;
V_L-CDR3: SEQ ID NO: 164.

In one embodiment, the DPP4-binding domain of the invention comprises a LCVR which comprises at least one, preferably at least two, more preferably the following three complementary-determining regions (CDRs):
V_L-CDR1: SEQ ID NO: 143;
V_L-CDR2: SEQ ID NO: 152;
V_L-CDR3: SEQ ID NO: 165.

In one embodiment, the DPP4-binding domain of the invention comprises a LCVR which comprises at least one, preferably at least two, more preferably the following three complementary-determining regions (CDRs):
V_L-CDR1: SEQ ID NO: 144;
V_L-CDR2: SEQ ID NO: 153;
V_L-CDR3: SEQ ID NO: 166.

In one embodiment, the DPP4-binding domain of the invention comprises a LCVR which comprises at least one, preferably at least two, more preferably the following three complementary-determining regions (CDRs):
V_L-CDR1: SEQ ID NO: 143;
V_L-CDR2: SEQ ID NO: 154;
V_L-CDR3: SEQ ID NO: 167.

In one embodiment, the DPP4-binding domain of the invention comprises a LCVR which comprises at least one, preferably at least two, more preferably the following three complementary-determining regions (CDRs):
V_L-CDR1: SEQ ID NO: 143;
V_L-CDR2: SEQ ID NO: 155;
V_L-CDR3: SEQ ID NO: 168.

In one embodiment, the DPP4-binding domain of the invention comprises a LCVR which comprises at least one, preferably at least two, more TABLE 3-continued Preferred combinations of HCVR's and LCVR's CDRs. The CDRs are defined by their SEQ ID NOs. First column indicates the clones name.

| Clone's name | V$_H$-CDR1 | V$_H$-CDR2 | V$_H$-CDR3 | V$_L$-CDR1 | V$_L$-CDR2 | V$_L$-CDR3 |
|---|---|---|---|---|---|---|
| 5826-13-R4A-H10 | 110 | 125 | 140 | 146 | 162 | 170 |
| 5826-13-R4A-H11 | 110 | 128 | 140 | 146 | 162 | 170 |
| 5826-13-R4A-H12 | 110 | 125 | 140 | 146 | 163 | 170 |

In one embodiment, the DPP4-binding domain of the invention comprises a combination of (i) three HCVR's CDRs and (ii) three LCVR's CDRs, said combination being that of any one of the following clones as defined in Table 3: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the DPP4-binding domain of the invention comprises a combination of (i) three HCVR's CDRs and (ii) three LCVR's CDRs, said combination being that of any one of the following clones as defined in Table 3: 5826-8-R6A-E10, 5826-8-R5A-G8, 5826-8-R6A-H11, 5826-13-R3A-D5, 5826-13-R4A-H5, and 5826-13-R4A-H12.

In one embodiment, the DPP4-binding domain of the invention comprises a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12.

In one embodiment, the DPP4-binding domain of the invention comprises a combination of (i) three HCVR's CDRs and (ii) three LCVR's CDRs, said combination being that of clone 5826-13-R3A-A10 as defined in Table 3. In one embodiment, the DPP4-binding domain of the invention comprises a combination of (i) three HCVR's CDRs and (ii) three LCVR's CDRs, said combination being that of clone 5826-13-R3A-B1 as defined in Table 3. In one embodiment, the DPP4-binding domain of the invention comprises a combination of (i) three HCVR's CDRs and (ii) three LCVR's CDRs, said combination being that of clone 5826-13-R3A-B3 as defined in Table 3. In one embodiment, the DPP4-binding domain of the invention comprises a combination of (i) three HCVR's CDRs and (ii) three LCVR's CDRs, said combination being that of clone 5826-13-R3A-D5 as defined in Table 3. In one embodiment, the DPP4-binding domain of the invention comprises a combination of (i) three HCVR's CDRs and (ii) three LCVR's CDRs, said combination being that of clone 5826-13-R3A-D6 as defined in Table 3. In one embodiment, the DPP4-binding domain of the invention comprises a combination of (i) three HCVR's CDRs and (ii) three LCVR's CDRs, said combination being that of clone 5826-13-R4A-E2 as defined in Table 3. In one embodiment, the DPP4-binding domain of the invention comprises a combination of (i) three HCVR's CDRs and (ii) three LCVR's CDRs, said combination being that of clone 5826-13-R4A-E6 as defined in Table 3. In one embodiment, the DPP4-binding domain of the invention comprises a combination of (i) three HCVR's CDRs and (ii) three LCVR's CDRs, said combination being that of clone 5826-13-R4A-E9 as defined in Table 3. In one embodiment, the DPP4-binding domain of the invention comprises a combination of (i) three HCVR's CDRs and (ii) three LCVR's CDRs, said combination being that of clone 5826-13-R4A-F10 as defined in Table 3. In one embodiment, the DPP4-binding domain of the invention comprises a combination of (i) three HCVR's CDRs and (ii) three LCVR's CDRs, said combination being that of clone 5826-13-R4A-G11 as defined in Table 3. In one embodiment, the DPP4-binding domain of the invention comprises a combination of (i) three HCVR's CDRs and (ii) three LCVR's CDRs, said combination being that of clone 5826-13-R4A-G12 as defined in Table 3. In one embodiment, the DPP4-binding domain of the invention comprises a combination of (i) three HCVR's CDRs and (ii) three LCVR's CDRs, said combination being that of clone 5826-13-R4A-H1 as defined in Table 3. In one embodiment, the DPP4-binding domain of the invention comprises a combination of (i) three HCVR's CDRs and (ii) three LCVR's CDRs, said combination being that of clone 5826-13-R4A-H2 as defined in Table 3. In one embodiment, the DPP4-binding domain of the invention comprises a combination of (i) three HCVR's CDRs and (ii) three LCVR's CDRs, said combination being that of clone 5826-13-R4A-H3 as defined in Table 3. In one embodiment, the DPP4-binding domain of the invention comprises a combination of (i) three HCVR's CDRs and (ii) three LCVR's CDRs, said combination being that of clone 5826-13-R4A-H4 as defined in Table 3. In one embodiment, the DPP4-binding domain of the invention comprises a combination of (i) three HCVR's CDRs and (ii) three LCVR's CDRs, said combination being that of clone 5826-13-R4A-H5 as defined in Table 3. In one embodiment, the DPP4-binding domain of the invention comprises a combination of (i) three HCVR's CDRs and (ii) three LCVR's CDRs, said combination being that of clone 5826-13-R4A-H6 as defined in Table 3. In one embodiment, the DPP4-binding domain of the invention comprises a combination of (i) three HCVR's CDRs and (ii) three LCVR's CDRs, said combination being that of clone 5826-13-R4A-H9 as defined in Table 3. In one embodiment, the DPP4-binding domain of the invention comprises a combination of (i) three HCVR's CDRs and (ii) three LCVR's CDRs, said combination being that of clone 5826-13-R4A-H10 as defined in Table 3. In one embodiment, the DPP4-binding domain of the invention comprises a combination of (i) three HCVR's CDRs and (ii) three LCVR's CDRs, said combination being that of clone 5826-13-R4A-H11 as defined in Table 3. In one embodiment, the DPP4-binding domain of the invention comprises a combination of (i) three HCVR's CDRs and (ii) three LCVR's CDRs, said combination being that of clone 5826-13-R4A-H12 as defined in Table 3.

In one embodiment, the DPP4-binding domain of the invention comprises a HCVR comprising or consisting of the sequence SEQ ID NO: 174; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 174.

SEQ ID NO: 174
EVQLEESGGGLVQPGRSLKLSCAASGFTFNNYGMAWVRQAPTKGLEWVATI

SYDGNDTYYRDSVKGRFTVSRDNAKSTLYLQMDSLRSEDTATYYCVRHRLI

YTTDYYYEVMDVWGQGASVTVSS

In one embodiment, the DPP4-binding domain of the invention comprises a HCVR comprising or consisting of the sequence SEQ ID NO: 175; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 175.

SEQ ID NO: 175
QVQLKESGGGLVQPGRSLKLSCAASGFTFSNYGMAWVRQAPTKGLEWVATT

SYDGNDTYYRDSVKGRFTVSRDNAKNTLYLQMDSLRSEDTATYYCVRHRLI

YTTDYYYEVMDAWGQGASVTVSS

In one embodiment, the DPP4-binding domain of the invention comprises a HCVR comprising or consisting of the sequence SEQ ID NO: 176; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 176.

SEQ ID NO: 176
QVTLKESGPGILQPSQTLSLTCSFSGFSLSTSDRCVSWIRQPSGKGLEWLA

TICWDDSKGYNPSLKNRLTISKDTSNNQAFLKITSVGTADIAKYYCARNSG

DGRFAYWGQGTLVTVSS

In one embodiment, the DPP4-binding domain of the invention comprises a HCVR comprising or consisting of the sequence SEQ ID NO: 177; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 177.

SEQ ID NO: 177
EVQLEESGGGLVQPGRSLKLSCAASGFTFSNYGMAWVRQAPTKGLEWVATI

NYDGRNTYYRDSVKGRFTISRDNAKSTLYLQVDSLQSEDTATYYCTRHKLI

YTTDYYYEVMDAWGQGASVTVSS

In one embodiment, the DPP4-binding domain of the invention comprises a HCVR comprising or consisting of the sequence SEQ ID NO: 178; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 178.

SEQ ID NO: 178
EVKLVESGGGLVQPGRSLKLSCAASGFSFTNYGMAWVRQAPTKGLEWVATI

NYDGSNTYYRDSVKGRFTISRDNAKRTLDLQMDSLRSEDTATYYCARHRLM

YTTDYYYEVMDDWGQGASVTVSS

In one embodiment, the DPP4-binding domain of the invention comprises a HCVR comprising or consisting of the sequence SEQ ID NO: 179; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 179.

SEQ ID NO: 179
EVKLVESGGGLVQPGRSLKLSCAASGFSFRNYGMAWVRQAPTKGQEWVATI

SYDGNDTYYRDSVKGRFTVSRDNAKSTLYLQMDSLRSEDTATYYCTRHRLI

YTTDYYYEVLDAWGQGASVTVSS

In one embodiment, the DPP4-binding domain of the invention comprises a HCVR comprising or consisting of the sequence SEQ ID NO: 180; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 180.

SEQ ID NO: 180
EVKLVESGGGLVQPGRSLKLSCTASGFTFSNYGMAWVRQAPTKGLEWVATI

NYDGRNTYYRDSVKGRFTISRDNAKSTLYLQVDSLQSEDTATYYCTRHKLI

YTTDYYYEVMDVWGQGASVAVSS

In one embodiment, the DPP4-binding domain of the invention comprises a HCVR comprising or consisting of the sequence SEQ ID NO: 181; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 181.

SEQ ID NO: 181
EVKLVESGGALVQPGRSLKLSCAASGFTFSNFGMAWVRQAPTKGLEWVATI

NYDGRDTYYRDSVKGRFTVSRDNAKSTLYLQMDSLRSEDTATYYCTRHRLI

YTTDYYYEVMDAWGRGASVTVSS

In one embodiment, the DPP4-binding domain of the invention comprises a HCVR comprising or consisting of the sequence SEQ ID NO: 182; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 182.

SEQ ID NO: 182
EVKLVESGPGLVKPSQSLSLACSITDYSITDNYWGWIRKFPGNKMEWIGHI

SHSGSSTYNPSLKSRISFTRDTSKNQFFLQLNSVTPEDTATYFCARYGAGA

SFDYWGQGVMVTVSS

In one embodiment, the DPP4-binding domain of the invention comprises a HCVR comprising or consisting of the sequence SEQ ID NO: 183; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 183.

SEQ ID NO: 183
EVQLQQSGAELTKPGSSVKISCKASGFTFTTYDIGWLKQRPGQALEWIGYI

NPGSGGIGYNEKFKGKATLTVDKSSSTAFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 184; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 184.

SEQ ID NO: 184
EVQLQQSGAGLTKPGASVKISCKASGYTFTTYDIGWIKQRPGQALEWIGSI

NPGSGGIAYSEKFKGKATLTVDKSSSTAFMQLSSLTPEDTAVYYCARPLRR

VLDYWGQGVLVTVSS

In one embodiment, the DPP4-binding domain of the invention comprises a HCVR comprising or consisting of the sequence SEQ ID NO: 185; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 185.

SEQ ID NO: 185
EVKLVESGPGLVKPSQSLSLTCSVTGYFITGNYLAWIRKFPGNKMEWIGHI

KSSGTTTYNPSLKSRVSITRDTSKNQFFLQLNSVTSEDTATYYCARHGHYV

MDVWGQGASVTVSS

In one embodiment, the DPP4-binding domain of the invention comprises a HCVR comprising or consisting of the sequence SEQ ID NO: 186; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 186.

SEQ ID NO: 186
EVQLQQSGAELTKPGSSVKISCKASGYTFTTYDIGWIKQRPGQALEWIGSI

NPGSGGIGYNERFKGKATLTVDKSSSTAFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 187; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 187.

SEQ ID NO: 187
QVQLKQSGAELTKPGSSVKISCKASGYTFTTYDIGWLKQRPGQALEWIGYI

NPGGGGIGYNEKFKGKATLTVDKSSSTAFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 188; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 188.

SEQ ID NO: 188
DVKLQESGPGLVKPSQSLSLTCSVTGHSITSNYWGWIRKFPGNKMEWIGQI

SHSGSTSYNPSLKSRISITRDTSKNQFFLQLNSVTTEDTATYYCGRYGAGS

SFDYWGQGVMVTVSS

In one embodiment, the DPP4-binding domain of the invention comprises a HCVR comprising or consisting of the sequence SEQ ID NO: 189; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 189.

SEQ ID NO: 189
EVQLQQSGAELTKPGSSVKISCKASGYTFTTYDIGWIKQRPGQALEWIGSI

NPGSGGIGYNEKFKGKATLTVDKSSSTVFMQLSSLTPEDTAVYYCARPLRR

VLDNWGQGVLVTVSS

In one embodiment, the DPP4-binding domain of the invention comprises a HCVR comprising or consisting of the sequence SEQ ID NO: 190; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 190.

SEQ ID NO: 190
EVQLQQSGAELAKPGSSVKISCKASGYTFTTYDIGWIKQRPGQALEWIGSI

NPGSGGIGYNEKFKGKATLTVDKSSRTVFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 191; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 191.

SEQ ID NO: 191
EVQLQQSGPELAKPGSSVKISCKASGYTFTTYDIGWIKQRPGQALEWIGSI

NPGSGGIGYNEKFKGKATLTVDKSSSTAFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 192; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 192.

SEQ ID NO: 192
EVQLQQSGAGLTKPGASVKISCTASGYTFTTYDRGWLRQRPGQALEWIGSI

NPGGGGTGYNEKFKGNATLTVDKSSSTAFMQLSSLTPEDTADYYCARPLRR

VLDYWGQGVLVTVSS

In one embodiment, the DPP4-binding domain of the invention comprises a HCVR comprising or consisting of the sequence SEQ ID NO: 193; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 193.

SEQ ID NO: 193
DVKLQESGPGLVKPSQSLSLTCSVTGHSITSNYWGWIRKLPGNKMEWIGQI

SHSGSTSYNPSLISRISITRDTSNQFFLQLNSVTTEDTATYYCGRYGAGSS

FDYWGQGVMVTVSS

In one embodiment, the DPP4-binding domain of the invention comprises a HCVR comprising or consisting of the sequence SEQ ID NO: 194; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 194.

SEQ ID NO: 194
EVQLQQSGAELTKPGSSVKISCKASGYTFTTYDIGWIKQRPGQALEWIGSI

NPGSGGIGYNEKFKGKATLTVDRSSSTAFMQLSSLTPEDTAVYYCARPLRR

VLDNWGQGVLVTVSS

In one embodiment, the DPP4-binding domain of the invention comprises a HCVR comprising or consisting of the sequence SEQ ID NO: 195; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 195.

SEQ ID NO: 195
EVQLQQSGGELTKPGSSVKISCKASGYTFSTYDIGWIKQRPGQALEWIGSI

NPGSGGIGYNEKFKGKATLTVDKSSSTAFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 196; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 196.

SEQ ID NO: 196
DVKLQESGPGLVKPSQSLSLTCSVTGHSITGNYWGWIRKFPGNKMEWIGQI

SHSGSTSYNPSLKSRISITRDTSKNQFFLQLNSVTTEDTATYYCGRYGAGS

SFDYWGQGVMVTVSS

In one embodiment, the DPP4-binding domain of the invention comprises a HCVR comprising or consisting of the sequence SEQ ID NO: 197; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 197.

SEQ ID NO: 197
EVQLQQSGAGLTKPGGSVKISCKVSGYTFTTYDIGWLKQRPGQALEWIGSI

NPGGGGTGYNEKFKGKATLTVDKSSSTAFMQLSSLTPEDTAVYYCARPLRR

VLDYWGQGVLVTVSS

In one embodiment, the DPP4-binding domain of the invention comprises a HCVR comprising or consisting of the sequence SEQ ID NO: 198; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 198.

SEQ ID NO: 198
EVQLQQSGAGLTKPGASVKISCKASGYTFTTYDIGWLKQRPGQALEWIGSI

NPGGGGTGYNEKFKGKATLTVDKSSSTAFMQLSSLTPEDTAVYYCARPLRV

LDYWGQGVLVTVSS

In one embodiment, the DPP4-binding domain of the invention comprises a HCVR comprising or consisting of the sequence SEQ ID NO: 199; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 199.

SEQ ID NO: 199
EVQLQQSGAELTKPGSSVKISCKASGYTFTTYDIGWIKQRPGQALEWIGSI

NPGSGGIGYNERFKGKATLTVDKSSSTAFMQLSSLTPEDTAVYYCARPLRR

VLDYWGRGVMVTVSS

In one embodiment, the DPP4-binding domain of the invention comprises a HCVR comprising or consisting of the sequence SEQ ID NO: 200; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 200.

SEQ ID NO: 200
EVQLEESGPGLVKPSQSLSLTCSVTGHSITSNYWGWIRKFPGNKMEWIGQI

SHSGSTSYNPSLKSRISITRDTSKNQFFLQLNSVTTEDTATYYCGRYGAGS

SFDYWGQGVMVTVSS

In one embodiment, the DPP4-binding domain of the invention comprises a HCVR comprising or consisting of the sequence SEQ ID NO: 201; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 201.

SEQ ID NO: 201
QVQLKESGPGLVKPSHSLSLTCSVTGHSITSNYWGWIRKFPGNKMEWIGQI

SHTGSSTYNPSLKSRISFTRDTSKNQFFLQLNSVTTEDSATYYCGRYGAGS

SFDYWGQGVMVTVSS

In one embodiment, the DPP4-binding domain of the invention comprises a LCVR comprising or consisting of the sequence SEQ ID NO: 202; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 202.

```
                                         SEQ ID NO: 202
DVLMTQTPSSQAASAGEKVTMSCKSSQSLLYNENKKNYLAWFQQKPGQSPK

LLIYWASTRESGVPDRFIGGGSGTDFTLTISSVQAEDLAVYYCQEYYKFPW

TFGGGTKLELK
```

In one embodiment, the DPP4-binding domain of the invention comprises a LCVR comprising or consisting of the sequence SEQ ID NO: 203; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 203.

```
                                         SEQ ID NO: 203
DIVMTQSPSSQAVSAGEKVTMSCKSSQSLLYNENKKNYLAWFQQKPGQSPK

LLIYWASTRESGVPDRFIGSGSGTDFTLTISSVQAEDLAVYYCQDYYHFPW

TFGGGTKLELK
```

In one embodiment, the DPP4-binding domain of the invention comprises a LCVR comprising or consisting of the sequence SEQ ID NO: 204; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 204.

```
                                         SEQ ID NO: 204
DVLMTQTPPTLSATIGQSVSISCKSSQSLLHSNGNTYLNWLLQRPGQSPQL

LIYSVSKLESGVPNRFSGSGSQTDFTLKISEVEAEDMGVYYCMQATHAPFT

FGSWTKLEIK
```

In one embodiment, the DPP4-binding domain of the invention comprises a LCVR comprising or consisting of the sequence SEQ ID NO: 205; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 205.

```
                                         SEQ ID NO: 205
DIVMTQAPSSQAVSPGEKVTMSCKSSQSLLYNENKKNYLAWYQQKPGQSPK

LLIYWASTREAGVPDRFIGSGSGTDFTLTISSVQAEDLAVYYCQQYYKFPW

PFGGGTKLELK
```

In one embodiment, the DPP4-binding domain of the invention comprises a LCVR comprising or consisting of the sequence SEQ ID NO: 206; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 206.

```
                                         SEQ ID NO: 206
DIVMTQAPSSQAVSAGEKVTMSCKSSQSLLYNENKKNYLAWFQQKPGQSPK

LLIYWASTRKSGVPDRFIGSGSGTDFTLTISSVQAEDLAVYYCQQYYKFPW

TFGGGTKLELR
```

In one embodiment, the DPP4-binding domain of the invention comprises a LCVR comprising or consisting of the sequence SEQ ID NO: 207; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 207.

```
                                         SEQ ID NO: 207
DIVMTQSPSSQAVSPGEKVTMNCKSSQSLLYNENKKNYLAWYQQKPGQSPK

LLIYWASTREAGVPDRFIGSGSGTDFTLTISSVQAEDLAVYYCQQYYKFPW

PFGGGTKLELK
```

In one embodiment, the DPP4-binding domain of the invention comprises a LCVR comprising or consisting of the sequence SEQ ID NO: 208; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 208.

```
                                         SEQ ID NO: 208
DVLMTQTPPTLSATIGQSVSISCRSSQSLLHSNGNTYLNWLLQRPGQSPQL

LIYSVSNLESGVPNRFSGSGSETDFTLKISGVEAEDLGVYYCMQATHAPFT

FGSGTKLEIK
```

In one embodiment, the DPP4-binding domain of the invention comprises a LCVR comprising or consisting of the sequence SEQ ID NO: 209; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 209.

```
                                         SEQ ID NO: 209
DIVMTQSPSSQAVSPGEKVTMNCKSSQSLLYNENKKNYLAWYQQKPGQSPK

LLIYWASTREAGVPDRFIGSGSGTDFTLTISSVQAEDLAVYYCQQYYKFPY

TFGAGTKLELK
```

In one embodiment, the DPP4-binding domain of the invention comprises a LCVR comprising or consisting of the sequence SEQ ID NO: 210; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 210.

```
                                         SEQ ID NO: 210
DIQLTQSPHSLSASLGETVSIECLASEGISNYLAWYQQKPGKSPQLLIYYT

SSLQDGVPSRFSGSGSGTQYSLKISNMQPEDEGVYYCQQGYKYPWTFGGGT

KLELK
```

In one embodiment, the DPP4-binding domain of the invention comprises a LCVR comprising or consisting of the sequence SEQ ID NO: 211; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 211.

SEQ ID NO: 211
DIVMTQSPSSLPASLGERVTISCRASQGISNKLNWYQQKPDGTIKPLIYYT

SRLQSGVPSRFSGSGSGTDYSLTISSLEPEDFAMYYCQQDASFPPTFGAGT

KVELK

In one embodiment, the DPP4-binding domain of the invention comprises a LCVR comprising or consisting of the sequence SEQ ID NO: 212; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 212.

SEQ ID NO: 212
DIQLTQSPSSLPASLGERVTISCRASQGISNKLNWYQQKPDGTIKPLIYYT

SNLQSGVPSRFSGSGSGTDYSLTISSLEPEDFAMYYCQQDASFPPTFGGGT

KLELK

In one embodiment, the DPP4-binding domain of the invention comprises a LCVR comprising or consisting of the sequence SEQ ID NO: 213; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 213.

SEQ ID NO: 213
DIVLTQSPVLAVSLGQRATISCRASQSVSTSTYNFMHWYQQKPGQQPRLLI

YDASHLASSVPARFSGSGSGTDFTLTINPVQADDIATYYCQQSRELPLTFG

SGTKLEIK

In one embodiment, the DPP4-binding domain of the invention comprises a LCVR comprising or consisting of the sequence SEQ ID NO: 214; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 214.

SEQ ID NO: 214
DILMTQSPSSLSASLGERVTISCRASQGIGNKLNWYQQKPDGTIKPLIYYT

SNLQSGVPSRFSGSGSGTDYSLTISSLEPEDFAMYYCQQDASFPPTFGGGT

KLELK

In one embodiment, the DPP4-binding domain of the invention comprises a LCVR comprising or consisting of the sequence SEQ ID NO: 215; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 215.

SEQ ID NO: 215
DIQLTQSPSSLPASLGERVTISCRASQGISNKLNWYQQKPDGTIKPLIYYT

SNLQSGVPSRFSGSGSGTDYSLTISSLEPEDFAMYFCQQDASFPPTFGGGT

KLELK

In one embodiment, the DPP4-binding domain of the invention comprises a LCVR comprising or consisting of the sequence SEQ ID NO: 216; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 216.

SEQ ID NO: 216
DIQMTQTPHSLSASLGETVSIECLASEGISNYLAWYQQKPGKSPQLLIYYT

SSFQDGVPSRFSGSGSGTQYSLKISNMQPEDEGVYYCQQGYKYPWTFGGGT

KLELK

In one embodiment, the DPP4-binding domain of the invention comprises a LCVR comprising or consisting of the sequence SEQ ID NO: 217; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 217.

SEQ ID NO: 217
DILMTQSPSSRPASLGERVTISCRASQGIGNKLNWYQQKPDGTIKPLIYYT

SNLQSGVPSRFSGSGSGTDYSLTISSLEPEDFAMYYCQQDASFPPTFGGGT

KLELK

In one embodiment, the DPP4-binding domain of the invention comprises a LCVR comprising or consisting of the sequence SEQ ID NO: 218; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 218.

SEQ ID NO: 218
DIQMTQTPSSLPASLGERVTISCRASQGISKKLNWYQQKPDGTIKPLIYYT

SNLQSGVPSRFSGSGSGTDYSLTISSLEPEDFAIYYCQQDASFPPTFGGGT

KLELK

In one embodiment, the DPP4-binding domain of the invention comprises a LCVR comprising or consisting of the sequence SEQ ID NO: 219; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 219.

SEQ ID NO: 219
DIQLTQSPSSLPASLGERVTISCRASQGISKKLNWYQQKPDGTIKPLIYYT

SNLQSGVPSRFSGSSGTDYSLTISSLEPEDFAMYYCQQDASFPPTFGGGTK

LELK

In one embodiment, the DPP4-binding domain of the invention comprises a LCVR comprising or consisting of the sequence SEQ ID NO: 220; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 220.

SEQ ID NO: 220
DILMTQSPSSLPASLGERVTISCGASQGIGNKVNWYQQKPDGTIKPLIYYT

SNLQSGVPSRFSGSGTGTDYSLTISSLEPEDFAMYYCQQDASFPPTFGGGT

KLELK

In one embodiment, the DPP4-binding domain of the invention comprises a LCVR comprising or consisting of the sequence SEQ ID NO: 221; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 221.

SEQ ID NO: 221
DIQMTQTPHSLSASLGETVSIECLASEGISNYLAWYQRKPGKSPQLLIYYT

ISLQDGVPSRFSGSGSGTQYSLKISNMQPEDEGVFYCQQGYKYPWTFGGGT

KLELK

In one embodiment, the DPP4-binding domain of the invention comprises a LCVR comprising or consisting of the sequence SEQ ID NO: 222; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 222.

SEQ ID NO: 222
DIQLTQSPSSLPASLGERVTISCRASQGIGNKLNWYQQKPDGTIKPLIYYT

SNLQSGVPSRFSGSGSGTDYSLTISSLEPEDFAMYYCQQDASFPPTFGGGT

KLELK

In one embodiment, the DPP4-binding domain of the invention comprises a LCVR comprising or consisting of the sequence SEQ ID NO: 223; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 223.

SEQ ID NO: 223
DILMTQSPSSLSASLGERVTISCRASQGIGNKLNWYQQKPDGTIKPLIYYT

SNLQSGVPSRFSGSGSGTDYSLTISSLEPEDFAMYYCQQDTSFPPTFGAGT

KLELK

In one embodiment, the DPP4-binding domain of the invention comprises a LCVR comprising or consisting of the sequence SEQ ID NO: 224; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 224.

SEQ ID NO: 224
DIQMTQTPHSLSASLGETVSIECLASEGISNYLAWYQQKPGKSPQLLIYYT

ISLQDGVPSRFSGSGSGTQYSLKISNMQPEDEGVFYCQQGYKYPWTFGGGT

KLELK

In one embodiment, the DPP4-binding domain of the invention comprises a LCVR comprising or consisting of the sequence SEQ ID NO: 225; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 225.

SEQ ID NO: 225
DIQMTQTPSSLPASLERVTISCRASQGISNKLNWYQKKPDGTIKPLIYYTS

NLQSGVPSRFSGSGSGTDYSLTISSLEPEDFAMYFCQQDASFPPTFGGGTQ

LELK

In one embodiment, the DPP4-binding domain of the invention comprises a LCVR comprising or consisting of the sequence SEQ ID NO: 226; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 226.

SEQ ID NO: 226
DIQLTQSPSSRPASLGERVTISCRASQGIGNKLNWYQQKPDGTIKPLIYYT

SNLQSGVPSRFSGSGSGTDYSLTISSLEPEDFAMYYCQQDASFPPTFGGGT

KLELK

In one embodiment, the DPP4-binding domain of the invention comprises a LCVR comprising or consisting of the sequence SEQ ID NO: 227; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 227.

SEQ ID NO: 227
DIQMTQTPHSLSASLGETVSIECLASEGISNYLAWYQQKPGKSPQLLIYYA

SSLQDGVPSRFSGSGSGTQYSLKISNMQPEDEGVYYCQQGYKYPWTFGGGT

KLELK

In one embodiment, the DPP4-binding domain of the invention comprises a combination of (i) a HCVR and (ii) a LCVR, said combination being as defined in Table 4.

TABLE 4

Preferred combinations of HCVR and LCVR. The HCVR and LCVR are defined by their SEQ ID NOs. First column indicates the clone's name.

| Clone's name | HCVR | LCVR |
|---|---|---|
| 5826-8-R6A-A10 | 174 | 202 |
| 5826-8-R6A-B11 | 175 | 203 |
| 5826-8-R6A-D12 | 176 | 204 |
| 5826-8-R6A-E10 | 177 | 205 |
| 5826-8-R5A-G6 | 178 | 203 |
| 5826-8-R5A-G8 | 179 | 206 |
| 5826-8-R6A-H9 | 180 | 207 |
| 5826-8-R6A-H11 | 176 | 208 |
| 5826-8-R6A-H12 | 181 | 209 |

TABLE 4-continued

Preferred combinations of HCVR and LCVR. The HCVR and LCVR are defined by their SEQ ID NOs. First column indicates the clone's name.

| Clone's name | HCVR | LCVR |
| --- | --- | --- |
| 5826-13-R3A-A10 | 182 | 210 |
| 5826-13-R3A-B1 | 183 | 211 |
| 5826-13-R3A-B3 | 184 | 212 |
| 5826-13-R3A-D5 | 185 | 213 |
| 5826-13-R3A-D6 | 186 | 214 |
| 5826-13-R4A-E2 | 187 | 215 |
| 5826-13-R4A-E6 | 188 | 216 |
| 5826-13-R4A-E9 | 189 | 217 |
| 5826-13-R4A-F10 | 190 | 218 |
| 5826-13-R4A-G11 | 191 | 219 |
| 5826-13-R4A-G12 | 192 | 220 |
| 5826-13-R4A-H1 | 193 | 221 |
| 5826-13-R4A-H2 | 194 | 222 |
| 5826-13-R4A-H3 | 195 | 223 |
| 5826-13-R4A-H4 | 196 | 224 |
| 5826-13-R4A-H5 | 197 | 212 |
| 5826-13-R4A-H6 | 198 | 225 |
| 5826-13-R4A-H9 | 199 | 226 |
| 5826-13-R4A-H10 | 200 | 224 |
| 5826-13-R4A-H11 | 201 | 224 |
| 5826-13-R4A-H12 | 200 | 227 |

In one embodiment, the DPP4-binding domain of the invention comprises a combination of (i) a HCVR and (ii) a LCVR, combination being that of any one of the following clones as defined in Table 4: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the DPP4-binding domain of the invention comprises a combination of (i) a HCVR and (ii) a LCVR, combination being that of any one of the following clones as defined in Table 4: 5826-8-R6A-E10, 5826-8-R5A-G8, 5826-8-R6A-H11, 5826-13-R3A-D5, 5826-13-R4A-H5, and 5826-13-R4A-H12.

In one embodiment, the DPP4-binding domain of the invention comprises a combination of (i) a HCVR and (ii) a LCVR, combination being that of any one of the following clones as defined in Table 4: 5826-13-R3A-D5, 5826-13-R4A-H5, and 5826-13-R4A-H12.

In one embodiment, the DPP4-binding domain of the invention comprises a combination of (i) a HCVR and (ii) a LCVR, combination being that of clone 5826-13-R3A-A10 as defined in Table 4. In one embodiment, the DPP4-binding domain of the invention comprises a combination of (i) a HCVR and (ii) a LCVR, combination being that of clone 5826-13-R3A-B1 as defined in Table 4. In one embodiment, the DPP4-binding domain of the invention comprises a combination of (i) a HCVR and (ii) a LCVR, combination being that of clone 5826-13-R3A-B3 as defined in Table 4. In one embodiment, the DPP4-binding domain of the invention comprises a combination of (i) a HCVR and (ii) a LCVR, combination being that of clone 5826-13-R3A-D5 as defined in Table 4. In one embodiment, the DPP4-binding domain of the invention comprises a combination of (i) a HCVR and (ii) a LCVR, combination being that of clone 5826-13-R3A-D6 as defined in Table 4. In one embodiment, the DPP4-binding domain of the invention comprises a combination of (i) a HCVR and (ii) a LCVR, combination being that of clone 5826-13-R4A-E2 as defined in Table 4. In one embodiment, the DPP4-binding domain of the invention comprises a combination of (i) a HCVR and (ii) a LCVR, combination being that of clone 5826-13-R4A-E6 as defined in Table 4. In one embodiment, the DPP4-binding domain of the invention comprises a combination of (i) a HCVR and (ii) a LCVR, combination being that of clone 5826-13-R4A-E9 as defined in Table 4. In one embodiment, the DPP4-binding domain of the invention comprises a combination of (i) a HCVR and (ii) a LCVR, combination being that of clone 5826-13-R4A-F10 as defined in Table 4. In one embodiment, the DPP4-binding domain of the invention comprises a combination of (i) a HCVR and (ii) a LCVR, combination being that of clone 5826-13-R4A-G11 as defined in Table 4. In one embodiment, the DPP4-binding domain of the invention comprises a combination of (i) a HCVR and (ii) a LCVR, combination being that of clone 5826-13-R4A-G12 as defined in Table 4. In one embodiment, the DPP4-binding domain of the invention comprises a combination of (i) a HCVR and (ii) a LCVR, combination being that of clone 5826-13-R4A-H1 as defined in Table 4. In one embodiment, the DPP4-binding domain of the invention comprises a combination of (i) a HCVR and (ii) a LCVR, combination being that of clone 5826-13-R4A-H2 as defined in Table 4. In one embodiment, the DPP4-binding domain of the invention comprises a combination of (i) a HCVR and (ii) a LCVR, combination being that of clone 5826-13-R4A-H3 as defined in Table 4. In one embodiment, the DPP4-binding domain of the invention comprises a combination of (i) a HCVR and (ii) a LCVR, combination being that of clone 5826-13-R4A-H4 as defined in Table 4. In one embodiment, the DPP4-binding domain of the invention comprises a combination of (i) a HCVR and (ii) a LCVR, combination being that of clone 5826-13-R4A-H5 as defined in Table 4. In one embodiment, the DPP4-binding domain of the invention comprises a combination of (i) a HCVR and (ii) a LCVR, combination being that of clone 5826-13-R4A-H6 as defined in Table 4. In one embodiment, the DPP4-binding domain of the invention comprises a combination of (i) a HCVR and (ii) a LCVR, combination being that of clone 5826-13-R4A-H9 as defined in Table 4. In one embodiment, the DPP4-binding domain of the invention comprises a combination of (i) a HCVR and (ii) a LCVR, combination being that of clone 5826-13-R4A-H10 as defined in Table 4. In one embodiment, the DPP4-binding domain of the invention comprises a combination of (i) a HCVR and (ii) a LCVR, combination being that of clone 5826-13-R4A-H11 as defined in Table 4. In one embodiment, the DPP4-binding domain of the invention comprises a combination of (i) a HCVR and (ii) a LCVR, combination being that of clone 5826-13-R4A-H12 as defined in Table 4.

Another object of the present invention is an isolated antibody or antigen-binding fragment thereof, wherein said antibody or antigen-binding fragment thereof recognizes and is capable of binding to a senescent cell-associated antigen, as defined hereinabove.

In one embodiment, the senescent cell-associated antigen is selected from the group comprising or consisting of DEP1 and DPP4.

In one embodiment, the isolated antibody or antigen-binding fragment thereof of the invention recognizes and is capable of binding to DEP1, such as, e.g., human DEP1, or orthologs thereof, including murine and rat DEP1. In one embodiment, the isolated antibody or antigen-binding fragment thereof of the invention recognizes and is capable of binding to human DEP1 (hDEP1) with SEQ ID NO: 1. In one embodiment, the isolated antibody or antigen-binding fragment thereof of the invention recognizes and is capable of binding to the extracellular domain of human DEP1 (hDEP1) comprising or consisting of amino acid residues 36-975 of SEQ ID NO: 1. Hence, the isolated antibody or antigen-binding fragment thereof of the invention is an isolated "anti-DEP1 antibody or antigen-binding fragment thereof".

In one embodiment, the isolated antibody or antigen-binding fragment thereof of the invention recognizes and is capable of binding to DPP4, such as, e.g., human DPP4 or orthologs thereof, including murine and rat DPP4. In one embodiment, the isolated antibody or antigen-binding fragment thereof of the invention recognizes and is capable of binding to human DPP4 (hDPP4) with SEQ ID NO: 101. In one embodiment, the isolated antibody or antigen-binding fragment thereof of the invention recognizes and is capable of binding to the extracellular domain of human DPP4 (hDPP4) comprising or consisting of amino acid residues 29-766 of SEQ ID NO: 101. Hence, the antigen-binding fragment of the invention is an isolated "anti-DPP4 antibody or antigen-binding fragment thereof".

In one embodiment, the isolated antibody or antigen-binding fragment thereof of the invention recognizes and is capable of binding to DEP1 and DPP4.

The binding between the anti-DEP1 antibody or antigen-binding fragment thereof of the invention and DEP1, or between the anti-DPP4 antibody or antigen-binding fragment thereof of the invention and DPP4, implies that said antibody or antigen-binding fragment thereof exhibits appreciable affinity for DEP1 or DPP4, respectively. In other words, the anti-DEP1 antibody or antigen-binding fragment thereof of the invention or the anti-DPP4 antibody or antigen-binding fragment thereof of the invention, is specific for, or is immunospecific for, or specifically binds to, DEP1 or DPP4, respectively.

An antibody or antigen-binding fragment thereof is said to be "specific for", "immunospecific for" or to "specifically bind to" an antigen if it reacts with said antigen (e.g., DEP1 and/or DPP4). An antibody or antigen-binding fragment thereof is said to be "specific for", "immunospecific for" or to "specifically bind to" an antigen if it recognizes and is capable of binding to antigen with a $K_D$-affinity constant less than or equal to $10^{-6}$ M, preferably less than or equal to $10^{-7}$ M, $5 \cdot 10^{-8}$ M, $10^{-8}$ M, $5 \cdot 10^{-9}$ M, $10^{-9}$ M or less; as may be determined, e.g., by biosensor analysis, particularly by Biacore Analysis.

In one embodiment, the isolated antibody or antigen-binding fragment thereof of the invention comprises an antigen-binding domain, as described hereinabove.

In one embodiment, the anti-DEP1 antibody or antigen-binding fragment thereof of the invention comprises a DEP1-binding domain, as described hereinabove.

In one embodiment, the anti-DEP1 antibody or antigen-binding fragment thereof of the invention comprises a DEP1-binding domain comprising a combination of (i) at least one, preferably at least two, more preferably three HCVR's CDRs and (ii) at least one, preferably at least two, more preferably three LCVR's CDRs, said combination being as defined in Table 1.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being as defined in Table 1.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of any one of the following clones as defined in Table 1: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of any one of the following clones as defined in Table 1: 5738-10-R3A-C6, 5738-10-R3A-D5, 5738-10-R4A-G12, 5738-13-R4A-D11, and 5738-13-R2A-H4.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of any one of the following clones as defined in Table 1: 5738-10-R4A-G12, 5738-13-R4A-D11, and 5738-13-R2A-H4.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of any one of the following clones as defined in Table 1: 5738-13-R4A-D11, and 5738-13-R2A-H4.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R2A-C1 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R2A-D3 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R4A-D11 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R3A-F5 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R4A-F11 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R2A-H3 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R2A-H4 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R4A-

H9 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R4A-H11 as defined in Table 1.

In one embodiment, the anti-DEP1 antibody or antigen-binding fragment thereof of the invention comprises a DEP1-binding domain comprising a combination of (i) a HCVR and (ii) a LCVR, said combination being as defined in Table 2.

In one embodiment, the anti-DEP1 antibody or antigen-binding fragment thereof of the invention comprises a DEP1-binding domain comprising a combination of (i) a HCVR and (ii) a LCVR, combination being that of any one of the following clones as defined in Table 2: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the anti-DEP1 antibody or antigen-binding fragment thereof of the invention comprises a DEP1-binding domain comprising a combination of (i) a HCVR and (ii) a LCVR, combination being that of any one of the following clones as defined in Table 2: 5738-10-R3A-C6, 5738-10-R3A-D5, 5738-10-R4A-G12, 5738-13-R4A-D11, and 5738-13-R2A-H4.

In one embodiment, the anti-DEP1 antibody or antigen-binding fragment thereof of the invention comprises a DEP1-binding domain comprising a combination of (i) a HCVR and (ii) a LCVR, combination being that of any one of the following clones as defined in Table 2: 5738-10-R4A-G12, 5738-13-R4A-D11, and 5738-13-R2A-H4.

In one embodiment, the anti-DEP1 antibody or antigen-binding fragment thereof of the invention comprises a DEP1-binding domain comprising a combination of (i) a HCVR and (ii) a LCVR, combination being that of any one of the following clones as defined in Table 2: 5738-13-R4A-D11, and 5738-13-R2A-H4.

In one embodiment, the anti-DEP1 antibody or antigen-binding fragment thereof of the invention comprises a DEP1-binding domain comprising a combination of (i) a HCVR and (ii) a LCVR, combination being that of clone 5738-13-R2A-C1 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R2A-D3 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R4A-D11 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R3A-F5 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R4A-F11 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R2A-H3 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R2A-H4 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R4A-H9 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R4A-H11 as defined in Table 2.

In one embodiment, the anti-DPP4 antibody or antigen-binding fragment thereof of the invention comprises a DPP4-binding domain, as described hereinabove.

In one embodiment, the anti-DPP4 antibody or antigen-binding fragment thereof of the invention comprises a DPP4-binding domain comprising a combination of (i) at least one, preferably at least two, more preferably three HCVR's CDRs and (ii) at least one, preferably at least two, more preferably three LCVR's CDRs, said combination being as defined in Table 3.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being as defined in Table 3.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of any one of the following clones as defined in Table 3: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of any one of the following clones as defined in Table 3: 5826-8-R6A-E10, 5826-8-R5A-G8, 5826-8-R6A-H11, 5826-13-R3A-D5, 5826-13-R4A-H5, and 5826-13-R4A-H12.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-A10 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-B1 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-B3 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-D5 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-D6 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-E2 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-E6 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-E9 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-F10 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-G11 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-G12 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H1 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H2 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H3 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H4 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H5 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H6 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H9 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H10 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H11 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H12 as defined in Table 3.

In one embodiment, the anti-DPP4 antibody or antigen-binding fragment thereof of the invention comprises a DPP4-binding domain comprising a combination of (i) a HCVR and (ii) a LCVR, said combination being as defined in Table 4.

In one embodiment, the anti-DPP4 antibody or antigen-binding fragment thereof of the invention comprises a DPP4-binding domain comprising a combination of (i) a HCVR and (ii) a LCVR, combination being that of any one of the following clones as defined in Table 4: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the anti-DPP4 antibody or antigen-binding fragment thereof of the invention comprises a DPP4-binding domain comprising a combination of (i) a HCVR and (ii) a LCVR, combination being that of any one of the following clones as defined in Table 4: 5826-8-R6A-E10, 5826-8-R5A-G8, 5826-8-R6A-H11, 5826-13-R3A-D5, 5826-13-R4A-H5, and 5826-13-R4A-H12.

In one embodiment, the anti-DPP4 antibody or antigen-binding fragment thereof of the invention comprises a DPP4-binding domain comprising a combination of (i) a HCVR and (ii) a LCVR, combination being that of any one of the following clones as defined in Table 4: 5826-13-R3A-D5, 5826-13-R4A-H5, and 5826-13-R4A-H12.

In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-A10 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-B1 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-B3 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-D5 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-D6 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-E2 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-E6 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-E9 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-F10 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-G11 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-G12 as defined in Table 4. 5826-13-R4A-H1 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H2 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H3 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H4 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H5 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H6 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H9 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H10 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H11 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H12 as defined in Table 4.

In one embodiment, the isolated antibody or antigen-binding fragment thereof of the invention is a molecule selected from the group comprising or consisting of a whole antibody, a single-chain variable fragment (scFv), a dimeric single-chain variable fragment (di-scFv, such as a tandem scFv or a diabody), a trimeric single-chain variable fragment (tri-scFv, such as a triabody), a tetrameric single-chain variable fragment (tetra-scFv, such as a tetrabody), a Fv, a Fab, a Fab', a Fab'-SH, a F(ab')$_2$, a Fabc, and a Fd.

In one embodiment, the isolated antibody or antigen-binding fragment thereof of the invention is a mimetic selected from the group comprising or consisting of an affibody, an alphabody, an armadillo repeat protein based scaffold, a knottin, a kunitz domain peptide, an affilin, an affitin, an adnectin, an atrimer, an evasin, a DARPin, an anticalin, an avimer, a fynomer, a versabody or a duocalin.

Antigen-binding fragment of antibodies comprising specific antigen-binding domains may be generated by known methods. Methods for producing such antigen-binding fragments of antibodies are known in the art, for example as described in Lo (Ed.), 2004. *Antibody Engineering: Methods and Protocols* (1$^{st}$ ed., Vol. 248). Totowa, N.J.: Humana Press; and McCafferty, Hoogenboom & Chiswell (Eds.), 1996. *Antibody Engineering: a Practical Approach* (1$^{st}$ ed., Vol. 169). Oxford: IRL Press at Oxford University Press. For example, F(ab')$_2$ fragments can be produced by pepsin digestion of the whole antibody molecule, and Fab fragments can be generated by reducing the disulfide bridges of the F(ab')$_2$ fragments. Alternatively, Fab expression libraries may be constructed to allow rapid and easy identification of monoclonal Fab fragments with the desired specificity, as described for example in Huse et al., 1989. *Science*. 246 (4935):1275-81.

Antibodies may be generated using known methods. For the production of antibodies, various hosts including goats, rabbits, rats, mice, humans, and others, may be immunized by injection with an appropriate antigen. Depending on the host species, various adjuvants may be used to increase an immunological response. Such adjuvants include Freund's adjuvant, mineral gels such as aluminium hydroxide, and surface-active substances such as lysolecithin, pluronic polyols, polyanions, peptides, oil emulsions, keyhole limpet hemocyanin, and dinitrophenol. Adjuvants are commercially available.

In one embodiment, the isolated antibody or antigen-binding fragment thereof of the invention is polyclonal. In another embodiment, the isolated antibody or antigen-binding fragment thereof of the invention is monoclonal.

Methods of producing polyclonal and monoclonal antibodies as well as fragments thereof are well known in the art (see, for example, Harlow and Lane, Antibodies: A Laboratory Manual, Cold Spring Harbor Laboratory, New York, 1988).

In one embodiment, the isolated antibody or antigen-binding fragment thereof of the invention is a purified antibody or a purified antigen-binding fragment thereof.

In one embodiment, the isolated antibody or antigen-binding fragment thereof of the invention is purified to:
(1) greater than 80%, 85%, 90%, 91%, 92%, 93%, 94%, 95% or more by weight of antibody or antigen-binding fragment thereof, as may be determined, e.g., by the Lowry method; and most preferably more than 96%, 97%, 98% or 99% by weight of antibody or antigen-binding fragment thereof;
(2) a degree sufficient to obtain at least 15 amino acid residues of the N-terminal, or of an internal, amino acid sequence, e.g., by use of a spinning cup sequenator; and/or
(3) homogeneity as shown, e.g., by SDS-PAGE under reducing or non-reducing conditions and using, e.g., Coomassie blue staining or more preferably silver staining.

In one embodiment, the isolated antibody or antigen-binding fragment thereof of the invention has an isotype selected from the group comprising or consisting of IgG (including IgG1, IgG2, IgG3 and IgG4), IgM, IgA (including IgA1 and IgA2), IgD and IgE. The immunoglobulin subclasses or "isotypes" (e.g., IgA1, etc.).

The constant region of an antibody is important in the ability of an antibody to fix complement and mediate cell-dependent cytotoxicity and phagocytosis. Thus, as discussed herein, the isotype of an antibody may be selected on the basis of whether it is desirable for the antibody to mediate cytotoxicity/phagocytosis. Determination or selection of the isotype of an antibody may be by known methods in the an.

In one embodiment, the isolated antibody or antigen-binding fragment thereof of the invention is a murine, a chimeric or a humanized antibody or antigen-binding fragment thereof.

In one embodiment, the isolated antibody or antigen-binding fragment thereof of the invention is a murine antibody or antigen-binding fragment thereof.

A "murine antibody or antigen-binding fragment thereof" refers to those antibodies or antigen-binding fragments thereof in which the variable region (including the CDRs and FRs) and the constant region are derived from a mouse.

In one embodiment, the isolated antibody or antigen-binding fragment thereof of the invention is a chimeric antibody or antigen-binding fragment thereof.

A "chimeric antibody or antigen-binding fragment thereof" broadly refers to an antibody or antigen-binding fragment thereof comprising a first amino acid sequence linked to a second amino acid sequence with which it is not naturally linked in nature. The amino acid sequences may normally exist in separate proteins that are brought together in the fusion protein or they may normally exist in the same protein but are placed in a new arrangement in the fusion protein. A chimeric protein may be created, for example, by chemical synthesis, or by creating and translating a polynucleotide in which the peptide regions are encoded in the desired relationship. The term "chimeric antibody or antigen-binding fragment thereof" encompasses herein antibodies and antigen-binding fragments thereof in which:
(a) the constant region (Fc), or a portion thereof, is altered, replaced or exchanged so that the variable region is linked to a constant region of a different or altered class, effector function and/or species, or an entirely different molecule which confers new properties to the chimeric antibody, e.g., an enzyme, toxin, hormone, growth factor, drug, etc.; or
(b) the variable region (Fv), or a portion thereof, is altered, replaced or exchanged with a variable region, or portion thereof, having a different or altered antigen specificity; or with corresponding sequences from another species or from another antibody class or subclass.

Method to produce chimeric antibodies are well known in the art. For example, chimeric antibodies may be produced as described in Morrison et al., 1984, *Proc Natl Acd Sci USA*. 81(21):6851-5; Neuberger et al., 1984. *Nature*. 312 (5995):604-608; and Takeda et al., 1985. *Nature*. 314(6010): 452-454.

In one embodiment, the isolated antibody or antigen-binding fragment thereof of the invention is a humanized antibody or antigen-binding fragment thereof.

A "humanized antibody or antigen-binding fragment thereof" refers to a chimeric antibody or antigen-binding fragment thereof which contains only minimal sequence derived from a non-human immunoglobulin. It includes antibodies made by a non-human cell having variable and constant regions which have been altered to more closely resemble antibodies that would be made by a human cell, e.g., by altering the non-human antibody amino acid sequence to incorporate amino acids found in human germline immunoglobulin sequences. Humanized antibodies or antigen-binding fragment thereof of the invention may include amino acid residues not encoded by human germline immunoglobulin sequences (e.g., mutations introduced by random or site-specific mutagenesis in vitro or by somatic mutation in vivo), for example in the CDRs. The term "humanized antibody or antigen-binding fragment thereof" also includes antibodies and antigen-binding fragment thereof in which CDR sequences derived from the germline of another mammalian species, such as a mouse, have been grafted onto human framework sequences. In other words, the term "humanized antibody or antigen-binding fragment thereof" refers to an antibody or antigen-binding fragment thereof in which the CDRs of a recipient human antibody are replaced by CDRs from a donor non-human antibody. Humanized antibodies or antigen-binding fragments thereof may also comprise residues of donor origin in the framework sequences. The humanized antibody or antigen-binding fragment thereof can also comprise at least a portion of a human immunoglobulin constant region. Humanized antibodies and or antigen-binding fragments thereof may also comprise residues which are found neither in the recipient antibody nor in the imported CDR or framework sequences. Humanization can be performed using methods known in the art (e.g., Jones et al., 1986. *Nature*. 321(6069):522-5; Riechmann et al., 1988. *Nature*. 332(6162):323-7; Verhoeyen et al., 1988. *Science*. 239(4847):1534-6; Presta, 1992. *Curr Opin Biotechnol*. 3(4):394-8; U.S. Pat. No. 4,816,567), including techniques such as "superhumanizing" antibodies (e.g., Tan et al., 2002. *J Immunol*. 169(2):1119-25) and "resurfacing" (e.g., Staelens et al., 2006. *Mol Immunol*. 43(8): 1243-57; Roguska et al., 1994. *Proc Natl Acad Sci USA*. 91(3):969-73). A "humanized antibody or antigen-binding fragment thereof" retains a similar antigenic specificity as the original antibody. However, using certain methods of humanization, the affinity and/or specificity of binding of the antibody may be increased.

Methods for humanizing the isolated antibody or antigen-binding fragment thereof of the invention are well-known in the art. The choice of human variable domains, both light and heavy, to be used in making the humanized antibody or antigen-binding fragment thereof is very important to reduce antigenicity. According to the so-called "best-fit" method, the sequence of the variable domain of an isolated antibody or antigen-binding fragment thereof of the invention is screened against the entire library of known human variable-domain sequences. The human sequence that is closest to the mouse sequence is then accepted as the human framework (FR) for the humanized antibody (Sims et al., 1993. *J Immunol.* 151(4):2296-308; Chothia & Lesk, 1987. *J Mol Biol.* 196(4):901-17).

Another method for humanizing the isolated antibody or antigen-binding fragment thereof of the invention uses a particular framework from the consensus sequence of all human antibodies of a particular subgroup of light or heavy chains. The same framework can be used for several different humanized antibodies (Carter et al., 1992. *Proc Natl Acad Sci USA.* 89(10):4285-9; Presta et al., 1993. *J Immunol.* 151(5):2623-32). It is further important that antibodies be humanized with retention of high affinity for DEP1 or DPP4 and other favorable biological properties. To achieve this goal, according to a preferred method, humanized antibodies and antigen-binding fragments thereof are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its epitope. In this way, CDR residues can be selected and combined from the consensus and import sequences so that the desired antibody characteristic, such as an increased affinity for DEP1 or DPP4, is achieved. In general, the CDR residues are directly and most substantially involved in influencing antigen binding.

Another method for humanizing the isolated antibody or antigen-binding fragment thereof of the invention is to use a transgenic or transchromosomic animal carrying parts of the human immune system for immunization. As a host, these animals have had their immunoglobulin genes replaced by functional human immunoglobulin genes. Thus, antibodies produced by these animals or in hybridomas made from the B cells of these animals are already humanized. Examples of such transgenic or transchromosomic animal include, without limitation:

the XenoMouse (Abgenix, Fremont, Calif.), described in U.S. Pat. Nos. 5,939,598, 6,075,181, 6,114,598, 6,150,584 and 6,162,963;

the HuMAb Mouse® (Medarex, Inc.), described in Lonberg et al., 1994. *Nature.* 368(6474):856-859; Lonberg & Huszar, 1995. *Int Rev Immunol.* 13(1):65-93; Harding & Lonberg, 1995. *Ann N Y Acad Sci.* 764:536-46; Taylor et al., 1992. *Nucleic Acids Res.* 20(23):6287-95; Chen et al., 1993. *Int Immunol.* 5(6):647-56; Tuaillon et al., 1993. *Proc Natl Acad Sci USA.* 90(8):3720-4; Choi et al., 1993. *Nat Genet.* 4(2):117-23; Chen et al., 1993. *EMBO J.* 12(3): 821-30; Tuaillon et al., 1994. *J Immunol.* 152(6):2912-20; Taylor et al., 1994. *Int Immunol.* 6(4):579-91; Fishwild et al., 1996. *Nat Biotechnol.* 14(7):845-51;

the KM Mouse®, described in Patent application WO2002043478;

the TC mice, described in Tomizuka et al., 2000. *Proc Natl Acad Sci USA.* 97(2):722-7; and the OmniRat™ (OMT, Inc.), described in Patent application WO2008151081; Geurts et al., 2009. *Science.* 325(5939):433; Menoret et al., 2010. *Eur J Immunol.* 40(10):2932-41.

Humanized antibodies and antigen-binding fragments thereof may also be produced according to various other techniques, such as by using, for immunization, other transgenic animals that have been engineered to express a human antibody repertoire (Jakobovitz et al., 1993. *Nature.* 362 (6417):255-8), or by selection of antibody repertoires using phage display methods. Such techniques are known to the skilled person and can be implemented starting from monoclonal antibodies or antigen-binding fragments thereof as disclosed in the present application.

Whether chimeric or humanized, the isolated antibody or antigen-binding fragment thereof of the invention may comprise a constant region (Fc) of human origin.

In one embodiment, especially when the isolated antibody or antigen-binding fragment thereof of the invention is intended for human therapeutic uses, it is typical for the entire constant region (Fc), or at least a part thereof, to have a fully or substantially human amino acid sequence. Therefore, one or more of, or any combination of, the $C_H1$ domain, hinge region, $C_H2$ domain, $C_H3$ domain and $C_L$ domain and $C_H4$ domain (when present) may be fully or substantially human with respect to its amino acid sequence. Advantageously, the $C_H1$ domain, hinge region, $C_H2$ domain, $C_H3$ domain and $C_L$ domain and $C_H4$ domain (when present) may all have a fully or substantially human amino acid sequence.

The term "substantially human", in the context of the constant region (Fc) of a chimeric or humanized antibody or antigen-binding fragment thereof, refers to an amino acid sequence identity of at least 70%, preferably at least 75%, 80%, 85%, 90%, 95%, 96%, 97%, 98%, 99% or more with a human constant region (Fc).

The term "human amino acid sequence", in this context, refers to an amino acid sequence which is encoded by a human immunoglobulin gene, which includes germline, rearranged and somatically mutated genes. The present invention also contemplates proteins comprising constant domains of "human" sequence which have been altered, by one or more amino acid additions, deletions or substitutions with respect to the human sequence, excepting those embodiments where the presence of a "fully human hinge region" is expressly required.

The presence of a "fully human hinge region" in the isolated antibody or antigen-binding fragment thereof of the invention may be beneficial both to minimize immunogenicity and to optimize stability of the antibody. It is considered that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g., by addition or deletion of N- or O-linked glycosylation sites). Depending on the intended use of the antibody or antigen-binding fragment thereof, it may be desirable to modify the isolated antibody or antigen-binding fragment thereof of the invention with respect to its binding properties to Fc receptors, for example to modulate effector function. For example, cysteine residue(s) may be introduced in the Fc region, thereby allowing interchain disulfide bond formation in this region. The homodimeric antibody thus generated may have improved effector function (Caron et al., 1992. *J Exp Med.* 176(4):1191-5; Shopes, 1992. *J Immunol.* 148(9): 2918-22).

In one embodiment, the isolated antibody or antigen-binding fragment thereof of the invention may be a bispecific antibody (BsAb) with antigen binding to at least two senescent cell-associated antigens. In one embodiment, the isolated antibody or antigen-binding fragment thereof of the invention may be a bispecific antibody (BsAb) which binds to both DEP1 and DPP4.

In one embodiment, the isolated antibody or antigen-binding fragment thereof of the invention may be a bispecific antibody (BsAb) with antigen binding to at one senescent cell-associated antigen and one non-senescent cell-associated antigen. In one embodiment, the isolated antibody or antigen-binding fragment thereof of the invention may be a bispecific antibody (BsAb) which binds to either of DEP1 or DPP4 on the one hand, and to one non-senescent cell-associated antigen on the other hand.

In one embodiment, the non-senescent cell-associated antigen is a T cell receptor or part thereof, such as, e.g., any one of the CD3δ, CD3γ, CD3ε or CD3ζ subunit.

Examples of bispecific antibodies (BsAb) include, but are not limited to, quadromas, knobs-in-holes, CrossMab Fab, CrossMab VH-VL, CrossMab $C_H1$-CL, TriMab, one-arm single-chain Fab-immunoglobulin gamma (OAscFab-IgG), disulfide stabilized Fv-IgG (dsFv-IgG), DuetMab, controlled Fab-arm exchanged-IgG1 (cFAE-IgG1), charged pair scFv-Fc, strand-exchange engineered domain body (SEED-body), two-arm leucine zipper heterodimeric monoclonal antibodies (two-arm LUZ-Y), kappa lambda body (κλ-body), bi-specific T cell engagers (BiTEs), diabodies, .tandab, dual-affinity retargeting molecules (DARTs), bispecific killer cell engagers (BiKEs), trispecific killer cell engagers (TriKEs), monomeric Fc-VH (mFc-VH) and Fc antigen binding (Fcab), all reviewed and described in Liu et al., 2017 (*Front Immunol.* 8:38).

Methods for producing bispecific antibodies (BsAb) are well known in the art.

In one embodiment, the isolated antibody or antigen-binding fragment thereof of the invention is a recombinant isolated antibody or antigen-binding fragment thereof.

Thus accordingly, the isolated antibody or antigen-binding fragment thereof of the invention may be produced recombinantly by methods known in the art, such as, e.g., by expression in *Escherichia coli* expression systems (see, e.g., U.S. Pat. No. 4,816,567). Antigen binding fragment may also be produced by phage display technologies, which are known in the art.

It will also be appreciated that the isolated antibody or antigen-binding fragment thereof of the invention can be modified using methods well known in the art, e.g., to improve the properties of the isolated antibody or antigen-binding fragment thereof. For example, to slow clearance in vivo and obtain a more desirable pharmacokinetic profile, the isolated antibody or antigen-binding fragment thereof may be modified with polyethylene glycol (PEG). Methods for coupling and site-specifically conjugating PEG to an antibody or antigen-binding fragment thereof are described in, e.g., Leong et al., 2001. *Cytokine.* 16(3):106-19; Delgado et al., 1996. *Br J Cancer.* 73(2):175-82. Another non-limiting example of modification consist in the modification of the human Fc region of the antibody in order to enhance their affinity for an Fcγ receptor. Methods of enhancing Fc receptor binding include Fc amino acid modification and modification of Fc carbohydrate structures. For immunoglobulins, it has been demonstrated that the attachment of an N-linked oligosaccharide to Asn-297 of the $C_H2$ domain is critical for ADCC activity. Removal of the N-linked oligosaccharide through mutation of the N-linked consensus site or by enzymatic means results in little or no ADCC activity. Removal of the core α-1,6-fucose moiety from IgG1 Fc oligosaccharides has been demonstrated to improve FcγRIII binding and ADCC activity (see, e.g., Carter, 2001. *Nat Rev Cancer.* 1(2):118-29; Kanda et al., 2007. *Glycobiology.* 17(1):104-18; Shields et al., 2002. *J Biol Chem.* 277(30): 26733-40; Shinkawa et al., 2003. *J Biol Chem.* 278(5):3466-73; Niwa et al., 2004. *Cancer Res.* 64(6):2127-33). The level of another glycoform, bisected N-linked carbohydrate, has also been suggested to increase ADCC (see, e.g., Umaña et al., 1999. *Nat Biotechnol.* 17(2): 176-80; Hodoniczky et al., 2005. *Biotechnol Prog.* 21(6): 1644-52).

A variety of Fc sequence variants with optimized binding affinity for FcγRs and/or enhanced ADCC have been described and are known in the art.

In one embodiment, the isolated antibody or antigen-binding fragment thereof of the invention targets, blocks, depletes and/or kills senescent cells to which it is bound.

In one embodiment, the isolated antibody or antigen-binding fragment thereof of the invention targets, blocks, depletes and/or kills senescent cells expressing at least one senescent cell-associated antigen, as defined hereinabove.

In one embodiment, the isolated antibody or antigen-binding fragment thereof of the invention may comprise human HCCRs (heavy chain constant regions) and allows to target, block, deplete and/or kill DEP1-expressing cells to which it is bound.

In one embodiment, the isolated antibody or antigen-binding fragment thereof of the invention may comprise human HCCRs (heavy chain constant regions) and allow to target, block, deplete and/or kill DPP4-expressing cells to which it is bound.

In one embodiment where the isolated antibody or antigen-binding fragment thereof is a bispecific antibody as described above, said bispecific antibody may comprise human HCCRs (heavy chain constant regions) and allow to target, block, and/or deplete DEP1- and/or DPP4-expressing cells to which it is bound.

In one embodiment, the isolated antibody or antigen-binding fragment thereof of the invention depletes and/or kills DEP1-expressing cells to which it is bound.

In one embodiment, the isolated antibody or antigen-binding fragment thereof of the invention depletes and/or kills DPP4-expressing cells to which it is bound.

In one embodiment where the isolated antibody or antigen-binding fragment thereof is a bispecific antibody as described above, said bispecific antibody depletes and/or kills DEP1- and/or DPP4-expressing cells to which it is bound.

By "deplete" or "depleting", it is referred to the killing, elimination, lysis, or induction of such killing, elimination or lysis, so as to negatively affect the number of cells to which the isolated antibody or antigen-binding fragment thereof is bound (such as, e.g., DEP1- and/or DPP4-expressing cells) present in a sample or in a subject. In one embodiment, such depletion occurs via ADCC. In one embodiment, such depletion occurs via ADCP. In one embodiment, such depletion occurs via CDC.

Thus, in one embodiment, the isolated antibody or antigen-binding fragment thereof of the invention leads, directly or indirectly, to the depletion of senescent cells, in particular of DEP1- and/or DPP4-expressing cells.

In one embodiment, the isolated antibody or antigen-binding fragment thereof of the invention leads, directly or indirectly, to the depletion of 10%, 20%, 30%, 40%, 50%, 60%, 70%, 80%, 90% or more of senescent cells, in particular of DEP1- and/or DPP4-expressing cells.

In one embodiment, the isolated antibody or antigen-binding fragment thereof of the invention leads, directly or indirectly, to a decrease by 10%, 20%, 30%, 40%, 50%, 60%, 70%, 80%, 90% or more elimination of the number of senescent cells, in particular of DEP1- and/or DPP4-expressing cells.

In one embodiment, the isolated antibody or antigen-binding fragment thereof of the invention induces any one or several, such as two or three, of:
- antibody dependent cellular cytotoxicity (ADCC);
- antibody-dependent cell-mediated phagocytosis (ADCP);
- complement-dependent cytotoxicity (CDC).

In one embodiment, the isolated antibody or antigen-binding fragment thereof of the invention is from the IgG1 subclass and has any one or several, such as two or three, of:
- antibody dependent cellular cytotoxicity (ADCC);
- antibody-dependent cell-mediated phagocytosis (ADCP);
- complement-dependent cytotoxicity (CDC).

In one embodiment, the isolated antibody or antigen-binding fragment thereof of the invention is linked/fused/conjugated to a payload, e.g., a therapeutic moiety. Such conjugates are referred to herein as an "antibody drug conjugates" or "ADCs".

In one embodiment, the payload is selected from chemotherapeutic agents, targeted therapy agents, cytotoxic agents, antibiotics, antivirals, cell cycle-synchronizing agents, ligands for cellular receptor(s), immunomodulatory agents, pro-apoptotic agents, anti-angiogenic agents, cytokines, growth factors, hormones, coding or non-coding oligonucleotides, photodetectable labels, contrast agents, radiolabels, and the like.

Another object of the present invention is a nucleic acid encoding the antigen-binding domain, the antibody or the antigen-binding fragment thereof of the invention.

Another object of the present invention is a vector comprising the nucleic acid encoding the antigen-binding domain, the antibody or the antigen-binding fragment thereof of the invention.

In one embodiment, the vector is an expression vector and further comprises regulatory elements allowing for expression of the antigen-binding domain, the antibody or the antigen-binding fragment thereof, in a cell.

In one embodiment, the expression vector may be monocistronic. By "monocistronic", it is meant that a single nucleic acid encoding a single protein is expressed in a single expression vector.

In one embodiment, the expression vector comprises a sequence encoding the HCVR of the antigen-binding domain, the antibody or the antigen-binding fragment thereof of the invention, preferably operably linked to regulatory elements.

In one embodiment, the expression vector comprises a sequence encoding the HCVR of the DEP1-binding domain, the anti-DEP1 antibody or the antigen-binding fragment thereof of the invention, preferably operably linked to regulatory elements.

In one embodiment, the expression vector comprises a sequence encoding the HCVR of the DEP1-binding domain, the anti-DEP1 antibody or the antigen-binding fragment of the invention, preferably operably linked to regulatory elements, said sequence being selected from the group comprising or consisting of SEQ ID NOs: 55 to 74.

In one embodiment, the expression vector comprises a sequence encoding the HCVR of the DPP4-binding domain, the anti-DPP4 antibody or the antigen-binding fragment of the invention, preferably operably linked to regulatory elements.

In one embodiment, the expression vector comprises a sequence encoding the HCVR of the DPP4-binding domain, the anti-DPP4 antibody or the antigen-binding fragment of the invention, preferably operably linked to regulatory elements, said sequence being selected from the group comprising or consisting of SEQ ID NOs: 174 to 201.

In one embodiment, the expression vector comprises a sequence encoding the LCVR of the antigen-binding domain, the antibody or the antigen-binding fragment thereof of the invention, preferably operably linked to regulatory elements.

In one embodiment, the expression vector comprises a sequence encoding the LCVR of the DEP1-binding domain, the anti-DEP1 antibody or the antigen-binding fragment of the invention, preferably operably linked to regulatory elements.

In one embodiment, the expression vector comprises a sequence encoding the LCVR of the DEP1-binding domain, the anti-DEP1 antibody or the antigen-binding fragment of the invention, preferably operably linked to regulatory elements, said sequence being selected from the group comprising or consisting of SEQ ID NOs: 75 to 94.

In one embodiment, the expression vector comprises a sequence encoding the LCVR of the DPP4-binding domain, the anti-DPP4 antibody or the antigen-binding fragment of the invention, preferably operably linked to regulatory elements.

In one embodiment, the expression vector comprises a sequence encoding the LCVR of the DPP4-binding domain, the anti-DPP4 antibody or the antigen-binding fragment of the invention, preferably operably linked to regulatory elements, said sequence being selected from the group comprising or consisting of SEQ ID NOs: 202 to 227.

In one embodiment, the expression vector may be polycistronic. By "polycistronic", it is meant that at least two or more nucleic acids, each encoding a single protein, are expressed in a single expression vector.

In one embodiment, the expression vector comprises:
- a sequence encoding the HCVR of the antigen-binding domain, the antibody or the antigen-binding fragment thereof of the invention, preferably operably linked to regulatory elements, and
- a sequence encoding the LCVR of the antigen-binding domain, the antibody or the antigen-binding fragment thereof of the invention, preferably operably linked to regulatory elements.

In one embodiment, the expression vector comprises:
- a sequence encoding the HCVR of the DEP1-binding domain, the anti-DEP1 antibody or the antigen-binding fragment of the invention, preferably operably linked to regulatory elements, and
- a sequence encoding the LCVR of the DEP1-binding domain, the anti-DEP1 antibody or the antigen-binding fragment of the invention, preferably operably linked to regulatory elements.

In one embodiment, the expression vector comprises:
- a sequence encoding the HCVR of the DEP1-binding domain, the anti-DEP1 antibody or the antigen-binding fragment of the invention, preferably operably linked to regulatory elements, said sequence being selected from the group comprising or consisting of SEQ ID NOs: 55 to 74, and a sequence encoding the LCVR of the DEP1-binding domain, the anti-DEP1 antibody or the antigen-binding fragment of the invention, preferably operably linked to regulatory elements, said sequence being selected from the group comprising or consisting of SEQ ID NOs: 75 to 94.

In one embodiment, the expression vector comprises:

a sequence encoding the HCVR of the DEP1-binding domain, the anti-DEP1 antibody or the antigen-binding fragment of the invention, preferably operably linked to regulatory elements, and a sequence encoding the LCVR of the DEP1-binding domain, the anti-DEP1 antibody or the antigen-binding fragment of the invention, preferably operably linked to regulatory elements, wherein said sequence encoding the HCVR and said sequence encoding the LCVR are selected from the group comprising or consisting of the combinations of HCVR and LCVR as defined in Table 2.

In one embodiment, the expression vector comprises:

a sequence encoding the HCVR of the DPP4-binding domain, the anti-DPP4 antibody or the antigen-binding fragment of the invention, preferably operably linked to regulatory elements, and a sequence encoding the LCVR of the DPP4-binding domain, the anti-DPP4 antibody or the antigen-binding fragment of the invention, preferably operably linked to regulatory elements.

In one embodiment, the expression vector comprises:

a sequence encoding the HCVR of the DPP4-binding domain, the anti-DPP4 antibody or the antigen-binding fragment of the invention, preferably operably linked to regulatory elements, said sequence being selected from the group comprising or consisting of SEQ ID NOs: 174 to 201, and a sequence encoding the LCVR of the DPP4-binding domain, the anti-DPP4 antibody or the antigen-binding fragment of the invention, preferably operably linked to regulatory elements, said sequence being selected from the group comprising or consisting of SEQ ID NOs: 202 to 227.

In one embodiment, the expression vector comprises:

a sequence encoding the HCVR of the DPP4-binding domain, the anti-DPP4 antibody or the antigen-binding fragment of the invention, preferably operably linked to regulatory elements, and a sequence encoding the LCVR of the DPP4-binding domain, the anti-DPP4 antibody or the antigen-binding fragment of the invention, preferably operably linked to regulatory elements, wherein said sequence encoding the HCVR and said sequence encoding the LCVR are selected from the group comprising or consisting of the combinations of HCVR and LCVR as defined in Table 4.

Another object of the invention is a method of producing and purifying the isolated antibody or antigen-binding fragment thereof of the invention.

In one embodiment, the method comprises:

culturing host cells comprising the nucleic acid or expression vector of the present invention, under conditions suitable for expression of the antibody or antigen-binding fragment thereof, and recovering the expressed antibody or antigen-binding fragment thereof.

This recombinant process can be used for large scale production of antibodies or antigen-binding fragments thereof, including monoclonal antibodies intended for in vitro, ex vivo and/or in vivo therapeutic and/or diagnostic uses.

The nucleic acid or expression vector encoding the antibody or antigen-binding fragment, as described herein, may be propagated and expressed according to any of a variety of routinely practiced procedures for nucleic acid excision, ligation, transformation, and transfection. In certain embodiments, expression of the antibody or antigen-binding fragment thereof may be carried out in a prokaryotic host cell (i.e., the host cell comprising the nucleic acid or expression vector of the present invention is a prokaryotic host cell), such as *Escherichia coli* (see, e.g., Plückthun et al., 1989. *Methods Enzymol.* 178:497-515). In certain other embodiments, the antibody or antigen-binding fragment thereof may be expressed in a eukaryotic host cell (i.e., the host cell comprising the nucleic acid or expression vector of the present invention is an eukaryotic host cell), including animal cells (such as mammalian cells), yeast (e.g., *Saccharomyces cerevisiae, Schizosaccharomyces pombe*, or *Pichia pastoris*); and plant cells. Examples of suitable animal cells include, but are not limited to, myeloma, HEK293, COS, or CHO cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the cellular polypeptide may be inserted. The regulatory elements will vary as appropriate for the particular host.

All these processes are well known in the art (Subramanian (Ed.), 2004. *Antibodies* (1st ed., Vol. 1: Production and Purification). New York, N.Y.: Springer US).

In an embodiment, the expressed antibody or antigen-binding fragment thereof is further purified.

Methods to purify the antibody or antigen-binding fragment thereof of the invention are well known in the art (Subramanian (Ed.), 2004. *Antibodies* (1st ed., Vol. 1: Production and Purification). New York, N.Y.: Springer US), and include, without limitation, chromatography, preferably by affinity chromatography, more preferably by affinity chromatography on protein L agarose.

Another object of the present invention is a chimeric antigen receptor (CAR) comprising:

(i) at least one extracellular binding domain, comprising or consisting of at least one antigen-binding domain directed to a senescent cell-associated antigen, (ii) an extracellular spacer domain, (iii) a transmembrane domain, (iv) optionally, at least one costimulatory domain, and (v) at least one intracellular signaling domain.

In one embodiment, the CAR of the invention comprises at least one extracellular binding domain (also called ectodomain), wherein said at least one extracellular binding domain recognizes and is capable of binding to a senescent cell-associated antigen, as defined hereinabove. In one embodiment, the extracellular binding domain comprises or consists of an antigen-binding domain directed to a senescent cell-associated antigen, which recognizes and is capable of binding to a senescent cell-associated antigen, as defined hereinabove.

In one embodiment, the senescent cell-associated antigen is selected from the group comprising or consisting of DEP1 and DPP4. Hence, in one embodiment, the at least one extracellular binding domain of the CAR of the invention recognizes and is capable of binding to DEP1 and/or DPP4. In one embodiment, the extracellular binding domain comprises or consists of an antigen-binding domain directed to DEP1 and/or DPP4, which recognizes and is capable of binding to DEP1 and/or DPP4, as defined hereinabove.

In one embodiment, the at least one extracellular binding domain in the CAR of the invention recognizes and is capable of binding to DEP1, such as, e.g., human DEP1, or orthologs thereof, including murine and rat DEP1. In one embodiment, the at least one extracellular binding domain in the CAR of the invention recognizes and is capable of binding to human DEP1 (hDEP1) with SEQ ID NO: 1. In one embodiment, the at least one extracellular binding domain in the CAR of the invention recognizes and is capable of binding to the extracellular domain of human DEP1 (hDEP1) comprising or consisting of amino acid residues 36-975 of SEQ ID NO: 1. In one embodiment, the extracellular binding domain comprises or consists of a DEP1-binding domain, as defined hereinabove. Hence, the CAR of the invention is an "anti-DEP1 chimeric antigen receptor (CAR)".

In one embodiment, the at least one extracellular binding domain in the CAR of the invention recognizes and is capable of binding to DPP4, such as, e.g., human DPP4 or orthologs thereof, including murine and rat DPP4. In one embodiment, the at least one extracellular binding domain in the CAR of the invention recognizes and is capable of binding to human DPP4 (hDPP4) with SEQ ID NO: 101. In one embodiment, the at least one extracellular binding domain in the CAR of the invention recognizes and is capable of binding to the extracellular domain of human DPP4 (hDPP4) comprising or consisting of amino acid residues 29-766 of SEQ ID NO: 101. In one embodiment, the extracellular binding domain comprises or consists of a DPP4-binding domain, as defined hereinabove. Hence, the CAR of the invention is an "anti-DDP4 chimeric antigen receptor (CAR)".

In one embodiment, the at least one extracellular binding domain in the CAR of the invention comprises an antigen-binding domain, as described hereinabove.

In one embodiment, the extracellular binding domain of the anti-DEP1 chimeric antigen receptor (CAR) of the invention comprises a DEP1-binding domain, as described hereinabove.

In one embodiment, the extracellular binding domain of the anti-DEP1 chimeric antigen receptor (CAR) of the invention comprises a DEP1-binding domain comprising a combination of (i) at least one, preferably at least two, more preferably three HCVR's CDRs and (ii) at least one, preferably at least two, more preferably three LCVR's CDRs, said combination being as defined in Table 1.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being as defined in Table 1.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of any one of the following clones as defined in Table 1: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of any one of the following clones as defined in Table 1: 5738-10-R3A-C6, 5738-10-R3A-D5, 5738-10-R4A-G12, 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of any one of the following clones as defined in Table 1: 5738-10-R4A-G12, 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of any one of the following clones as defined in Table 1: 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R2A-C1 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R2A-D3 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R4A-D11 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R3A-F5 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R4A-F11 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R2A-H3 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R2A-H4 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R4A-H9 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii)

three LCVR's CDRs, said combination being that of clone 5738-13-R4A-H11 as defined in Table 1.

In one embodiment, the extracellular binding domain of the anti-DEP1 chimeric antigen receptor (CAR) of the invention comprises a DEP1-binding domain comprising a combination of (i) a HCVR and (ii) a LCVR, said combination being as defined in Table 2.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of any one of the following clones as defined in Table 2: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of any one of the following clones as defined in Table 2: 5738-10-R3A-C6, 5738-10-R3A-D5, 5738-10-R4A-G12, 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of any one of the following clones as defined in Table 2: 5738-10-R4A-G12, 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of any one of the following clones as defined in Table 2: 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R2A-C1 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R2A-D3 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R4A-D11 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R3A-F5 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R4A-F11 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R2A-H3 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R2A-H4 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R4A-H9 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R4A-H11 as defined in Table 2.

In one embodiment, the extracellular binding domain of the anti-DPP4 chimeric antigen receptor (CAR) of the invention comprises a DPP4-binding domain, as described hereinabove.

In one embodiment, the extracellular binding domain of the anti-DPP4 chimeric antigen receptor (CAR) of the invention comprises a DPP4-binding domain comprising a combination of (i) at least one, preferably at least two, more preferably three HCVR's CDRs and (ii) at least one, preferably at least two, more preferably three LCVR's CDRs, said combination being as defined in Table 3.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being as defined in Table 3.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of any one of the following clones as defined in Table 3: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of any one of the following clones as defined in Table 3: 5826-8-R6A-E10, 5826-8-R5A-G8, 5826-8-R6A-H11, 5826-13-R3A-D5, 5826-13-R4A-H5, and 5826-13-R4A-H12.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-A10 as defined in Table 3. In one embodiment, the extracellular binding domain of the anti-DPP4 chimeric antigen receptor (CAR) of the invention comprises a DPP4- binding domain comprising a combination of (i) three HCVR's CDRs and (ii) three LCVR's CDRs, said combination being that of clone 5826-13-R3A-B1 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-B3 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-D5 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-D6 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-E2 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-E6 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-E9 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-F10 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-G11 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-G12 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H1 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H2 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H3 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H4 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H5 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H6 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H9 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H10 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H11 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H12 as defined in Table 3.

In one embodiment, the extracellular binding domain of the anti-DPP4 chimeric antigen receptor (CAR) of the invention comprises a DPP4-binding domain comprising a combination of (i) a HCVR and (ii) a LCVR, said combination being as defined in Table 4.

In one embodiment, the extracellular binding domain of the anti-DPP4 chimeric antigen receptor (CAR) of the invention comprises a DPP4-binding domain comprising a combination of (i) a HCVR and (ii) a LCVR, combination being that of any one of the following clones as defined in Table 4: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the extracellular binding domain of the anti-DPP4 chimeric antigen receptor (CAR) of the invention comprises a DPP4-binding domain comprising a combination of (i) a HCVR and (ii) a LCVR, combination being that of any one of the following clones as defined in Table 4: 5826-8-R6A-E10, 5826-8-R5A-G8, 5826-8-R6A-H11, 5826-13-R3A-D5, 5826-13-R4A-H5, and 5826-13-R4A-H12.

In one embodiment, the extracellular binding domain of the anti-DPP4 chimeric antigen receptor (CAR) of the invention comprises a DPP4-binding domain comprising a combination of (i) a HCVR and (ii) a LCVR, combination being that of any one of the following clones as defined in Table 4: 5826-13-R3A-D5, 5826-13-R4A-H5, and 5826-13-R4A-H12.

In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-A10 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-B1 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-B3 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-D5 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-D6 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-E2 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-E6 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-E9 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-F10 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-G11 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-G12 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H1 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H2 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H3 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H4 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H5 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H6 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H9 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H10 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H11 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H12 as defined in Table 4.

In one embodiment, the extracellular binding domain of the CAR of the invention comprises or consists a single chain variable region (scFv) or a Fab fragment, preferably a scFv, comprising an one antigen-binding domain as defined hereinabove.

In one embodiment, the CAR of the invention comprises more than one extracellular binding domain, such as 2 extracellular binding domains, 3 extracellular binding domains or more. Such CARs are called "tandem CARs" or "multispecific CARs", such as bispecific, trispecific, etc.

In this embodiment, the CAR of the invention is multispecific and comprises extracellular binding domains, wherein at least one of the extracellular binding domains recognizes and is capable of binding to a senescent cell-associated antigen.

In one embodiment, the CAR of the invention is multispecific and comprises extracellular binding domains, each of which recognizes and is capable of binding to a different senescent cell-associated antigen.

In one embodiment, the CAR of the invention is multispecific and comprises extracellular binding domains, wherein one extracellular binding domain recognizes and is capable of binding to either of DEP1 or DPP4, and at least one other extracellular binding domain recognizes and is capable of binding to another senescent cell-associated antigen.

In one embodiment, the CAR of the invention is multi-specific and comprises extracellular binding domains, wherein one extracellular binding domain recognizes and is capable of binding to DEP1, and at least one other extracellular binding domain recognizes and is capable of binding to DPP4.

In one embodiment, the CAR of the invention is bispecific and comprises two extracellular binding domains, wherein one extracellular binding domain recognizes and is capable of binding to DEP1, and the other extracellular binding domain recognizes and is capable of binding to DPP4.

In this embodiment,
a) one extracellular binding domain of the bispecific CAR of the invention comprises a DEP1-binding domain comprising a combination of (i) at least one, preferably at least two, more preferably three HCVR's CDRs and (ii) at least one, preferably at least two, more preferably three LCVR's CDRs, said combination being as defined in Table 1; and
b) one extracellular binding domain of the bispecific CAR of the invention comprises a DPP4-binding domain comprising a combination of (i) at least one, preferably at least two, more preferably three HCVR's CDRs and (ii) at least one, preferably at least two, more preferably three LCVR's CDRs, said combination being as defined in Table 3,
as described and defined hereinabove.

In this embodiment,
a) one extracellular binding domain of the bispecific CAR of the invention comprises a DEP1-binding domain comprising a combination of (i) three HCVR's CDRs and (ii) three LCVR's CDRs, said combination being as defined in Table 1; and
b) one extracellular binding domain of the bispecific CAR of the invention comprises a DPP4-binding domain comprising a combination of (i) three HCVR's CDRs and (ii) three LCVR's CDRs, said combination being as defined in Table 3,
as described and defined hereinabove.

In this embodiment,
a) one extracellular binding domain of the bispecific CAR of the invention comprises a DEP1-binding domain comprising a combination of (i) three HCVR's CDRs and (ii) three LCVR's CDRs, said combination being that of any one of the following clones as defined in Table 1: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11; and
b) one extracellular binding domain of the bispecific CAR of the invention comprises a DPP4-binding domain comprising a combination of (i) three HCVR's CDRs and (ii) three LCVR's CDRs, said combination being that of any one of the following clones as defined in Table 3: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12,
as described and defined hereinabove.

In this embodiment,
a) one extracellular binding domain of the bispecific CAR of the invention comprises a DEP1-binding domain comprising a combination of (i) three HCVR's CDRs and (ii) three LCVR's CDRs, said combination being that of any one of the following clones as defined in Table 1: 5738-10-R3A-C6, 5738-10-R3A-D5, 5738-10-R4A-G12, 5738-13-R4A-D11, and 5738-13-R2A-H4; and
b) one extracellular binding domain of the bispecific CAR of the invention comprises a DPP4-binding domain comprising a combination of (i) three HCVR's CDRs and (ii) three LCVR's CDRs, said combination being that of any one of the following clones as defined in Table 3: 5826-8-R6A-E10, 5826-8-R5A-G8, 5826-8-R6A-H11, 5826-13-R3A-D5, 5826-13-R4A-H5, and 5826-13-R4A-H12,
as described and defined hereinabove.

In this embodiment,
a) one extracellular binding domain of the bispecific CAR of the invention comprises a DEP1-binding domain comprising a combination of (i) three HCVR's CDRs and (ii) three LCVR's CDRs, said combination being that of any one of the following clones as defined in Table 1: 5738-10-R4A-G12, 5738-13-R4A-D11, and 5738-13-R2A-H4; and
b) one extracellular binding domain of the bispecific CAR of the invention comprises a DPP4-binding domain comprising a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12,
as described and defined hereinabove.

In this embodiment,
a) one extracellular binding domain of the bispecific CAR of the invention comprises a DEP1-binding domain comprising a combination of (i) three HCVR's CDRs and (ii) three LCVR's CDRs, said combination being that of any one of the following clones as defined in Table 1: 5738-13-R4A-D11, and 5738-13-R2A-H4; and
b) one extracellular binding domain of the bispecific CAR of the invention comprises a DPP4-binding domain comprising a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12,
as described and defined hereinabove.

In this embodiment,
a) one extracellular binding domain of the bispecific CAR of the invention comprises a DEP1-binding domain comprising a combination of (i) a HCVR and (ii) a LCVR, said combination being as defined in Table 2; and
b) one extracellular binding domain of the bispecific CAR of the invention comprises a DPP4-binding domain comprising a combination of (i) a HCVR and (ii) a LCVR, said combination being as defined in Table 4,
as described and defined hereinabove.

In this embodiment,
a) one extracellular binding domain of the bispecific CAR of the invention comprises a DEP1-binding domain comprising a combination of (i) a HCVR and (ii) a LCVR, combination being that of any one of the following clones as defined in Table 2: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11; and
b) one extracellular binding domain of the bispecific CAR of the invention comprises a DPP4-binding domain comprising a combination of (i) a HCVR and (ii) a LCVR, combination being that of any one of the following clones as defined in Table 4: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12, as described and defined hereinabove.

In this embodiment, a) one extracellular binding domain of the bispecific CAR of the invention comprises a DEP1-binding domain comprising a combination of (i) a HCVR and (ii) a LCVR, combination being that of any one of the following clones as defined in Table 2: 5738-10-R3A-C6, 5738-10-R3A-D5, 5738-10-R4A-G12, 5738-13-R4A-D11, and 5738-13-R2A-H4; and b) one extracellular binding domain of the bispecific CAR of the invention comprises a DPP4-binding domain comprising a combination of (i) a HCVR and (ii) a LCVR, combination being that of any one of the following clones as defined in Table 4: 5826-8-R6A-E10, 5826-8-R5A-G8, 5826-8-R6A-H11, 5826-13-R3A-D5, 5826-13-R4A-H5, and 5826-13-R4A-H12, as described and defined hereinabove.

In this embodiment, a) one extracellular binding domain of the bispecific CAR of the invention comprises a DEP1-binding domain comprising a combination of (i) a HCVR and (ii) a LCVR, combination being that of any one of the following clones as defined in Table 2: 5738-10-R4A-G12, 5738-13-R4A-D11, and 5738-13-R2A-H4; and b) one extracellular binding domain of the bispecific CAR of the invention comprises a DPP4-binding domain comprising a combination of (i) a HCVR and (ii) a LCVR, combination being that of any one of the following clones as defined in Table 4: 5826-13-R3A-D5, 5826-13-R4A-H5, and 5826-13-R4A-H12, as described and defined hereinabove.

In this embodiment, a) one extracellular binding domain of the bispecific CAR of the invention comprises a DEP1-binding domain comprising a combination of (i) a HCVR and (ii) a LCVR, combination being that of any one of the following clones as defined in Table 2: 5738-13-R4A-D11, and 5738-13-R2A-H4; and b) one extracellular binding domain of the bispecific CAR of the invention comprises a DPP4-binding domain comprising a combination of (i) a HCVR and (ii) a LCVR, combination being that of any one of the following clones as defined in Table 4: 5826-13-R3A-D5, 5826-13-R4A-H5, and 5826-13-R4A-H12, as described and defined hereinabove.

Additionally or alternatively, the CAR of the invention is multispecific and comprises extracellular binding domains, wherein at least two extracellular binding domains recognize and are capable of binding to the same senescent cell-associated antigen, but on different epitopes of said senescent cell-associated antigen.

Such multispecific CARs typically comprise:

(i) two of more extracellular binding domains, as defined hereinabove, (ii) one extracellular spacer domain, (iii) one transmembrane domain, (iv) optionally, at least one costimulatory domain, and (v) at least one intracellular signaling domain.

In a multispecific CAR, each extracellular binding domain comprises or consists of a single chain variable region (scFv) or a Fab fragment, preferably a scFv, comprising the antigen-binding domain as defined hereinabove.

In one embodiment, the extracellular binding domains in the multispecific CAR of the invention are linked or fused together through a flexible peptidic linker, enabling each extracellular binding domain to form the desired structure for antigen binding (Plückthun, 1994. "Antibodies from *Escherichia coli*". In Rosenberg & Moore (Eds.), *The pharmacology of monoclonal antibodies*. Handbook of Experimental Pharmacology, 113:269-315. Springer: Berlin, Heidelberg). Flexible peptidic linkers are generally composed of small, non-polar (e.g., glycine, Gly, G) or polar (e.g., serine, Ser, S; or threonine, Thr, T) amino acids, as suggested by Argos (1990. *J Mol Biol.* 211(4):943-958). The small size of these amino acids provides flexibility, and allows for mobility of the connecting functional domains, such as the extracellular binding domains. In one embodiment, the flexible peptidic linker may be a short oligo- or polypeptide, preferably having a length ranging from 2 to 30 amino acids. In one embodiment, the flexible peptidic linker comprises glycine-serine repeats. In one embodiment, the flexible peptidic linker comprises one, or several repeats of, such as 2, 3, 4, 5 or more repeats of, GS linker(s) (i.e., a sequence of one Gly and one Ser), G25 linker(s) (i.e., a sequence of two Gly and one Ser), $G_3S$ linker(s) (i.e., a sequence of three Gly and one Ser), $G_4S$ linker(s) (i.e., a sequence of four Gly and one Ser), or $G_5S$ linker(s) (i.e., a sequence of five Gly and one Ser).

In one embodiment, the CAR of the invention comprises an extracellular spacer domain (also called hinge domain).

In one embodiment, the at least one extracellular binding domain is connected to one transmembrane domain through one extracellular spacer domain.

The extracellular spacer domain typically facilitates proper protein folding, provides flexibility to the at least one extracellular binding domain and helps avoiding steric hindrance. It typically comprises a hydrophilic region linking the at least one extracellular binding domain and the transmembrane domain.

Extracellular spacer domains may include, but are not limited to, Fc fragments of antibodies or fragments or derivatives thereof, hinge regions of antibodies or fragments or derivatives thereof, $C_H2$ regions of antibodies, $C_H3$ regions antibodies, artificial spacer sequences or combinations thereof.

Examples of extracellular spacer domains include, but are not limited to, CD8α hinge; CD28 hinge; flexible peptidic linkers (such as, e.g., Gly3); or hinge region, $C_H1$, $C_H2$ and/or $C_H3$ domains of IgG's (such as human IgG4).

In one embodiment, the extracellular spacer domain is selected from the group comprising or consisting of (i) a hinge region, $C_H2$ domain and $C_H3$ domain of IgG4, (ii) a hinge region of IgG4, (iii) a hinge region and $C_H2$ domain of IgG4, (iv) a hinge region of CD8α, (v) a hinge region, $C_H2$ domain and $C_H3$ domain of IgG1, (vi) a hinge region of IgG1 (vii) a hinge region and $C_H2$ domain of IgG1, and (viii) a hinge region of CD28; and combinations thereof.

Additional extracellular spacer domains will be apparent to those skilled in the art and may be used in connection with alternate embodiments of the invention.

In one embodiment, the CAR of the invention comprises a transmembrane domain.

In one embodiment, the transmembrane domain comprises an amino acid sequence derived from the transmembrane domain of any protein which has such transmembrane domain, including any of the type I, type II or type III transmembrane proteins.

In one embodiment, the transmembrane domain may also comprise an artificial hydrophobic sequence.

Examples of transmembrane domains that are suitable in the CAR of the invention include, but are not limited to, transmembrane domains of an α, β or ζ chain of a T cell receptor, or of CD28, CD3γ, CD3δ, CD3ε, CD3ζ, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR (CD357), CD40, BAFFR, HVEM (LIGHTR), SLAMF7, NKp80 (KLRF1), CD160, CD19, IL2Rβ, IL2Rγ, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, PD1, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM (CD355), Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D or NKG2C.

In one embodiment, the transmembrane domain comprises an amino acid sequence derived from the transmembrane domain of CD28 or CD3ζ.

Additional transmembrane domains will be apparent to those skilled in the art and may be used in connection with alternate embodiments of the invention.

In one embodiment, the transmembrane domain may be recombinant, in which case it will comprise predominantly hydrophobic amino acids, such as, e.g., valine, Val, V or leucine, Leu, L.

In one embodiment, the CAR of the invention can optionally comprise one or several costimulatory domain(s).

Costimulatory domains enhance cell proliferation, cell survival and development of memory cells.

Examples of costimulatory domains that are suitable in the CAR of the invention include, but are not limited to, costimulatory domains of any of the members of the TNFR super family, CD28, CD137 (4-1BB), CD134 (OX40), Dap10, CD27, CD2, CD5, ICAM-1, Lck, TNFR-1, TNFR-II, Fas, CD30, CD40, CTLA-4, ICOS, PD-1, and combinations thereof.

Costimulatory domains from other proteins may also be used with the CARs of the invention. Additional costimulatory domains will be apparent to those skilled in the art and may be used in connection with alternate embodiments of the invention.

If the CAR of the invention comprises more than one costimulatory domain, these domains may be arranged in tandem, optionally separated by a linker, such as a flexible peptidic linker as has been described above.

In one embodiment, the costimulatory domain comprises a T cell costimulatory molecule, or a sequence derived therefrom.

In one embodiment, the CAR of the invention comprises at least one costimulatory domain selected from the group comprising or consisting of 4-1BB, ICOS, CD27, OX40, CD28, CTLA4 and PD-1.

In one embodiment, the CAR of the invention comprises at least one intracellular signaling domain (also called endodomain).

The intracellular signaling domain is cytoplasmic, and allows to transduce the effector function signal and direct the cell to perform its specialized function upon binding of the extracellular binding domain to its antigen.

Examples of intracellular signaling domains that are suitable in the CAR of the invention include, but are not limited to, ζ chain of the T cell receptor or any of its homologs (such as, e.g., η chain, FcεR1γ and β chains, MB1 (Igα) chain, B29 (Igβ) chain, etc.), CD3 polypeptides (such as, e.g., Δ, δ and ε), syk family tyrosine kinases (such as, e.g., Syk, ZAP 70, etc.), src family tyrosine kinases (such as, e.g., Lck, Fyn, Lyn, etc.) and other molecules involved in T cell transduction, such as, e.g., CD2, CD5 and CD28.

In one embodiment, the intracellular signaling domain may be human CD3ζ chain, FcγRIII, FcεRI, cytoplasmic tails of Fc receptors, immunoreceptor tyrosine-based activation motif (ITAM) bearing cytoplasmic receptors or combinations thereof. Additional intracellular signaling domains will be apparent to those skilled in the art and may be used in connection with alternate embodiments of the invention.

In one embodiment, the at least one intracellular signaling domain may comprise the entire intracellular portion, or the entire native intracellular signaling domain, of the molecule from which it is derived, or a functional fragment or derivative thereof.

In one embodiment, the at least one intracellular signaling domain comprises or consists of a T cell primary signaling domain (or a sequence derived therefrom).

In one embodiment, the T cell primary signaling domain comprises or consists of a signaling domain of a protein selected in the group of CD3ζ, CD3γ, CD3δ, CD3ε, common FcRγ (FCER1G), FcRε (Fc Epsilon Rib), CD79a, CD79b, FcγRIIa, DAP10, DAP12, and sequences derived therefrom.

In one embodiment, the T cell primary signaling domain comprises or consists of a functional signaling domain of CD3ζ.

T cell primary signaling domains that act in a stimulatory manner may comprise signaling motifs known as immunoreceptor tyrosine-based activation motifs (ITAMS).

Examples of ITAM containing T cell primary intracellular signaling domains that are of particular use in the invention include, but are not limited to, those of (or derived from) CD3ζ, common FcRγ (FCER1G), FcγRIIa, FcRβ (FcεR1b), CD3γ, CD3δ, CD3ε, CD5, CD22, CD66b, CD79a, CD79b, DAP10, and DAP12.

In one embodiment, the T cell primary signaling domain comprises a modified ITAM domain (e.g., a mutated ITAM domain which has altered e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In one embodiment, a primary signaling domain comprises one, two, three, four or more ITAM motifs.

In one embodiment, the at least one intracellular signaling domain and the at least one costimulatory domain, if present, may be linked to each other in tandem, in a random or in a specified order.

Optionally, a linker, such as a flexible peptidic linker as has been described above, may form the linkage between distinct intracellular signaling domains, and/or between a costimulatory domain and an intracellular signaling domain. Besides flexible peptidic linkers described above, a single amino acid (such as, e.g., alanine, Ala, A or glycine, Gly, G) may also be a suitable linker.

In one embodiment, the CAR of the invention comprises more than one intracellular signaling domain, such as 2, 3, 4, 5, or more, intracellular signaling domains.

In one embodiment, the CAR of the invention may further comprise a tag, such as, e.g., a tag for quality control, enrichment, tracking in vivo and the like.

In one embodiment, said tag is localized N-terminally, C-terminally and/or internally.

Examples of tags that that are suitable in the CAR of the invention include, but are not limited to, hemagglutinin tag, poly-arginine tag, poly-histidine tag, Myc tag, strep tag, S-tag, HAT tag, 3xFlag tag, calmodulin-binding peptide (CBP) tag, SBP tag, chitin binding domain (CBD) tag, GST tag, maltose-binding protein (MBP) tag, fluorescent protein tag, T7 tag, V5 tag and Xpress tag.

The CAR of the invention may be a first-generation, second-generation or third-generation CAR.

The first generation of CARs was developed more than 30 years ago (Kuwana et al., 1987. *Biochem Biophys Res Commun.* 149(3):960-968; Gross et al., 1989. *Transplant Proc.* 21(1 Pt 1):127-130; Gross et al., 1989. *Proc Natl Acad Sci USA.* 86(24):10024-10028).

In one embodiment, the CAR of the invention is a first-generation CAR and comprises:
(i) at least one extracellular binding domain,
(ii) an extracellular spacer domain,
(iii) a transmembrane domain, and
(iv) one or more intracellular signaling domain(s).

A first-generation CAR can be, for example, a CAR in which signaling is provided by CD3ζ, i.e., the intracellular signaling domain is CD3ζ.

Second-generation CARs add a co-stimulatory domain, such as, e.g., CD28 or 4-1BB. The involvement of these intracellular signaling domains improve T cell proliferation, cytokine secretion, resistance to apoptosis, and in vivo persistence.

In one embodiment, the CAR of the invention is a second-generation CAR and comprises:
(i) at least one extracellular binding domain,
(ii) an extracellular spacer domain,
(iii) a transmembrane domain,
(iv) a costimulatory domain(s), and
(v) one or more intracellular signaling domain(s).

Third-generation CARs combine multiple co-stimulatory domains, such as, e.g., CD28-4-1BB or CD28-OX40, to increase T cell activity.

In one embodiment, the CAR of the invention is a third-generation CAR and comprises:
(i) at least one extracellular binding domain,
(ii) an extracellular spacer domain,
(iii) a transmembrane domain,
(iv) at least two costimulatory domains, and
(v) one or more intracellular signaling domain(s).

Another object of the present invention is a nucleic acid encoding the CAR of the invention.

Another object of the present invention is a vector comprising the nucleic acid encoding the CAR of the invention.

In one embodiment, the nucleic acid or vector of the invention comprises a nucleic acid sequence of the extracellular binding domain(s) operably linked to the nucleic acid sequence of an extracellular spacer domain, operably linked to the nucleic acid sequence of a transmembrane domain, operably linked to the nucleic acid sequence of a cytoplasmic domain (i.e., at least one intracellular signaling domain and optionally, at least one costimulatory domain).

The nucleic acid or the vector of the invention can be prepared in conventional ways (e.g., recombinant methods), where the genes and regulatory regions may be isolated, as appropriate, ligated, and cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. Alternatively, the gene of interest can be produced synthetically, rather than cloned.

In one embodiment, the vector comprises a first nucleic acid encoding a CAR of the invention, and further comprises a second nucleic acid encoding an antibody or antigen-binding fragment thereof, a bispecific antibody (e.g., a BiTE), a cytokine or a costimulatory ligand. In one embodiment, the first nucleic acid and the second nucleic acid are each operably linked to a promoter. In one embodiment, the first nucleic acid is operably linked to a first promoter and the second nucleic acid is operably linked to a second promoter. The promoter can be a constitutively-expressed promoter (e.g., an EF1a promoter) or an inducibly-expressed promoter (e.g., a NFAT promoter).

In one embodiment, expression of the CAR and expression of the antibody or antigen-binding fragment thereof, bispecific antibody (e.g., a BiTE), cytokine or costimulatory ligand are driven by the same promoter, e.g., a constitutively expressed promoter (e.g., an EF1a promoter). In one embodiment, expression of the CAR and expression of the antibody or antigen-binding fragment thereof, bispecific antibody (e.g., a BiTE), cytokine or costimulatory ligand are driven by different promoters.

In one embodiment, the nucleic acid encoding the CAR can be located upstream or downstream of the second nucleic acid encoding the antibody or antigen-binding fragment thereof, the bispecific antibody (e.g., a BiTE), the cytokine or the costimulatory ligand.

Another object of the present invention is an immune cell, preferably an isolated immune cell engineered to express the chimeric antigen receptor (CAR) of the invention at its surface.

In one embodiment, the immune cell of the invention expresses at its cell surface a CAR comprising an extracellular binding domain comprising or consisting of an antigen-binding domain directed to a senescent cell-associated antigen, which recognizes and is capable of binding to a senescent cell-associated antigen, as defined hereinabove.

In one embodiment, the immune cell of the invention expresses at its cell surface an anti-DEP1 chimeric antigen receptor (CAR), as defined hereinabove.

In one embodiment, the immune cell of the invention expresses at its cell surface an anti-DPP4 chimeric antigen receptor (CAR), as defined hereinabove.

In one embodiment, the immune cell of the invention expresses at its cell surface at least two CARs, wherein the first CAR and the second CAR recognize two different senescent cell-associated antigens.

In one embodiment, the immune cell of the invention expresses at its cell surface at least two CARs, wherein the first CAR is an anti-DEP1 chimeric antigen receptor, and the second CAR is an anti-DPP4 chimeric antigen receptor, as defined hereinabove.

In one embodiment, the immune cell of the invention expresses at its cell surface a multispecific CAR, as defined hereinabove.

In one embodiment, the immune cell of the invention expresses at its cell surface a bispecific CAR, comprising two extracellular binding domains, wherein one extracellular binding domain recognizes and is capable of binding to DEP1, and the other extracellular binding domain recognizes and is capable of binding to DPP4, as defined hereinabove.

In one embodiment, the immune cell of the invention further expresses at its cell surface a bispecific T cell engager (BiTE).

In one embodiment, the BiTE binds to at least one senescent cell-associated antigen and at least one non-senescent cell-associated antigen, as defined hereinabove.

In one embodiment, the immune cell of the invention is a T cell, preferably an isolated T cell. In one embodiment, the immune cell is a $CD8^+$ T cell, a $CD4^+$ T cells, a natural killer (NK) cell or an NKT cell.

In one embodiment, the immune cell of the invention is a cytotoxic T cell (also known as TC, cytotoxic T lymphocyte, CTL, T-killer cell, cytolytic T cell, $CD8^+$ T cells or killer T cell). NK cells and NKT cells are also encompassed in the invention.

In one embodiment, the T cell is a $CD8^+$ T cytotoxic lymphocyte cell selected from the group comprising or consisting of naive $CD8^+$ T cells, $CD8^+$ memory T cells, central memory $CD8^+$ T cells, regulatory $CD8^+$ T cells, IPS-derived $CD8^+$ T cells, effector memory $CD8^+$ T cells and bulk $CD8^+$ T cells.

In one embodiment, the T cell is a $CD4^+$ T helper lymphocyte cell selected from the group comprising or consisting of naive $CD4^+$ T cells, $CD4^+$ memory T cells, central memory $CD4^+$ T cells, regulatory $CD4^+$ T cells, IPS-derived $CD4^+$ T cells, effector memory $CD4^+$ T cells and bulk $CD4^+$ T cells.

In one embodiment, the immune cell of the invention is cytotoxic for cells expressing at their surface the senescent cell-associated antigen recognized by the CAR (such as, e.g., DEP1 and/or DPP4). In one embodiment, the immune cell of the invention is not cytotoxic for cells expressing at their surface the senescent cell-associated antigen recognized by the CAR (such as, e.g., DEP1 and/or DPP4).

In one embodiment, the immune cell of the invention is a phagocytic cell.

In one embodiment, the immune cell of the invention is a phagocytic cell selected from the group comprising or consisting of macrophages, monocytes, histiocytes, Kupffer cells, alveolar macrophages, microglial cells and dendritic cells.

In one embodiment, the immune cell of the invention is a mammal immune cell, preferably a human immune cell.

In one embodiment, the immune cells of the invention is an autologous cell, a syngeneic cell, an allogenic cell, or a xenogeneic cell.

Another object of the present invention is a population of immune cells, comprising a plurality of immune cells of the invention.

In one embodiment, the population of immune cells may be homogeneous, i.e., composed at more than 50%, such as more than 60%, 70%, 80%, 90%, 95% or more of the same immune cells, i.e., immune cells of same nature, origin, and/or expressing the same CAR at their cell surface.

In one embodiment, the population of immune cells may be heterogeneous, i.e., composed of a mix of different immune cells, i.e., immune cells of different nature, origin, and/or expressing a different CAR at their cell surface.

Another object of the present invention is a method of obtaining an immune cell expressing the CAR of the invention at its surface, or a population of such immune cells.

Means and methods to obtain immune cells expressing the CAR of the invention at its surface, or a population of such immune cells, are well known in the art.

In one embodiment, the method for obtaining an immune cell expressing the CAR of the invention at its surface, or a population of such immune cells, comprises one or several of:

a step of isolating an immune cell or population of immune cells (e.g., T cells or phagocytic cells) from a sample obtained from a subject, optionally, a step of selecting a specific subpopulation of immune cells, a step of transducing the immune cell or population of immune cells with a nucleic acid encoding the CAR of the invention, optionally, a step of expanding the transduced immune cell or population of immune cells, optionally, a step of washing the immune cell or population of immune cells, optionally, a step of cryopreserving the immune cell or population of immune cells.

Prior to transduction and expansion of the immune cell of the invention, a source of immune cells (e.g., T cells or phagocytic cells) is obtained from a subject. Thus, in one embodiment, the immune cell or the population of immune cells of the invention is isolated and/or substantially purified.

T cells and/or phagocytic cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In one embodiment, any number of T cell and/or phagocytic cells lines available in the art may be used.

In one embodiment, T cells and/or phagocytic cells can be obtained from a unit of blood collected from a subject using any number of techniques known to those skilled in the art, such as Ficoll™ separation.

In one embodiment, cells from the circulating blood of a subject are obtained by apheresis. The apheresis product typically contains lymphocytes, including T cells, monocytes, granulocytes, B cells, other nucleated white blood cells, red blood cells, and platelets.

In one embodiment, cells from the circulating blood of a subject are obtained by leukapheresis. In one embodiment, cells collected by leukapheresis may be washed to remove the plasma fraction and to place the cells in an appropriate buffer or media for subsequent processing steps. In one embodiment of the invention, the cells are washed with phosphate buffered saline (PBS). In one embodiment, the wash solution lacks calcium, and may lack magnesium or many if not all divalent cations. After washing, the cells may be resuspended in a variety of biocompatible buffers, such as, e.g., $Ca^{2+}$-free, $Mg^{2+}$-free PBS, PlasmaLyte A, or other saline solution with or without buffer. Alternatively, the undesirable components of the leukapheresis sample may be removed and the cells directly resuspended in culture media.

In one embodiment, T cells and/or phagocytic cells are isolated from peripheral blood lymphocytes by lysing the red blood cells and depleting the monocytes, e.g., by centrifugation through a PERCOLL™ gradient or by counter-flow centrifugal elutriation. A specific subpopulation of T cells can be further isolated by positive or negative selection techniques. Those skilled in the art would recognize that multiple rounds of selection can also be used in the context of this invention.

In one embodiment, it may be desirable to perform the selection procedure and use the "unselected" cells in the activation and expansion process. "Unselected" cells can also be subjected to further rounds of selection. Enrichment of a T cell population by negative selection can be accomplished with a combination of antibodies directed to surface markers unique to the negatively selected cells. One method is cell sorting and/or selection via negative magnetic immuno-adherence or flow cytometry that uses a cocktail of monoclonal antibodies directed to cell surface markers present on the cells negatively selected.

For example, to enrich CD4$^+$ cells by negative selection, a monoclonal antibody cocktail typically includes antibodies directed to CD14, CD20, CD11b, CD16, HLA-DR, and CD8. To deplete T regulatory cells, anti-CD25 conjugated beads or other similar method of selection can be used. To enrich a population of monocytes, macrophages and/or dendritic cells by negative selection, a monoclonal antibody cocktail typically includes antibodies to CD34, CD3, CD4, CD8, CD14, CD19 or CD20. Those skilled in the art are familiar with such means and methods.

In one embodiment, the immune cell or population of immune cells of the invention is transduced with a nucleic acid encoding the CAR of the invention, or with a vector comprising the nucleic acid encoding the CAR of the invention, and optionally expanded.

Methods for transfecting eukaryotic cells and tissues removed from an organism in an ex vivo method are known to those skilled in the art. In one embodiment, the method is an ex vivo method. Thus, it is contemplated that cells or tissues may be removed and transfected ex vivo using nucleic acids or vectors of the invention. In one embodiment, the transplanted cells or tissues may be placed into an organism. In one embodiment, a nucleic acid is expressed in the transplanted immune cell population.

The nucleic acid encoding the CAR of the invention, once completed and demonstrated to have the appropriate sequences, may be introduced into the immune cell by any convenient means, including, but not limited to, by fusion, electroporation, biolistics, transfection, lipofection, or the like. Alternatively, the nucleic acid encoding the CAR of the invention may also be integrated and packaged into non-replicating, defective viral genomes like adenovirus, adeno-associated virus (AAV), or herpes simplex virus (HSV) or others, including retroviral vectors or lentiviral vectors, for infection or transduction into cells. The nucleic acid encoding the CAR of the invention may include viral sequences for transfection, if desired. The engineered cells may be grown and expanded in culture before introduction of the construct(s), followed by the appropriate treatment for introduction of the construct(s) and integration of the construct(s). The engineered cells are then expanded and screened by virtue of a marker present in the construct. Various markers that may be used successfully include hprt, neomycin resistance, thymidine kinase, hygromycin resistance, etc.

In one embodiment, one may have a target site for homologous recombination, where it is desired that a nucleic acid be integrated at a particular locus. For example, one can knock-out an endogenous gene and replace it (at the same locus or elsewhere) with the gene encoded for by the construct using materials and methods as are known in the art for homologous recombination. For homologous recombination, one may use either OMEGA or O-vectors. See, e.g., Thomas & Capecchi, 1987. *Cell*. 51(3):503-12; Mansour et al., 1988. *Nature*. 336(6197):348-352; and Joyner et al., 1989. *Nature*. 338(6211):153-156.

The nucleic acid encoding the CAR of the invention may be introduced as a single DNA molecule encoding at least the CAR of the invention and optionally another gene, or different DNA molecules having one or more genes. Other genes include genes that encode therapeutic molecules or suicide genes, for example. The constructs may be introduced simultaneously or consecutively, each with the same or different markers.

In one embodiment, suicide gene technology may be used. Different suicide gene technologies are described in the art depending on their mechanism of action (Jones et al., 2014. *Front Pharmacol*. 5:254). Examples of gene-directed enzyme prodrug therapy (GDEPT) converting a nontoxic drug to a toxic drug include herpes simplex virus thymidine kinase (HSV-TK) and cytosine deaminase (CD). Other examples are chimeric proteins composed of a drug binding domain linked to apoptotic components such as for example the inducible Fas (iFas) or the inducible Caspase 9 (iCasp9) systems. Other examples include systems mediated by therapeutic antibodies such as inducing overexpression of c-myc at the surface of the engineered cell to induce their deletion by administration of an anti-c-myc antibody. The use of EGFR is described as a similar system compared to the c-myc system.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

In one embodiment, the step of transducing the immune cell or population of immune cells corresponds to a gene disruption step, a gene correction step or a gene addition step, preferably a gene addition step.

The immune cells that have been transduced with the nucleic acid encoding the CAR of the invention are then grown in culture under selective conditions, to retain only those cells which were successfully transduced.

In one embodiment, the immune cell or the population of immune cells of the invention is or comprises or consists of a genetically modified immune cell.

In one embodiment, the genetically modified immune cell or the population of immune cells of the invention can be or comprise or consist of an allogeneic immune cell. For example, the allogeneic immune cell can be an immune cell lacking expression of a functional human leukocyte antigen (HLA), e.g., HLA class I and/or HLA class II or a T cell receptor (TCR).

In one embodiment, the immune cell or the population of immune cells of the invention can be engineered such that the immune cell does not express a functional HLA and/or TCR on its surface. For example, an immune cell can be engineered such that cell surface expression HLA, e.g., HLA class 1 and/or HLA class II or non-classical HLA molecules, is downregulated.

Modified immune cells that lack expression of a functional HLA and/or TCR can be obtained by any suitable means, including a knock-out or knock-down of one or more subunit of HLA. For example, the immune cell can include a knock-down of HLA using siRNA, shRNA, clustered regularly interspaced short palindromic repeats (CRISPR) transcription-activator like effector nuclease (TALEN), zinc finger endonuclease (ZFN), meganuclease (mn, also known as homing endonuclease), or megaTAL (combining a TAL effector with a mn cleavage domain). Such systems are well known in the art.

In one embodiment, the nucleic acid encoding a CAR as described herein is inserted at a specific locus in the genome of an immune cell, such as, e.g., at the locus of a gene to be deleted. In one embodiment, the nucleic acid encoding a CAR as described herein is inserted within an HLA locus, thereby resulting in the inhibition of HLA expression.

In one embodiment, the CAR of the invention, when expressed by a T cell or phagocytic cell, confers to the T cell or phagocytic cell the ability to bind to cells expressing DEP1 and/or DPP4 on their cell surface and be activated by DEP1 and/or DPP4, differently from the antigen that the T cells or phagocytic cell are or would have been specific or activated by.

The immune cell population of the invention may thus be defined as a redirected immune cell population. The term "redirected" refers to such immune cells, e.g., a T cell or phagocytic cell, which carries a CAR as described herein, conferring to the immune cell the ability to bind to and be activated by a ligand that is different from the one the immune cell is or would have been specific or be activated by.

In one embodiment, the immune cell or population of immune cell of the invention can express certain gene products that can kill the modified cells under controlled conditions, such as inducible suicide genes.

In one embodiment, the immune cell or the population of immune cells of the invention is cultured for expansion. In one embodiment, the immune cell or the population of immune cells of the invention comprises or consists of progenitor cells, which are cultured for differentiation and expansion of the immune cells or population of immune cells as described herein.

Whether prior to or after transduction of the immune cells (i.e., T cells or phagocytic cells) to express a desirable CAR as described herein, the immune cells (i.e., T cells and/or phagocytic cells) can be activated and expanded generally using methods as described, e.g., in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and 7,572,631.

In one embodiment, immune cells may be cryopreserved, either after isolation and optionally, selection, and/or after transduction and expansion.

In one embodiment, cryopreserved cells are thawed and washed as described herein and allowed to rest for one hour at room temperature prior to activation.

Also contemplated in the context of the invention is the collection of blood samples or leukapheresis product from a subject at a time period prior to when the expanded cells as described herein might be needed. As such, the source of the cells to be expanded can be collected at any time point necessary, and desired cells, such as T cells and/or phagocytic cells, isolated and frozen for later use in cell therapy for any number of diseases or conditions that would benefit from cell therapy, such as those described herein.

In one embodiment, a blood sample or a leukapheresis product is taken from a generally healthy subject. In one embodiment, a blood sample or a leukapheresis product is taken from a healthy subject who is at risk of developing a disease, but who has not yet developed said disease, and the cells of interest are isolated and cryopreserved for later use. In one embodiment, the T cells and/or phagocytic cells may be expanded, frozen, and used at a later time.

Another object of the invention is a composition comprising, consisting of or consisting essentially of:
  an antigen-binding domain, as described above;
  an antibody or antigen-binding fragment thereof, as described above;
  a nucleic acid encoding the antigen-binding domain, the antibody or the antigen-binding fragment thereof, as described above;
  a vector comprising the nucleic acid encoding the antigen-binding domain, the antibody or the antigen-binding fragment thereof, as described above;
  a CAR, as described above;
  a nucleic acid encoding the CAR, as described above;
  a vector comprising the nucleic acid encoding the CAR, as described above;
  an immune cell engineered to express the CAR at its cell surface, as described above;
  a population of immune cells engineered to express the CAR at their cell surface, as described above.

In one embodiment, the composition comprises, consists of or consists essentially of:
  a DEP1-binding domain, as described above;
  an anti-DEP1 antibody or antigen-binding fragment thereof, as described above;
  a nucleic acid encoding the DEP1-binding domain, the anti-DEP1 antibody or the antigen-binding fragment thereof, as described above;
  a vector comprising the nucleic acid encoding the DEP1-binding domain, the anti-DEP1 antibody or the antigen-binding fragment thereof, as described above; an anti-DEP1 CAR, as described above;
  a nucleic acid encoding the anti-DEP1 CAR, as described above;
  a vector comprising the nucleic acid encoding the anti-DEP1 CAR, as described above;
  an immune cell engineered to express the anti-DEP1 CAR at its cell surface, as described above;
  a population of immune cells engineered to express the anti-DEP1 CAR at their cell surface, as described above.

In one embodiment, the composition comprises, consists of or consists essentially of:
  a DPP4-binding domain, as described above;
  an anti-DPP4 antibody or antigen-binding fragment thereof, as described above;
  a nucleic acid encoding the DPP4-binding domain, the anti-DPP4 antibody or the antigen-binding fragment thereof, as described above;
  a vector comprising the nucleic acid encoding the DPP4-binding domain, the anti-DPP4 antibody or the antigen-binding fragment thereof, as described above;
  an anti-DPP4 CAR, as described above;
  a nucleic acid encoding the anti-DPP4 CAR, as described above;
  a vector comprising the nucleic acid encoding the anti-DPP4 CAR, as described above;
  an immune cell engineered to express the anti-DPP4 CAR at its cell surface, as described above;
  a population of immune cells engineered to express the anti-DPP4 CAR at their cell surface, as described above.

In one embodiment, the composition comprises, consists of or consists essentially of:
  a DEP1-binding domain and a DPP4-binding domain, as described above;
  an anti-DEP1 antibody or antigen-binding fragment thereof and an anti-DPP4 antibody or antigen-binding fragment thereof, as described above;
  an anti-DEP1/anti-DPP4 bispecific antibody;
  a nucleic acid encoding the DEP1-binding domain, the anti-DEP1 antibody or the antigen-binding fragment thereof and a nucleic acid encoding the DPP4-binding domain, the anti-DPP4 antibody or the antigen-binding fragment thereof, as described above;

a nucleic acid encoding the anti-DEP1/anti-DPP4 bispecific antibody, as described above;

a vector comprising the nucleic acid encoding the DEP1-binding domain, the anti-DEP1 antibody or the antigen-binding fragment thereof and a vector comprising the nucleic acid encoding the DPP4-binding domain, the anti-DPP4 antibody or the antigen-binding fragment thereof, as described above;

a vector comprising the nucleic acid encoding the DEP1-binding domain, the anti-DEP1 antibody or the antigen-binding fragment thereof and the nucleic acid encoding the DPP4-binding domain, the anti-DPP4 antibody or the antigen-binding fragment thereof, as described above;

a vector comprising the nucleic acid the anti-DEP1/anti-DPP4 bispecific antibody, as described above;

an anti-DEP1 CAR and an anti-DPP4 CAR, as described above;

an anti-DEP1/anti-DPP4 bispecific CAR, as described above;

a nucleic acid encoding the anti-DEP1 CAR and the anti-DPP4 CAR, as described above;

a nucleic acid encoding the anti-DEP1/anti-DPP4 bispecific CAR, as described above;

a vector comprising a nucleic acid encoding the anti-DEP1 CAR and a vector comprising the nucleic acid encoding the anti-DPP4 CAR, as described above;

a vector comprising a nucleic acid encoding the anti-DEP1 CAR and the nucleic acid encoding the anti-DPP4 CAR, as described above;

a vector comprising a nucleic acid encoding the anti-DEP1/anti-DPP4 bispecific CAR, as described above;

an immune cell engineered to express the anti-DEP1 CAR and an immune cell engineered to express the anti-DPP4 CAR, as described above;

an immune cell engineered to express the anti-DEP1 CAR and the anti-DPP4 CAR, as described above;

an immune cell engineered to express the anti-DEP1/anti-DPP4 bispecific CAR, as described above;

a population of immune cells engineered to express the anti-DEP1 CAR and a population of immune cells engineered to express the anti-DPP4 CAR, as described above;

a population of immune cells engineered to express the anti-DEP1 CAR and the anti-DPP4 CAR, as described above;

a population of immune cells engineered to express the anti-DEP1/anti-DPP4 bispecific CAR, as described above.

In one embodiment, the composition has been frozen and thawed. In one embodiment, the composition is lyophilized.

In one embodiment, the compositions of the invention are pharmaceutical compositions and further comprise at least one pharmaceutically acceptable excipient.

The term "pharmaceutically acceptable excipient" includes any and all solvents, dispersion media, coatings, antibacterial and antifungal agents, isotonic and absorption delaying agents and the like. Said excipient does not produce an adverse, allergic or other untoward reaction when administered to an animal, preferably a human. For human administration, preparations should meet sterility, pyrogenicity, and general safety and purity standards as required by regulatory offices, such as, for example, FDA Office or EMA.

Pharmaceutically acceptable excipients that may be used in the pharmaceutical composition of the invention include, without being not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In one embodiment, the compositions according to the present invention are medicaments.

As used herein, the term "consisting essentially of", with reference to a composition, pharmaceutical composition or medicament, means that the antigen-binding domain, antibody or antigen-binding fragment thereof, nucleic acid, vector, CAR, immune cell or population of immune cells of the invention is/are the only therapeutic agent, or agent with a biologic activity, within said composition, pharmaceutical composition or medicament.

Such compositions and medicaments may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Since the present invention selectively target senescent cells, it is contemplated that the compositions according to the present invention may be cosmetic compositions, and further comprise at least one dermatologically acceptable excipient.

The term "dermatologically acceptable excipient" refers to excipient which are suitable for external topical application. Examples of dermatologically acceptable excipients include, but are not limited to, sebum-regulating agents, antibacterial agents, antifungal agents, keratolytic agents, keratoregulating agents, astringents, anti-inflammatory agents, anti-irritants, antioxidants, free-radical scavengers, cicatrizing agents, anti-aging agents and moisturizing agents.

The administration of the composition, pharmaceutical composition, medicament or cosmetic composition of the invention may be carried out in any convenient manner, including by injection, aerosol inhalation, topical delivery (such as, for example, by transdermal delivery), oral delivery, rectal delivery, nasal delivery, or vaginal delivery.

In one embodiment, the composition, pharmaceutical composition, medicament or cosmetic composition of the present invention is in a form adapted for injection, such as, e.g., for trans-arterial, intravenous (i.v.), intramuscular, intraperitoneal (i.p.), intrapleural, intradermal, subcutaneous, transdermal injection or infusion.

Examples of forms suitable for injectable use include, but are not limited to, sterile solutions or dispersions and sterile powders for the extemporaneous preparation of sterile injectable solutions or dispersions. The prevention against contamination by microorganisms can be brought about by adding in the composition preservatives such as, e.g., various antibacterial and antifungal agents (e.g., parabens, chlorobutanol, phenol, sorbic acid, thimerosal and the like). In one embodiment, it may be preferable to include isotonic agents, e.g., sugars or sodium chloride, to reduce pain during injection. In one embodiment, prolonged absorption of the injectable compositions can be brought about by the use in the compositions of agents delaying absorption, e.g., aluminum monostearate and gelatin.

In one embodiment, the composition, pharmaceutical composition, medicament or cosmetic composition of the present invention is in an adapted form for a parenteral administration. Thus, in one embodiment, the composition, pharmaceutical composition, medicament or cosmetic composition of the invention is to be administered parenterally.

In one embodiment, the composition, pharmaceutical composition, medicament or cosmetic composition of the invention is in an adapted form for an intravenous administration. Thus, in one embodiment, the composition, pharmaceutical composition, medicament or cosmetic composition of the present invention is to be administered intravenously.

In one embodiment, the composition, pharmaceutical composition, medicament or cosmetic composition of the present invention may be injected directly into the site of the disease or disorder to be treated.

In one embodiment, a lyophilized composition, a lyophilized pharmaceutical composition, a lyophilized medicament or a lyophilized cosmetic composition of the invention is solubilized in water for injection and gently mixed, the mixture is gently mixed and charged into a suitable syringe. This invention thus also relates to a medical device, including a syringe filled or prefilled with a composition, pharmaceutical composition, medicament or cosmetic composition of the invention.

In one embodiment, the composition, pharmaceutical composition, medicament or cosmetic composition of the invention is formulated for topical administration. Thus, in one embodiment, the composition, pharmaceutical composition, medicament or cosmetic composition is to be administered topically.

Examples of forms adapted for topical administration include, without being limited to, liquid, paste or solid compositions, and more particularly aqueous solutions, drops, dispersions, sprays, microcapsules, micro- or nanoparticles, polymeric patch, or controlled-release patch, and the like.

In particular embodiments where the compositions of the invention comprise a CAR, an immune cell or a population of immune cells as described above, such compositions may be administered by intradermal or subcutaneous injection, such as by i.v. injection.

In one embodiment, the compositions comprising a CAR, an immune cell or a population of immune cells may be injected directly into a lymph node, site of infection, site of inflammation or site of tissue or organ rejection. In one embodiment, the compositions comprising a CAR, an immune cell or a population of immune cells may be injected directly into the site of the autoimmune and/or inflammatory disease.

In one embodiment, the subject is administered, or is to be administered, with autologous cells. In some embodiments, the subject is administered, or is to be administered, with allogenic cells.

In one embodiment, the subject may be a mammal. In one embodiment, the subject may be a human.

Another object of the present invention is the use of the composition, pharmaceutical composition or medicament described herein, as a medicament.

Another object of the present invention is the use of the composition, pharmaceutical composition or medicament described herein, in treating, preventing or alleviating senescence-related diseases or disorders.

Another object of the present invention is a method of treating, preventing or alleviating senescence-related diseases or disorders in a subject in need thereof, comprising administering to said subject the composition, pharmaceutical composition or medicament described herein.

As used herein, the term "senescence-associated", "senescence-related" or "age-related" diseases, disorders, or conditions refers to a physiological condition that presents with one or more symptoms or signs, wherein a subject having the condition needs or would benefit from a lessening of such symptoms or signs. The condition is senescence-associated if it is caused or mediated in part by senescent cells, which may be induced by multiple etiologic factors including age, DNA damage, oxidative stress, genetic defects, etc. Lists of senescence-associated disorders that can potentially be treated or managed using the methods and products taught in this disclosure include those discussed in this disclosure and the previous disclosures to which this application claims priority.

Non-limiting examples of senescence-related diseases include: fibrotic diseases, chronic inflammatory diseases (e.g., arthritis or arthrosis), cancer, premalignant lesions, atherosclerosis, osteoarthritis, diabetes, diabetic ulcers, kyphosis, scoliosis, hepatic insufficiency, cirrhosis, Hutchinson-Gilford progeria syndrome (HGPS), laminopathies, osteoporosis, dementia, (cardio)vascular diseases (e.g., angina, arrhythmia, atherosclerosis, cardiomyopathy, congestive heart failure, coronary artery disease (CAD), carotid artery disease, endocarditis, heart attack, coronary thrombosis, myocardial infarction, high blood pressure/hypertension, hypercholesterolemia/hyperlipidemia, mitral valve prolapsed, peripheral artery disease (PAD) and stroke), obesity, metabolic syndrome, acute myocardial infarction, emphysema, insulin sensitivity, boutonneuse fever, sarcopenia, neurodegenerative diseases (e.g., Alzheimer's, Huntington's or Parkinson's disease), cataract, anemia, hypertension, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

Another object of the present invention is the use of the composition, pharmaceutical composition or medicament described herein, in treating, preventing or alleviating fibrotic diseases, premalignant lesions, inflammatory diseases and cancers.

Another object of the present invention is a method of treating, preventing or alleviating fibrotic diseases, premalignant lesions, inflammatory diseases and cancers in a subject in need thereof, comprising administering to said subject the composition, pharmaceutical composition or medicament described herein.

Senescent cells are present in fibrosis of many tissues including, but not limited to, skin, liver, lung, pancreas and prostate.

Thus, in one embodiment, the senescence-related disease or disorder to be treated is a fibrotic disease. Exemplary fibrotic diseases which may be treated by the invention include but are not limited to eosinophilic esophagitis, hypereosinophilic syndromes (HES), Loeffler's endomyocarditis, endomyocardial fibrosis, idiopathic pulmonary fibrosis, and scleroderma.

In one embodiment, the pulmonary fibrotic disease to be treated, prevented or alleviated is selected from the group comprising idiopathic pulmonary fibrosis (IPF), chronic obstructive pulmonary disease (COPD) acute respiratory distress syndrome (ARDS), combined pulmonary fibrosis and emphysema (CPFR), pulmonary edema, Loffler's syndrome, eosinophilic pneumonia, respiratory hypersensitivity, allergic bronchopulmonary aspergillosis (ABPA), Hamman-Rich syndrome, sarcoidosis, pneumoconiosis, and hypersensitivity pneumonitis (HP).

In one embodiment, the pulmonary fibrotic disease to be treated, prevented or alleviated is chronic obstructive pulmonary disease (COPD) or idiopathic pulmonary fibrosis.

In one embodiment, the senescence-related disease or disorder to be treated is a premalignant lesion.

As used herein, the phrase "premalignant lesion" refers to a mass of cells and/or tissue having increased probability of transforming into a malignant tumor.

Examples of premalignant lesions include, but are not limited to, adenomatous polyps, Barrett's esophagus, pancreatic intraepithelial neoplasia (PanIN), IPMN (intraductal papillary mucinus neoplasia), DCIS (ductal carcinoma in situ) in the breast, leukoplakia and erythroplakia. Thus, the premalignant lesion to be treated by the invention can transform into a malignant solid or non-solid (e.g., hematological malignancies) cancer (or tumor).

In one embodiment, the premalignant lesion which is to be treated is an adenomatous polyp of the colon, an adenomatous polyp of the rectum, an adenomatous polyp of the small bowel or Barrett's esophagus.

As used herein, the term "inflammatory diseases" refers to any abnormality associated with inflammation, such as, for example, chronic inflammatory diseases, acute inflammatory diseases.

Examples of inflammatory disorders include, but are not limited to, rheumatic diseases, neurological diseases, cardiovascular diseases, uro-gynecological diseases, eye and ear diseases, mucocutaneous diseases, infectious diseases, graft rejection diseases and allergic diseases.

Examples of rheumatic diseases include, but are not limited to, arthritis, osteoarthritis, rheumatoid arthritis, osteoporosis, fibromyalgia, lupus, systemic lupus erythematosus and scleroderma.

Examples of neurological diseases include, but are not limited to, multiple sclerosis, Alzheimer's disease, Parkinson's disease, Huntington's disease, stroke, traumatic brain injury, spinal cord injury, dystonia, chronic regional pain syndrome, motor neuron disease/amyotrophic lateral sclerosis, Guillain-Barre syndrome, muscular dystrophy, cerebral palsy, neuropathy and myositis.

Examples of cardiovascular diseases include, but are not limited to, coronary heart disease, stroke, hypertensive heart disease, inflammatory heart disease, rheumatic heart disease, aortic aneurysm and dissection, congenital heart disease, deep vein thrombosis and pulmonary embolism and atherosclerosis.

Examples of uro-gynecological diseases include, but are not limited to, glomerulonephritis, urinary incontinence and prolapse.

Examples of eye and ear diseases include, but are not limited to, cataract, glaucoma, age-related macular degeneration (AMD), presbyopia, dry eyes, corneal diseases, diabetic retinopathy, vertigo, tinnitus and Meniere's disease.

Examples of mucocutaneous diseases include, but are not limited to, eczema, xeroderma pigmentosum, oral lichen planus, mucous membrane pemphigoid and pemphigus vulgaris.

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Examples of diseases associated with transplantation of a graft include, but are not limited to, graft rejection, chronic graft rejection, subacute graft rejection, hyperacute graft rejection, acute graft rejection and graft versus host disease.

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

In one embodiment, the senescence-related disease or disorder to be treated is cancer.

Non-limiting examples of cancers which may be treated according to this aspect of the present invention include, but are not limited to, adenocarcinoma, adrenal gland tumor, ameloblastoma, anaplastic, anaplastic carcinoma of the thyroid, angiofibroma, angioma, angiosarcoma, apudoma, argentaffmoma, arrhenoblastoma, ascites tumor cell, ascitic tumor, astroblastoma, astrocytoma, ataxia-telangiectasia, atrial myxoma, a basal cell carcinoma cell, bone cancer, brainstem glioma, brain tumor, breast cancer, Burkitt's lymphoma, cerebellar astrocytoma, cervical cancer, cherry angioma, cholangiocarcinoma, cholangioma, chondroblastoma, chondroma, chondrosarcoma, chorioblastoma, choriocarcinoma, colon cancer, common acute lymphoblastic leukemia, craniopharyngioma, cystocarcinoma, cystofbroma, cystoma, ductal carcinoma in situ, ductal papilloma, dysgerminoma, encephaloma, endometrial carcinoma, endothelioma, ependymoma, epithelioma, erythroleukemia, Ewing's sarcoma, extra nodal lymphoma, feline sarcoma, fibro adenoma, fibro sarcoma, follicular cancer of the thyroid, ganglioglioma, gastrinoma cell, glioblastoma multiform, glioma, gonadoblastoma, haemangioblastoma, haemangioendothelioblastoma, haemangioendothelioma, haemangiopericytoma, haematolymphangioma, haemocytoblastoma, haemocytoma, hairy cell leukemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angioforoma, Kaposi sarcoma, kidney tumor, large cell lymphoma, leukemia, a leukemia, acute leukemia, lipoma, liver cancer, liver metastases, Lucke carcinoma, lymphadenoma, lymphangioma, lymphocytic leukemia, lymphocytic lymphoma, lymphoeytoma, lymphoedema, lymphoma, lung cancer, malignant mesothelioma, malignant teratoma, mastocytoma, medulloblastome, melanoma, meningioma, mesothelioma, Morton's neuroma, multiple myeloma, myeloblastoma, myeloid leukemia, myelolipoma, myeloma, myoblastoma, myxoma, nasopharyngeal carcinoma, neoplastic, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteosarcoma, ovarian cancer, Paget's disease of the nipple, pancoast tumor, pancreatic cancer, phaeochromocytoma, pheoehromocytoma, plasmacytoma, primary brain tumor, progonoma, prolactinoma, renal cell carcinoma, retinoblastoma, rhabdomyosarcoma, rhabdo sarcoma, a solid tumor, sarcoma, a secondary tumor, seminoma, skin cancer, small cell carcinoma, squamous cell carcinoma, strawberry haemangioma, T cell lymphoma, teratoma, testicular cancer, thymoma, trophoblastic tumor, and Wilm's tumor.

In one embodiment, the composition, pharmaceutical composition or medicament described herein is used alone.

In one embodiment, the composition, pharmaceutical composition, or medicament described herein is used in combination with at least one anti-cancer agent.

Indeed, many of existing and potential anti-cancer agents induce senescence of cancer cells, therefore the present invention can be used in combination with these agents to increase the efficacy of an anti-cancer treatment. Treatment by these agents can also reduce side effects of radiotherapy or chemotherapy with DNA-damaging agents.

Thus, the composition, pharmaceutical composition or medicament described herein can be used as an adjuvant therapy along with other treatment modalities for cancers, which are selected based on cancer type, location, the cell type and the grade of malignancy. Conventional therapies include surgery, radiation therapy, and chemotherapy.

Exemplary anti-cancer drugs that can be co-administered with the composition, pharmaceutical composition or medicament described herein include, but are not limited to, acivicin, aclarubicin, acodazole hydrochloride, acronine, adriamycin, adozelesin, aldesleukin, altretamine, ambomycin, ametantrone acetate, aminoglutethimide, amsacrine, anastrozole, anthramycin, asparaginase, asperlin, azacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interferon alfa-2a, interferon alfa-2b, interferon alfa-n1, interferon alfa-n3, interferon beta-1a, interferon gamma-1b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, taxol, tecogalan sodium, tegafur, teloxantrone hydrochloride, temoporfin, teniposide, teroxirone, testolactone, thiamiprine, thioguanine, thiotepa, tiazofuirin, tirapazamine, topotecan hydrochloride, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, and zorubicin hydrochloride.

Additional antineoplastic agents include those disclosed in Chabner et al., 2001. "Antineoplastic agents". In Goodman et al. (Eds.), Goodman & Gilman's The pharmacological basis of therapeutics (10$^{th}$ ed., pp. 1315-1404). New York, N.Y.: McGraw-Hill.

Another object of the present invention is the use of the cosmetic composition described herein, as cosmetics.

Indeed, since the present invention selectively target senescent cells, it is contemplated that the present invention can be used for skin care, skin anti-aging and/or skin rejuvenation.

Another object of the present invention is thus a method for rejuvenating the skin in a subject in need thereof, comprising administering to the subject the cosmetic composition described herein.

Because senescent cells drive age-related pathologies, a selective elimination of these cells can prevent or delay age-related deterioration. Thus, senescent cells may be therapeutic targets in the treatment of aging and age-related disease. As such, removal of senescent cells may delay tissue dysfunction and extend health span. Clearance of senescent cells is expected to improve tissue milieu, thereby improving the function of the remaining non-senescent cells.

Another object of the present invention is thus the use of the composition, pharmaceutical composition or medicament described herein, for depleting and/or killing senescent cells.

Another object of the present invention is thus a method for depleting and/or killing senescent cells in a subject, comprising administering to the subject the composition, pharmaceutical composition or medicament described herein.

In one embodiment, the composition, pharmaceutical composition, medicament or cosmetic composition described herein is to be administered to a subject in need thereof in a therapeutically effective amount.

It will be however understood that the total daily usage of the composition, pharmaceutical composition, medicament or cosmetic composition described herein will be decided by the attending physician within the scope of sound medical judgment. The specific therapeutically effective dose level for any particular patient will depend upon a variety of factors including the disease being treated and the severity of the disease; activity of the therapeutic agent in the composition, pharmaceutical composition, medicament or cosmetic composition (antigen-binding domain, antibody or antigen-binding fragment thereof, nucleic acid, vector, CAR, immune cell or population of immune cells of the invention) employed; the age, body weight, general health, sex and diet of the subject; the time of administration, route of administration, and rate of excretion of the specific composition, pharmaceutical composition, medicament or cosmetic composition employed; the duration of the treatment; drugs used in combination or coincidental with the composition, pharmaceutical composition, medicament or cosmetic composition employed; and like factors well known in the medical arts. For example, it is well within the skill of the art to start doses of the compound at levels lower than those required to achieve the desired therapeutic effect and to gradually increase the dosage until the desired effect is achieved. The total dose required for each treatment may be administered by multiple doses or in a single dose.

Disclosed herein is a chimeric antigen receptor (CAR) comprising:
(i) at least one extracellular binding domain, comprising at least one antigen-binding domain directed to a senescent cell-associated antigen, preferably to DEP1 and/or DPP4,
(ii) an extracellular spacer domain,
(iii) a transmembrane domain,
(iv) optionally at least one costimulatory domain, and
(v) at least one intracellular signaling domain.

In one embodiment, said at least one antigen-binding domain is directed to DEP1.

In one embodiment, said at least one antigen-binding domain is directed to DPP4.

In one embodiment, said CAR is a bispecific CAR comprising two antigen-binding domains.

In one embodiment, each of the at least two antigen-binding domains binds to a different antigen, preferably to DEP1 and DPP4.

Also disclosed herein is an isolated immune cell population expressing at least one CAR according to the present disclosure, preferably the isolated immune cell population expresses:
at least one CAR directed to DEP1 and at least one CAR directed to DPP4; or
at least one bispecific CAR comprising two antigen-binding domains, preferably wherein each of the at least two antigen-binding domains binds to a different antigen, preferably to DEP1 and DPP4.

In one embodiment, the isolated immune cell population according to the present disclosure comprises immune cells selected from the group comprising T cells, natural killer (NK) cells, or a combination thereof.

Also disclosed herein is an isolated bispecific antibody or a fragment thereof, comprising at least two antigen binding domains directed to at least two senescent cell-associated antigens, preferably the at least two senescent cell-associated antigens are DEP1 and DPP4.

In one embodiment, the isolated bispecific antibody or fragment thereof according to the present disclosure comprises:
(i) an antigen-binding domain of an anti-human DEP1 antibody or a fragment thereof and
(ii) an antigen-binding domain of an anti-human DPP4 antibody or a fragment thereof.

Also disclosed herein is a composition comprising:
the isolated immune cell population according to the present disclosure;
the isolated bispecific antibody or fragment thereof according to the present disclosure; or
a mixture of an isolated anti-human DEP1 antibody or a fragment thereof and an isolated anti-human DPP4 antibody or a fragment thereof.

In one embodiment, the composition according to the present disclosure is a pharmaceutical composition and further comprises at least one pharmaceutically acceptable excipient.

In one embodiment, the composition or pharmaceutical composition according to the present disclosure is for use as a medicament.

In one embodiment, the composition or pharmaceutical composition according to the present disclosure is:
for use in treating, preventing or alleviating senescence-related diseases or disorders; or
for depleting and/or killing senescent cells.

In one embodiment, senescence-related diseases or disorders are selected from the group comprising fibrotic diseases, premalignant lesions, inflammatory diseases and cancers.

BRIEF DESCRIPTION OF THE DRAWINGS

FIG. 9A: staining with monoclonal antibody (Creative Biolabs);

FIG. 9B: staining with 5826-13-R3A-D5;

FIG. 9C: staining with 5826-13-R4A-H5.

FIG. 10A: staining with monoclonal antibody(AbCam)

FIG. 10B: staining with 5738-10-R3A-D5;

FIG. 10C: staining with 5738-13-R4A-D11;

FIG. 10D: staining with 5738-13-R2A-H4.

EXAMPLES

The present invention is further illustrated by the following examples.

Example 1

DPP4 is Expressed on the Surface of Senescent Cells

Materials and Methods

Expression of DPP4 (rhuMAB 41) Antibody and Antigen

The full-length of the antigen was synthesized and subcloned into an expression vector. The insert was confirmed by Sanger sequencing. After the vector was verified by sequencing, the vector was expressed in CHO-S cell line with chemically defined culture media. After 9 days cultivation, the protein was purified by Nickel columns, ultrafiltration and then subjected to 0.2-micron sterile filtration to get the bulk of high purity.

The heavy chain and light chain of the rhuMAB 41 antibody (Creative Biolabs) were synthesized and subcloned into Creative Biolabs property expression vector, respectively. The insert was confirmed by Sanger sequencing. After the vectors were verified by sequencing, they were expressed in HEK293 cell line with chemically defined culture media. After 9 days of cultivation, the protein was purified by Protein A affinity chromatography, ultrafiltration and then subjected to 0.2-micron sterile filtration to get the bulk of high purity.

Expression of DPP4 (rhuMAB 41) scFv

The scFv consists of variable regions of heavy and light chains that are joined together by a flexible peptide linker. In the scFv, the order of the domains can be either VH-linker-VL or VL-linker-VH. The affinity of the two construction types to the target might be different. Hence, the two construction types can lead to secretory expression in different level.

The scFv(s) were expressed and tested by flow cytometry to evaluate the binding affinity to target cells. $5\times10^5$ WI-38 cells were co-cultured with rhuMAB 41 antibody (humanized antibody), VL-Linker-VH antibody and VH-Linker-VL antibody (1 µg/tube), respectively, and then analyzed by using PE-anti-human IgG Fc as secondary antibody.

The results indicated that VH-linker-VL antibody has higher affinity for target cell WI-38 and was chosen for CAR development.

CAR-T Cell Preparation and Construction

Primary human T cells were used for CAR-T generation. Human primary T cells were isolated from PBMCs of healthy donors by magnetic beads and stimulated in growth medium supplemented with IL-2. Activated T cells were then transduced with lentivirus expressing customized chimeric antigen receptor. After CAR-T cell expansion, CAR-transduction efficiency was examined by FACS and qPCR.

Figure 1:
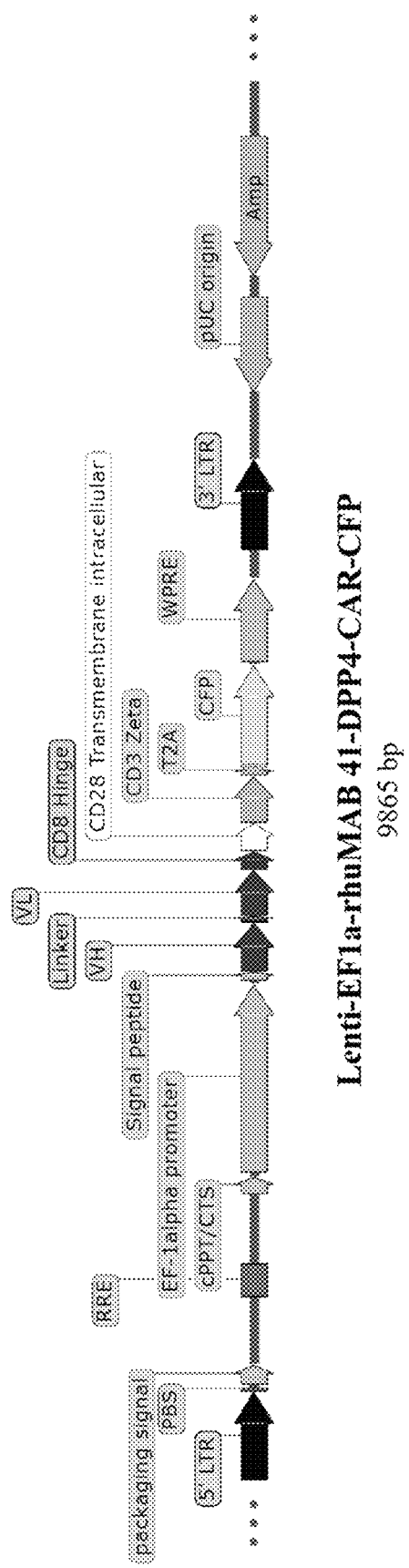
FIG. 1—'The structure of CAR vector'—is a schema illustrating the construction of the full-length CAR expression cassette, subcloned into Lenti-EF1a-rhuMAB 41-VH-Linker-VL-CFPCART, pCDCAR1. The full length of chimeric antigen receptor was synthesized and subcloned into lentivirus vector. The insert was confirmed by Sanger sequencing and is schematically illustrated in the figure. This CAR vector was used in the CAR-T assays for the proof-of-concept experiments.

The full-length of chimeric antigen receptor was synthesized and subcloned into lentivirus vector. The insert was confirmed by Sanger sequencing. The structure of CAR vector is schematically illustrated in FIG. 1.

Lentiviral vectors, which were derived from immunodeficiency viruses, were used for their relatively high efficiency for T cell transduction and their ability of infection of the non-proliferating cells. A second generation of the packaging system was utilized to generate transduction-ready pseudoviral particles in HEK293T cells. The titer of the lentivirus particle was determined by qPCR and cell-based titration assay. The results of lentivirus titration showed that prepared virus stock was at a high titer of $3.27\times10^8$ TU/mL.

Primary Human T Lymphocytes Preparation and CAR-T Preparation

PBMC from a healthy human donor was stimulated with anti-CD3/CD28 magnetic beads and the T cells were isolated using magnetic cell separation system. To generate CAR-T cells, the lentivirus particles with DPP4-CAR coding gene were incubated with the T cells in the presence of polybrene. After T cell expansion, the CAR-T cells were used for in vitro cytotoxicity assays.

Target Cell Preparation

WI-38 target cells were obtained at population doubling 19 (PD19) and passaged until they stopped proliferating. They were further analyzed by FACS for the detection of their surface antigen DPP4 and by qRT-PCT for the detection of their relative DPP4 mRNA expression level.

Cellular senescence induced by DNA damage was also induced in GM21808 fibroblasts by adding etoposide, as previously described (Robles et al., 1999. *Biochem Pharmacol.* 58(4):675-685; Gey & Seeger, 2013. *Mech Ageing Dev.* 134(3-4):130-138). Untreated (control) and treated cells were further analyzed by qRT-PCT for the detection of their relative DPP4 mRNA expression level.

Natural Killer (NK) Cell Preparation

Effector cells (NK cells) were freshly prepared before the ADCC assay. By using EasySep™ Human NK Cell Isolation Kit (STEMCELL, Catalog:17955), NK cells were isolated from a healthy human donor and resuspended in RPMI 1640 medium at $5\times10^6$/mL.

ADCC Assay

The target cells (WI-38), i.e., the senescent cells and proliferating cells, were plated into a 24-well plate at $1\times10^5$ cell/well in 100 µL RPMI-1640 supplied with 5% FBS 24 hour and cultured overnight. On the day of the assay, anti-DPP4 antibody (rhuMAB 41) was added into each well at a final concentration of 0 µg/mL, 0.05 µg/mL, and 0.5 µg/mL. After 30 minutes of incubation at 37° C. with 5% $CO_2$, 100 µL NK cells ($5 \times 10^5$ cell/well) were added to each well at E/T=5:1. After incubation for 6 hours at 37° C. with 5% $CO_2$, the cells were stained with eBioscience™ Annexin V Apoptosis Detection Kit PE (Invitrogen, Catalog: 88-8102-74) with 7-AAD and analyzed by flow cytometry.

In Vitro CAR-T Activity Assay by FACS

In vitro analysis was used for evaluation of the targeting effect of DPP4-CAR-T. The target cells (WI-38 or GM21808), i.e., the senescent cells and proliferating cells, were plated into a 24-well plate at $1 \times 10^5$ cell/well in 100 µL RPMI-1640 supplied with 5% FBS and cultured overnight. On the day of the assay, effector cells ($5 \times 10^5$ cell/well) were added to each well at E/T=5:1. After incubation for 6 hours at 37° C. with 5% $CO_2$, the cells were stained with eBioscience™ Annexin V Apoptosis Detection Kit PE (Invitrogen, Catalog: 88-8102-74) with 7-AAD and analyzed by flow cytometry. The relative percentage was quantified by normalizing the results to control CAR-T.

Results

Assessment of Senescent State and DPP4 Levels in Target Cells

Figure 2:
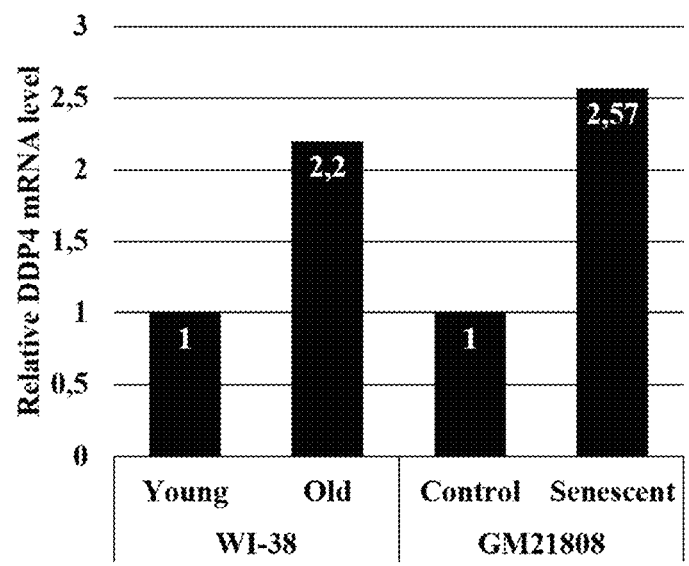
FIG. 2—'The assessment of senescent state and DPP4 levels in target cells'—is a graph showing the senescent state of WI-38 and GM21808 cells, confirmed by senescence associated β-galactosidase activity. Representative results of control versus senescent fibroblasts are shown. DPP4 levels of the cells were monitored by quantitative RT-PCR. Relative quantities of DPP4 in young WI-38 (low passage number: PDL<20) or old WI-38 (high passage number: PDL>50) and in GM21808 cells, untreated or cultured with DNA-damaging agent etoposide (adding etoposide every two days for fourteen days) were calculated. Fold-change, or relative quantity, of DPP4 in each sample was calculated relative to young WI-38 or untreated GM21808.

The senescent state of the cells was confirmed by senescence associated β-galactosidase activity. DPP4 levels were monitored by quantitative RT-PCR. FIG. 2 shows that DPP4 is expressed selectively in senescent cells, but not in proliferating human diploid fibroblasts or healthy foreskin fibroblasts.

ADCC Assay

In vitro Antibody-Dependent Cell-Mediated Cytotoxicity (ADCC) assays are common tools for immunotherapeutic drug discovery and biosimilar development. For this experiment, cytotoxicity is defined as apoptosis monitored by annexin-V positive and 7-ADD negative cells counted.

Figure 3:
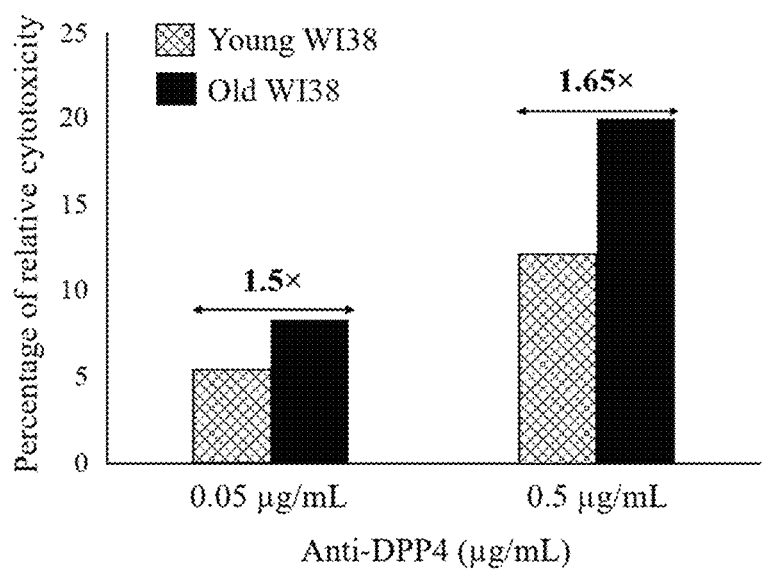
FIG. 3—'The ADCC Assay'—is a graph showing the relative toxicity in young and old fibroblast cells (WI-38 cells), using 0.05 μg/mL or 0.5 μg/ml of anti-DPP4 antibody.

Results of a standard ADCC assay are shown in FIG. 3. This experiment depicts a difference between young and old fibroblast cells at indicated antibody concentration as listed 1.5 and 1.65-fold, respectively.

Our results show that high abundance of DPP4 on the surface of senescent cells lead to a 1.5-fold selective elimination of senescent cells using anti-DPP4 antibody under optimal conditions.

DPP4-CAR-T Assay

Figure 4:
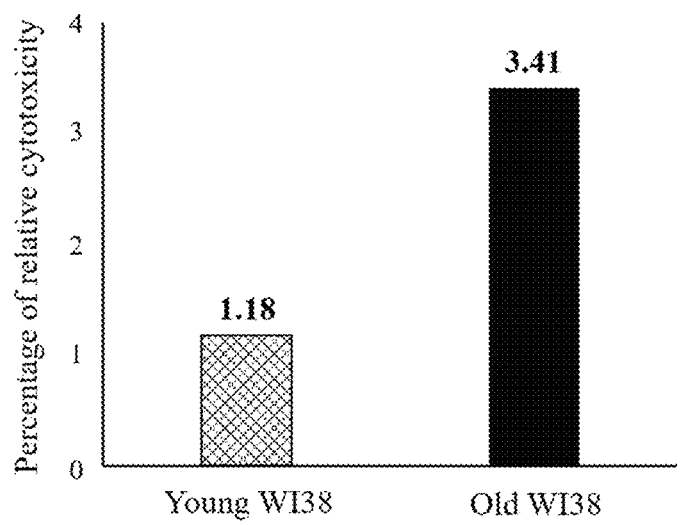
FIG. 4—'The CAR-T assay'—is a graph showing the results of selective elimination of senescent cells by engineered CAR-T against DPP4.
Figure 5:
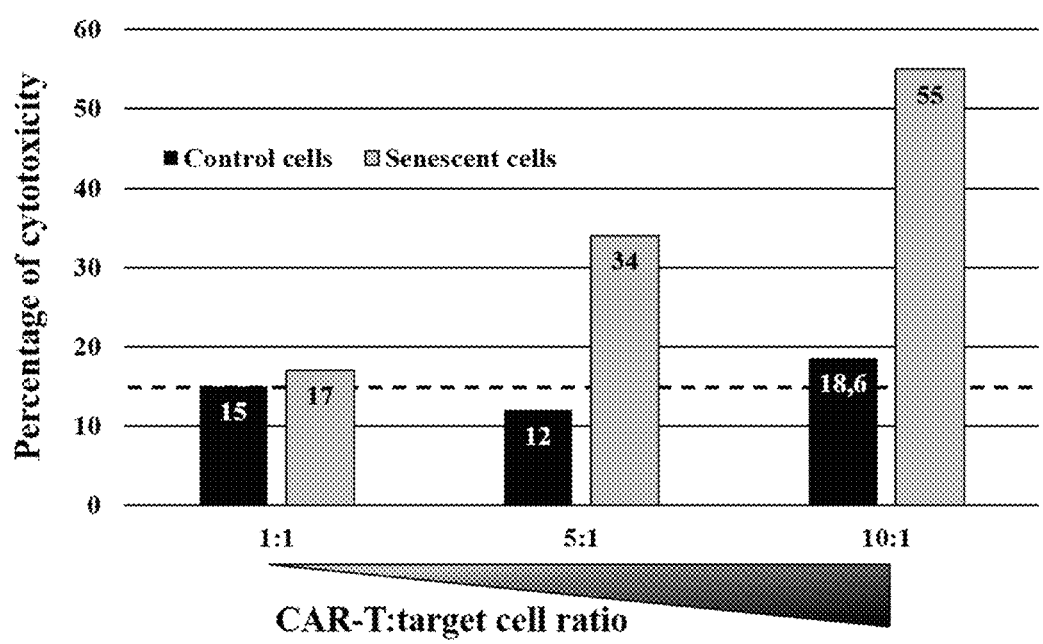
FIG. 5—'The quantification of experimental CAR-T assay results'—is a graph showing the results of the CAR-T assay on control (WI-38/GM21808) versus senescent cells. Cells were incubated with increasing ratios of CAR-T to target cells (1:1, 5:1 and 10:1).

When we used the same cells with control and DPP4-CAR-T cells, we observe a 3-fold selective elimination of old senescent cells with respect to the young ones. CAR-T cells engineered against DPP4 show high specificity against DPP4-bearing senescent cells (FIG. 4). The quantification of experimental results also shows that increasing CAR-T levels are only cytotoxic to senescent cells, but not to control cells (FIG. 5). This indicates that the CAR-T assay selectively eliminates target cells, i.e., senescent cells.

Conclusion

DPP4 is a novel senescent surface marker identified in human fibroblasts both in replicative and oncogene-induced (RAS) senescence. DPP4 is robustly upregulated on the plasma membrane of senescent cells.

DPP4 is expressed selectively in senescent cells, but not proliferating human diploid fibroblasts, making it a suitable target for senolytic therapy (FIG. 2). We showed that, upon two different senescent-inducing stimuli in two different types of fibroblasts, CAR-T cell therapy against DPP4 selectively eliminates DPP4-positive senescent cells (FIG. 5).

Example 2

Development of scFv Against Human DEP1

Materials
Rat Immunization and Splenectomy
"hDEP1 Peptide #1": amino acid residues 36-48 of SEQ ID NO: 1, conjugated to BSA
"hDEP1 Peptide #2": amino acid residues 436-452 of SEQ ID NO: 1, conjugated to BSA
"hDEP1 Peptide #3": amino acid residues 728-741 of SEQ ID NO: 1, conjugated to BSA
"hDEP1 Peptide #4": amino acid residues 864-881 of SEQ ID NO: 1, conjugated to BSA
"hDEP1-ECD-Fc": amino acid residues 621-969 of SEQ ID NO: 1 conjugated to an IgG1 Fc domain (SEQ ID NO: 2), produced recombinantly in CHO cells and purified on protein A resin
"hDEP1-ECD-His": amino acid residues 621-969 of SEQ ID NO: 1 conjugated to a 6× His tag through a linker (SEQ ID NO: 3), produced recombinantly in CHO cells and purified on Ni-NTA resin
BSA (NEB)
Freund's complete and incomplete adjuvants (Sigma, F5881 and F5506)
Standard ELISA material
Fc-specific polyclonal anti-rat immunoglobulin G (IgG) (Jackson 112-036-071; 1/5000)
RNA Extraction
RNAse AWAY (Molecular Bio-products, Cat. no 7002)
Tri reagent (Molecular research center Inc, Cat. no TR118)
BCP (Molecular research center Inc, Cat. no BP-ISI)
Isopropanol, ethanol 75% (molecular grade)
RT-PCR, Library Pre-Cloning
SuperScript Reverse Transcriptase (Invitrogen, Cat. no 18064-014)
Murine Primers set
Taq DNA polymerase, recombinant (Invitrogen, Cat. 10342-020)
pGemT Vector System (Promega, Cat. A3600)
Electroporation device and material
Electrocompetent Sure bacteria (*E. coli*) (Stratagene, Cat. 200227)
Nucleobond AX (Macherey-Nagel, Cat. 740 573-100)
Amplifying VH and VL
Red Taq (Sigma, Hamburg)+10× buffer
dNTP mix (10 mM each)
Oligonucleotide primer
Agarose (Serva, Heidelberg)
TAE-buffer 50× (2 M TrisHCl, 1 M acetic acid, 0.05 M EDTA pH 8)
Nucleospin Extract 2 Kit (Macherey-Nagel, Düren)
Cloning VH and VL
NotI, MluI, NcoI, HindIII (NEB)
Buffer 2, Buffer 3 (NEB)
BSA (NEB)
Calf intestine phosphatase (CIP) (MBI Fermentas, St. Leon-Rot)
T4 ligase (Promega, Mannheim)
3 M sodium acetate pH 5.2
*E. coli* XL1-Blue MRF (Stratagene, Amsterdam), genotype: Δ(mcrA)183 Δ(mcrCB-hsdSMR-mrr)173 endA1 supE44 thi-1 recA1 gyrA96 relA1 lac [F′ proAB lacIqZΔM15 Tn10 (Tetr)]
Electroporator MicroPulser (BIO-RAD, München)
2 M glucose (sterile filtered)
2 M magnesium solution (1 M MgCl, 1 M MgSO4)
SOC medium pH 7.0 (2% w/v tryptone, 0.5% w/v yeast extract, 0.05% w/v NaCl, 20 mM Mg solution, 20 mM glucose)
2×YT-medium pH 7.0 (1.6% w/v tryptone, 1% w/v yeast extract, 0.5% w/v NaCl)
2×YT-GAT (2×YT+100 mM glucose+100 μg/mL ampiciline+20 μg/mL tetracycline)
Ampiciline (100 mg/mL stock)
Tetracycline (10 mg/mL stock)
9 cm-Petrie dishes
25 cm-square Petri dishes ("pizza plates")
2×YT-GAT agar plates (2×YT-GAT, 1.5% w/v agar-agar)
Nucleobond Plasmid Midi Kit (Macherey-Nagel)
Glycerol 99.5% (Roth, Karlsruhe)
Library Packaging
2×YT-medium pH 7.0 (1.6% w/v tryptone, 1% w/v yeast extract, 0.5% w/v NaCl)
2×TY-GA (2×TY, 100 mM glucose, 100 μg/mL ampicillin)
M13K07 Helperphage for monovalent display (Stratagene)
2× TY-AK (2× TY+100 μg/mL ampicillin+50 μg/mL kanamycin)
Sorval Centrifuge RCSB Plus, rotor GS3 and SS34 (Thermo Scientific, Waltham)
Polyethylenglycol (PEG) solution (20% w/v PEG 6000, 2.5 M NaCl)
Phage dilution buffer (10 mM Tris-HCl pH 7.5, 20 mM NaCl, 2 mM EDTA)
Library Screening
Microtiter plate (Nunc Maxisorp)
3% BSA in TBS (50 mM Tris; 137 mM NaCl; 2.7 mM KCl; pH adjusted to 8.0)
TBS supplemented with 0.1% Tween20
E. coli (SURE strain, Stratagene)
SB (super broth) supplemented with tetracycline (10 μg/mL) and carbenicillin (50 μg/mL).
SB supplemented with tetracycline (10 μg/mL), carbenicillin (50 μg/mL) and kanamycin (70 μg/mL)
Polyethylenglycol (PEG) solution (20% w/v PEG 6000, 2.5 M NaCl)
Sorval Centrifuge RCSB Plus, rotor GS3 and SS34 (Thermo Scientific, Waltham)
scFv Production and Purification
E. coli strain HB2151
SB (super broth) supplemented with carbenicillin (50 μg/mL) and 1% glucose
1 mM IPTG
Polymyxin B sulfate
His-Trap column (GE Healthcare, Buckinghamshire, UK)
Methods
Rat Immunization
12 rats were immunized with i.p. injections of 50 μg of hDEP1 Peptide #1, Peptide #2, Peptide #3 or Peptide #4 (3 rats/peptide). In parallel, 5 rats were immunized with i.p. injections of 50 μg of hDEP1-ECD-Fc.

The three first injections were administered at 14 days intervals (D0, D14 and D28). A fourth injection was administered after animal selection according to the titer reached.

The first injection at D0 was mixed with complete Freund's adjuvant. The remaining injections were carried out with incomplete Freund's adjuvant.

The rat immune response was evaluated by ELISA performed in 96-well microtiter plates using hDEP1 Peptide #1, Peptide #2, Peptide #3, Peptide #4, hDEP1-ECD-His, or BSA. Pre-immune serum was used as a negative control. For detection, Fc-specific polyclonal anti-rat IgG was used and the titer was measured as the reciprocal of the highest dilution of immune serum giving a signal at 50% of the highest OD.

RNA Extraction, RT-PCR, Library Pre-Cloning

After the fourth injection, RNA was isolated with Tri Reagent/BCP method from the spleen of the immunized rats and used for reverse transcription. Oligonucleotides sets were used for amplification of the DNA encoding the κ and λ light chain and to amplify the DNA encoding Fd fragments of the heavy γ chain. To obtain two sub-libraries encoding the Fd fragment and light chain, the corresponding PCR products were pooled and sub-cloned into the pGEMT vector.

Library Construction

The final library was constructed starting from these two sub-libraries. The DNA encoding the Fd fragment and the light chain was re-amplified with two individual oligonucleotide sets introducing the required restrictions sites for library-cloning using the pTH1 vector. First the pTH1 vector and the VL-amplified repertoire were digested with MluI and NotI. Afterwards, the enzyme reaction was terminated and the vector was dephosphorylated with calf intestinal phosphatase. The vector and the VL-repertoire were purified using NucleoSpinII Gel and PCR Clean-up Kit (Macherey-Nagel) and 270 ng of the VL-repertoire was cloned into 1 μg of dephosphorylated vector using T4 DNA-ligase. The pellet was washed twice with 70% ethanol and resuspended in 30 μL H$_2$O before it was used for electroporation (1.7 kV) with 25 μL of XL1-BlueMRF'. The transformed bacteria were cultured on 2×YT agar plates supplemented with 100 μg/mL ampicillin, 20 μg/mL tetracycline and 100 mM glucose. The colonies were harvested by resuspension in 40 mL of 2×YT medium with a Drigalsky spatula and plasmids were isolated with the Nucleobond Plasmid Midi Kit. Following this, the VL-library and the VH-repertoire were digested with SfiI and HindIII, ligated and electroporated as described for VL, but this time 250 ng of the digested and purified VH-repertoire was inserted into 1 μg of the VL-library. The harvested bacteria of the final scFv antibody gene library were pooled, aliquoted and stored at −80° C. The library was packaged with M13K07.

Library Packaging

To package the library, inoculate 400 mL 2× TY-GA in a 1 L Erlenmeyer flask with 1 mL antibody gene library stock and then infect 25 mL bacteria culture (~1.25×10$^{10}$ cells) with 2.5×10$^{11}$ colony forming units (cfu) of the helper phage M13K07.

Produce scFv-phage overnight at 250 rpm and 30° C. Pellet the bacteria by centrifugation for 10 minutes at 10000 g. Precipitate the phage from the supernatant by adding ⅕ volume PEG solution. Incubate for 1 hour at 4° C. with gentle shaking, followed by centrifugation for 1 hour at 10000 g. Discard the supernatant, resolve each pellet in 10 mL phage dilution buffer and add ⅕ volume PEG solution. Incubate on ice for 20 minutes and pellet the phage by centrifugation for 30 minutes at 10000 g. Discard the supernatant and put the open tubes upside down on tissue paper. Let the viscous PEG solution move out completely. Resuspend the phage pellet in 1 mL phage dilution buffer.

Library Screening

For isolation of anti-DEP1 specific scFv, microtiter plates were coated overnight with hDEP1-ECD-His or Peptide #4 at 10 µg/mL in PBS at 4° C. The plates were then blocked with 3% BSA in TBS for 2 hours at 37° C. After a washing step, the antibody phage display library was added and incubated for an additional 2 hours at 37° C.

During the first round of panning, the plates were washed 5 times with TBS supplemented with 0.1% Tween20. The plates were finally rinsed with sterile PBS and phage were eluted with trypsin (1 mg/mL in TBS) for 30 minutes at 37° C. The eluted phages were used to infect E. coli cultured in SB supplemented with tetracycline and carbenicillin.

For the production of new phage particles, infected E. coli were co-infected with M13K07 and cultured overnight at 37° C. in SB supplemented with tetracycline, carbenicillin and kanamycin. Phage particles were precipitated in PEG/NaCl (4% w/v PEG8000, 3% w/v NaCl) and used for the next round of panning. This was performed as described above, with the exception that the plates were washed with increasing stringency.

The infected E. coli of the last round of panning were grown on SB media in petri dishes and used for screening by ELISA using hDEP1-ECD-His or Peptide #4.

scFv Production and Purification

For expression of soluble scFv, the DNA encoding the selected scFv was used to transform the non-suppressor E. coli strain HB2151. Transformed E. coli were then used to inoculate 500 mL of SB medium and cultivated at 30° C. until $OD_{600} \approx 1.5$. Then, 1 mM IPTG was added to induce the expression of scFv and the culture was incubated overnight at 22° C. After harvesting by centrifugation at 2500 g for 15 minutes at 4° C., scFv were extracted with polymyxin B sulfate and purified using a His-Trap column according to the manufacturer's instructions. Purified scFv were quantified by $OD_{280}$ and controlled by SDS-PAGE analysis.

Confirmation of Selected scFv by ELISA Against Screening Peptide

The soluble anti-DEP1 scFv were tested in indirect ELISA for reactivities against the 4 peptides (Peptide #1, Peptide #2, Peptide #3, and Peptide #4), against hDEP1-ECD-His and its murine counterpart with SEQ ID NO: 4; and against BSA as negative control. Reactivity was assessed by $OD_{450}$, in serial dilutions.

Results

Serum of the 17 rats was collected on D38 (after the third immunization, on D28) and Fc-specific polyclonal anti-rat IgG was used to measure the titer at 50% of maximum signal. Results are given in Table 5.

TABLE 5

| | | hDEP1 Peptide #1 | hDEP1 Peptide #2 | hDEP1 Peptide #3 | hDEP1 Peptide #4 | hDEP1-ECD-His | BSA |
|---|---|---|---|---|---|---|---|
| hDEP1 Peptide #1 | Rat 1 | 380000 | ND | ND | ND | ND | ND |
| | Rat 2 | 55000 | ND | ND | ND | ND | ND |
| | Rat 3 | 11000 | ND | ND | ND | ND | ND |
| hDEP1 Peptide #2 | Rat 4 | ND | 27000 | ND | ND | ND | ND |
| | Rat 5 | ND | 23000 | ND | ND | ND | ND |
| | Rat 6 (dead) | ND | 170000 | ND | ND | ND | ND |
| hDEP1 Peptide #3 | Rat 7 | ND | ND | 12000 | ND | 500 | ND |
| | Rat 8 | ND | ND | 18000 | ND | 500 | ND |
| | Rat 9 | ND | ND | 22000 | ND | 500 | ND |
| hDEP1 Peptide #4 | Rat 10 | ND | ND | ND | 113000 | 6000 | ND |
| | Rat 11 | ND | ND | ND | 110000 | 4500 | ND |
| | Rat 12 | ND | ND | ND | 113000 | 5000 | 500 |
| hDEP1-ECD-Fc | Rat 13 | 500 | 500 | 500 | ND | 321000 | ND |
| | Rat 14 | ND | ND | 500 | ND | 64000 | 500 |
| | Rat 15 | ND | ND | 500 | ND | 180000 | 500 |
| | Rat 16 | 500 | 500 | 500 | 500 | 82000 | ND |
| | Rat 17 | ND | ND | 500 | ND | 40000 | ND |

High titers were harvested against each immunogenic peptide.

Peptides #1 and #4 appeared to be more immunogenic than Peptides #2 and #3, allowing better immune responses. Rats immunized with Peptide #4 also presented a positive immune response for the recombinant hDEP1-ECD-His protein, while rats immunized with Peptides #1 and #2 did not present such positive immune response. Overall, rat 10 seemed to be the best candidate among rats 1 to 12.

High titers were also harvested against the recombinant protein hDEP1-ECD-His, ranging from ¹⁄₄₀₀₀₀ to ¹⁄₃₂₁₀₀₀. Overall, rat 13 seemed to be the best candidate among rats 13 to 17.

A splenectomy was carried out on rats 10 and 13. RNA were extracted from the spleens, and total RNA was quantified (Table 6) and controlled on agarose gel (not shown).

TABLE 6

| Sample | Concentration (µg/mL) | $A_{260nm}$ | $A_{280nm}$ | $A_{260nm}/A_{280nm}$ | $A_{260nm}/A_{230nm}$ |
|---|---|---|---|---|---|
| Rat 10 | 2108.9 | 52.7 | 29.5 | 1.78 | 1.55 |
| Rat 13 | 2370.77 | 59.3 | 33.4 | 1.77 | 1.42 |

The first step of the library construction consisted of the VL fragments cloning in a phagemid vector, and then the VH fragments were inserted into the vector containing the VL repertoire. The vector format VH/VL-6×His-Flag was selected for constructions.

Rat 10

The final scFv library consisted of $1 \times 10^7$ independent clones with a full-size insert rate of 92% (by colony-PCR) and was finally packaged in M13K07 phage.

Figure 6:
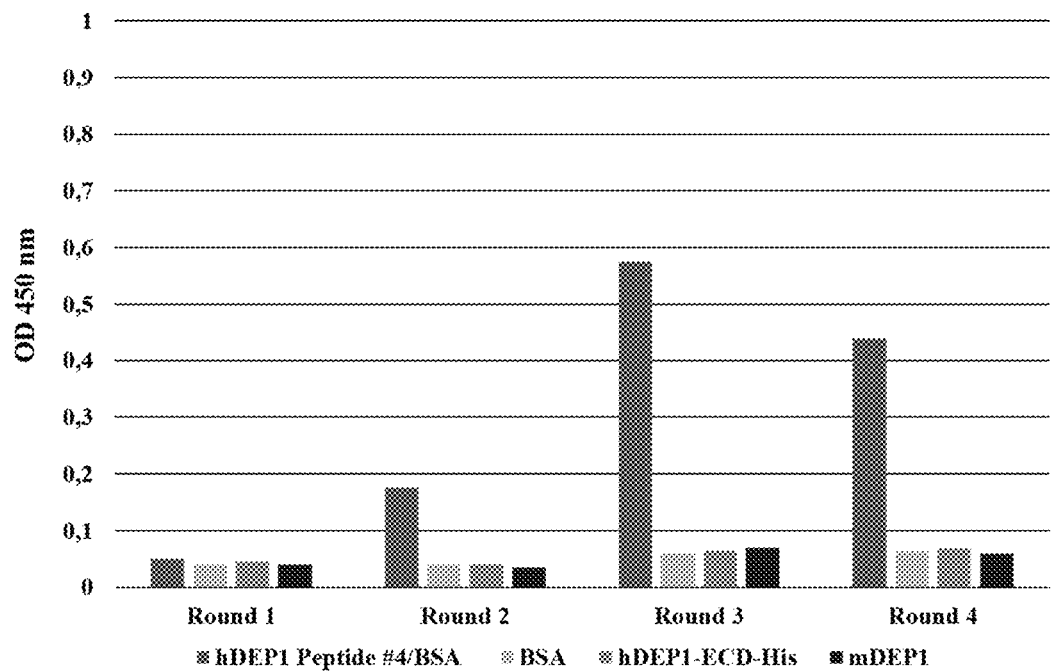
FIG. 6—'scFv library screening by phage display'—is a graph showing the panning using hDEP1 Peptide #4/BSA as target and standard elution strategy. Four rounds were carried out in order to isolate specific binders. The reactivity of phages eluted after each round against the targeted peptide was assessed in phage-ELISA.

The panning was performed using hDEP1 Peptide #4/BSA as target and standard elution strategy. Four rounds were carried out in order to isolate specific binders. After each round, only the phages having interacted with hDEP1 Peptide #4/BSA were eluted. Between the first and the last round of panning, the number of eluted phages increased, indicating that amplification/selection of reactive phages was expected from this panning. The reactivity of the phages eluted after each round against the targeted peptide was assessed in phage-ELISA and confirmed that potential binders were eluted in rounds 3 and 4 (FIG. 6).

96 isolated clones from the second, third and fourth rounds of panning were hand-picked and used to produce the respective soluble scFv in microtiter plate. Each clone was then tested in ELISA against hDEP1 Peptide #4/BSA.

48 isolated clones showing a specific signal against hDEP1 Peptide #4/BSA compared to negative control (BSA) were selected. Their DNA was extracted and sequenced. Sequences with an early stop codon or with an incorrect size were considered as recombined. The non-recombined sequences were aligned for redundancy analysis in order to identify the identical sequences (referred to as "redundant" sequences).

Twelve sequences corresponding to non-recombined and non-redundant scFv sequences were identified, grouped into two clusters (Table 7).

TABLE 7

HCVR and LCVR column indicate the amino acid sequence of the heavy chain and light chain variable regions, respectively.

| Cluster | Clone's name | Redundancy | HCVR | LCVR |
|---|---|---|---|---|
| Cluster 1 | 5738-10-R3A-C6 | 2 | 56 | 76 |
| | 5738-10-R3A-D8 | 1 | 59 | 79 |

TABLE 7-continued

HCVR and LCVR column indicate the amino acid sequence of
the heavy chain and light chain variable regions, respectively.

| Cluster | Clone's name | Redundancy | HCVR | LCVR |
|---|---|---|---|---|
| Cluster 2 | 5738-10-R3A-B2 | 1 | 55 | 75 |
| | 5738-10-R3A-D1 | 1 | 57 | 77 |
| | 5738-10-R3A-D5 | 1 | 58 | 78 |
| | 5738-10-R3A-D11 | 3 | 60 | 80 |
| | 5738-10-R4A-E7 | 1 | 61 | 81 |
| | 5738-10-R4A-E9 | 1 | 60 | 82 |
| | 5738-10-R4A-F12 | 5 | 62 | 83 |
| | 5738-10-R4A-G4 | 2 | 63 | 84 |
| | 5738-10-R4A-G11 | 7 | 64 | 85 |
| | 5738-10-R4A-G12 | 18 | 65 | 86 |

According to sequence and redundancy analysis, the following clones were selected:

5738-10-R3A-C6 (cluster 1)

5738-10-R3A-D5 (cluster 2)

5738-10-R4A-G12 (cluster 2)

After transformation of the 3 selected clones DNA in an E. coli strain dedicated to production, the clones were expressed as soluble scFv and purified using the His tag on an Ni-NTA column. These soluble anti-hDEP1 scFv were tested in indirect ELISA for reactivities against the 4 peptides and DEP1 proteins (human and murine) and against the negative control (BSA only).

All three scFv were reactive against hDEP1 Peptide #4, as expected, especially the two scFv of cluster 2. No reactivity could be observed against the 3 other peptides. Only clone 5738-10-R4A-G12 showed a reactivity against hDEP1, with no response for the mDEP1 or the negative control.

Rat 13

The final scFv library consisted of 1×10⁷ independent clones with a full-size insert rate of 88% (by colony-PCR) and was finally packaged in M13K07 phage.

Figure 7:
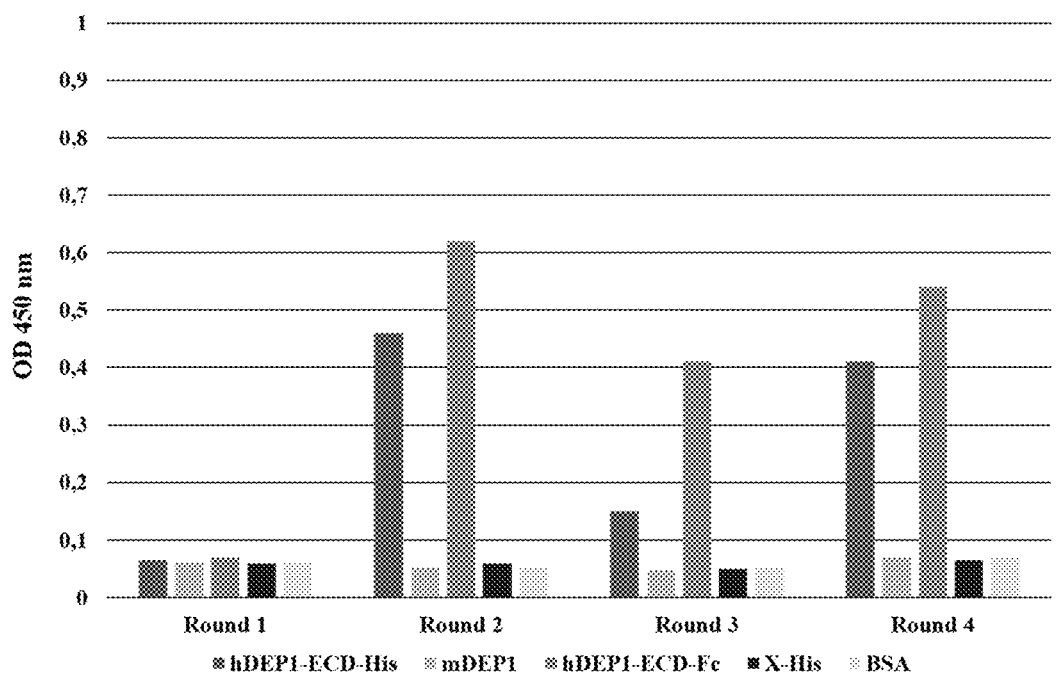
FIG. 7—'scFv library screening by phage display'—is a graph showing the panning using hDEP1-ECD-His as target and standard elution strategy. Four rounds were carried out in order to isolate specific binders. The reactivity of phages eluted after each round against the targeted peptide was assessed in phage-ELISA.

The panning was performed using hDEP1-ECD-His as target and standard elution strategy. Four rounds were carried out in order to isolate specific binders. After each round, only the phages having interacted with hDEP1-ECD-His were eluted. Between the first and the last round of panning, the number of eluted phages increased, indicating that amplification/selection of reactive phages was expected from this panning. The reactivity of the phages eluted after each round against the targeted peptide was assessed in phage-ELISA and confirmed that potential binders were eluted in rounds 2, 3 and 4 (FIG. 7).

96 isolated clones from the second, third and fourth rounds of panning were hand-picked and used to produce the respective soluble scFv in microtiter plate. Each clone was then tested in ELISA against hDEP1-ECD-His.

48 isolated clones showing a specific signal against hDEP1-ECD-His compared to negative control (BSA) were selected. Their DNA was extracted and sequenced. Sequences with an early stop codon or with an incorrect size were considered as recombined. The non-recombined sequences were aligned for redundancy analysis in order to identify the identical sequences (referred to as "redundant" sequences).

Nine sequences corresponding to non-recombined and non-redundant scFv sequences were identified, grouped into two clusters (Table 8).

TABLE 8

HCVR and LCVR column indicate the amino acid sequence of the
heavy chain and light chain variable regions, respectively.

| Cluster | Clone's name | Redundancy | HCVR | LCVR |
|---|---|---|---|---|
| Cluster 1 | 5738-13-R2A-C1 | 1 | 66 | 87 |
| | 5738-13-R4A-D11 | 1 | 68 | 89 |
| Cluster 2 | 5738-13-R2A-D3 | 1 | 67 | 88 |
| | 5738-13-R3A-F5 | 1 | 69 | 90 |
| | 5738-13-R4A-F11 | 1 | 70 | 91 |
| | 5738-13-R2A-H3 | 3 | 71 | 92 |
| | 5738-13-R2A-H4 | 21 | 72 | 93 |
| | 5738-13-R4A-H9 | 2 | 73 | 94 |
| | 5738-13-R4A-H11 | 15 | 74 | 94 |

According to sequence and redundancy analysis, the following clones were selected:

5738-13-R4A-D11 (cluster 1)

5738-13-R2A-H4 (cluster 2)

After transformation of the 2 selected clones DNA in an E. coli strain dedicated to production, the clones were expressed as soluble scFv and purified using the His tag on an Ni-NTA column. These soluble anti-hDEP1 scFv were tested in indirect ELISA for reactivities against the 4 peptides and DEP1 proteins (human and murine) and against the negative control (BSA only).

The two scFv were reactive against hDEP1, as expected. No reactivity could be observed against any of the 4 peptides, the mDEP1 or the negative control.

Example 3

Development of scFv Against Human DPP4

Materials
Rat Immunization and Splenectomy
"hDPP4 Peptide P2": amino acid residues 170-191 of SEQ ID NO: 101, conjugated to BSA
"hDPP4 Peptide P3": amino acid residues 235-254 of SEQ ID NO: 101, conjugated to BSA
"hDPP4 Peptide P5": amino acid residues 492-517 of SEQ ID NO: 101, conjugated to BSA
"hDPP4 Peptide P6": amino acid residues 533-551 of SEQ ID NO: 101, conjugated to BSA
"hDPP4-ECD-His": SEQ ID NO: 102
"mDPP4": murine DDP with SEQ ID NO: 103
BSA (NEB)
Freund's complete and incomplete adjuvants (Sigma, F5881 and F5506)
Standard ELISA material
Fc-specific polyclonal anti-rat immunoglobulin G (IgG) (Jackson 112-036-071; 1/5000)
RNA Extraction
RNAse AWAY (Molecular Bio-products, Cat. no 7002)
Tri reagent (Molecular research center Inc, Cat. no TR118)
BCP (Molecular research center Inc, Cat. no BP-ISI)
Isopropanol, ethanol 75% (molecular grade)
RT-PCR, Library Pre-Cloning
SuperScript Reverse Transcriptase (Invitrogen, Cat. no 18064-014)
Murine Primers set
Taq DNA polymerase, recombinant (Invitrogen, Cat. 10342-020)
pGemT Vector System (Promega, Cat. A3600)

Electroporation device and material
Electrocompetent Sure bacteria (*E. coli*) (Stratagene, Cat. 200227)
Nucleobond AX (Macherey-Nagel, Cat. 740 573-100)
Amplifying VH and VL
Red Taq (Sigma, Hamburg)+10× buffer
dNTP mix (10 mM each)
Oligonucleotide primer
Agarose (Serva, Heidelberg)
TAE-buffer 50× (2 M TrisHCl, 1 M acetic acid, 0.05 M EDTA pH 8)
Nucleospin Extract 2 Kit (Macherey-Nagel, Duren)
Cloning VH and VL
NotI, MluI, NcoI, HindIII (NEB)
Buffer 2, Buffer 3 (NEB)
BSA (NEB)
Calf intestine phosphatase (CIP) (MBI Fermentas, St. Leon-Rot)
T4 ligase (Promega, Mannheim)
3 M sodium acetate pH 5.2
*E. coli* XL1-Blue MRF (Stratagene, Amsterdam), genotype: Δ(mcrA)183 Δ(mcrCB-hsdSMR-mrr)173 endA1 supE44 thi-1 recA1 gyrA96 relA1 lac [F' proAB lacIqZΔM15 Tn10 (Tetr)]
Electroporator MicroPulser (BIO-RAD, München)
2 M glucose (sterile filtered)
2 M magnesium solution (1 M MgCl, 1 M MgSO4)
SOC medium pH 7.0 (2% w/v tryptone, 0.5% w/v yeast extract, 0.05% w/v NaCl, 20 mM Mg solution, 20 mM glucose)
2×YT-medium pH 7.0 (1.6% w/v tryptone, 1% w/v yeast extract, 0.5% w/v NaCl)
2×YT-GAT (2×YT+100 mM glucose+100 µg/mL ampiciline+20 µg/mL tetracycline)
Ampiciline (100 mg/mL stock)
Tetracycline (10 mg/mL stock)
9 cm-Petrie dishes
25 cm-square Petri dishes ("pizza plates")
2×YT-GAT agar plates (2×YT-GAT, 1.5% w/v agar-agar)
Nucleobond Plasmid Midi Kit (Macherey-Nagel)
Glycerol 99.5% (Roth, Karlsruhe)
Library Packaging
2×YT-medium pH 7.0 (1.6% w/v tryptone, 1% w/v yeast extract, 0.5% w/v NaCl)
2×TY-GA (2×TY, 100 mM glucose, 100 µg/mL ampicillin)
M13K07 Helperphage for monovalent display (Stratagene)
2×TY-AK (2×TY+100 µg/mL ampicillin+50 µg/mL kanamycin)
Sorval Centrifuge RCSB Plus, rotor GS3 and SS34 (Thermo Scientific, Waltham)
Polyethylenglycol (PEG) solution (20% w/v PEG 6000, 2.5 M NaCl)
Phage dilution buffer (10 mM Tris-HCl pH 7.5, 20 mM NaCl, 2 mM EDTA)
Library Screening
Microtiter plate (Nunc Maxisorp)
3% BSA in TBS (50 mM Tris; 137 mM NaCl; 2.7 mM KCl; pH adjusted to 8.0)
TBS supplemented with 0.1% Tween20
*E. coli* (SURE strain, Stratagene)
SB (super broth) supplemented with tetracycline (10 µg/mL) and carbenicillin (50 µg/mL).
SB supplemented with tetracycline (10 µg/mL), carbenicillin (50 µg/mL) and kanamycin (70 µg/mL)
Polyethylenglycol (PEG) solution (20% w/v PEG 6000, 2.5 M NaCl)
Sorval Centrifuge RCSB Plus, rotor GS3 and SS34 (Thermo Scientific, Waltham)
scFv Production and Purification
*E. coli* strain HB2151
SB (super broth) supplemented with carbenicillin (50 µg/mL) and 1% glucose
1 mM IPTG
Polymyxin B sulfate
His-Trap column (GE Healthcare, Buckinghamshire, UK)
Methods
Rat Immunization 12 rats were immunized with i.p. injections of 50 µg of hDDP4 Peptide P1, Peptide P3, Peptide P5 or Peptide P6 (3 rats/peptide). In parallel, 5 rats were immunized with i.p. injections of 50 µg of hDDP4-ECD-His.

The three first injections were administered at 14 days intervals (D0, D14 and D28). A fourth injection was administered after animal selection according to the titer reached.

The first injection at D0 was mixed with complete Freund's adjuvant. The remaining injections were carried out with incomplete Freund's adjuvant.

The rat immune response was evaluated by ELISA performed in 96-well microtiter plates using hDDP4 Peptide P1, Peptide P3, Peptide P5, Peptide P6, hDPP4-ECD-His, mDPP4, or BSA.

Pre-immune serum was used as a negative control. For detection, Fc-specific polyclonal anti-rat IgG was used and the titer was measured as the reciprocal of the highest dilution of immune serum giving a signal at 50% of the highest OD.

RNA Extraction, RT-PCR, Library Pre-Cloning

After the fourth injection, RNA was isolated with Tri Reagent/BCP method from the spleen of the immunized rats and used for reverse transcription. Oligonucleotides sets were used for amplification of the DNA encoding the κ and λ light chain and to amplify the DNA encoding Fd fragments of the heavy γ chain. To obtain two sub-libraries encoding the Fd fragment and light chain, the corresponding PCR products were pooled and sub-cloned into the pGEMT vector.

Library Construction

The final library was constructed starting from these two sub-libraries. The DNA encoding the Fd fragment and the light chain was re-amplified with two individual oligonucleotide sets introducing the required restrictions sites for library-cloning using the pTH1 vector. First the pTH1 vector and the VL-amplified repertoire were digested with MluI and NotI. Afterwards, the enzyme reaction was terminated and the vector was dephosphorylated with calf intestinal phosphatase. The vector and the VL-repertoire were purified using NucleoSpinII Gel and PCR Clean-up Kit (Macherey-Nagel) and 270 ng of the VL-repertoire was cloned into 1 µg of dephosphorylated vector using T4 DNA-ligase. The pellet was washed twice with 70% ethanol and resuspended in 30 µL H₂O before it was used for electroporation (1.7 kV) with 25 µL of XL1-BlueMRF'. The transformed bacteria were cultured on 2×YT agar plates supplemented with 100 µg/mL ampicillin, 20 µg/mL tetracycline and 100 mM glucose. The colonies were harvested by resuspension in 40 mL of 2×YT medium with a Drigalsky spatula and plasmids were isolated with the Nucleobond Plasmid Midi Kit. Following this, the VL-library and the VH-repertoire were digested with SfiI and HindIII, ligated and electroporated as described for VL, but this time 250 ng of the digested and purified VH-repertoire was inserted into 1 µg of the VL-library. The harvested bacteria of the final scFv antibody gene library were pooled, aliquoted and stored at −80° C. The library was packaged with M13K07.

Library Packaging

To package the library, inoculate 400 mL 2×TY-GA in a 1 L Erlenmeyer flask with 1 mL antibody gene library stock and then infect 25 mL bacteria culture (~1.25×10$^{10}$ cells) with 2.5×10$^{11}$ colony forming units (cfu) of the helper phage M13K07.

Produce scFv-phage overnight at 250 rpm and 30° C. Pellet the bacteria by centrifugation for 10 minutes at 10000 g. Precipitate the phage from the supernatant by adding ⅕ volume PEG solution. Incubate for 1 hour at 4° C. with gentle shaking, followed by centrifugation for 1 hour at 10000 g. Discard the supernatant, resolve each pellet in 10 mL phage dilution buffer and add ⅕ volume PEG solution. Incubate on ice for 20 minutes and pellet the phage by centrifugation for 30 minutes at 10000 g. Discard the supernatant and put the open tubes upside down on tissue paper. Let the viscous PEG solution move out completely. Resuspend the phage pellet in 1 mL phage dilution buffer.

Library Screening

For isolation of anti-DPP4 specific scFv, microtiter plates were coated overnight with hDPP4-ECD-His or Peptide P5 at 10 µg/mL in PBS at 4° C. The plates were then blocked with 3% BSA in TBS for 2 hours at 37° C. After a washing step, the antibody phage display library was added and incubated for an additional 2 hours at 37° C.

During the first round of panning, the plates were washed 5 times with TBS supplemented with 0.1% Tween20. The plates were finally rinsed with sterile PBS and phage were eluted with trypsin (1 mg/mL in TBS) for 30 minutes at 37° C. The eluted phages were used to infect *E. coli* cultured in SB supplemented with tetracycline and carbenicillin.

For the production of new phage particles, infected *E. coli* were co-infected with M13K07 and cultured overnight at 37° C. in SB supplemented with tetracycline, carbenicillin and kanamycin. Phage particles were precipitated in PEG/NaCl (4% w/v PEG8000, 3% w/v NaCl) and used for the next round of panning. This was performed as described above, with the exception that the plates were washed with increasing stringency.

The infected *E. coli* of the last round of panning were grown on SB media in petri dishes and used for screening by ELISA using hDPP4-ECD-His or Peptide P5.

scFv Production and Purification

For expression of soluble scFv, the DNA encoding the selected scFv was used to transform the non-suppressor *E. coli* strain HB2151. Transformed *E. coli* were then used to inoculate 500 mL of SB medium and cultivated at 30° C. until $OD_{600}\approx1.5$. Then, 1 mM IPTG was added to induce the expression of scFv and the culture was incubated overnight at 22° C. After harvesting by centrifugation at 2500 g for 15 minutes at 4° C., scFv were extracted with polymyxin B sulfate and purified using a His-Trap column according to the manufacturer's instructions. Purified scFv were quantified by $OD_{280}$ and controlled by SDS-PAGE analysis.

Confirmation of Selected scFv by ELISA Against Screening Peptide

The soluble anti-DPP4 scFv were tested in indirect ELISA for reactivities against the 4 peptides (Peptide P2, Peptide P3, Peptide P5, and Peptide P6), against hDPP4-ECD-His and its murine counterpart mDPP4 with SEQ ID NO: 103; and against BSA as negative control. Reactivity was assessed by $OD_{450}$, in serial dilutions.

Results

Serum of the 17 rats was collected on D38 (after the third immunization, on D28) and Fc-specific polyclonal anti-rat IgG was used to measure the titer at 50% of maximum signal. Results are given in Table 9.

TABLE 9

| | | hDEP4 Peptide P2 | hDEP4 Peptide P3 | hDEP4 Peptide P5 | hDEP4 Peptide P6 | hDEP4-ECD-His | mDPP4 |
|---|---|---|---|---|---|---|---|
| hDPP4 Peptide P2 | Rat 1 | 10045 | ND | ND | ND | 3663 | ND |
| | Rat 2 | 5023 | ND | ND | ND | <423 | ND |
| | Rat 3 | 3949 | <380 | ND | ND | 820 | ND |
| hDPP4 Peptide P3 | Rat 4 | ND | <1545 | ND | ND | <950 | <515 |
| | Rat 5 | ND | <1456 | ND | ND | 1423 | <606 |
| | Rat 6 | ND | <677 | ND | ND | <429 | ND |
| hDPP4 Peptide P5 | Rat 7 | ND | ND | 38114 | ND | <954 | <1238 |
| | Rat 8 | ND | ND | 54322 | ND | 2363 | <1591 |
| | Rat 9 | ND | ND | 6844 | ND | <532 | <584 |
| hDPP4 Peptide P6 | Rat 10 | ND | ND | ND | <634 | ND | ND |
| | Rat 11 | ND | ND | ND | <1252 | ND | ND |
| | Rat 12 | ND | ND | ND | 3183 | <506 | <578 |
| hDPP4-ECD-His | Rat 13 | ND | ND | <1887 | ND | 278332 | <1497 |
| | Rat 14 | ND | ND | <1503 | ND | 22112 | <468 |
| | Rat 15 | ND | <526 | 4592 | ND | 69570 | <708 |
| | Rat 16 | ND | <537 | 2737 | ND | 198247 | <1719 |
| | Rat 17 | ND | <763 | <647 | ND | 40687 | <1635 |

Relatively low titers were harvested against each immunogenic peptide. Peptide P5 however appeared to be more immunogenic than Peptides P2, P3 and P6, allowing better immune responses. Overall, rat 8 seemed to be the best candidate among rats 1 to 12.

High titers were harvested against the recombinant protein hDPP4-ECD-His, ranging from 1/22000 to 1/278000. Overall, rat 13 seemed to be the best candidate among rats 13 to 17.

A splenectomy was carried out on rats 8 and 13. RNA were extracted from the spleens, and total RNA was quantified (Table 10) and controlled on agarose gel (not shown).

TABLE 10

| Sample | Concentration (μg/mL) | $A_{260nm}$ | $A_{280nm}$ | $A_{260nm}/A_{280nm}$ | $A_{260nm}/A_{230nm}$ |
|---|---|---|---|---|---|
| Rat 8 | 2051 | 51.2 | 29.0 | 1.78 | 1.29 |
| Rat 13 | 2107 | 52.7 | 29.8 | 1.77 | 1.29 |

The first step of the library construction consisted of the VL fragments cloning in a phagemid vector, and then the VH fragments were inserted into the vector containing the VL repertoire. The vector format VH/VL-6× His-Flag was selected for constructions.

Rat 8

The final scFv library consisted of $5.2\times10^{7}$ independent clones with a full-size insert rate of 75% (by colony-PCR) and was finally packaged in M13K07 phage.

The panning was performed using hDPP4 Peptide P5/BSA as target and standard elution strategy. Six rounds were carried out in order to isolate specific binders. After each round, only the phages having interacted with hDPP4 Peptide P5/BSA were eluted. Between the first and the last round of panning, the number of eluted phages increased, indicating that amplification/selection of reactive phages was expected from this panning. The reactivity of the phages eluted after each round against the targeted peptide was assessed in phage-ELISA and confirmed that potential binders were eluted in rounds 4, 5 and 6.

96 isolated clones from the second, third and fourth rounds of panning were hand-picked and used to produce the respective soluble scFv in microtiter plate. Each clone was then tested in ELISA against hDPP4 Peptide P5/BSA.

48 isolated clones showing a specific signal against hDPP4 Peptide P5/BSA compared to negative control (BSA) were selected. Their DNA was extracted and sequenced. Sequences with an early stop codon or with an incorrect size were considered as recombined. The non-recombined sequences were aligned for redundancy analysis in order to identify the identical sequences (referred to as "redundant" sequences).

Nine sequences corresponding to non-recombined and non-redundant scFv sequences were identified, grouped into two clusters (Table 11).

TABLE 11

HCVR and LCVR column indicate the amino acid sequence of the heavy chain and light chain variable regions, respectively.

| Cluster | Clone's name | HCVR | LCVR |
|---|---|---|---|
| Cluster 1 | 5826-8-R6A-D12 | 176 | 204 |
|  | 5826-8-R6A-H11 | 176 | 208 |
| Cluster 2 | 5826-8-R6A-A10 | 174 | 202 |
|  | 5826-8-R6A-B11 | 175 | 203 |
|  | 5826-8-R6A-E10 | 177 | 205 |
|  | 5826-8-R5A-G6 | 178 | 203 |
|  | 5826-8-R5A-G8 | 179 | 206 |
|  | 5826-8-R6A-H9 | 180 | 207 |
|  | 5826-8-R6A-H12 | 181 | 209 |

According to sequence and redundancy analysis, the following clones were selected:
5826-8-R6A-H11 (cluster 1)
5826-8-R6A-E10 (cluster 2)
5826-8-R5A-G8 (cluster 2)

After transformation of the 3 selected clones DNA in an E. coli strain dedicated to production, the clones were expressed as soluble scFv and purified using the His tag on an Ni-NTA column. These soluble anti-hDPP4 scFv were tested in indirect ELISA for reactivities against the 4 peptides and DPP4 proteins (human and murine) and against the negative control (BSA only).

All three scFv were reactive against hDPP4 Peptide P5, as expected. No reactivity could be observed against the 3 other peptides, the DPP4 proteins (human or murine) or the negative control.

Rat 13

The final scFv library consisted of $4 \times 10^7$ independent clones with a full-size insert rate of 88% (by colony-PCR) and was finally packaged in M13K07 phage.

The panning was performed using hDPP4-ECD-His as target and standard elution strategy. Four rounds were carried out in order to isolate specific binders. After each round, only the phages having interacted with hDEP1-ECD-His were eluted. Between the first and the last round of panning, the number of eluted phages increased, indicating that amplification/selection of reactive phages was expected from this panning. The reactivity of the phages eluted after each round against the targeted peptide was assessed in phage-ELISA and confirmed that potential binders were eluted in rounds 2, 3 and 4.

96 isolated clones from the second, third and fourth rounds of panning were hand-picked and used to produce the respective soluble scFv in microtiter plate. Each clone was then tested in ELISA against hDPP4-ECD-His.

48 isolated clones showing a specific signal against hDPP4-ECD-His compared to negative control (BSA) were selected. Their DNA was extracted and sequenced. Sequences with an early stop codon or with an incorrect size were considered as recombined. The non-recombined sequences were aligned for redundancy analysis in order to identify the identical sequences (referred to as "redundant" sequences).

Twenty-one sequences corresponding to non-recombined and non-redundant scFv sequences were identified, grouped into three clusters (Table 12).

TABLE 12

HCVR and LCVR column indicate the amino acid sequence of the heavy chain and light chain variable regions, respectively.

| Cluster | Clone's name | HCVR | LCVR |
|---|---|---|---|
| Cluster 1 | 5826-13-R3A-A10 | 182 | 210 |
|  | 5826-13-R4A-E6 | 188 | 216 |
|  | 5826-13-R4A-H1 | 193 | 221 |
|  | 5826-13-R4A-H4 | 196 | 224 |
|  | 5826-13-R4A-H10 | 200 | 224 |
|  | 5826-13-R4A-H11 | 201 | 224 |
|  | 5826-13-R4A-H12 | 200 | 227 |
| Cluster 2 | 5826-13-R3A-D5 | 185 | 213 |
| Cluster 3 | 5826-13-R3A-B1 | 183 | 211 |
|  | 5826-13-R3A-B3 | 184 | 212 |
|  | 5826-13-R3A-D6 | 186 | 214 |
|  | 5826-13-R4A-E2 | 187 | 215 |
|  | 5826-13-R4A-E9 | 189 | 217 |
|  | 5826-13-R4A-F10 | 190 | 218 |
|  | 5826-13-R4A-G11 | 191 | 219 |
|  | 5826-13-R4A-G12 | 192 | 220 |
|  | 5826-13-R4A-H2 | 194 | 222 |
|  | 5826-13-R4A-H3 | 195 | 223 |
|  | 5826-13-R4A-H5 | 197 | 212 |
|  | 5826-13-R4A-H6 | 198 | 225 |
|  | 5826-13-R4A-H9 | 199 | 226 |

According to sequence and redundancy analysis, the following clones were selected:
5826-13-R4A-H12 (cluster 1)
5826-13-R3A-D5 (cluster 2)
5826-13-R4A-H5 (cluster 3)

After transformation of the 3 selected clones DNA in an E. coli strain dedicated to production, the clones were expressed as soluble scFv and purified using the His tag on an Ni-NTA column. These soluble anti-hDPP4 scFv were tested in indirect ELISA for reactivities against the 4 peptides and DPP4 proteins (human and murine) and against the negative control (BSA only).

The three scFv were reactive against hDPP4, as expected. No reactivity could be observed against any of the 4 peptides, the mDPP4 protein or the negative control.

Example 4

Antibody Screening in Fibroblasts

Material and Methods
Screening of scFv Against Human DPP4

WI-38 and GM21808 fibroblast cell lines and primary fibroblasts from healthy and diseased patients (COPD subjects—chronic obstructive pulmonary disease; and IPF subjects—idiopathic pulmonary fibrosis) were purchased from ethically sourced suppliers. GM21808 cells were treated with 20 μM etoposide and cultured for a further 15 days to instigate chemical-induced senescence, or left untreated. WI-38 is a diploid human cell line composed of fibroblasts derived from lung tissue and GM21808 is a healthy human foreskin fibroblast line. Senescence can be induced in both of these cell lines, by two different methods: replicative senescence via repeated passaging for WI-38 and damage-induced senescence via etoposide treatment for GM21808.

Cultures of expanding fibroblasts were gently detached using a cell scraper and harvested for staining with the following panel of anti-DPP4 antibodies:
commercial mAb (Creative Biolabs);
5826-13-R3A-D5, comprising a $V_H$-CDR1 with SEQ ID NO: 109, a $V_H$-CDR2 with SEQ ID NO: 122, a $V_H$-CDR3 with SEQ ID NO: 139, a $V_L$-CDR1 with SEQ ID NO: 148, a $V_L$-CDR2 with SEQ ID NO: 160 and a $V_L$-CDR3 with SEQ ID NO: 172; and
5826-13-R4A-H5, comprising a $V_H$-CDR1 with SEQ ID NO: 108, a $V_H$-CDR2 with SEQ ID NO: 127, a $V_H$-CDR3 with SEQ ID NO: 138, a $V_L$-CDR1 with SEQ ID NO: 147, a $V_L$-CDR2 with SEQ ID NO: 159 and a $V_L$-CDR3 with SEQ ID NO: 171.

Briefly, cells were incubated with a fixable viability dye (eF780, eBioscience) in a protein-free solution at 4° C. for 15 minutes. Samples were then washed once before addition of Fc block (Miltenyi Biotec) for 5 minutes at 4° C. Each test antibody or ScFV recognizing DPP4 was then added (0.5 μg per test) and staining was performed for 30 minutes at 4° C. Samples were then washed and stained with a secondary anti-human-PE antibody (Biolegend) for the monoclonal antibody, or with an anti-6× His tag PE antibody (R&D systems) for 5826-13-R3A-D5 and 5826-13-R4A-H5.

At the end of the incubation, cells were washed and fixed with 1% PFA before analysis using a BD LSR-Fortessa cytometer (Becton Dickinson). Data was analyzed using FlowJo software (Treestar) and was presented as percentage binding of anti-DPP4 antibody versus binding of secondary antibody.

Screening of scFv Against Human DEPT

WI-38 and GM21808 fibroblast cell lines and primary fibroblasts from healthy and diseased patients (COPD subjects—chronic obstructive pulmonary disease; and IPF subjects—idiopathic pulmonary fibrosis) were purchased from ethically sourced suppliers. GM21808 cells were treated with 20 μM etoposide and cultured for a further 15 days to instigate chemical-induced senescence, or left untreated. WI-38 is a diploid human cell line composed of fibroblasts derived from lung tissue and GM21808 is a healthy human foreskin fibroblast line. Senescence can be induced in both of these cell lines, by two different methods: replicative senescence via repeated passaging for WI-38 and damage-induced senescence via etoposide treatment for GM21808.

Cultures of expanding fibroblasts were gently detached using a cell scraper and harvested for staining with the following panel of anti-DEP1 antibodies:
commercial mAb (AbCam);
5738-10-R3A-D5, comprising a $V_H$-CDR1 with SEQ ID NO: 5, a $V_H$-CDR2 with SEQ ID NO: 12, a $V_H$-CDR3 with SEQ ID NO: 29, a $V_L$-CDR1 with SEQ ID NO: 33, a $V_L$-CDR2 with SEQ ID NO: 40 and a $V_L$-CDR3 with SEQ ID NO: 49;
5738-13-R4A-D11, comprising a $V_H$-CDR1 with SEQ ID NO: 10, a $V_H$-CDR2 with SEQ ID NO: 21, a $V_H$-CDR3 with SEQ ID NO: 30, a $V_L$-CDR1 with SEQ ID NO: 37, a $V_L$-CDR2 with SEQ ID NO: 44 and a $V_L$-CDR3 with SEQ ID NO: 53; and
5738-13-R2A-H4, comprising a $V_H$-CDR1 with SEQ ID NO: 11, a $V_H$-CDR2 with SEQ ID NO: 25, a $V_H$-CDR3 with SEQ ID NO: 32, a $V_L$-CDR1 with SEQ ID NO: 38, a $V_L$-CDR2 with SEQ ID NO: 46 and a $V_L$-CDR3 with SEQ ID NO: 52.

Briefly, cells were incubated with a fixable viability dye (eF780, eBioscience) in a protein-free solution at 4° C. for 15 minutes. Samples were then washed once before addition of Fc block (Miltenyi Biotec) for 5 minutes at 4° C. Each test antibody or ScFV recognizing DEP1 was then added (0.5 μg per test) and staining was performed for 30 minutes at 4° C. Samples were then washed and stained with a secondary anti-human-PE antibody (Biolegend) for the monoclonal antibody, or with an anti-6× His tag PE antibody (R&D systems) for 5738-10-R3A-D5, 5738-13-R4A-D11 and 5738-13-R2A-H4.

At the end of the incubation, cells were washed and fixed with 1% PFA before analysis using a BD LSR-Fortessa cytometer (Becton Dickinson). Data was analyzed using FlowJo software (Treestar) and was presented as percentage binding of anti-DEP1 antibody versus binding of secondary antibody.

Results

Both DPP4 and DEP1 are Specifically Increased in Lung Fibrosis Cells

Figure 8:
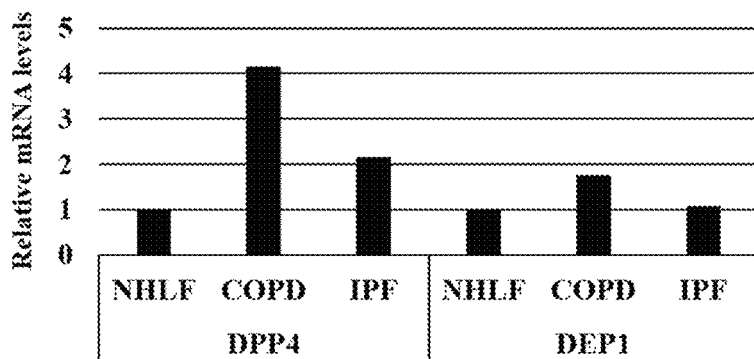
FIG. 8—'DPP4 and DEP1 mRNA levels in normal and diseased primary human lung fibroblasts'—is a graph showing the relative quantity of DPP4 and DEP-1 in normal and diseased human lung fibroblasts. Expression levels in NHLF (normal human lung fibroblast), idiopathic pulmonary fibroblast (IPF) and chronic obstructive pulmonary disease (COPD) human fibroblast cells were calculated relative to NHLF.

As seen in FIG. 8, DPP4, but also DEP1, another novel surface antigen, are specifically increased in lung fibrosis cells with respect to normal lung cells.

DPP4/DEP1 Staining in Fibroblasts

Figure 9A:
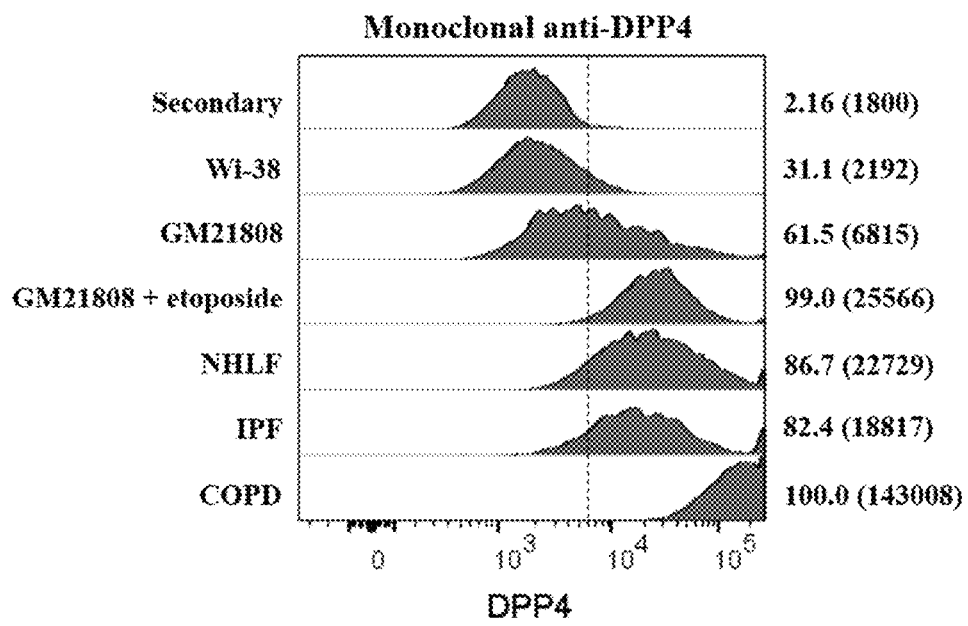
FIGS. 9A-C—'DPP4 staining in fibroblasts' are three graphs showing the staining of various primary human fibroblasts and different senescence-stressors in terms of DPP4 surface antigen presentation in target senescent cells versus normal/young cells. The data also include normal human cells versus human lung fibrosis disease cells. WI-38 (PDL<20), GM21808 (±etoposide), normal human lung fibroblast (NHLF), idiopathic pulmonary fibroblast (IPF) and chronic obstructive pulmonary disease (COPD) human fibroblast cells were stained with anti-DPP4 antibodies or scFv. Control staining comprising secondary antibody only was included for all cell types, but only the control staining for NHLF cells is shown for illustration. Percentage of positive cells is indicated on the right side, with MFI indicated in parenthesis.
Figure 9B:
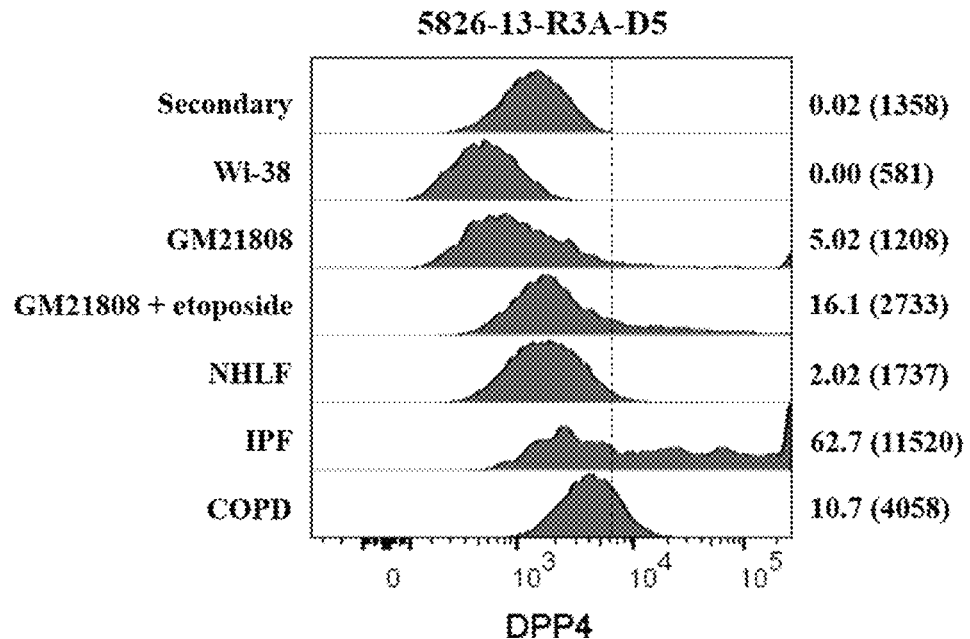
Figure 9C:
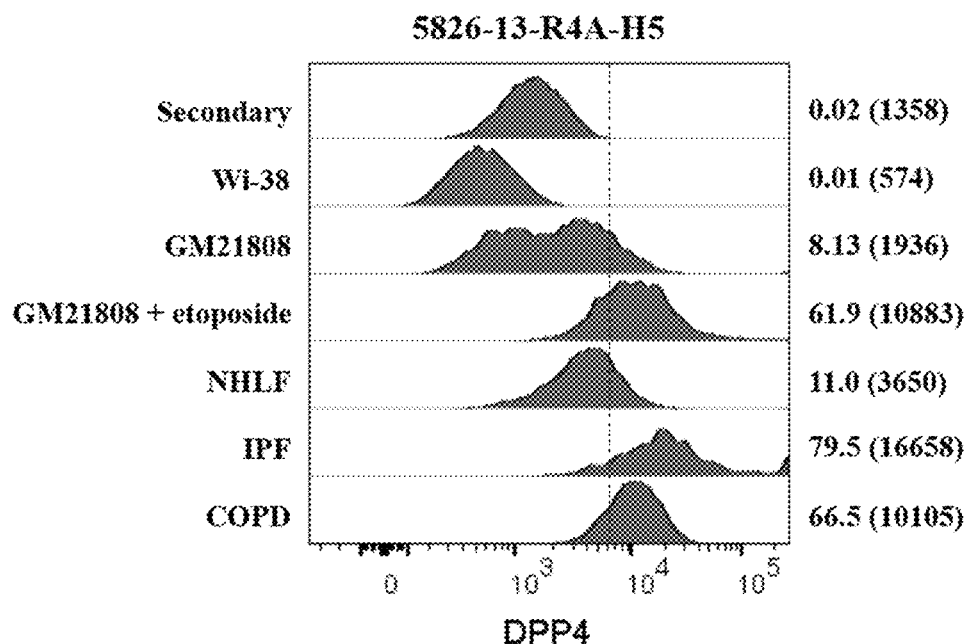
Figure 10A:
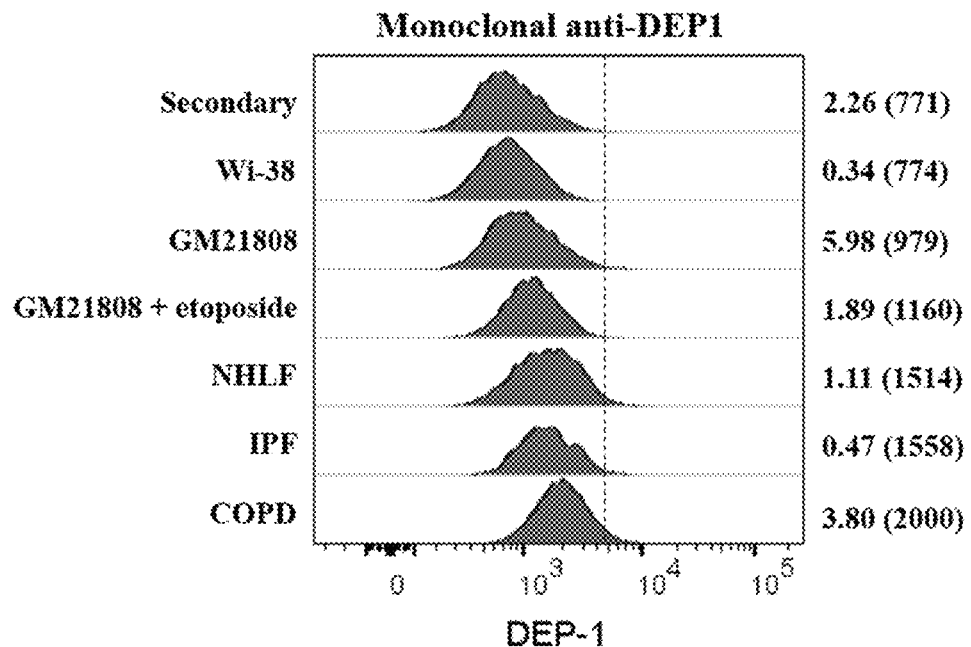
FIGS. 10A-D—'DEPT staining in fibroblasts' are four graphs showing the staining of various primary human fibroblasts and different senescence-stressors in terms of DEP1 surface antigen presentation in target senescent cells versus normal/young cells. The data also include normal human cells versus human lung fibrosis disease cells. WI-38 (PDL<20), GM21808 (±etoposide), normal human lung fibroblast (NHLF), idiopathic pulmonary fibroblast (IPF) and chronic obstructive pulmonary disease (COPD) human fibroblast cells were stained with anti-DEP1 antibodies or scFv. Control staining comprising secondary antibody only was included for all cell types, but only the control staining for NHLF cells is shown for illustration. Percentage of positive cells is indicated on the right side, with MFI indicated in parenthesis.
Figure 10B:
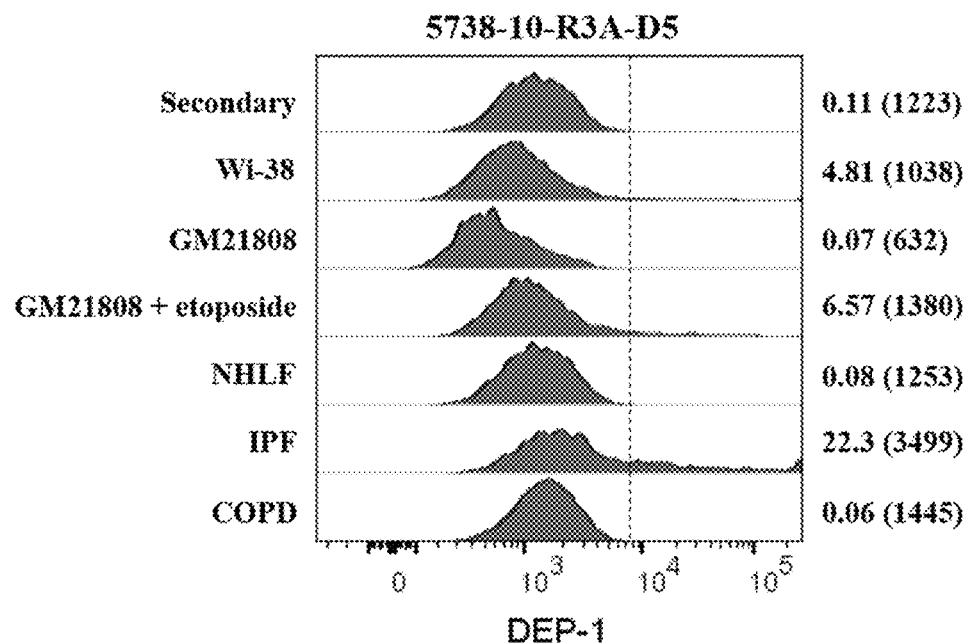
Figure 10C:
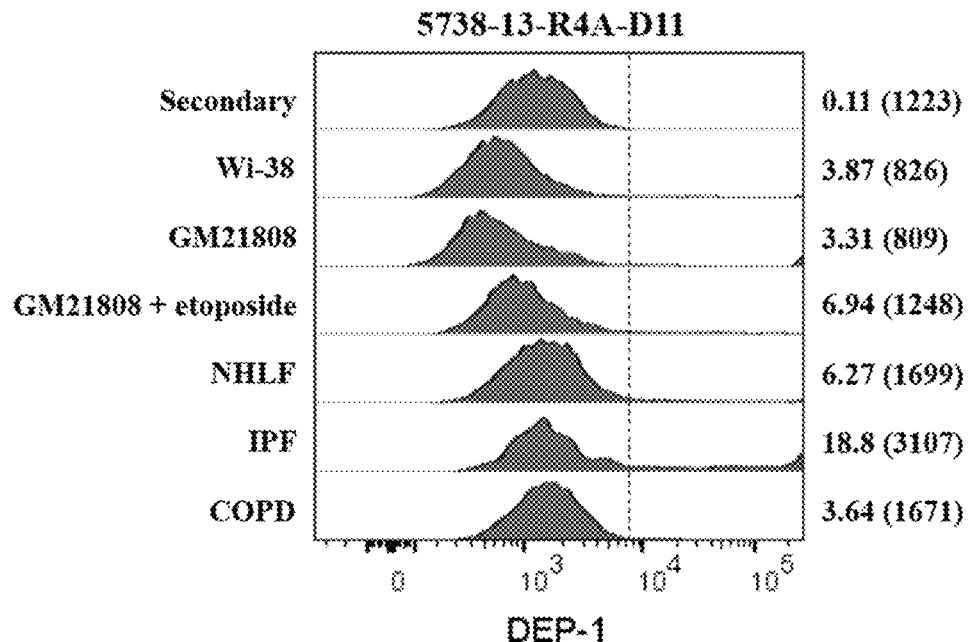
Figure 10D:
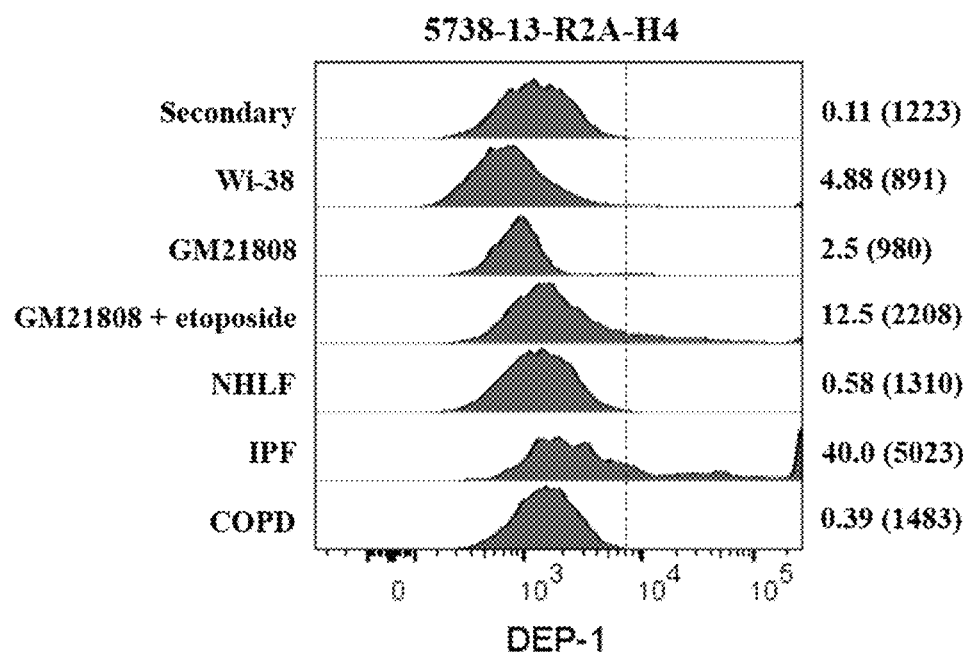

The anti-DPP4 scFv described herein detect the DPP4 surface antigen in both disease human lung fibroblasts cells (COPD and IPF) with less background than the commercial antibody (see for comparison, staining in young WI-38, untreated GM21808 and NHLF cells) (FIGS. 9A to 9C).

The anti-DEP1 scFv described herein also performed substantially better at detecting the DEP1 surface antigen in disease human lung fibroblasts cells than the commercial antibody (FIGS. 10A to 10D).

Conclusion

Fibroblasts are key effector cells in the progression of fibrotic diseases. CAR-T cell-based immunotherapy approach using specific surface markers to target senescent cells in lung fibrosis disease state has a significant potential for the exploration of novel anti-fibrotic strategies.

Example 5

Analysis of DPP4 and DEP1 Expression by qPCR

Material and Methods

Analysis of DPP4 Expression by qPCR

WI-38 and GM21808 fibroblast cell lines and primary fibroblasts from healthy and diseased patients (COPD subjects—chronic obstructive pulmonary disease; and IPF subjects—idiopathic pulmonary fibrosis) were purchased from ethically sourced suppliers. GM21808 cells were treated with 20 μM etoposide and cultured for a further 15 days to instigate chemical-induced senescence, or left untreated.

RNA was isolated using a RNeasy plus kit (Qiagen) following manufacturer's instructions. RNA was quantified using a NanoDrop One (Thermofisher Scientific) by measuring absorbance at 260 nm. 100-500 ng of RNA was reversed-transcribed using QuantiTect Reverse Transcription kit (Qiagen) in a final reaction volume of 20 μL following manufacturer's instructions.

Gene expression of DPP4 in each cell type was determined by qPCR using a SYBR green assay. Briefly, 10 ng cDNA (5 μl) from each cell type was mixed in a BrightWhite qPCR 96-well plate with 15 μL master mix containing PrecisionFAST SYBR master mix (PrimerDesign), DPP4 SYBR green forward and reverse primers (300 nM each; Integrated DNA technologies) and PCR water.

Expression of GAPDH was also assessed as a housekeeping gene using a TaqMan assay. Briefly, 10 ng cDNA (5 μL)

from each cell type was mixed in a BrightWhite qPCR 96-well plate with 15 µL master mix containing TaqMan Fast Advanced master mix, 300 nM GAPDH TaqMan gene expression assays and PCR water, all sourced from ThermoFisher Scientific.

The plate was then sealed with an optical seal and amplification was performed on a QuantStudio 3 Real-Time system using the following protocols:

for DPP4 SYBR green gene expression assays: initial denaturation at 95° C. for 20 seconds; followed by 40 cycles of (i) denaturation at 95° C. for 3 seconds and (ii) annealing/extension at 54.5° C. for 30 seconds; followed by a step of melt curve comprising (i) a denaturation step at 95° C. for 1 second and (ii) a ramp from 95° C. to 60° C. with a 0.15° C. decrease per second.

for GAPDH TaqMan expression assays: initial denaturation at 95° C. for 2 minutes; followed by 40 cycles of (i) denaturation at 95° C. for 5 seconds and (ii) annealing/extension at 60° C. for 20 seconds.

Data was analyzed using the $2^{-\Delta\Delta Ct}$ method. The signal from DPP4 was normalized against the GAPDH reference gene. These values for each cell type were then further normalized against the level of expression in the WI-38 sample to give a relative quantification (RQ) value.

Analysis of DEP1 Expression by qPCR

WI-38 and GM21808 fibroblast cell lines and primary fibroblasts from healthy and diseased patients (COPD subjects—chronic obstructive pulmonary disease; and IPF subjects—idiopathic pulmonary fibrosis) were purchased from ethically sourced suppliers. GM21808 cells were treated with 20 µM etoposide and cultured for a further 15 days to instigate chemical-induced senescence, or left untreated.

RNA was isolated using a RNeasy plus kit (Qiagen) following manufacturer's instructions. RNA was quantified using a NanoDrop One (ThermoFisher Scientific) by measuring absorbance at 260 nm. 100-500 ng of RNA was reversed-transcribed using QuantiTect Reverse Transcription kit (Qiagen) in a final reaction volume of 20 µL following manufacturer's instructions.

Gene expression of DEP1 and GAPDH in each cell type was determined by qPCR using a TaqMan assay. Briefly, 10 ng cDNA (5 µl) from each cell type was mixed in a BrightWhite qPCR 96-well plate with 15 µL master mix containing TaqMan Fast Advanced master mix, 300 nM GAPDH/DEP1 TaqMan gene expression assays and PCR water, all sourced from ThermoFisher Scientific.

The plate was then sealed with an optical seal and amplification was performed on a QuantStudio 3 Real-Time system using the following protocol: initial denaturation at 95° C. for 2 minutes; followed by 40 cycles of (i) denaturation at 95° C. for 5 seconds and (ii) annealing/extension at 60° C. for 20 seconds.

The signal from DEP1 was normalized against the GAPDH reference gene. These values for each cell type were then further normalized against the level of expression in the WI-38 sample to give a relative quantification (RQ) value.

The invention claimed is:

1. A DPP4-binding domain, comprising a combination of three heavy chain variable region (HCVR)'s complementary-determining regions (CDRs) and three light chain variable region (LCVR)'s CDRs, said combination being as defined in any row of the table below, wherein the CDRs are defined by their SEQ ID NO:

| Clone's name | $V_H$-CDR1 | $V_H$-CDR2 | $V_H$-CDR3 | $V_L$-CDR1 | $V_L$-CDR2 | $V_L$-CDR3 |
|---|---|---|---|---|---|---|
| 5826-13-R3A-A10 | 107 | 119 | 137 | 146 | 157 | 170 |
| 5826-13-R3A-B1 | 108 | 120 | 138 | 147 | 158 | 171 |
| 5826-13-R3A-B3 | 108 | 121 | 138 | 147 | 159 | 171 |
| 5826-13-R3A-D5 | 109 | 122 | 139 | 148 | 160 | 172 |
| 5826-13-R3A-D6 | 108 | 123 | 138 | 149 | 159 | 171 |
| 5826-13-R4A-E2 | 108 | 124 | 138 | 147 | 159 | 171 |
| 5826-13-R4A-E6 | 110 | 125 | 140 | 146 | 161 | 170 |
| 5826-13-R4A-E9 | 108 | 126 | 141 | 149 | 159 | 171 |
| 5826-13-R4A-F10 | 108 | 126 | 138 | 150 | 159 | 171 |
| 5826-13-R4A-G11 | 108 | 126 | 138 | 150 | 159 | 171 |
| 5826-13-R4A-G12 | 111 | 127 | 138 | 151 | 159 | 171 |
| 5826-13-R4A-H1 | 110 | 128 | 140 | 146 | 162 | 170 |
| 5826-13-R4A-H2 | 108 | 126 | 141 | 149 | 159 | 171 |
| 5826-13-R4A-H3 | 108 | 126 | 138 | 149 | 159 | 173 |
| 5826-13-R4A-H4 | 112 | 125 | 140 | 146 | 162 | 170 |
| 5826-13-R4A-H5 | 108 | 127 | 138 | 147 | 159 | 171 |
| 5826-13-R4A-H6 | 108 | 127 | 142 | 147 | 159 | 171 |
| 5826-13-R4A-H9 | 108 | 123 | 138 | 149 | 159 | 171 |
| 5826-13-R4A-H10 | 110 | 125 | 140 | 146 | 162 | 170 |
| 5826-13-R4A-H11 | 110 | 128 | 140 | 146 | 162 | 170 |
| 5826-13-R4A-H12 | 110 | 125 | 140 | 146 | 163 | 170. |

2. A DPP4-binding domain according to claim 1, comprising:
   a) HCVR which comprises the following three CDRs:
      $V_H$-CDR1 selected from the group consisting of SEQ ID NO: 109, 108, and 110;
      $V_H$-CDR2 selected from the group consisting of SEQ ID NO: 122, 127, and 125;
      $V_H$-CDR3 selected from the group consisting of SEQ ID NO: 139, 138, and 140;
   b) a LCVR which comprises the following three CDRs:
      $V_L$-CDR1 selected from the group consisting of SEQ ID NO: 148, 147, and 146;
      $V_L$-CDR2 selected from the group consisting of SEQ ID NO: 160, 159, and 163;
      $V_L$-CDR3 selected from the group consisting of SEQ ID NO: 172, 171, and 170.

3. The DPP4-binding domain according to claim 1, being selected from the group consisting of:
  i. DPP4-binding domain comprising a $V_H$-CDR1 with SEQ ID NO: 109, a $V_H$-CDR2 with SEQ ID NO: 122, a $V_H$-CDR3 with SEQ ID NO: 139, a $V_L$-CDR1 with SEQ ID NO: 148, a $V_L$-CDR2 with SEQ ID NO: 160 and a $V_L$-CDR3 with SEQ ID NO: 172;
  ii. DPP4-binding domain comprising a $V_H$-CDR1 with SEQ ID NO: 108, a $V_H$-CDR2 with SEQ ID NO: 127, a $V_H$-CDR3 with SEQ ID NO: 138, a $V_L$-CDR1 with SEQ ID NO: 147, a $V_L$-CDR2 with SEQ ID NO: 159 and a $V_L$-CDR3 with SEQ ID NO: 171; and
  iii a DPP4-binding domain comprising a $V_H$-CDR1 with SEQ ID NO: 110, a $V_H$-CDR2 with SEQ ID NO: 125, a $V_H$-CDR3 with SEQ ID NO: 140, a $V_L$-CDR1 with SEQ ID NO: 146, a $V_L$-CDR2 with SEQ ID NO: 163 and a $V_L$-CDR3 with SEQ ID NO: 170.

4. The DPP4-binding domain according to claim 1, being selected from the group consisting of:
  i. a DPP4-binding domain comprising a HCVR with a sequence sharing at least 80% of sequence identity with the non-CDR regions of SEQ ID NO: 185 and a LCVR with a sequence sharing at least 80% of sequence identity with the non-CDR regions of SEQ ID NO: 213;
  ii. a DPP4-binding domain comprising a HCVR with a sequence sharing at least 80% of sequence identity with the non-CDR regions of SEQ ID NO: 197 and a LCVR with a sequence sharing at least 80% of sequence identity with the non-CDR regions of SEQ ID NO: 212; and
  iii. a DPP4-binding domain comprising a HCVR with a sequence sharing at least 80% of sequence identity with the non-CDR regions of SEQ ID NO: 200 and a LCVR with a sequence sharing at least 80% of sequence identity with the non-CDR regions of SEQ ID NO: 227.

5. An isolated antibody or antigen-binding fragment thereof comprising the DPP4-binding domain according to claim 1.

6. The isolated antibody or antigen-binding fragment thereof-comprising the DPP4-binding domain according to claim 1, being a bispecific antibody comprising a DPP4-binding domain comprising a combination of three heavy chain variable region (HCVR)'s complementary-determining regions (CDRs) and three light chain variable region (LCVR)'s CDRs, said combination being as defined in claim 1 and an antigen-binding domain to a non-senescent cell-associated antigen.

7. The isolated antibody or antigen-binding fragment thereof comprising the DPP4-binding domain according to claim 1, being a bispecific antibody comprising the DPP4-binding domain comprising a combination of three heavy chain variable region (HCVR)'s complementary-determining regions (CDRs) and three light chain variable region (LCVR)'s CDRs, said combination being as defined in claim 1 and an antigen-binding domain to another senescent cell-associated antigen.

8. A chimeric antigen receptor (CAR) comprising:
  a. at least one extracellular binding domain, comprising at least one DPP4-binding domain according to claim 1,
  b. an extracellular spacer domain,
  c. a transmembrane domain,
  d. optionally, at least one costimulatory domain, and
  e. at least one intracellular signaling domain.

9. The CAR according to claim 8, wherein said CAR is multispecific and comprises at least one DPP4-binding domain according to claim 1 and at least one antigen-binding domain to a non-senescent cell-associated antigen.

10. The CAR according to claim 8, wherein said CAR is multispecific and comprises at least one DPP4-binding domain according to claim 1 and at least one antigen-binding domain to another senescent cell-associated antigen.

11. An immune cell engineered to express the CAR of claim 8 at its surface.

12. A population of immune cells, comprising a plurality of immune cells according to claim 11.

13. A composition comprising:
  the isolated antibody or antigen-binding fragment thereof comprising the DPP4-binding domain according to claim 1,
  an immune cell engineered to express at its surface a chimeric antigen receptor (CAR) comprising:
    (a) at least one extracellular binding domain, comprising at least one DPP4-binding domain, comprising a combination of three heavy chain variable region (HCVR)'s complementary-determining regions (CDRs) and three light chain variable region (LCVR)'s CDRs, said combination being as defined in claim 1,
    (b) an extracellular spacer domain,
    (c) a transmembrane domain,
    (d) optionally, at least one costimulatory domain, and
    (e) at least one intracellular signaling domain, and/or
  a population of immune cells comprising a plurality of immune cells engineered to express at each cell's surface a chimeric antigen receptor (CAR) comprising:
    (a) at least one extracellular binding domain, comprising at least one DPP4-binding domain, comprising a combination of three heavy chain variable region (HCVR)'s complementary-determining regions (CDRs) and three light chain variable region (LCVR)'s CDRs, said combination being as defined in claim 1,
    (b) an extracellular spacer domain,
    (c) a transmembrane domain,
    (d) optionally, at least one costimulatory domain, and
    (e) at least one intracellular signaling domain.

14. The composition according to claim 13, being a pharmaceutical composition and further comprising at least one pharmaceutically acceptable excipient.

15. A method of depleting and/or killing senescent cells, comprising contacting the senescent cells with the composition according to claim 13.

* * * * *

SEQUENCE LISTING

```
<160> NUMBER OF SEQ ID NOS: 227

<210> SEQ ID NO 1
<211> LENGTH: 1337
<212> TYPE: PRT
<213> ORGANISM: Homo sapiens
<220> FEATURE:
<221> NAME/KEY: DOMAIN
<222> LOCATION: 1..35
<223> OTHER INFORMATION: Signal peptide
<220> FEATURE:
<223> OTHER INFORMATION: hDEP1
<220> FEATURE:
<221> NAME/KEY: SITE
<222> LOCATION: 36..48
<223> OTHER INFORMATION: hDEP1 Peptide #1
<220> FEATURE:
<221> NAME/KEY: DOMAIN
<222> LOCATION: 36..975
<223> OTHER INFORMATION: Extracellular domain
<220> FEATURE:
<221> NAME/KEY: SITE
<222> LOCATION: 436..452
<223> OTHER INFORMATION: hDEP1 Peptide #2
<220> FEATURE:
<221> NAME/KEY: SITE
<222> LOCATION: 728..741
<223> OTHER INFORMATION: hDEP1 Peptide #3
<220> FEATURE:
<221> NAME/KEY: SITE
<222> LOCATION: 864..881
<223> OTHER INFORMATION: hDEP1 Peptide #4
<220> FEATURE:
<221> NAME/KEY: DOMAIN
<222> LOCATION: 976..996
<223> OTHER INFORMATION: Transmembrane domain
<220> FEATURE:
<221> NAME/KEY: DOMAIN
<222> LOCATION: 997..1337
<223> OTHER INFORMATION: Cytoplasmic domain
```

```
<400> SEQUENCE: 1

Met Lys Pro Ala Ala Arg Glu Ala Arg Leu Pro Pro Arg Ser Pro Gly
1               5                   10                  15

Leu Arg Trp Ala Leu Pro Leu Leu Leu Leu Arg Leu Gly Gln
            20                  25                  30

Ile Leu Cys Ala Gly Gly Thr Pro Ser Pro Ile Pro Asp Pro Ser Val
            35                  40                  45

Ala Thr Val Ala Thr Gly Glu Asn Gly Ile Thr Gln Ile Ser Ser Thr
        50                  55                  60

Ala Glu Ser Phe His Lys Gln Asn Gly Thr Gly Thr Pro Gln Val Glu
65                  70                  75                  80

Thr Asn Thr Ser Glu Asp Gly Glu Ser Ser Gly Ala Asn Asp Ser Leu
                85                  90                  95

Arg Thr Pro Glu Gln Gly Ser Asn Gly Thr Asp Gly Ala Ser Gln Lys
                100                 105                 110

Thr Pro Ser Ser Thr Gly Pro Ser Pro Val Phe Asp Ile Lys Ala Val
            115                 120                 125

Ser Ile Ser Pro Thr Asn Val Ile Leu Thr Trp Lys Ser Asn Asp Thr
        130                 135                 140

Ala Ala Ser Glu Tyr Lys Tyr Val Val Lys His Lys Met Glu Asn Glu
145                 150                 155                 160

Lys Thr Ile Thr Val Val His Gln Pro Trp Cys Asn Ile Thr Gly Leu
                165                 170                 175

Arg Pro Ala Thr Ser Tyr Val Phe Ser Ile Thr Pro Gly Ile Gly Asn
                180                 185                 190

Glu Thr Trp Gly Asp Pro Arg Val Ile Lys Val Ile Thr Glu Pro Ile
            195                 200                 205

Pro Val Ser Asp Leu Arg Val Ala Leu Thr Gly Val Arg Lys Ala Ala
        210                 215                 220

Leu Ser Trp Ser Asn Gly Asn Gly Thr Ala Ser Cys Arg Val Leu Leu
225                 230                 235                 240

Glu Ser Ile Gly Ser His Glu Glu Leu Thr Gln Asp Ser Arg Leu Gln
                245                 250                 255

Val Asn Ile Ser Gly Leu Lys Pro Gly Val Gln Tyr Asn Ile Asn Pro
                260                 265                 270

Tyr Leu Leu Gln Ser Asn Lys Thr Lys Gly Asp Pro Leu Gly Thr Glu
            275                 280                 285

Gly Gly Leu Asp Ala Ser Asn Thr Glu Arg Ser Arg Ala Gly Ser Pro
        290                 295                 300

Thr Ala Pro Val His Asp Glu Ser Leu Val Gly Pro Val Asp Pro Ser
305                 310                 315                 320

Ser Gly Gln Gln Ser Arg Asp Thr Glu Val Leu Leu Val Gly Leu Glu
                325                 330                 335

Pro Gly Thr Arg Tyr Asn Ala Thr Val Tyr Ser Gln Ala Ala Asn Gly
                340                 345                 350

Thr Glu Gly Gln Pro Gln Ala Ile Glu Phe Arg Thr Asn Ala Ile Gln
            355                 360                 365

Val Phe Asp Val Thr Ala Val Asn Ile Ser Ala Thr Ser Leu Thr Leu
        370                 375                 380

Ile Trp Lys Val Ser Asp Asn Glu Ser Ser Ser Asn Tyr Thr Tyr Lys
385                 390                 395                 400

Ile His Val Ala Gly Glu Thr Asp Ser Ser Asn Leu Asn Val Ser Glu
                405                 410                 415
```

```
Pro Arg Ala Val Ile Pro Gly Leu Arg Ser Thr Phe Tyr Asn Ile
            420                 425                 430

Thr Val Cys Pro Val Leu Gly Asp Ile Glu Gly Thr Pro Gly Phe Leu
            435                 440                 445

Gln Val His Thr Pro Pro Val Pro Val Ser Asp Phe Arg Val Thr Val
            450                 455                 460

Val Ser Thr Thr Glu Ile Gly Leu Ala Trp Ser Ser His Asp Ala Glu
465             470                 475                 480

Ser Phe Gln Met His Ile Thr Gln Glu Gly Ala Gly Asn Ser Arg Val
                485                 490                 495

Glu Ile Thr Thr Asn Gln Ser Ile Ile Gly Gly Leu Phe Pro Gly
                500                 505                 510

Thr Lys Tyr Cys Phe Glu Ile Val Pro Lys Gly Pro Asn Gly Thr Glu
            515                 520                 525

Gly Ala Ser Arg Thr Val Cys Asn Arg Thr Val Pro Ser Ala Val Phe
            530                 535                 540

Asp Ile His Val Val Tyr Val Thr Thr Thr Glu Met Trp Leu Asp Trp
545             550                 555                 560

Lys Ser Pro Asp Gly Ala Ser Glu Tyr Val Tyr His Leu Val Ile Glu
                565                 570                 575

Ser Lys His Gly Ser Asn His Thr Ser Thr Tyr Asp Lys Ala Ile Thr
                580                 585                 590

Leu Gln Gly Leu Ile Pro Gly Thr Leu Tyr Asn Ile Thr Ile Ser Pro
            595                 600                 605

Glu Val Asp His Val Trp Gly Asp Pro Asn Ser Thr Ala Gln Tyr Thr
            610                 615                 620

Arg Pro Ser Asn Val Ser Asn Ile Asp Val Ser Thr Asn Thr Thr Ala
625             630                 635                 640

Ala Thr Leu Ser Trp Gln Asn Phe Asp Asp Ala Ser Pro Thr Tyr Ser
                645                 650                 655

Tyr Cys Leu Leu Ile Glu Lys Ala Gly Asn Ser Ser Asn Ala Thr Gln
            660                 665                 670

Val Val Thr Asp Ile Gly Ile Thr Asp Ala Thr Val Thr Glu Leu Ile
            675                 680                 685

Pro Gly Ser Ser Tyr Thr Val Glu Ile Phe Ala Gln Val Gly Asp Gly
            690                 695                 700

Ile Lys Ser Leu Glu Pro Gly Arg Lys Ser Phe Cys Thr Asp Pro Ala
705             710                 715                 720

Ser Met Ala Ser Phe Asp Cys Glu Val Val Pro Lys Glu Pro Ala Leu
                725                 730                 735

Val Leu Lys Trp Thr Cys Pro Pro Gly Ala Asn Ala Gly Phe Glu Leu
            740                 745                 750

Glu Val Ser Ser Gly Ala Trp Asn Asn Ala Thr His Leu Glu Ser Cys
            755                 760                 765

Ser Ser Glu Asn Gly Thr Glu Tyr Arg Thr Glu Val Thr Tyr Leu Asn
            770                 775                 780

Phe Ser Thr Ser Tyr Asn Ile Ser Ile Thr Thr Val Ser Cys Gly Lys
785             790                 795                 800

Met Ala Ala Pro Thr Arg Asn Thr Cys Thr Thr Gly Ile Thr Asp Pro
                805                 810                 815

Pro Pro Pro Asp Gly Ser Pro Asn Ile Thr Ser Val Ser His Asn Ser
            820                 825                 830
```

Val Lys Val Lys Phe Ser Gly Phe Glu Ala Ser His Gly Pro Ile Lys
         835                 840                 845

Ala Tyr Ala Val Ile Leu Thr Thr Gly Glu Ala Gly His Pro Ser Ala
    850                 855                 860

Asp Val Leu Lys Tyr Thr Tyr Glu Asp Phe Lys Lys Gly Ala Ser Asp
865                 870                 875                 880

Thr Tyr Val Thr Tyr Leu Ile Arg Thr Glu Lys Gly Arg Ser Gln
                885                 890                 895

Ser Leu Ser Glu Val Leu Lys Tyr Glu Ile Asp Val Gly Asn Glu Ser
            900                 905                 910

Thr Thr Leu Gly Tyr Tyr Asn Gly Lys Leu Glu Pro Leu Gly Ser Tyr
        915                 920                 925

Arg Ala Cys Val Ala Gly Phe Thr Asn Ile Thr Phe His Pro Gln Asn
    930                 935                 940

Lys Gly Leu Ile Asp Gly Ala Glu Ser Tyr Val Ser Phe Ser Arg Tyr
945                 950                 955                 960

Ser Asp Ala Val Ser Leu Pro Gln Asp Pro Gly Val Ile Cys Gly Ala
                965                 970                 975

Val Phe Gly Cys Ile Phe Gly Ala Leu Val Ile Val Thr Val Gly Gly
            980                 985                 990

Phe Ile Phe Trp Arg Lys Lys Arg Lys Asp Ala Lys Asn Asn Glu Val
        995                 1000                1005

Ser Phe Ser Gln Ile Lys Pro Lys Ser Lys Leu Ile Arg Val Glu
    1010                1015                1020

Asn Phe Glu Ala Tyr Phe Lys Lys Gln Ala Asp Ser Asn Cys Gly
1025                1030                1035                1040

Phe Ala Glu Glu Tyr Glu Asp Leu Lys Leu Val Gly Ile Ser Gln Pro
                1045                1050                1055

Lys Tyr Ala Ala Glu Leu Ala Glu Asn Arg Gly Lys Asn Arg Tyr Asn
                1060                1065                1070

Asn Val Leu Pro Tyr Asp Ile Ser Arg Val Lys Leu Ser Val Gln Thr
            1075                1080                1085

His Ser Thr Asp Asp Tyr Ile Asn Ala Asn Tyr Met Pro Gly Tyr His
    1090                1095                1100

Ser Lys Lys Asp Phe Ile Ala Thr Gln Gly Pro Leu Pro Asn Thr Leu
1105                1110                1115                1120

Lys Asp Phe Trp Arg Met Val Trp Glu Lys Asn Val Tyr Ala Ile Ile
                1125                1130                1135

Met Leu Thr Lys Cys Val Glu Gln Gly Arg Thr Lys Cys Glu Glu Tyr
            1140                1145                1150

Trp Pro Ser Lys Gln Ala Gln Asp Tyr Gly Asp Ile Thr Val Ala Met
        1155                1160                1165

Thr Ser Glu Ile Val Leu Pro Glu Trp Thr Ile Arg Asp Phe Thr Val
    1170                1175                1180

Lys Asn Ile Gln Thr Ser Glu Ser His Pro Leu Arg Gln Phe His Phe
1185                1190                1195                1200

Thr Ser Trp Pro Asp His Gly Val Pro Asp Thr Thr Asp Leu Leu Ile
                1205                1210                1215

Asn Phe Arg Tyr Leu Val Arg Asp Tyr Met Lys Gln Ser Pro Pro Glu
            1220                1225                1230

Ser Pro Ile Leu Val His Cys Ser Ala Gly Val Gly Arg Thr Gly Thr
        1235                1240                1245

Phe Ile Ala Ile Asp Arg Leu Ile Tyr Gln Ile Glu Asn Glu Asn Thr

```
                    1250                1255                1260
Val Asp Val Tyr Gly Ile Val Tyr Asp Leu Arg Met His Arg Pro Leu
1265                1270                1275                1280

Met Val Gln Thr Glu Asp Gln Tyr Val Phe Leu Asn Gln Cys Val Leu
                    1285                1290                1295

Asp Ile Val Arg Ser Gln Lys Asp Ser Lys Val Asp Leu Ile Tyr Gln
                    1300                1305                1310

Asn Thr Thr Ala Met Thr Ile Tyr Glu Asn Leu Ala Pro Val Thr Thr
            1315                1320                1325

Phe Gly Lys Thr Asn Gly Tyr Ile Ala
        1330                1335

<210> SEQ ID NO 2
<211> LENGTH: 583
<212> TYPE: PRT
<213> ORGANISM: Artificial Sequence
<220> FEATURE:
<223> OTHER INFORMATION: hDEP1-ECD-Fc (Amino acid residues 621-969 of
      SEQ ID NO: 1 + Fc domain)

<400> SEQUENCE: 2

Ala Gln Tyr Thr Arg Pro Ser Asn Val Ser Asn Ile Asp Val Ser Thr
1               5                   10                  15

Asn Thr Thr Ala Ala Thr Leu Ser Trp Gln Asn Phe Asp Asp Ala Ser
            20                  25                  30

Pro Thr Tyr Ser Tyr Cys Leu Leu Ile Glu Lys Ala Gly Asn Ser Ser
        35                  40                  45

Asn Ala Thr Gln Val Val Thr Asp Ile Gly Ile Thr Asp Ala Thr Val
50                  55                  60

Thr Glu Leu Ile Pro Gly Ser Ser Tyr Thr Val Glu Ile Phe Ala Gln
65                  70                  75                  80

Val Gly Asp Gly Ile Lys Ser Leu Glu Pro Gly Arg Lys Ser Phe Cys
                85                  90                  95

Thr Asp Pro Ala Ser Met Ala Ser Phe Asp Cys Glu Val Val Pro Lys
            100                 105                 110

Glu Pro Ala Leu Val Leu Lys Trp Thr Cys Pro Pro Gly Ala Asn Ala
        115                 120                 125

Gly Phe Glu Leu Glu Val Ser Ser Gly Ala Trp Asn Asn Ala Thr His
130                 135                 140

Leu Glu Ser Cys Ser Ser Glu Asn Gly Thr Glu Tyr Arg Thr Glu Val
145                 150                 155                 160

Thr Tyr Leu Asn Phe Ser Thr Ser Tyr Asn Ile Ser Ile Thr Thr Val
                165                 170                 175

Ser Cys Gly Lys Met Ala Ala Pro Thr Arg Asn Thr Cys Thr Thr Gly
            180                 185                 190

Ile Thr Asp Pro Pro Pro Pro Asp Gly Ser Pro Asn Ile Thr Ser Val
        195                 200                 205

Ser His Asn Ser Val Lys Val Lys Phe Ser Gly Phe Glu Ala Ser His
210                 215                 220

Gly Pro Ile Lys Ala Tyr Ala Val Ile Leu Thr Thr Gly Glu Ala Gly
225                 230                 235                 240

His Pro Ser Ala Asp Val Leu Lys Tyr Thr Tyr Glu Asp Phe Lys Lys
                245                 250                 255

Gly Ala Ser Asp Thr Tyr Val Thr Tyr Leu Ile Arg Thr Glu Glu Lys
            260                 265                 270
```

Gly Arg Ser Gln Ser Leu Ser Glu Val Leu Lys Tyr Glu Ile Asp Val
            275                 280                 285

Gly Asn Glu Ser Thr Thr Leu Gly Tyr Tyr Asn Gly Lys Leu Glu Pro
    290                 295                 300

Leu Gly Ser Tyr Arg Ala Cys Val Ala Gly Phe Thr Asn Ile Thr Phe
305                 310                 315                 320

His Pro Gln Asn Lys Gly Leu Ile Asp Gly Ala Glu Ser Tyr Val Ser
                325                 330                 335

Phe Ser Arg Tyr Ser Asp Ala Val Ser Leu Pro Gln Asp Gly Ser Glu
            340                 345                 350

Pro Lys Ser Cys Asp Lys Thr His Thr Cys Pro Pro Cys Pro Ala Pro
        355                 360                 365

Glu Leu Leu Gly Gly Pro Ser Val Phe Leu Phe Pro Pro Lys Pro Lys
370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Ala Leu
    450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Asp Glu Leu Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
            580

<210> SEQ ID NO 3
<211> LENGTH: 359
<212> TYPE: PRT
<213> ORGANISM: Artificial Sequence
<220> FEATURE:
<223> OTHER INFORMATION: hDEP1-ECD-6His (Amino acid residues 621-969 of
      SEQ ID NO: 1 + Linker + 6His tag)

<400> SEQUENCE: 3

Ala Gln Tyr Thr Arg Pro Ser Asn Val Ser Asn Ile Asp Val Ser Thr
1               5                   10                  15

Asn Thr Thr Ala Ala Thr Leu Ser Trp Gln Asn Phe Asp Asp Ala Ser
            20                  25                  30

Pro Thr Tyr Ser Tyr Cys Leu Leu Ile Glu Lys Ala Gly Asn Ser Ser
        35                  40                  45

```
Asn Ala Thr Gln Val Val Thr Asp Ile Gly Ile Thr Asp Ala Thr Val
    50                  55                  60

Thr Glu Leu Ile Pro Gly Ser Ser Tyr Thr Val Glu Ile Phe Ala Gln
65                  70                  75                  80

Val Gly Asp Gly Ile Lys Ser Leu Glu Pro Gly Arg Lys Ser Phe Cys
                85                  90                  95

Thr Asp Pro Ala Ser Met Ala Ser Phe Asp Cys Glu Val Val Pro Lys
            100                 105                 110

Glu Pro Ala Leu Val Leu Lys Trp Thr Cys Pro Pro Gly Ala Asn Ala
        115                 120                 125

Gly Phe Glu Leu Glu Val Ser Ser Gly Ala Trp Asn Asn Ala Thr His
    130                 135                 140

Leu Glu Ser Cys Ser Ser Glu Asn Gly Thr Glu Tyr Arg Thr Glu Val
145                 150                 155                 160

Thr Tyr Leu Asn Phe Ser Thr Ser Tyr Asn Ile Ser Ile Thr Thr Val
                165                 170                 175

Ser Cys Gly Lys Met Ala Ala Pro Thr Arg Asn Thr Cys Thr Thr Gly
            180                 185                 190

Ile Thr Asp Pro Pro Pro Pro Asp Gly Ser Pro Asn Ile Thr Ser Val
        195                 200                 205

Ser His Asn Ser Val Lys Val Lys Phe Ser Gly Phe Glu Ala Ser His
    210                 215                 220

Gly Pro Ile Lys Ala Tyr Ala Val Ile Leu Thr Thr Gly Glu Ala Gly
225                 230                 235                 240

His Pro Ser Ala Asp Val Leu Lys Tyr Thr Tyr Glu Asp Phe Lys Lys
                245                 250                 255

Gly Ala Ser Asp Thr Tyr Val Thr Tyr Leu Ile Arg Thr Glu Glu Lys
            260                 265                 270

Gly Arg Ser Gln Ser Leu Ser Glu Val Leu Lys Tyr Glu Ile Asp Val
        275                 280                 285

Gly Asn Glu Ser Thr Thr Leu Gly Tyr Tyr Asn Gly Lys Leu Glu Pro
    290                 295                 300

Leu Gly Ser Tyr Arg Ala Cys Val Ala Gly Phe Thr Asn Ile Thr Phe
305                 310                 315                 320

His Pro Gln Asn Lys Gly Leu Ile Asp Gly Ala Glu Ser Tyr Val Ser
                325                 330                 335

Phe Ser Arg Tyr Ser Asp Ala Val Ser Leu Pro Gln Asp Val Ala Ala
            340                 345                 350

Ala His His His His His His
        355

<210> SEQ ID NO 4
<211> LENGTH: 357
<212> TYPE: PRT
<213> ORGANISM: Artificial Sequence
<220> FEATURE:
<223> OTHER INFORMATION: mDEP1-ECD-6His

<400> SEQUENCE: 4

Thr Gln Tyr Thr Arg Pro Ser Ser Val Ser His Ile Glu Val Asn Thr
1               5                   10                  15

Thr Thr Thr Thr Ala Ala Ile Arg Trp Lys Asn Glu Asp Ala Ala Ser
            20                  25                  30

Ala Ser Tyr Ala Tyr Ser Val Leu Ile Leu Lys Thr Gly Asp Gly Ser
        35                  40                  45
```

```
Asn Val Thr Ser Asn Phe Thr Lys Asp Pro Ser Ile Leu Ile Pro Glu
 50                  55                  60

Leu Ile Pro Gly Val Ser Tyr Thr Val Lys Ile Leu Thr Gln Val Gly
 65                  70                  75                  80

Asp Gly Thr Thr Ser Leu Val Pro Gly Trp Asn Leu Phe Cys Thr Glu
                 85                  90                  95

Pro Glu Pro Val Thr Ser Phe His Cys Glu Val Val Pro Lys Glu Pro
            100                 105                 110

Ala Leu Val Leu Lys Trp Ala Cys Pro Phe Gly Met Tyr Thr Gly Phe
            115                 120                 125

Glu Leu Gly Val Arg Ser Asp Ser Trp Asp Asn Met Thr Arg Leu Glu
            130                 135                 140

Asn Cys Thr Ser Asp Asp Thr Glu Cys Arg Thr Glu Val Ala Tyr
145                 150                 155                 160

Leu Asn Phe Ser Thr Ser Tyr Asn Ile Ser Ile Ala Thr Leu Ser Cys
                165                 170                 175

Gly Lys Met Ala Leu Pro Ala Gln Asn Ile Cys Thr Thr Gly Ile Thr
            180                 185                 190

Asp Pro Pro Thr Pro Asp Gly Ser Pro Asn Ile Thr Ser Val Ser His
            195                 200                 205

Asn Ser Val Lys Val Lys Phe Ser Gly Phe Glu Ala Ser His Gly Pro
210                 215                 220

Ile Lys Ala Tyr Ala Val Ile Leu Thr Thr Gly Glu Ala Ala Gln Pro
225                 230                 235                 240

Ser Ala Asp Val Leu Lys Tyr Thr Tyr Glu Asp Phe Lys Arg Gly Ala
            245                 250                 255

Ser Asp Thr Tyr Val Thr Tyr Leu Ile Arg Ile Glu Glu Lys Gly Gln
            260                 265                 270

Ser Gln Gly Leu Ser Glu Val Leu Asn Tyr Glu Ile Asp Val Gly Asn
            275                 280                 285

Gln Ser Thr Thr Leu Gly Tyr Tyr Asn Gly Arg Leu Glu Pro Leu Gly
            290                 295                 300

Ser Tyr Arg Ala Cys Val Ala Gly Phe Thr Asn Ile Thr Tyr Asn Leu
305                 310                 315                 320

Gln Asn Asp Gly Leu Ile Asn Gly Asp Glu Ser Tyr Val Ser Phe Ser
                325                 330                 335

Pro Tyr Ser Glu Ala Val Phe Leu Pro Gln Asp Val Ala Ala Ala His
            340                 345                 350

His His His His His
        355

<210> SEQ ID NO 5
<211> LENGTH: 5
<212> TYPE: PRT
<213> ORGANISM: Artificial Sequence
<220> FEATURE:
<223> OTHER INFORMATION: HCDR1

<400> SEQUENCE: 5

Ser Tyr Tyr Ile Ser
1               5

<210> SEQ ID NO 6
<211> LENGTH: 5
<212> TYPE: PRT
<213> ORGANISM: Artificial Sequence
```

```
<220> FEATURE:
<223> OTHER INFORMATION: HCDR1

<400> SEQUENCE: 6

Asn Ile Ala Met Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: HCDR1

<400> SEQUENCE: 7

Asn Tyr Thr Ile Ser
1               5

<210> SEQ ID NO 8
<211> LENGTH: 5
<212> TYPE: PRT
<213> ORGANISM: Artificial Sequence
<220> FEATURE:
<223> OTHER INFORMATION: HCDR1

<400> SEQUENCE: 8

Ser Asp Ser Ile Ser
1               5

<210> SEQ ID NO 9
<211> LENGTH: 5
<212> TYPE: PRT
<213> ORGANISM: Artificial Sequence
<220> FEATURE:
<223> OTHER INFORMATION: HCDR1

<400> SEQUENCE: 9

Asn Tyr Ser Ile Ser
1               5

<210> SEQ ID NO 10
<211> LENGTH: 5
<212> TYPE: PRT
<213> ORGANISM: Artificial Sequence
<220> FEATURE:
<223> OTHER INFORMATION: HCDR1

<400> SEQUENCE: 10

Asp Tyr Asn Met Ala
1               5

<210> SEQ ID NO 11
<211> LENGTH: 5
<212> TYPE: PRT
<213> ORGANISM: Artificial Sequence
<220> FEATURE:
<223> OTHER INFORMATION: HCDR1

<400> SEQUENCE: 11

Asn Tyr Tyr Met Ala
1               5

<210> SEQ ID NO 12
<211> LENGTH: 17
<212> TYPE: PRT
<213> ORGANISM: Artificial Sequence
<220> FEATURE:
```

```
<223> OTHER INFORMATION: HCDR2

<400> SEQUENCE: 12

Tyr Ile Asn Thr Gly Ser Gly Gly Thr Asn Tyr Asn Glu Lys Phe Lys
1               5                   10                  15
Gly

<210> SEQ ID NO 13
<211> LENGTH: 19
<212> TYPE: PRT
<213> ORGANISM: Artificial Sequence
<220> FEATURE:
<223> OTHER INFORMATION: HCDR2

<400> SEQUENCE: 13

His Ile Arg Thr Lys Pro His Asn Phe Ala Thr Tyr Tyr Ala Asn Ser
1               5                   10                  15
Val Lys Gly

<210> SEQ ID NO 14
<211> LENGTH: 17
<212> TYPE: PRT
<213> ORGANISM: Artificial Sequence
<220> FEATURE:
<223> OTHER INFORMATION: HCDR2

<400> SEQUENCE: 14

Tyr Ile Tyr Ala Gly Thr Gly Asp Thr Asn Tyr Asn Glu Lys Phe Lys
1               5                   10                  15
Gly

<210> SEQ ID NO 15
<211> LENGTH: 19
<212> TYPE: PRT
<213> ORGANISM: Artificial Sequence
<220> FEATURE:
<223> OTHER INFORMATION: HCDR2

<400> SEQUENCE: 15

His Ile Arg Thr Lys Pro His Asn Tyr Ala Thr Tyr Tyr Ala Asp Ser
1               5                   10                  15
Val Lys Gly

<210> SEQ ID NO 16
<211> LENGTH: 17
<212> TYPE: PRT
<213> ORGANISM: Artificial Sequence
<220> FEATURE:
<223> OTHER INFORMATION: HCDR2

<400> SEQUENCE: 16

Tyr Ile His Pro Gly Ser Gly Val Thr Asn Tyr Asn Glu Lys Phe Lys
1               5                   10                  15
Gly

<210> SEQ ID NO 17
<211> LENGTH: 17
<212> TYPE: PRT
<213> ORGANISM: Artificial Sequence
<220> FEATURE:
<223> OTHER INFORMATION: HCDR2

<400> SEQUENCE: 17
```

Tyr Ile His Pro Gly Ser Gly Val Thr Asn Tyr Asn Glu Lys Phe Arg
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: HCDR2

<400> SEQUENCE: 18

Tyr Ile Tyr Pro Gly Ser Gly Asp Thr Asn Tyr Asn Glu Lys Phe Lys
1               5                   10                  15

Gly

<210> SEQ ID NO 19
<211> LENGTH: 17
<212> TYPE: PRT
<213> ORGANISM: Artificial Sequence
<220> FEATURE:
<223> OTHER INFORMATION: HCDR2

<400> SEQUENCE: 19

Thr Ile Ser Tyr Asp Asp Ser Arg Thr Tyr Tyr Arg Asp Ser Val Lys
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: HCDR2

<400> SEQUENCE: 20

Tyr Ile Thr Asn Ser Phe Gly Ser Ala Tyr Tyr Arg Asp Ser Val Lys
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: HCDR2

<400> SEQUENCE: 21

Thr Ile Ser Tyr Asp Asp Tyr Arg Thr Tyr Tyr Arg Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: HCDR2

<400> SEQUENCE: 22

Tyr Ile Thr Asn Ser Leu Gly Ser Ala Tyr Tyr Arg Asp Ser Val Lys
1               5                   10                  15

Gly

```
<210> SEQ ID NO 23
<211> LENGTH: 17
<212> TYPE: PRT
<213> ORGANISM: Artificial Sequence
<220> FEATURE:
<223> OTHER INFORMATION: HCDR2

<400> SEQUENCE: 23

Tyr Ile Thr Asn Ser Phe Gly Ser Thr Tyr Tyr Arg Asp Ser Val Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: HCDR2

<400> SEQUENCE: 24

Tyr Ile Thr Asn Gly Tyr Gly Ser Thr Tyr Tyr Arg Asp Ser Val Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: HCDR2

<400> SEQUENCE: 25

Tyr Ile Thr Asn Gly Phe Gly Ser Thr Tyr Tyr Arg Asp Ser Val Lys
1               5                   10                  15

Gly

<210> SEQ ID NO 26
<211> LENGTH: 4
<212> TYPE: PRT
<213> ORGANISM: Artificial Sequence
<220> FEATURE:
<223> OTHER INFORMATION: HCDR3

<400> SEQUENCE: 26

Tyr Phe Asp Tyr
1

<210> SEQ ID NO 27
<211> LENGTH: 5
<212> TYPE: PRT
<213> ORGANISM: Artificial Sequence
<220> FEATURE:
<223> OTHER INFORMATION: HCDR3

<400> SEQUENCE: 27

Gly Phe Gly Asp Tyr
1               5

<210> SEQ ID NO 28
<211> LENGTH: 4
<212> TYPE: PRT
<213> ORGANISM: Artificial Sequence
<220> FEATURE:
<223> OTHER INFORMATION: HCDR3
```

```
<400> SEQUENCE: 28

Tyr Phe Asp His
1

<210> SEQ ID NO 29
<211> LENGTH: 5
<212> TYPE: PRT
<213> ORGANISM: Artificial Sequence
<220> FEATURE:
<223> OTHER INFORMATION: HCDR3

<400> SEQUENCE: 29

Asp Lys Trp Val Asp
1               5

<210> SEQ ID NO 30
<211> LENGTH: 12
<212> TYPE: PRT
<213> ORGANISM: Artificial Sequence
<220> FEATURE:
<223> OTHER INFORMATION: HCDR3

<400> SEQUENCE: 30

Gln Gly Gly Ile Ile Arg Gly Val Trp Phe Pro Tyr
1               5                   10

<210> SEQ ID NO 31
<211> LENGTH: 8
<212> TYPE: PRT
<213> ORGANISM: Artificial Sequence
<220> FEATURE:
<223> OTHER INFORMATION: HCDR3

<400> SEQUENCE: 31

Val Pro Leu Gly Ala Phe Val Tyr
1               5

<210> SEQ ID NO 32
<211> LENGTH: 8
<212> TYPE: PRT
<213> ORGANISM: Artificial Sequence
<220> FEATURE:
<223> OTHER INFORMATION: HCDR3

<400> SEQUENCE: 32

Val Pro Leu Gly Ala Phe Val Ser
1               5

<210> SEQ ID NO 33
<211> LENGTH: 11
<212> TYPE: PRT
<213> ORGANISM: Artificial Sequence
<220> FEATURE:
<223> OTHER INFORMATION: LCDR1

<400> SEQUENCE: 33

Arg Ala Ser Gln Asp Val Gly Ile Tyr Val Asn
1               5                   10

<210> SEQ ID NO 34
<211> LENGTH: 16
<212> TYPE: PRT
<213> ORGANISM: Artificial Sequence
<220> FEATURE:
<223> OTHER INFORMATION: LCDR1
```

```
<400> SEQUENCE: 34

Lys Ser Ser Gln Ser Leu Lys His Ser Asp Gly Lys Thr Tyr Leu Asn
1               5                   10                  15

<210> SEQ ID NO 35
<211> LENGTH: 11
<212> TYPE: PRT
<213> ORGANISM: Artificial Sequence
<220> FEATURE:
<223> OTHER INFORMATION: LCDR1

<400> SEQUENCE: 35

Gln Ala Ser Gln Asp Ile Gly Asn Asn Leu Ile
1               5                   10

<210> SEQ ID NO 36
<211> LENGTH: 16
<212> TYPE: PRT
<213> ORGANISM: Artificial Sequence
<220> FEATURE:
<223> OTHER INFORMATION: LCDR1

<400> SEQUENCE: 36

Arg Ser Ser Gln Ser Leu Lys His Ser Asp Gly Lys Thr Tyr Leu Asn
1               5                   10                  15

<210> SEQ ID NO 37
<211> LENGTH: 11
<212> TYPE: PRT
<213> ORGANISM: Artificial Sequence
<220> FEATURE:
<223> OTHER INFORMATION: LCDR1

<400> SEQUENCE: 37

Gln Ala Ser Gln Asp Ile Gly Asn Trp Leu Ala
1               5                   10

<210> SEQ ID NO 38
<211> LENGTH: 11
<212> TYPE: PRT
<213> ORGANISM: Artificial Sequence
<220> FEATURE:
<223> OTHER INFORMATION: LCDR1

<400> SEQUENCE: 38

Leu Ala Ser Glu Gly Ile Ser Asn Tyr Leu Ala
1               5                   10

<210> SEQ ID NO 39
<211> LENGTH: 11
<212> TYPE: PRT
<213> ORGANISM: Artificial Sequence
<220> FEATURE:
<223> OTHER INFORMATION: LCDR1

<400> SEQUENCE: 39

Leu Ala Ser Glu Asp Ile Tyr Ser Tyr Leu Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: LCDR2

<400> SEQUENCE: 40
```

Arg Ala Thr Asn Leu Ala Asp
1               5

<210> SEQ ID NO 41
<211> LENGTH: 7
<212> TYPE: PRT
<213> ORGANISM: Artificial Sequence
<220> FEATURE:
<223> OTHER INFORMATION: LCDR2

<400> SEQUENCE: 41

Gln Val Ser Lys Leu Asp Ser
1               5

<210> SEQ ID NO 42
<211> LENGTH: 7
<212> TYPE: PRT
<213> ORGANISM: Artificial Sequence
<220> FEATURE:
<223> OTHER INFORMATION: LCDR2

<400> SEQUENCE: 42

Tyr Ala Thr Asn Leu Ala Asn
1               5

<210> SEQ ID NO 43
<211> LENGTH: 7
<212> TYPE: PRT
<213> ORGANISM: Artificial Sequence
<220> FEATURE:
<223> OTHER INFORMATION: LCDR2

<400> SEQUENCE: 43

Arg Ala Thr Thr Leu Ala Asp
1               5

<210> SEQ ID NO 44
<211> LENGTH: 7
<212> TYPE: PRT
<213> ORGANISM: Artificial Sequence
<220> FEATURE:
<223> OTHER INFORMATION: LCDR2

<400> SEQUENCE: 44

Gly Ala Thr Thr Leu Ala Asp
1               5

<210> SEQ ID NO 45
<211> LENGTH: 7
<212> TYPE: PRT
<213> ORGANISM: Artificial Sequence
<220> FEATURE:
<223> OTHER INFORMATION: LCDR2

<400> SEQUENCE: 45

His Ala Asn Pro Leu His Asp
1               5

<210> SEQ ID NO 46
<211> LENGTH: 7
<212> TYPE: PRT
<213> ORGANISM: Artificial Sequence
<220> FEATURE:
<223> OTHER INFORMATION: LCDR2

<400> SEQUENCE: 46

Tyr Ala Asn Pro Leu His Asp
1               5

<210> SEQ ID NO 47
<211> LENGTH: 9
<212> TYPE: PRT
<213> ORGANISM: Artificial Sequence
<220> FEATURE:
<223> OTHER INFORMATION: LCDR3

<400> SEQUENCE: 47

Leu Gln Tyr Asp Glu Phe Pro Pro Thr
1               5

<210> SEQ ID NO 48
<211> LENGTH: 9
<212> TYPE: PRT
<213> ORGANISM: Artificial Sequence
<220> FEATURE:
<223> OTHER INFORMATION: LCDR3

<400> SEQUENCE: 48

Cys Gln Gly Ser Tyr Ser Pro Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: LCDR3

<400> SEQUENCE: 49

Leu Gln Tyr Asp Glu Trp Pro Tyr Thr
1               5

<210> SEQ ID NO 50
<211> LENGTH: 9
<212> TYPE: PRT
<213> ORGANISM: Artificial Sequence
<220> FEATURE:
<223> OTHER INFORMATION: LCDR3

<400> SEQUENCE: 50

Leu Gln Tyr Asp Glu Tyr Pro Pro Thr
1               5

<210> SEQ ID NO 51
<211> LENGTH: 9
<212> TYPE: PRT
<213> ORGANISM: Artificial Sequence
<220> FEATURE:
<223> OTHER INFORMATION: LCDR3

<400> SEQUENCE: 51

Gln Gln Thr Ser Ser Thr Pro Trp Thr
1               5

<210> SEQ ID NO 52
<211> LENGTH: 9
<212> TYPE: PRT
<213> ORGANISM: Artificial Sequence
<220> FEATURE:
<223> OTHER INFORMATION: LCDR3

<400> SEQUENCE: 52

Gln Gln Gly Tyr Lys Phe Pro Tyr Thr

```
<210> SEQ ID NO 53
<211> LENGTH: 9
<212> TYPE: PRT
<213> ORGANISM: Artificial Sequence
<220> FEATURE:
<223> OTHER INFORMATION: LCDR3

<400> SEQUENCE: 53

Gln Gln Ala Ser Ser Ala Pro Trp Thr
1               5

<210> SEQ ID NO 54
<211> LENGTH: 9
<212> TYPE: PRT
<213> ORGANISM: Artificial Sequence
<220> FEATURE:
<223> OTHER INFORMATION: LCDR3

<400> SEQUENCE: 54

Gln Gln Gly Tyr Lys Phe Pro Tyr Ser
1               5

<210> SEQ ID NO 55
<211> LENGTH: 113
<212> TYPE: PRT
<213> ORGANISM: Artificial Sequence
<220> FEATURE:
<223> OTHER INFORMATION: 5738-10-R3A-B2 HCVR

<400> SEQUENCE: 55

Gln Val Gln Leu Lys Gln Ser Gly Ala Glu Leu Ala Lys Pro Gly Ser
1               5                   10                  15

Ser Val Lys Ile Ser Cys Lys Ala Ser Gly Tyr Thr Phe Thr Ser Tyr
            20                  25                  30

Tyr Ile Ser Trp Ile Lys Gln Thr Thr Gly Gln Gly Leu Glu Tyr Ile
        35                  40                  45

Gly Tyr Ile Asn Thr Gly Ser Gly Thr Asn Tyr Asn Glu Lys Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Asp Asp Ser Ala Val Tyr Tyr Cys
                85                  90                  95

Ala Arg Tyr Phe Asp Tyr Trp Gly Gln Gly Val Met Val Thr Val Ser
            100                 105                 110

Ser

<210> SEQ ID NO 56
<211> LENGTH: 116
<212> TYPE: PRT
<213> ORGANISM: Artificial Sequence
<220> FEATURE:
<223> OTHER INFORMATION: 5738-10-R3A-C6 HCVR

<400> SEQUENCE: 56

Glu Val Lys Leu Val Glu Ser Gly Gly Gly Leu Val Gln Pro Lys Glu
1               5                   10                  15

Ser Leu Lys Ile Ser Cys Ala Ala Ser Gly Phe Thr Phe Ser Asn Ile
            20                  25                  30

Ala Met Tyr Trp Val Arg Gln Ala Pro Gly Lys Gly Leu Glu Trp Val
        35                  40                  45
```

```
Ala His Ile Arg Thr Lys Pro His Asn Phe Ala Thr Tyr Tyr Ala Asn
         50                  55                  60

Ser Val Lys Gly Arg Phe Thr Ile Ser Arg Asp Asp Ser Lys Asn Met
 65                  70                  75                  80

Val Tyr Leu Gln Met Asp Asn Leu Lys Pro Glu Asp Thr Ala Met Tyr
                 85                  90                  95

Tyr Cys Ser Val Gly Phe Gly Asp Tyr Trp Gly Gln Gly Val Met Val
            100                 105                 110

Thr Val Ser Ser
        115

<210> SEQ ID NO 57
<211> LENGTH: 113
<212> TYPE: PRT
<213> ORGANISM: Artificial Sequence
<220> FEATURE:
<223> OTHER INFORMATION: 5738-10-R3A-D1 HCVR

<400> SEQUENCE: 57

Glu Val Gln Leu Gln Gln Ser Gly Ala Glu Leu Ala Lys Pro Gly Ser
 1               5                  10                  15

Ser Val Lys Ile Ser Cys Lys Ala Ser Gly Tyr Thr Phe Thr Asn Tyr
                20                  25                  30

Thr Ile Ser Trp Ile Lys Gln Thr Thr Gly Gln Gly Leu Glu Tyr Ile
            35                  40                  45

Gly Tyr Ile Tyr Ala Gly Thr Gly Asp Thr Asn Tyr Asn Glu Lys Phe
        50                  55                  60

Lys Gly Lys Ala Thr Leu Thr Val Asp Lys Ser Ser Asn Thr Ala Phe
 65                  70                  75                  80

Met Gln Leu Ser Ser Leu Thr Pro Asp Asp Ser Ala Val Tyr Tyr Cys
                 85                  90                  95

Ala Arg Tyr Phe Asp His Trp Gly Gln Gly Val Met Val Thr Val Ser
            100                 105                 110

Ser

<210> SEQ ID NO 58
<211> LENGTH: 114
<212> TYPE: PRT
<213> ORGANISM: Artificial Sequence
<220> FEATURE:
<223> OTHER INFORMATION: 5738-10-R3A-D5 HCVR

<400> SEQUENCE: 58

Glu Val Gln Leu Gln Gln Ser Gly Ala Glu Leu Ala Lys Pro Gly Ser
 1               5                  10                  15

Ser Val Lys Ile Ser Cys Lys Ala Ser Gly Tyr Thr Phe Thr Ser Tyr
                20                  25                  30

Tyr Ile Ser Trp Ile Lys Gln Thr Thr Gly Gln Gly Leu Glu Tyr Ile
            35                  40                  45

Gly Tyr Ile Asn Thr Gly Ser Gly Thr Asn Tyr Asn Glu Lys Phe
        50                  55                  60

Lys Gly Lys Ala Thr Leu Thr Val Asp Lys Ser Ser Thr Ala Phe
 65                  70                  75                  80

Met Gln Leu Ser Ser Leu Thr Pro Asp Asp Ser Ala Val Tyr Tyr Cys
                 85                  90                  95

Ala Arg Asp Lys Trp Val Asp Trp Gly Gln Gly Val Met Val Thr Val
            100                 105                 110
```

Ser Ser

<210> SEQ ID NO 59
<211> LENGTH: 116
<212> TYPE: PRT
<213> ORGANISM: Artificial Sequence
<220> FEATURE:
<223> OTHER INFORMATION: 5738-10-R3A-D8 HCVR

<400> SEQUENCE: 59

Glu Val Gln Leu Glu Glu Ser Gly Gly Gly Leu Val Gln Pro Lys Glu
1               5                   10                  15

Ser Leu Lys Ile Ser Cys Ala Val Ser Gly Phe Thr Phe Ser Asn Ile
            20                  25                  30

Ala Met Tyr Trp Val Arg Gln Ala Pro Gly Lys Gly Leu Glu Trp Val
        35                  40                  45

Gly His Ile Arg Thr Lys Pro His Asn Tyr Ala Thr Tyr Tyr Ala Asp
    50                  55                  60

Ser Val Lys Gly Arg Phe Thr Ile Ser Arg Asp Asp Ser Asn Asn Met
65                  70                  75                  80

Val Tyr Leu Glu Met Asp Asn Leu Lys Pro Glu Asp Thr Ala Met Tyr
                85                  90                  95

Tyr Cys Ser Val Gly Phe Gly Asp Tyr Trp Gly Gln Gly Val Met Val
            100                 105                 110

Thr Val Ser Ser
        115

<210> SEQ ID NO 60
<211> LENGTH: 113
<212> TYPE: PRT
<213> ORGANISM: Artificial Sequence
<220> FEATURE:
<223> OTHER INFORMATION: 5738-10-R3A-D11 HCVR & 5738-10-R4A-E9 HCVR

<400> SEQUENCE: 60

Gln Val Gln Leu Lys Gln Ser Gly Ala Glu Leu Ala Lys Pro Gly Ser
1               5                   10                  15

Ser Val Lys Ile Ser Cys Lys Ala Ser Gly Tyr Thr Phe Thr Ser Tyr
            20                  25                  30

Tyr Ile Ser Trp Ile Lys Gln Thr Gly Gln Gly Leu Glu Tyr Ile
        35                  40                  45

Gly Tyr Ile His Pro Gly Ser Gly Val Thr Asn Tyr Asn Glu Lys Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Asp Asp Ser Ala Ile Tyr Tyr Cys
                85                  90                  95

Ala Arg Tyr Phe Asp Tyr Trp Gly Gln Gly Val Met Val Thr Val Ser
            100                 105                 110

Ser

<210> SEQ ID NO 61
<211> LENGTH: 113
<212> TYPE: PRT
<213> ORGANISM: Artificial Sequence
<220> FEATURE:
<223> OTHER INFORMATION: 5738-10-R4A-E7 HCVR

<400> SEQUENCE: 61

Gln Val Gln Leu Lys Gln Ser Gly Val Glu Leu Ala Lys Pro Gly Ser
1               5                   10                  15

Ser Val Lys Ile Ser Cys Lys Ala Ser Gly Tyr Thr Phe Thr Ser Asp
                20                  25                  30

Ser Ile Ser Trp Ile Lys Gln Thr Thr Gly Gln Gly Leu Glu Tyr Ile
            35                  40                  45

Gly Tyr Ile His Pro Gly Ser Gly Val Thr Asn Tyr Asn Glu Lys Phe
        50                  55                  60

Lys Gly Lys Ala Thr Leu Thr Val Asp Lys Ser Ser Thr Ala Phe
65                  70                  75                  80

Met Gln Leu Ser Ser Leu Thr Pro Asp Asp Ser Ala Ile Tyr Tyr Cys
                85                  90                  95

Ala Arg Tyr Phe Asp Tyr Trp Gly Gln Gly Val Met Val Thr Val Ser
            100                 105                 110

Ser

<210> SEQ ID NO 62
<211> LENGTH: 113
<212> TYPE: PRT
<213> ORGANISM: Artificial Sequence
<220> FEATURE:
<223> OTHER INFORMATION: 5738-10-R4A-F12 HCVR

<400> SEQUENCE: 62

Glu Val Gln Leu Gln Gln Ser Gly Val Glu Leu Ala Lys Pro Gly Ser
1               5                   10                  15

Ser Val Lys Ile Ser Cys Lys Ala Ser Gly Tyr Thr Phe Thr Ser Asp
                20                  25                  30

Ser Ile Ser Trp Ile Lys Gln Thr Thr Gly Gln Gly Leu Glu Tyr Ile
            35                  40                  45

Gly Tyr Ile His Pro Gly Ser Gly Val Thr Asn Tyr Asn Glu Lys Phe
        50                  55                  60

Lys Gly Lys Ala Thr Leu Thr Val Asp Lys Ser Ser Thr Ala Phe
65                  70                  75                  80

Met Gln Leu Ser Ser Leu Thr Pro Asp Asp Ser Ala Ile Tyr Tyr Cys
                85                  90                  95

Ala Arg Tyr Phe Asp Tyr Trp Gly Gln Gly Val Met Val Thr Val Ser
            100                 105                 110

Ser

<210> SEQ ID NO 63
<211> LENGTH: 113
<212> TYPE: PRT
<213> ORGANISM: Artificial Sequence
<220> FEATURE:
<223> OTHER INFORMATION: 5738-10-R4A-G4 HCVR

<400> SEQUENCE: 63

Glu Val Gln Leu Gln Gln Ser Gly Val Glu Leu Ala Lys Pro Gly Ser
1               5                   10                  15

Ser Val Lys Ile Ser Cys Lys Ala Ser Gly Tyr Thr Phe Thr Ser Asp
                20                  25                  30

Ser Ile Ser Trp Ile Lys Gln Thr Thr Gly Gln Gly Leu Glu Tyr Ile
            35                  40                  45

Gly Tyr Ile His Pro Gly Ser Gly Val Thr Asn Tyr Asn Glu Lys Phe
        50                  55                  60

Arg Gly Lys Ala Thr Leu Thr Val Asp Lys Ser Ser Thr Ala Phe
65                  70                  75                  80

Met Gln Leu Ser Ser Leu Thr Pro Asp Asp Ser Ala Ile Tyr Tyr Cys
                85                  90                  95

Ala Arg Tyr Phe Asp Tyr Trp Gly Gln Gly Val Met Val Thr Val Ser
            100                 105                 110

Ser

<210> SEQ ID NO 64
<211> LENGTH: 113
<212> TYPE: PRT
<213> ORGANISM: Artificial Sequence
<220> FEATURE:
<223> OTHER INFORMATION: 5738-10-R4A-G11 HCVR

<400> SEQUENCE: 64

Gln Val Gln Leu Gln Gln Pro Arg Ala Glu Leu Ala Lys Pro Gly Ser
1               5                   10                  15

Ser Val Lys Ile Ser Cys Lys Ala Ser Gly Tyr Thr Phe Thr Asn Tyr
                20                  25                  30

Ser Ile Ser Trp Ile Lys Gln Thr Thr Gly Gln Gly Leu Glu Tyr Ile
            35                  40                  45

Gly Tyr Ile Tyr Pro Gly Ser Gly Asp Thr Asn Tyr Asn Glu Lys Phe
        50                  55                  60

Lys Gly Lys Ala Thr Leu Thr Val Asp Lys Ser Ser Thr Ala Phe
65                  70                  75                  80

Met Gln Leu Ser Ser Leu Thr Pro Asp Asp Ser Ala Val Tyr Tyr Cys
                85                  90                  95

Ala Arg Tyr Phe Asp His Trp Gly Gln Gly Thr Leu Val Thr Val Ser
            100                 105                 110

Ser

<210> SEQ ID NO 65
<211> LENGTH: 113
<212> TYPE: PRT
<213> ORGANISM: Artificial Sequence
<220> FEATURE:
<223> OTHER INFORMATION: 5738-10-R4A-G12 HCVR

<400> SEQUENCE: 65

Gln Val Gln Leu Lys Glu Ser Gly Ala Glu Leu Ala Lys Pro Gly Ser
1               5                   10                  15

Ser Val Lys Ile Ser Cys Lys Ala Ser Gly Tyr Thr Phe Thr Ser Asp
                20                  25                  30

Ser Ile Ser Trp Ile Lys Gln Thr Thr Gly Gln Gly Leu Glu Tyr Ile
            35                  40                  45

Gly Tyr Ile His Pro Gly Ser Gly Val Thr Asn Tyr Asn Glu Lys Phe
        50                  55                  60

Lys Gly Lys Ala Thr Leu Thr Val Asp Lys Ser Ser Thr Ala Phe
65                  70                  75                  80

Met Gln Leu Ser Ser Leu Thr Pro Asp Asp Ser Ala Ile Tyr Tyr Cys
                85                  90                  95

Ala Arg Tyr Phe Asp Tyr Trp Gly Gln Gly Val Met Val Thr Val Ser
            100                 105                 110

Ser

<210> SEQ ID NO 66

```
<211> LENGTH: 121
<212> TYPE: PRT
<213> ORGANISM: Artificial Sequence
<220> FEATURE:
<223> OTHER INFORMATION: 5738-13-R2A-C1 HCVR

<400> SEQUENCE: 66

Gln Val Gln Leu Lys Glu Ser Gly Gly Gly Leu Val Gln Pro Gly Arg
1               5                   10                  15

Ser Leu Lys Leu Ser Cys Ala Ala Ser Gly Phe Thr Phe Ser Asp Tyr
            20                  25                  30

Asn Met Ala Trp Val Arg Gln Ala Pro Lys Lys Gly Leu Glu Trp Val
        35                  40                  45

Ala Thr Ile Ser Tyr Asp Asp Ser Arg Thr Tyr Tyr Arg Asp Ser Val
    50                  55                  60

Lys Gly Arg Phe Ala Ile Ser Arg Asp Asp Ala Lys Thr Leu Asn
65                  70                  75                  80

Leu Gln Met Asp Ser Leu Arg Ser Glu Asp Thr Ala Thr Tyr Tyr Cys
                85                  90                  95

Ala Arg Gln Gly Gly Ile Ile Arg Gly Val Trp Phe Pro Tyr Trp Gly
            100                 105                 110

Gln Gly Thr Leu Val Thr Val Ser Ser
        115                 120

<210> SEQ ID NO 67
<211> LENGTH: 117
<212> TYPE: PRT
<213> ORGANISM: Artificial Sequence
<220> FEATURE:
<223> OTHER INFORMATION: 5738-13-R2A-D3 HCVR

<400> SEQUENCE: 67

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Tyr Ile Thr Asn Ser Phe Gly Ser Ala Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ser Thr Val Pro Leu Gly Ala Phe Val Tyr Trp Gly Gln Gly Thr Leu
            100                 105                 110

Val Thr Val Ser Ser
        115

<210> SEQ ID NO 68
<211> LENGTH: 121
<212> TYPE: PRT
<213> ORGANISM: Artificial Sequence
<220> FEATURE:
<223> OTHER INFORMATION: 5738-13-R4A-D11 HCVR

<400> SEQUENCE: 68

Gln Val Gln Leu Lys Glu Ser Gly Gly Gly Leu Val Gln Pro Gly Arg
1               5                   10                  15
```

-continued

Ser Leu Lys Leu Ser Cys Ala Ala Ser Gly Phe Ser Phe Gly Asp Tyr
            20                  25                  30

Asn Met Ala Trp Val Arg Gln Ala Pro Lys Gly Leu Glu Trp Val
        35                  40                  45

Ala Thr Ile Ser Tyr Asp Asp Tyr Arg Thr Tyr Tyr Arg Asp Ser Val
50                  55                  60

Lys Gly Arg Phe Thr Ile Ser Arg Asp Asp Ala Lys Ala Thr Leu Tyr
65                  70                  75                  80

Leu Gln Met Asp Ser Leu Arg Ser Glu Asp Thr Ala Thr Tyr Tyr Cys
                85                  90                  95

Ala Arg Gln Gly Gly Ile Ile Arg Gly Val Trp Phe Pro Tyr Trp Gly
            100                 105                 110

Gln Gly Thr Leu Val Thr Val Ser Ser
        115                 120

<210> SEQ ID NO 69
<211> LENGTH: 117
<212> TYPE: PRT
<213> ORGANISM: Artificial Sequence
<220> FEATURE:
<223> OTHER INFORMATION: 5738-13-R3A-F5 HCVR

<400> SEQUENCE: 69

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Tyr Ile Thr Asn Ser Leu Gly Ser Ala Tyr Tyr Arg Asp Ser Val
50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ser Thr Val Pro Leu Gly Ala Phe Val Tyr Trp Gly Gln Gly Thr Leu
            100                 105                 110

Val Thr Val Ser Ser
        115

<210> SEQ ID NO 70
<211> LENGTH: 117
<212> TYPE: PRT
<213> ORGANISM: Artificial Sequence
<220> FEATURE:
<223> OTHER INFORMATION: 5738-13-R4A-F11 HCVR

<400> SEQUENCE: 70

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Tyr Ile Thr Asn Ser Phe Gly Ser Thr Tyr Tyr Arg Asp Ser Val
50                  55                  60

Lys Gly Arg Phe Thr Ile Ser Arg Asp Asn Ala Lys Ser Thr Leu Tyr
65                  70                  75                  80

```
Leu Gln Met Asp Ser Leu Arg Ser Glu Asp Thr Ala Thr Tyr Tyr Cys
            85                  90                  95

Ser Thr Val Pro Leu Gly Ala Phe Val Tyr Trp Gly Gln Gly Thr Leu
            100                 105                 110

Val Thr Val Ser Ser
        115

<210> SEQ ID NO 71
<211> LENGTH: 117
<212> TYPE: PRT
<213> ORGANISM: Artificial Sequence
<220> FEATURE:
<223> OTHER INFORMATION: 5738-13-R2A-H3 HCVR

<400> SEQUENCE: 71

Glu Val Lys Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
            35                  40                  45

Ala Tyr Ile Thr Asn Gly Tyr Gly Ser Thr Tyr Tyr Arg Asp Ser Val
        50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
            85                  90                  95

Ser Thr Val Pro Leu Gly Ala Phe Val Tyr Trp Gly Gln Gly Thr Leu
            100                 105                 110

Val Thr Val Ser Ser
        115

<210> SEQ ID NO 72
<211> LENGTH: 117
<212> TYPE: PRT
<213> ORGANISM: Artificial Sequence
<220> FEATURE:
<223> OTHER INFORMATION: 5738-13-R2A-H4 HCVR

<400> SEQUENCE: 72

Glu Val Lys Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
            35                  40                  45

Ala Tyr Ile Thr Asn Gly Phe Gly Ser Thr Tyr Tyr Arg Asp Ser Val
        50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
            85                  90                  95

Ser Thr Val Pro Leu Gly Ala Phe Val Ser Trp Gly Gln Gly Thr Leu
            100                 105                 110

Val Thr Val Ser Ser
        115
```

```
<210> SEQ ID NO 73
<211> LENGTH: 117
<212> TYPE: PRT
<213> ORGANISM: Artificial Sequence
<220> FEATURE:
<223> OTHER INFORMATION: 5738-13-R4A-H9 HCVR

<400> SEQUENCE: 73

Glu Val Lys Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Tyr Ile Thr Asn Gly Phe Gly Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Ala Ala Thr Tyr Tyr Cys
                85                  90                  95

Ser Thr Val Pro Leu Gly Ala Phe Val Ser Trp Gly Gln Gly Thr Leu
            100                 105                 110

Val Thr Val Ser Ser
        115

<210> SEQ ID NO 74
<211> LENGTH: 117
<212> TYPE: PRT
<213> ORGANISM: Artificial Sequence
<220> FEATURE:
<223> OTHER INFORMATION: 5738-13-R4A-H11 HCVR

<400> SEQUENCE: 74

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Tyr Ile Thr Asn Gly Phe Gly Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ser Thr Val Pro Leu Gly Ala Phe Val Ser Trp Gly Gln Gly Thr Leu
            100                 105                 110

Val Thr Val Ser Ser
        115

<210> SEQ ID NO 75
<211> LENGTH: 107
<212> TYPE: PRT
<213> ORGANISM: Artificial Sequence
<220> FEATURE:
<223> OTHER INFORMATION: 5738-10-R3A-B2 LCVR

<400> SEQUENCE: 75

Asp Ile Val Met Thr Gln Ser Pro Ser Ser Met Ser Val Ser Leu Gly
1               5                   10                  15
```

-continued

Asp Thr Val Thr Ile Thr Cys Arg Ala Ser Gln Asp Val Gly Ile Tyr
            20                  25                  30

Val Asn Trp Phe Gln Gln Lys Pro Gly Lys Pro Arg Met Ile
        35                  40                  45

Tyr Arg Ala Thr Asn Leu Ala Asp Gly Val Pro Ser Arg Phe Ser Gly
    50                  55                  60

Thr Arg Ser Gly Ser Asp Tyr Ser Leu Thr Ile Ser Ser Leu Glu Ser
65                  70                  75                  80

Glu Asp Val Ala Asp Tyr His Cys Leu Gln Tyr Asp Glu Phe Pro Pro
                85                  90                  95

Thr Phe Gly Ser Gly Thr Lys Leu Asp Ile Lys
            100                 105

<210> SEQ ID NO 76
<211> LENGTH: 112
<212> TYPE: PRT
<213> ORGANISM: Artificial Sequence
<220> FEATURE:
<223> OTHER INFORMATION: 5738-10-R3A-C6 LCVR

<400> SEQUENCE: 76

Asp Ile Val Met Thr Gln Ala Pro Leu Ser Leu Ser Val Ala Ile Gly
1               5                   10                  15

Gln Ser Ala Ser Ile Ser Cys Lys Ser Ser Gln Ser Leu Lys His Ser
            20                  25                  30

Asp Gly Lys Thr Tyr Leu Asn Trp Ile Phe Gln Ser Pro Gly Gln Ser
        35                  40                  45

Pro Lys Arg Leu Ile Tyr Gln Val Ser Lys Leu Asp Ser Gly Val Pro
    50                  55                  60

Asp Arg Phe Ser Gly Thr Gly Ser Glu Thr Asp Phe Thr Leu Lys Ile
65                  70                  75                  80

Ser Arg Val Glu Ala Glu Asp Leu Gly Val Tyr Tyr Cys Cys Gln Gly
                85                  90                  95

Ser Tyr Ser Pro Tyr Thr Phe Gly Ala Gly Thr Lys Leu Glu Leu Lys
            100                 105                 110

<210> SEQ ID NO 77
<211> LENGTH: 107
<212> TYPE: PRT
<213> ORGANISM: Artificial Sequence
<220> FEATURE:
<223> OTHER INFORMATION: 5738-10-R3A-D1 LCVR

<400> SEQUENCE: 77

Asp Ile Leu Met Thr Gln Ser Pro Ser Ser Met Ser Ala Ser Leu Gly
1               5                   10                  15

Asp Arg Val Thr Ile Thr Cys Gln Ala Ser Gln Asp Ile Gly Asn Asn
            20                  25                  30

Leu Ile Trp Phe Gln Gln Lys Pro Gly Lys Ser Arg Arg Met Ile
        35                  40                  45

Tyr Tyr Ala Thr Asn Leu Ala Asn Gly Val Pro Ser Arg Phe Ser Gly
    50                  55                  60

Ser Arg Ser Gly Ser Asp Tyr Ser Leu Ser Ile Ser Ser Leu Glu Ser
65                  70                  75                  80

Glu Asp Val Ala Asp Tyr His Cys Leu Gln Tyr Asp Glu Phe Pro Pro
                85                  90                  95

Thr Phe Gly Ser Gly Thr Lys Leu Glu Ile Lys

```
<210> SEQ ID NO 78
<211> LENGTH: 107
<212> TYPE: PRT
<213> ORGANISM: Artificial Sequence
<220> FEATURE:
<223> OTHER INFORMATION: 5738-10-R3A-D5 LCVR

<400> SEQUENCE: 78

Asp Ile Leu Met Thr Gln Ser Pro Ser Ser Met Ser Val Ser Leu Gly
1               5                   10                  15

Asp Thr Val Thr Ile Thr Cys Arg Ala Ser Gln Asp Val Gly Ile Tyr
            20                  25                  30

Val Asn Trp Phe Gln Gln Lys Pro Gly Lys Pro Pro Arg Arg Met Ile
        35                  40                  45

Tyr Arg Ala Thr Asn Leu Ala Asp Gly Val Pro Ser Arg Phe Ser Gly
    50                  55                  60

Ser Arg Ser Gly Ser Asn Tyr Ser Leu Thr Ile Arg Ser Leu Glu Ser
65                  70                  75                  80

Glu Asp Val Ala Asp Tyr His Cys Leu Gln Tyr Asp Glu Trp Pro Tyr
                85                  90                  95

Thr Phe Gly Ala Gly Thr Lys Leu Glu Leu Lys
            100                 105

<210> SEQ ID NO 79
<211> LENGTH: 112
<212> TYPE: PRT
<213> ORGANISM: Artificial Sequence
<220> FEATURE:
<223> OTHER INFORMATION: 5738-10-R3A-D8 LCVR

<400> SEQUENCE: 79

Asp Ile Val Met Thr Gln Ala Pro Leu Ser Leu Ser Val Asp Ile Gly
1               5                   10                  15

Gln Ser Ala Ser Ile Ser Cys Arg Ser Ser Gln Ser Leu Lys His Ser
            20                  25                  30

Asp Gly Lys Thr Tyr Leu Asn Trp Val Phe Gln Ser Pro Gly Gln Ser
        35                  40                  45

Pro Lys Arg Leu Ile Tyr Gln Val Ser Lys Leu Asp Ser Gly Val Pro
    50                  55                  60

Asp Arg Phe Ser Gly Ser Gly Ser Glu Ala Asp Phe Thr Leu Lys Ile
65                  70                  75                  80

Ser Arg Val Glu Ala Glu Asp Leu Gly Val Tyr Tyr Cys Cys Gln Gly
                85                  90                  95

Ser Tyr Ser Pro Tyr Thr Phe Gly Ala Gly Thr Lys Leu Glu Leu Lys
            100                 105                 110

<210> SEQ ID NO 80
<211> LENGTH: 107
<212> TYPE: PRT
<213> ORGANISM: Artificial Sequence
<220> FEATURE:
<223> OTHER INFORMATION: 5738-10-R3A-D11 LCVR

<400> SEQUENCE: 80

Asp Ile Gln Leu Thr Gln Ser Pro Ser Ser Met Ser Val Ser Gln Gly
1               5                   10                  15

Asp Thr Val Thr Ile Thr Cys Arg Ala Ser Gln Asp Val Gly Ile Tyr
            20                  25                  30
```

```
Val Asn Trp Phe Gln Gln Lys Pro Gly Lys Ser Pro Arg Arg Met Ile
        35                  40                  45

Tyr Arg Ala Thr Asn Leu Ala Asp Gly Val Pro Ser Arg Phe Ser Gly
    50                  55                  60

Ser Arg Ser Gly Ser Asp Tyr Ser Leu Thr Ile Ala Ser Leu Glu Ser
65                  70                  75                  80

Glu Asp Val Ala Asp Tyr His Cys Leu Gln Tyr Asp Glu Phe Pro Pro
                85                  90                  95

Thr Phe Gly Ser Gly Thr Asn Leu Glu Ile Lys
            100                 105

<210> SEQ ID NO 81
<211> LENGTH: 107
<212> TYPE: PRT
<213> ORGANISM: Artificial Sequence
<220> FEATURE:
<223> OTHER INFORMATION: 5738-10-R4A-E7 LCVR

<400> SEQUENCE: 81

Asp Ile Leu Met Thr Gln Ser Pro Ser Ser Met Ser Val Ser Leu Gly
1               5                   10                  15

Asp Thr Val Thr Ile Thr Cys Arg Ala Ser Gln Asp Val Gly Ile Tyr
                20                  25                  30

Val Asn Trp Phe Gln Gln Ile Pro Gly Lys Ser Pro Arg Arg Leu Ile
        35                  40                  45

Tyr Arg Ala Thr Asn Leu Ala Asp Gly Val Pro Ser Arg Phe Ser Gly
    50                  55                  60

Ser Arg Ser Gly Ser Asp Tyr Ser Leu Thr Ile Ala Ser Leu Glu Ser
65                  70                  75                  80

Glu Asp Val Ala Asp Tyr His Cys Leu Gln Tyr Asp Glu Phe Pro Pro
                85                  90                  95

Thr Phe Gly Ser Gly Thr Lys Leu Glu Ile Lys
            100                 105

<210> SEQ ID NO 82
<211> LENGTH: 107
<212> TYPE: PRT
<213> ORGANISM: Artificial Sequence
<220> FEATURE:
<223> OTHER INFORMATION: 5738-10-R4A-E9 LCVR

<400> SEQUENCE: 82

Asp Ile Leu Met Thr Gln Ser Pro Ser Ser Met Ser Val Ser Gln Gly
1               5                   10                  15

Asp Thr Val Thr Ile Thr Cys Arg Ala Ser Gln Asp Val Gly Ile Tyr
                20                  25                  30

Val Asn Trp Phe Gln Gln Lys Pro Gly Lys Ser Pro Arg Arg Met Ile
        35                  40                  45

His Arg Ala Thr Asn Leu Ala Asp Gly Val Pro Ser Arg Phe Ser Gly
    50                  55                  60

Ser Arg Ser Gly Ser Asp Tyr Ser Leu Thr Ile Thr Ser Leu Glu Ser
65                  70                  75                  80

Glu Asp Val Ala Asp Tyr His Cys Leu Gln Tyr Asp Glu Tyr Pro Pro
                85                  90                  95

Thr Phe Gly Ser Gly Thr Asn Leu Glu Ile Lys
            100                 105
```

```
<210> SEQ ID NO 83
<211> LENGTH: 107
<212> TYPE: PRT
<213> ORGANISM: Artificial Sequence
<220> FEATURE:
<223> OTHER INFORMATION: 5738-10-R4A-F12 LCVR

<400> SEQUENCE: 83

Asp Ile Leu Met Thr Gln Ser Pro Ser Ser Met Ser Val Ser Leu Gly
1               5                   10                  15

Asp Thr Val Thr Ile Thr Cys Arg Ala Ser Gln Asp Val Gly Ile Tyr
            20                  25                  30

Val Asn Trp Phe Gln Gln Lys Pro Gly Lys Ser Pro Arg Arg Met Ile
        35                  40                  45

His Arg Ala Thr Asn Leu Ala Asp Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Val Ala Asp Tyr His Cys Leu Gln Tyr Asp Glu Tyr Pro Pro
                85                  90                  95

Thr Phe Gly Ser Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
<223> OTHER INFORMATION: 5738-10-R4A-G4 LCVR

<400> SEQUENCE: 84

Asp Ile Val Met Thr Gln Ser Pro Ser Ser Met Ser Val Ser Leu Gly
1               5                   10                  15

Asp Thr Val Thr Ile Thr Cys Arg Ala Ser Gln Asp Val Gly Ile Tyr
            20                  25                  30

Val Asn Trp Phe Gln Gln Lys Pro Gly Lys Ser Pro Arg Arg Met Ile
        35                  40                  45

Tyr Arg Ala Thr Asn Leu Ala Asp Gly Val Pro Ser Arg Phe Ser Gly
    50                  55                  60

Ser Arg Ser Gly Ser Asp Tyr Ser Leu Thr Ile Ala Ser Leu Glu Ser
65                  70                  75                  80

Glu Asp Val Ala Asp Tyr His Cys Leu Gln Tyr Asp Glu Phe Pro Pro
                85                  90                  95

Thr Phe Gly Ser Gly Thr Lys Leu Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: 5738-10-R4A-G11 LCVR

<400> SEQUENCE: 85

Asp Ile Leu Met Thr Gln Ser Pro Ser Ser Met Ser Val Ser Leu Gly
1               5                   10                  15

Asp Thr Val Thr Ile Thr Cys Arg Ala Ser Gln Asp Val Gly Ile Tyr
            20                  25                  30

Val Asn Trp Phe Gln Gln Lys Pro Gly Lys Ser Pro Arg Arg Met Ile
        35                  40                  45
```

```
Tyr Arg Ala Thr Thr Leu Ala Asp Gly Val Pro Ser Arg Phe Ser Gly
            50                  55                  60

Ser Arg Ser Gly Ser Asp Tyr Ser Leu Thr Ile Ser Ser Leu Glu Ser
 65                  70                  75                  80

Glu Asp Val Ala Asp Tyr His Cys Leu Gln Tyr Asp Glu Tyr Pro Pro
                 85                  90                  95

Thr Phe Gly Ser Gly Thr Lys Leu Glu Ile Lys
            100                 105
```

<210> SEQ ID NO 86
<211> LENGTH: 107
<212> TYPE: PRT
<213> ORGANISM: Artificial Sequence
<220> FEATURE:
<223> OTHER INFORMATION: 5738-10-R4A-G12 LCVR

<400> SEQUENCE: 86

```
Asp Ile Leu Met Thr Gln Ser Pro Ser Ser Met Ser Val Ser Leu Gly
 1               5                  10                  15

Asp Thr Val Thr Ile Thr Cys Arg Ala Ser Gln Asp Val Gly Ile Tyr
                20                  25                  30

Val Asn Trp Phe Gln Gln Lys Pro Gly Lys Ser Pro Arg Arg Met Ile
            35                  40                  45

Tyr Arg Ala Thr Asn Leu Ala Asp Gly Val Pro Ser Arg Phe Ser Gly
            50                  55                  60

Ser Arg Ser Gly Ser Asp Tyr Ser Leu Thr Ile Ser Ser Leu Glu Ser
 65                  70                  75                  80

Glu Asp Val Ala Asp Tyr His Cys Leu Gln Tyr Asp Glu Tyr Pro Pro
                 85                  90                  95

Thr Phe Gly Gly Gly Thr Lys Leu Glu Leu Lys
            100                 105
```

<210> SEQ ID NO 87
<211> LENGTH: 106
<212> TYPE: PRT
<213> ORGANISM: Artificial Sequence
<220> FEATURE:
<223> OTHER INFORMATION: 5738-13-R2A-C1 LCVR

<400> SEQUENCE: 87

```
Asp Ile Gln Leu Thr Gln Ser Pro Ala Ser Leu Ser Ala Ser Leu Glu
 1               5                  10                  15

Glu Ile Val Thr Ile Thr Cys Gln Ala Ser Gln Asp Ile Gly Asn Trp
                20                  25                  30

Leu Ala Trp Tyr Gln Gln Lys Pro Gly Lys Ser Pro His Leu Leu Ile
            35                  40                  45

Tyr Gly Ala Thr Thr Leu Ala Asp Gly Val Pro Ser Arg Ser Gly Ser
            50                  55                  60

Arg Ser Gly Thr Gln Tyr Ser Leu Lys Ile Ser Arg Leu Gln Val Glu
 65                  70                  75                  80

Asp Val Gly Met Tyr Tyr Cys Gln Gln Thr Ser Ser Thr Pro Trp Thr
                 85                  90                  95

Phe Gly Gly Gly Thr Lys Leu Glu Leu Lys
            100                 105
```

<210> SEQ ID NO 88
<211> LENGTH: 107
<212> TYPE: PRT

<213> ORGANISM: Artificial Sequence
<220> FEATURE:
<223> OTHER INFORMATION: 5738-13-R2A-D3 LCVR

<400> SEQUENCE: 88

Asp Ile Gln Met Thr Gln Thr Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Tyr Gln Gln Lys Pro Gly Lys Ser Pro Gln Leu Leu Ile
        35                  40                  45

Ser His Ala Asn Pro Leu His Asp Gly Val Pro Ser Arg Phe Ser Gly
50                  55                  60

Asp Gly Ser Gly Thr Gln Tyr Ser Leu Lys Ile Arg Asn Met Gln Pro
65                  70                  75                  80

Glu Asp Glu Gly Val Tyr Tyr Cys Gln Gln Gly Tyr Lys Phe Pro Tyr
                85                  90                  95

Thr Phe Gly Ala Gly Thr Lys Leu Glu Leu Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: 5738-13-R4A-D11 LCVR

<400> SEQUENCE: 89

Asp Ile Gln Met Thr Gln Thr Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro His Leu Leu Ile
        35                  40                  45

Tyr Gly Ala Thr Thr Leu Ala Asp Gly Val Pro Ser Arg Phe Ser Gly
50                  55                  60

Ser Arg Ser Gly Thr Gln Tyr Ser Leu Lys Ile Ser Arg Leu Gln Ala
65                  70                  75                  80

Glu Asp Ile Gly Ile Tyr Tyr Cys Gln Gln Ala Ser Ser Ala Pro Trp
                85                  90                  95

Thr Phe Gly Gly Gly Thr Lys Leu Glu Leu Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: 5738-13-R3A-F5 LCVR

<400> SEQUENCE: 90

Asp Ile Gln Met Thr Gln Thr Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Tyr Gln Gln Lys Pro Gly Lys Ser Pro Gln Leu Leu Ile
        35                  40                  45

Ser His Ala Asn Pro Leu His Asp Gly Val Pro Ser Arg Phe Ser Gly
50                  55                  60

```
Ser Gly Ser Gly Thr Gln Tyr Ser Leu Lys Ile Arg Asn Met Gln Pro
65                  70                  75                  80

Glu Asp Glu Gly Val Tyr Tyr Cys Gln Gln Gly Tyr Lys Phe Pro Tyr
                85                  90                  95

Ser Phe Gly Ala Gly Thr Lys Leu Glu Leu Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: 5738-13-R4A-F11 LCVR

<400> SEQUENCE: 91

Asp Ile Gln Leu Thr Gln Ser Pro Ala Ser Leu Ser Ala Ser Leu Gly
1               5                   10                  15

Glu Thr Val Ser Ile Glu Cys Leu Ala Ser Glu Asp Ile Tyr Ser Tyr
                20                  25                  30

Leu Ala Trp Tyr Gln Gln Lys Pro Gly Lys Ser Pro Gln Leu Leu Ile
            35                  40                  45

Ser His Ala Asn Pro Leu His Asp Gly Val Pro Ser Arg Phe Ser Gly
        50                  55                  60

Ser Gly Ser Gly Thr Gln Tyr Ser Leu Lys Ile Arg Asn Met Gln Pro
65                  70                  75                  80

Glu Asp Glu Gly Val Tyr Tyr Cys Gln Gln Gly Tyr Lys Phe Pro Tyr
                85                  90                  95

Thr Phe Gly Ala Gly Thr Lys Leu Glu Leu Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: 5738-13-R2A-H3 LCVR

<400> SEQUENCE: 92

Asp Ile Gln Met Thr Gln Thr Pro His Ser Leu Ser Ala Ser Leu Gly
1               5                   10                  15

Glu Thr Val Ser Ile Glu Cys Leu Ala Ser Glu Gly Ile Ser Asn Tyr
                20                  25                  30

Leu Ala Trp Tyr Gln Gln Lys Pro Gly Lys Ser Pro Gln Leu Leu Ile
            35                  40                  45

Ser His Ala Asn Pro Leu His Asp Gly Val Pro Ser Arg Phe Ser Gly
        50                  55                  60

Ser Gly Ser Gly Thr Gln Tyr Ser Leu Lys Ile Arg Asn Met Gln Pro
65                  70                  75                  80

Glu Asp Glu Gly Val Tyr Tyr Cys Gln Gln Gly Tyr Lys Phe Pro Tyr
                85                  90                  95

Thr Phe Gly Ala Gly Thr Lys Leu Glu Leu Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: 5738-13-R2A-H4 LCVR
```

<400> SEQUENCE: 93

Asp Ile Gln Met Thr Gln Thr Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Tyr Gln Gln Lys Pro Gly Lys Ser Pro Gln Leu Leu Ile
        35                  40                  45

Ser Tyr Ala Asn Pro Leu His Asp Gly Val Pro Ser Arg Phe Ser Gly
    50                  55                  60

Ser Gly Ser Gly Thr Gln Phe Ser Leu Lys Ile Arg Asn Met Gln Pro
65                  70                  75                  80

Glu Asp Glu Gly Val Tyr Tyr Cys Gln Gln Gly Tyr Lys Phe Pro Tyr
                85                  90                  95

Thr Phe Gly Ala Gly Thr Lys Leu Glu Leu Thr
            100                 105

<210> SEQ ID NO 94
<211> LENGTH: 107
<212> TYPE: PRT
<213> ORGANISM: Artificial Sequence
<220> FEATURE:
<223> OTHER INFORMATION: 5738-13-R4A-H9 LCVR & 5738-13-R4A-H11 LCVR

<400> SEQUENCE: 94

Asp Ile Gln Met Thr Gln Thr Pro His Ser Leu Ser Ala Ser Leu Gly
1               5                   10                  15

Glu Thr Val Ser Ile Glu Cys Leu Ala Ser Gly Ile Ser Asn Tyr
            20                  25                  30

Leu Ala Trp Tyr Gln Gln Lys Pro Gly Lys Ser Pro Gln Leu Leu Ile
        35                  40                  45

Ser His Ala Asn Pro Leu His Asp Gly Val Pro Ser Arg Phe Ser Gly
    50                  55                  60

Ser Gly Ser Gly Thr Gln Phe Ser Leu Lys Ile Arg Asn Met Gln Pro
65                  70                  75                  80

Glu Asp Glu Gly Val Tyr Tyr Cys Gln Gln Gly Tyr Lys Phe Pro Tyr
                85                  90                  95

Thr Phe Gly Ala Gly Thr Lys Leu Glu Leu Lys
            100                 105

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

```
<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 766
<212> TYPE: PRT
<213> ORGANISM: Homo sapiens
<220> FEATURE:
<221> NAME/KEY: DOMAIN
<222> LOCATION: 1..6
<223> OTHER INFORMATION: Cytoplasmic domain
<220> FEATURE:
<223> OTHER INFORMATION: hDPP4
<220> FEATURE:
<221> NAME/KEY: DOMAIN
<222> LOCATION: 7..28
<223> OTHER INFORMATION: Transmembrane domain
<220> FEATURE:
<221> NAME/KEY: DOMAIN
<222> LOCATION: 29..766
<223> OTHER INFORMATION: Extracellular domain
<220> FEATURE:
<221> NAME/KEY: SITE
<222> LOCATION: 170..191
<223> OTHER INFORMATION: hDPP4 Peptide P2
<220> FEATURE:
<221> NAME/KEY: SITE
<222> LOCATION: 235..254
<223> OTHER INFORMATION: hDPP4 Peptide P3
<220> FEATURE:
<221> NAME/KEY: SITE
<222> LOCATION: 492..517
<223> OTHER INFORMATION: hDPP4 Peptide P5
<220> FEATURE:
<221> NAME/KEY: SITE
<222> LOCATION: 533..551
<223> OTHER INFORMATION: hDPP4 Peptide P6

<400> SEQUENCE: 101

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125
```

```
Thr Ala Ser Tyr Asp Ile Tyr Asp Leu Asn Lys Arg Gln Leu Ile Thr
        130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asp Ile Tyr Val Lys Ile
                165                 170                 175

Glu Pro Asn Leu Pro Ser Tyr Arg Ile Thr Trp Thr Gly Lys Glu Asp
                180                 185                 190

Ile Ile Tyr Asn Gly Ile Thr Asp Trp Val Tyr Glu Glu Val Phe
        195                 200                 205

Ser Ala Tyr Ser Ala Leu Trp Trp Ser Pro Asn Gly Thr Phe Leu Ala
        210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
                260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
        340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
        370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
                420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
        450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
                500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
        530                 535                 540
```

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
            565                 570                 575

Ser Phe Asp Gly Arg Gly Ser Gly Tyr Gln Gly Asp Lys Ile Met His
        580                 585                 590

Ala Ile Asn Arg Arg Leu Gly Thr Phe Glu Val Glu Asp Gln Ile Glu
    595                 600                 605

Ala Ala Arg Gln Phe Ser Lys Met Gly Phe Val Asp Asn Lys Arg Ile
610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765

<210> SEQ ID NO 102
<211> LENGTH: 736
<212> TYPE: PRT
<213> ORGANISM: Artificial Sequence
<220> FEATURE:
<223> OTHER INFORMATION: hDPP4-ECD_6xHis

<400> SEQUENCE: 102

His His His His His His Ala Asp Ser Arg Lys Thr Tyr Thr Leu Thr
1               5                   10                  15

Asp Tyr Leu Lys Asn Thr Tyr Arg Leu Lys Leu Tyr Ser Leu Arg Trp
            20                  25                  30

Ile Ser Asp His Glu Tyr Leu Tyr Lys Gln Glu Asn Asn Ile Leu Val
        35                  40                  45

Phe Asn Ala Glu Tyr Gly Asn Ser Ser Val Phe Leu Glu Asn Ser Thr
    50                  55                  60

Phe Asp Glu Phe Gly His Ser Ile Asn Asp Tyr Ser Ile Ser Pro Asp
65                  70                  75                  80

Gly Gln Phe Ile Leu Leu Glu Tyr Asn Tyr Val Lys Gln Trp Arg His
                85                  90                  95

Ser Tyr Thr Ala Ser Tyr Asp Ile Tyr Asp Leu Asn Lys Arg Gln Leu
            100                 105                 110

Ile Thr Glu Glu Arg Ile Pro Asn Asn Thr Gln Trp Val Thr Trp Ser
        115                 120                 125

Pro Val Gly His Lys Leu Ala Tyr Val Trp Asn Asn Asp Ile Tyr Val
    130                 135                 140

-continued

```
Lys Ile Glu Pro Asn Leu Pro Ser Tyr Arg Ile Thr Trp Thr Gly Lys
145                 150                 155                 160

Glu Asp Ile Ile Tyr Asn Gly Ile Thr Asp Trp Val Tyr Glu Glu
            165                 170                 175

Val Phe Ser Ala Tyr Ser Ala Leu Trp Trp Ser Pro Asn Gly Thr Phe
            180                 185                 190

Leu Ala Tyr Ala Gln Phe Asn Asp Thr Glu Val Pro Leu Ile Glu Tyr
            195                 200                 205

Ser Phe Tyr Ser Asp Glu Ser Leu Gln Tyr Pro Lys Thr Val Arg Val
            210                 215                 220

Pro Tyr Pro Lys Ala Gly Ala Val Asn Pro Thr Val Lys Phe Phe Val
225                 230                 235                 240

Val Asn Thr Asp Ser Leu Ser Ser Val Thr Asn Ala Thr Ser Ile Gln
            245                 250                 255

Ile Thr Ala Pro Ala Ser Met Leu Ile Gly Asp His Tyr Leu Cys Asp
            260                 265                 270

Val Thr Trp Ala Thr Gln Glu Arg Ile Ser Leu Gln Trp Leu Arg Arg
            275                 280                 285

Ile Gln Asn Tyr Ser Val Met Asp Ile Cys Asp Tyr Asp Glu Ser Ser
290                 295                 300

Gly Arg Trp Asn Cys Leu Val Ala Arg Gln His Ile Glu Met Ser Thr
305                 310                 315                 320

Thr Gly Trp Val Gly Arg Phe Arg Pro Ser Glu Pro His Phe Thr Leu
            325                 330                 335

Asp Gly Asn Ser Phe Tyr Lys Ile Ile Ser Asn Glu Glu Gly Tyr Arg
            340                 345                 350

His Ile Cys Tyr Phe Gln Ile Asp Lys Lys Asp Cys Thr Phe Ile Thr
            355                 360                 365

Lys Gly Thr Trp Glu Val Ile Gly Ile Glu Ala Leu Thr Ser Asp Tyr
            370                 375                 380

Leu Tyr Tyr Ile Ser Asn Glu Tyr Lys Gly Met Pro Gly Gly Arg Asn
385                 390                 395                 400

Leu Tyr Lys Ile Gln Leu Ser Asp Tyr Thr Lys Val Thr Cys Leu Ser
            405                 410                 415

Cys Glu Leu Asn Pro Glu Arg Cys Gln Tyr Tyr Ser Val Ser Phe Ser
            420                 425                 430

Lys Glu Ala Lys Tyr Tyr Gln Leu Arg Cys Ser Gly Pro Gly Leu Pro
            435                 440                 445

Leu Tyr Thr Leu His Ser Ser Val Asn Asp Lys Gly Leu Arg Val Leu
            450                 455                 460

Glu Asp Asn Ser Ala Leu Asp Lys Met Leu Gln Asn Val Gln Met Pro
465                 470                 475                 480

Ser Lys Lys Leu Asp Phe Ile Ile Leu Asn Glu Thr Lys Phe Trp Tyr
            485                 490                 495

Gln Met Ile Leu Pro Pro His Phe Asp Lys Ser Lys Tyr Pro Leu
            500                 505                 510

Leu Leu Asp Val Tyr Ala Gly Pro Cys Ser Gln Lys Ala Asp Thr Val
            515                 520                 525

Phe Arg Leu Asn Trp Ala Thr Tyr Leu Ala Ser Thr Glu Asn Ile Ile
            530                 535                 540

Val Ala Ser Phe Asp Gly Arg Gly Ser Gly Tyr Gln Gly Asp Lys Ile
545                 550                 555                 560

Met His Ala Ile Asn Arg Arg Leu Gly Thr Phe Glu Val Glu Asp Gln
```

-continued

```
                565                 570                 575
Ile Glu Ala Ala Arg Gln Phe Ser Lys Met Gly Phe Val Asp Asn Lys
            580                 585                 590

Arg Ile Ala Ile Trp Gly Trp Ser Tyr Gly Gly Tyr Val Thr Ser Met
        595                 600                 605

Val Leu Gly Ser Gly Ser Gly Val Phe Lys Cys Gly Ile Ala Val Ala
    610                 615                 620

Pro Val Ser Arg Trp Glu Tyr Tyr Asp Ser Val Tyr Thr Glu Arg Tyr
625                 630                 635                 640

Met Gly Leu Pro Thr Pro Glu Asp Asn Leu Asp His Tyr Arg Asn Ser
                645                 650                 655

Thr Val Met Ser Arg Ala Glu Asn Phe Lys Gln Val Glu Tyr Leu Leu
            660                 665                 670

Ile His Gly Thr Ala Asp Asp Asn Val His Phe Gln Gln Ser Ala Gln
        675                 680                 685

Ile Ser Lys Ala Leu Val Asp Val Gly Val Asp Phe Gln Ala Met Trp
    690                 695                 700

Tyr Thr Asp Glu Asp His Gly Ile Ala Ser Ser Thr Ala His Gln His
705                 710                 715                 720

Ile Tyr Thr His Met Ser His Phe Ile Lys Gln Cys Phe Ser Leu Pro
                725                 730                 735
```

<210> SEQ ID NO 103
<211> LENGTH: 760
<212> TYPE: PRT
<213> ORGANISM: Mus musculus
<220> FEATURE:
<223> OTHER INFORMATION: mDPP4

<400> SEQUENCE: 103

```
Met Lys Thr Pro Trp Lys Val Leu Leu Gly Leu Leu Gly Val Ala Ala
1               5                   10                  15

Leu Val Thr Ile Ile Thr Val Pro Ile Val Leu Leu Ser Lys Asp Glu
            20                  25                  30

Ala Ala Ala Asp Ser Arg Arg Thr Tyr Ser Leu Ala Asp Tyr Leu Lys
        35                  40                  45

Ser Thr Phe Arg Val Lys Ser Tyr Ser Leu Trp Trp Val Ser Asp Phe
    50                  55                  60

Glu Tyr Leu Tyr Lys Gln Glu Asn Asn Ile Leu Leu Asn Ala Glu
65                  70                  75                  80

His Gly Asn Ser Ser Ile Phe Leu Glu Asn Ser Thr Phe Glu Ser Phe
                85                  90                  95

Gly Tyr His Ser Val Ser Pro Asp Arg Leu Phe Val Leu Leu Glu Tyr
            100                 105                 110

Asn Tyr Val Lys Gln Trp Arg His Ser Tyr Thr Ala Ser Tyr Asn Ile
        115                 120                 125

Tyr Asp Val Asn Lys Arg Gln Leu Ile Thr Glu Glu Lys Ile Pro Asn
    130                 135                 140

Asn Thr Gln Trp Ile Thr Trp Ser Pro Glu Gly His Lys Leu Ala Tyr
145                 150                 155                 160

Val Trp Lys Asn Asp Ile Tyr Val Lys Val Glu Pro His Leu Pro Ser
                165                 170                 175

His Arg Ile Thr Ser Thr Gly Glu Glu Asn Val Ile Tyr Asn Gly Ile
            180                 185                 190

Thr Asp Trp Val Tyr Glu Glu Glu Val Phe Gly Ala Tyr Ser Ala Leu
```

```
            195                 200                 205
Trp Trp Ser Pro Asn Asn Thr Phe Leu Ala Tyr Ala Gln Phe Asn Asp
    210                 215                 220

Thr Gly Val Pro Leu Ile Glu Tyr Ser Phe Tyr Ser Asp Glu Ser Leu
225                 230                 235                 240

Gln Tyr Pro Lys Thr Val Trp Ile Pro Tyr Pro Lys Ala Gly Ala Val
                    245                 250                 255

Asn Pro Thr Val Lys Phe Phe Ile Val Asn Ile Asp Ser Leu Ser Ser
                260                 265                 270

Ser Ser Ser Ala Ala Pro Ile Gln Ile Pro Ala Pro Ala Ser Val Ala
            275                 280                 285

Arg Gly Asp His Tyr Leu Cys Asp Val Val Trp Ala Thr Glu Glu Arg
        290                 295                 300

Ile Ser Leu Gln Trp Leu Arg Arg Ile Gln Asn Tyr Ser Val Met Ala
305                 310                 315                 320

Ile Cys Asp Tyr Asp Lys Ile Asn Leu Thr Trp Asn Cys Pro Ser Glu
                    325                 330                 335

Gln Gln His Val Glu Met Ser Thr Thr Gly Trp Val Gly Arg Phe Arg
                340                 345                 350

Pro Ala Glu Pro His Phe Thr Ser Asp Gly Ser Ser Phe Tyr Lys Ile
            355                 360                 365

Ile Ser Asp Lys Asp Gly Tyr Lys His Ile Cys His Phe Pro Lys Asp
        370                 375                 380

Lys Lys Asp Cys Thr Phe Ile Thr Lys Gly Ala Trp Glu Val Ile Ser
385                 390                 395                 400

Ile Glu Ala Leu Thr Ser Asp Tyr Leu Tyr Tyr Ile Ser Asn Gln Tyr
                    405                 410                 415

Lys Glu Met Pro Gly Gly Arg Asn Leu Tyr Lys Ile Gln Leu Thr Asp
                420                 425                 430

His Thr Asn Val Lys Cys Leu Ser Cys Asp Leu Asn Pro Glu Arg Cys
            435                 440                 445

Gln Tyr Tyr Ala Val Ser Phe Ser Lys Glu Ala Lys Tyr Tyr Gln Leu
        450                 455                 460

Gly Cys Trp Gly Pro Gly Leu Pro Leu Tyr Thr Leu His Arg Ser Thr
465                 470                 475                 480

Asp His Lys Glu Leu Arg Val Leu Glu Asp Asn Ser Ala Leu Asp Arg
                    485                 490                 495

Met Leu Gln Asp Val Gln Met Pro Ser Lys Lys Leu Asp Phe Ile Val
                500                 505                 510

Leu Asn Glu Thr Arg Phe Trp Tyr Gln Met Ile Leu Pro Pro His Phe
            515                 520                 525

Asp Lys Ser Lys Lys Tyr Pro Leu Leu Leu Asp Val Tyr Ala Gly Pro
        530                 535                 540

Cys Ser Gln Lys Ala Asp Ala Ser Phe Arg Leu Asn Trp Ala Thr Tyr
545                 550                 555                 560

Leu Ala Ser Thr Glu Asn Ile Ile Val Ala Ser Phe Asp Gly Arg Gly
                    565                 570                 575

Ser Gly Tyr Gln Gly Asp Lys Ile Met His Ala Ile Asn Arg Arg Leu
                580                 585                 590

Gly Thr Leu Glu Val Glu Asp Gln Ile Glu Ala Ala Arg Gln Phe Val
            595                 600                 605

Lys Met Gly Phe Val Asp Ser Lys Arg Val Ala Ile Trp Gly Trp Ser
        610                 615                 620
```

```
Tyr Gly Gly Tyr Val Thr Ser Met Val Leu Gly Ser Gly Ser Gly Val
625                 630                 635                 640

Phe Lys Cys Gly Ile Ala Val Ala Pro Val Ser Arg Trp Glu Tyr Tyr
                645                 650                 655

Asp Ser Val Tyr Thr Glu Arg Tyr Met Gly Leu Pro Ile Pro Glu Asp
                660                 665                 670

Asn Leu Asp His Tyr Arg Asn Ser Thr Val Met Ser Arg Ala Glu His
                675                 680                 685

Phe Lys Gln Val Glu Tyr Leu Leu Ile His Gly Thr Ala Asp Asp Asn
                690                 695                 700

Val His Phe Gln Gln Ser Ala Gln Ile Ser Lys Ala Leu Val Asp Ala
705                 710                 715                 720

Gly Val Asp Phe Gln Ala Met Trp Tyr Thr Asp Glu Asp His Gly Ile
                725                 730                 735

Ala Ser Ser Thr Ala His Gln His Ile Tyr Ser His Met Ser His Phe
                740                 745                 750

Leu Gln Gln Cys Phe Ser Leu His
                755                 760

<210> SEQ ID NO 104
<211> LENGTH: 5
<212> TYPE: PRT
<213> ORGANISM: Artificial Sequence
<220> FEATURE:
<223> OTHER INFORMATION: HCDR1

<400> SEQUENCE: 104

Asn Tyr Gly Met Ala
1               5

<210> SEQ ID NO 105
<211> LENGTH: 7
<212> TYPE: PRT
<213> ORGANISM: Artificial Sequence
<220> FEATURE:
<223> OTHER INFORMATION: HCDR1

<400> SEQUENCE: 105

Thr Ser Asp Arg Cys Val Ser
1               5

<210> SEQ ID NO 106
<211> LENGTH: 5
<212> TYPE: PRT
<213> ORGANISM: Artificial Sequence
<220> FEATURE:
<223> OTHER INFORMATION: HCDR1

<400> SEQUENCE: 106

Asn Phe Gly Met Ala
1               5

<210> SEQ ID NO 107
<211> LENGTH: 5
<212> TYPE: PRT
<213> ORGANISM: Artificial Sequence
<220> FEATURE:
<223> OTHER INFORMATION: HCDR1

<400> SEQUENCE: 107

Asp Asn Tyr Trp Gly
1               5
```

<210> SEQ ID NO 108
<211> LENGTH: 5
<212> TYPE: PRT
<213> ORGANISM: Artificial Sequence
<220> FEATURE:
<223> OTHER INFORMATION: HCDR1

<400> SEQUENCE: 108

Thr Tyr Asp Ile Gly
1               5

<210> SEQ ID NO 109
<211> LENGTH: 5
<212> TYPE: PRT
<213> ORGANISM: Artificial Sequence
<220> FEATURE:
<223> OTHER INFORMATION: HCDR1

<400> SEQUENCE: 109

Gly Asn Tyr Leu Ala
1               5

<210> SEQ ID NO 110
<211> LENGTH: 5
<212> TYPE: PRT
<213> ORGANISM: Artificial Sequence
<220> FEATURE:
<223> OTHER INFORMATION: HCDR1

<400> SEQUENCE: 110

Ser Asn Tyr Trp Gly
1               5

<210> SEQ ID NO 111
<211> LENGTH: 5
<212> TYPE: PRT
<213> ORGANISM: Artificial Sequence
<220> FEATURE:
<223> OTHER INFORMATION: HCDR1

<400> SEQUENCE: 111

Thr Tyr Asp Arg Gly
1               5

<210> SEQ ID NO 112
<211> LENGTH: 5
<212> TYPE: PRT
<213> ORGANISM: Artificial Sequence
<220> FEATURE:
<223> OTHER INFORMATION: HCDR1

<400> SEQUENCE: 112

Gly Asn Tyr Trp Gly
1               5

<210> SEQ ID NO 113
<211> LENGTH: 17
<212> TYPE: PRT
<213> ORGANISM: Artificial Sequence
<220> FEATURE:
<223> OTHER INFORMATION: HCDR2

<400> SEQUENCE: 113

Thr Ile Ser Tyr Asp Gly Asn Asp Thr Tyr Tyr Arg Asp Ser Val Lys
1               5                   10                  15

Gly

```
<210> SEQ ID NO 114
<211> LENGTH: 17
<212> TYPE: PRT
<213> ORGANISM: Artificial Sequence
<220> FEATURE:
<223> OTHER INFORMATION: HCDR2

<400> SEQUENCE: 114
```

Thr Thr Ser Tyr Asp Gly Asn Asp Thr Tyr Tyr Arg Asp Ser Val Lys
1               5                   10                  15

Gly

```
<210> SEQ ID NO 115
<211> LENGTH: 16
<212> TYPE: PRT
<213> ORGANISM: Artificial Sequence
<220> FEATURE:
<223> OTHER INFORMATION: HCDR2

<400> SEQUENCE: 115
```

Thr Ile Cys Trp Asp Asp Ser Lys Gly Tyr Asn Pro Ser Leu Lys Asn
1               5                   10                  15

```
<210> SEQ ID NO 116
<211> LENGTH: 17
<212> TYPE: PRT
<213> ORGANISM: Artificial Sequence
<220> FEATURE:
<223> OTHER INFORMATION: HCDR2

<400> SEQUENCE: 116
```

Thr Ile Asn Tyr Asp Gly Arg Asn Thr Tyr Tyr Arg Asp Ser Val Lys
1               5                   10                  15

Gly

```
<210> SEQ ID NO 117
<211> LENGTH: 17
<212> TYPE: PRT
<213> ORGANISM: Artificial Sequence
<220> FEATURE:
<223> OTHER INFORMATION: HCDR2

<400> SEQUENCE: 117
```

Thr Ile Asn Tyr Asp Gly Ser Asn Thr Tyr Tyr Arg Asp Ser Val Lys
1               5                   10                  15

Gly

```
<210> SEQ ID NO 118
<211> LENGTH: 17
<212> TYPE: PRT
<213> ORGANISM: Artificial Sequence
<220> FEATURE:
<223> OTHER INFORMATION: HCDR2

<400> SEQUENCE: 118
```

Thr Ile Asn Tyr Asp Gly Arg Asp Thr Tyr Tyr Arg Asp Ser Val Lys
1               5                   10                  15

Gly

```
<210> SEQ ID NO 119
<211> LENGTH: 16
<212> TYPE: PRT
```

-continued

```
<213> ORGANISM: Artificial Sequence
<220> FEATURE:
<223> OTHER INFORMATION: HCDR2

<400> SEQUENCE: 119

His Ile Ser His Ser Gly Ser Ser Thr Tyr Asn Pro Ser Leu Lys Ser
1               5                   10                  15

<210> SEQ ID NO 120
<211> LENGTH: 17
<212> TYPE: PRT
<213> ORGANISM: Artificial Sequence
<220> FEATURE:
<223> OTHER INFORMATION: HCDR2

<400> SEQUENCE: 120

Tyr Ile Asn Pro Gly Ser Gly Gly Ile Gly Tyr Asn Glu Lys Phe Lys
1               5                   10                  15

Gly

<210> SEQ ID NO 121
<211> LENGTH: 17
<212> TYPE: PRT
<213> ORGANISM: Artificial Sequence
<220> FEATURE:
<223> OTHER INFORMATION: HCDR2

<400> SEQUENCE: 121

Ser Ile Asn Pro Gly Ser Gly Gly Ile Ala Tyr Ser Glu Lys Phe Lys
1               5                   10                  15

Gly

<210> SEQ ID NO 122
<211> LENGTH: 16
<212> TYPE: PRT
<213> ORGANISM: Artificial Sequence
<220> FEATURE:
<223> OTHER INFORMATION: HCDR2

<400> SEQUENCE: 122

His Ile Lys Ser Ser Gly Thr Thr Thr Tyr Asn Pro Ser Leu Lys Ser
1               5                   10                  15

<210> SEQ ID NO 123
<211> LENGTH: 17
<212> TYPE: PRT
<213> ORGANISM: Artificial Sequence
<220> FEATURE:
<223> OTHER INFORMATION: HCDR2

<400> SEQUENCE: 123

Ser Ile Asn Pro Gly Ser Gly Gly Ile Gly Tyr Asn Glu Arg Phe Lys
1               5                   10                  15

Gly

<210> SEQ ID NO 124
<211> LENGTH: 17
<212> TYPE: PRT
<213> ORGANISM: Artificial Sequence
<220> FEATURE:
<223> OTHER INFORMATION: HCDR2

<400> SEQUENCE: 124

Tyr Ile Asn Pro Gly Gly Gly Gly Ile Gly Tyr Asn Glu Lys Phe Lys
1               5                   10                  15
```

Gly

<210> SEQ ID NO 125
<211> LENGTH: 16
<212> TYPE: PRT
<213> ORGANISM: Artificial Sequence
<220> FEATURE:
<223> OTHER INFORMATION: HCDR2

<400> SEQUENCE: 125

Gln Ile Ser His Ser Gly Ser Thr Ser Tyr Asn Pro Ser Leu Lys Ser
1               5                   10                  15

<210> SEQ ID NO 126
<211> LENGTH: 17
<212> TYPE: PRT
<213> ORGANISM: Artificial Sequence
<220> FEATURE:
<223> OTHER INFORMATION: HCDR2

<400> SEQUENCE: 126

Ser Ile Asn Pro Gly Ser Gly Gly Ile Gly Tyr Asn Glu Lys Phe Lys
1               5                   10                  15

Gly

<210> SEQ ID NO 127
<211> LENGTH: 17
<212> TYPE: PRT
<213> ORGANISM: Artificial Sequence
<220> FEATURE:
<223> OTHER INFORMATION: HCDR2

<400> SEQUENCE: 127

Ser Ile Asn Pro Gly Gly Gly Gly Thr Gly Tyr Asn Glu Lys Phe Lys
1               5                   10                  15

Gly

<210> SEQ ID NO 128
<211> LENGTH: 16
<212> TYPE: PRT
<213> ORGANISM: Artificial Sequence
<220> FEATURE:
<223> OTHER INFORMATION: HCDR2

<400> SEQUENCE: 128

Gln Ile Ser His Ser Gly Ser Thr Ser Tyr Asn Pro Ser Leu Ile Ser
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: HCDR2

<400> SEQUENCE: 129

Gln Ile Ser His Thr Gly Ser Ser Thr Tyr Asn Pro Ser Leu Lys Ser
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: HCDR3

<400> SEQUENCE: 130

His Arg Leu Ile Tyr Thr Thr Asp Tyr Tyr Glu Val Met Asp Val
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: HCDR3

<400> SEQUENCE: 131

His Arg Leu Ile Tyr Thr Thr Asp Tyr Tyr Glu Val Met Asp Ala
1               5                   10                  15

<210> SEQ ID NO 132
<211> LENGTH: 9
<212> TYPE: PRT
<213> ORGANISM: Artificial Sequence
<220> FEATURE:
<223> OTHER INFORMATION: HCDR3

<400> SEQUENCE: 132

Asn Ser Gly Asp Gly Arg Phe Ala Tyr
1               5

<210> SEQ ID NO 133
<211> LENGTH: 16
<212> TYPE: PRT
<213> ORGANISM: Artificial Sequence
<220> FEATURE:
<223> OTHER INFORMATION: HCDR3

<400> SEQUENCE: 133

His Lys Leu Ile Tyr Thr Thr Asp Tyr Tyr Glu Val Met Asp Ala
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: HCDR3

<400> SEQUENCE: 134

His Arg Leu Met Tyr Thr Thr Asp Tyr Tyr Glu Val Met Asp Asp
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: HCDR3

<400> SEQUENCE: 135

His Arg Leu Ile Tyr Thr Thr Asp Tyr Tyr Glu Val Leu Asp Ala
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: HCDR3

<400> SEQUENCE: 136

His Lys Leu Ile Tyr Thr Thr Asp Tyr Tyr Glu Val Met Asp Val
1               5                   10                  15

<210> SEQ ID NO 137
<211> LENGTH: 9
<212> TYPE: PRT
<213> ORGANISM: Artificial Sequence
<220> FEATURE:
<223> OTHER INFORMATION: HCDR3

<400> SEQUENCE: 137

Tyr Gly Ala Gly Ala Ser Phe Asp Tyr
1               5

<210> SEQ ID NO 138
<211> LENGTH: 8
<212> TYPE: PRT
<213> ORGANISM: Artificial Sequence
<220> FEATURE:
<223> OTHER INFORMATION: HCDR3

<400> SEQUENCE: 138

Pro Leu Arg Arg Val Leu Asp Tyr
1               5

<210> SEQ ID NO 139
<211> LENGTH: 8
<212> TYPE: PRT
<213> ORGANISM: Artificial Sequence
<220> FEATURE:
<223> OTHER INFORMATION: HCDR3

<400> SEQUENCE: 139

His Gly His Tyr Val Met Asp Val
1               5

<210> SEQ ID NO 140
<211> LENGTH: 9
<212> TYPE: PRT
<213> ORGANISM: Artificial Sequence
<220> FEATURE:
<223> OTHER INFORMATION: HCDR3

<400> SEQUENCE: 140

Tyr Gly Ala Gly Ser Ser Phe Asp Tyr
1               5

<210> SEQ ID NO 141
<211> LENGTH: 8
<212> TYPE: PRT
<213> ORGANISM: Artificial Sequence
<220> FEATURE:
<223> OTHER INFORMATION: HCDR3

<400> SEQUENCE: 141

Pro Leu Arg Arg Val Leu Asp Asn
1               5

<210> SEQ ID NO 142
<211> LENGTH: 7
<212> TYPE: PRT
<213> ORGANISM: Artificial Sequence
<220> FEATURE:
<223> OTHER INFORMATION: HCDR3

<400> SEQUENCE: 142

```
-continued

Pro Leu Arg Val Leu Asp Tyr
1               5

<210> SEQ ID NO 143
<211> LENGTH: 17
<212> TYPE: PRT
<213> ORGANISM: Artificial Sequence
<220> FEATURE:
<223> OTHER INFORMATION: LCDR1

<400> SEQUENCE: 143

Lys Ser Ser Gln Ser Leu Leu Tyr Asn Glu Asn Lys Asn Tyr Leu
1               5                   10                  15

Ala

<210> SEQ ID NO 144
<211> LENGTH: 16
<212> TYPE: PRT
<213> ORGANISM: Artificial Sequence
<220> FEATURE:
<223> OTHER INFORMATION: LCDR1

<400> SEQUENCE: 144

Lys Ser Ser Gln Ser Leu Leu His Ser Asn Gly Asn Thr Tyr Leu Asn
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: LCDR1

<400> SEQUENCE: 145

Arg Ser Ser Gln Ser Leu Leu His Ser Asn Gly Asn Thr Tyr Leu Asn
1               5                   10                  15

<210> SEQ ID NO 146
<211> LENGTH: 11
<212> TYPE: PRT
<213> ORGANISM: Artificial Sequence
<220> FEATURE:
<223> OTHER INFORMATION: LCDR1

<400> SEQUENCE: 146

Leu Ala Ser Glu Gly Ile Ser Asn Tyr Leu Ala
1               5                   10

<210> SEQ ID NO 147
<211> LENGTH: 11
<212> TYPE: PRT
<213> ORGANISM: Artificial Sequence
<220> FEATURE:
<223> OTHER INFORMATION: LCDR1

<400> SEQUENCE: 147

Arg Ala Ser Gln Gly Ile Ser Asn Lys Leu Asn
1               5                   10

<210> SEQ ID NO 148
<211> LENGTH: 15
<212> TYPE: PRT
<213> ORGANISM: Artificial Sequence
<220> FEATURE:
<223> OTHER INFORMATION: LCDR1
```

```
<400> SEQUENCE: 148

Arg Ala Ser Gln Ser Val Ser Thr Ser Thr Tyr Asn Phe Met His
1               5                   10                  15

<210> SEQ ID NO 149
<211> LENGTH: 11
<212> TYPE: PRT
<213> ORGANISM: Artificial Sequence
<220> FEATURE:
<223> OTHER INFORMATION: LCDR1

<400> SEQUENCE: 149

Arg Ala Ser Gln Gly Ile Gly Asn Lys Leu Asn
1               5                   10

<210> SEQ ID NO 150
<211> LENGTH: 11
<212> TYPE: PRT
<213> ORGANISM: Artificial Sequence
<220> FEATURE:
<223> OTHER INFORMATION: LCDR1

<400> SEQUENCE: 150

Arg Ala Ser Gln Gly Ile Ser Lys Lys Leu Asn
1               5                   10

<210> SEQ ID NO 151
<211> LENGTH: 11
<212> TYPE: PRT
<213> ORGANISM: Artificial Sequence
<220> FEATURE:
<223> OTHER INFORMATION: LCDR1

<400> SEQUENCE: 151

Gly Ala Ser Gln Gly Ile Gly Asn Lys Val Asn
1               5                   10

<210> SEQ ID NO 152
<211> LENGTH: 7
<212> TYPE: PRT
<213> ORGANISM: Artificial Sequence
<220> FEATURE:
<223> OTHER INFORMATION: LCDR2

<400> SEQUENCE: 152

Trp Ala Ser Thr Arg Glu Ser
1               5

<210> SEQ ID NO 153
<211> LENGTH: 7
<212> TYPE: PRT
<213> ORGANISM: Artificial Sequence
<220> FEATURE:
<223> OTHER INFORMATION: LCDR2

<400> SEQUENCE: 153

Ser Val Ser Lys Leu Glu Ser
1               5

<210> SEQ ID NO 154
<211> LENGTH: 7
<212> TYPE: PRT
<213> ORGANISM: Artificial Sequence
<220> FEATURE:
<223> OTHER INFORMATION: LCDR2

<400> SEQUENCE: 154
```

Trp Ala Ser Thr Arg Glu Ala
1               5

<210> SEQ ID NO 155
<211> LENGTH: 7
<212> TYPE: PRT
<213> ORGANISM: Artificial Sequence
<220> FEATURE:
<223> OTHER INFORMATION: LCDR2

<400> SEQUENCE: 155

Trp Ala Ser Thr Arg Lys Ser
1               5

<210> SEQ ID NO 156
<211> LENGTH: 7
<212> TYPE: PRT
<213> ORGANISM: Artificial Sequence
<220> FEATURE:
<223> OTHER INFORMATION: LCDR2

<400> SEQUENCE: 156

Ser Val Ser Asn Leu Glu Ser
1               5

<210> SEQ ID NO 157
<211> LENGTH: 7
<212> TYPE: PRT
<213> ORGANISM: Artificial Sequence
<220> FEATURE:
<223> OTHER INFORMATION: LCDR2

<400> SEQUENCE: 157

Tyr Thr Ser Ser Leu Gln Asp
1               5

<210> SEQ ID NO 158
<211> LENGTH: 7
<212> TYPE: PRT
<213> ORGANISM: Artificial Sequence
<220> FEATURE:
<223> OTHER INFORMATION: LCDR2

<400> SEQUENCE: 158

Tyr Thr Ser Arg Leu Gln Ser
1               5

<210> SEQ ID NO 159
<211> LENGTH: 7
<212> TYPE: PRT
<213> ORGANISM: Artificial Sequence
<220> FEATURE:
<223> OTHER INFORMATION: LCDR2

<400> SEQUENCE: 159

Tyr Thr Ser Asn Leu Gln Ser
1               5

<210> SEQ ID NO 160
<211> LENGTH: 7
<212> TYPE: PRT
<213> ORGANISM: Artificial Sequence
<220> FEATURE:
<223> OTHER INFORMATION: LCDR2

<400> SEQUENCE: 160

Asp Ala Ser His Leu Ala Ser
1               5

<210> SEQ ID NO 161
<211> LENGTH: 7
<212> TYPE: PRT
<213> ORGANISM: Artificial Sequence
<220> FEATURE:
<223> OTHER INFORMATION: LCDR2

<400> SEQUENCE: 161

Tyr Thr Ser Ser Phe Gln Asp
1               5

<210> SEQ ID NO 162
<211> LENGTH: 7
<212> TYPE: PRT
<213> ORGANISM: Artificial Sequence
<220> FEATURE:
<223> OTHER INFORMATION: LCDR2

<400> SEQUENCE: 162

Tyr Thr Ile Ser Leu Gln Asp
1               5

<210> SEQ ID NO 163
<211> LENGTH: 7
<212> TYPE: PRT
<213> ORGANISM: Artificial Sequence
<220> FEATURE:
<223> OTHER INFORMATION: LCDR2

<400> SEQUENCE: 163

Tyr Ala Ser Ser Leu Gln Asp
1               5

<210> SEQ ID NO 164
<211> LENGTH: 9
<212> TYPE: PRT
<213> ORGANISM: Artificial Sequence
<220> FEATURE:
<223> OTHER INFORMATION: LCDR3

<400> SEQUENCE: 164

Gln Glu Tyr Tyr Lys Phe Pro Trp Thr
1               5

<210> SEQ ID NO 165
<211> LENGTH: 9
<212> TYPE: PRT
<213> ORGANISM: Artificial Sequence
<220> FEATURE:
<223> OTHER INFORMATION: LCDR3

<400> SEQUENCE: 165

Gln Asp Tyr Tyr His Phe Pro Trp Thr
1               5

<210> SEQ ID NO 166
<211> LENGTH: 9
<212> TYPE: PRT
<213> ORGANISM: Artificial Sequence
<220> FEATURE:
<223> OTHER INFORMATION: LCDR3

<400> SEQUENCE: 166

Met Gln Ala Thr His Ala Pro Phe Thr

```
1               5
```

<210> SEQ ID NO 167
<211> LENGTH: 9
<212> TYPE: PRT
<213> ORGANISM: Artificial Sequence
<220> FEATURE:
<223> OTHER INFORMATION: LCDR3

<400> SEQUENCE: 167

```
Gln Gln Tyr Tyr Lys Phe Pro Trp Pro
1               5
```

<210> SEQ ID NO 168
<211> LENGTH: 9
<212> TYPE: PRT
<213> ORGANISM: Artificial Sequence
<220> FEATURE:
<223> OTHER INFORMATION: LCDR3

<400> SEQUENCE: 168

```
Gln Gln Tyr Tyr Lys Phe Pro Trp Thr
1               5
```

<210> SEQ ID NO 169
<211> LENGTH: 9
<212> TYPE: PRT
<213> ORGANISM: Artificial Sequence
<220> FEATURE:
<223> OTHER INFORMATION: LCDR3

<400> SEQUENCE: 169

```
Gln Gln Tyr Tyr Lys Phe Pro Tyr Thr
1               5
```

<210> SEQ ID NO 170
<211> LENGTH: 9
<212> TYPE: PRT
<213> ORGANISM: Artificial Sequence
<220> FEATURE:
<223> OTHER INFORMATION: LCDR3

<400> SEQUENCE: 170

```
Gln Gln Gly Tyr Lys Tyr Pro Trp Thr
1               5
```

<210> SEQ ID NO 171
<211> LENGTH: 9
<212> TYPE: PRT
<213> ORGANISM: Artificial Sequence
<220> FEATURE:
<223> OTHER INFORMATION: LCDR3

<400> SEQUENCE: 171

```
Gln Gln Asp Ala Ser Phe Pro Pro Thr
1               5
```

<210> SEQ ID NO 172
<211> LENGTH: 9
<212> TYPE: PRT
<213> ORGANISM: Artificial Sequence
<220> FEATURE:
<223> OTHER INFORMATION: LCDR3

<400> SEQUENCE: 172

```
Gln Gln Ser Arg Glu Leu Pro Leu Thr
1               5
```

<210> SEQ ID NO 173
<211> LENGTH: 9
<212> TYPE: PRT
<213> ORGANISM: Artificial Sequence
<220> FEATURE:
<223> OTHER INFORMATION: LCDR3

<400> SEQUENCE: 173

Gln Gln Asp Thr Ser Phe Pro Pro Thr
1               5

<210> SEQ ID NO 174
<211> LENGTH: 125
<212> TYPE: PRT
<213> ORGANISM: Artificial Sequence
<220> FEATURE:
<223> OTHER INFORMATION: 5826-8-R6A-A10 HCVR

<400> SEQUENCE: 174

Glu Val Gln Leu Glu Glu Ser Gly Gly Gly Leu Val Gln Pro Gly Arg
1               5                   10                  15

Ser Leu Lys Leu Ser Cys Ala Ala Ser Gly Phe Thr Phe Asn Asn Tyr
            20                  25                  30

Gly Met Ala Trp Val Arg Gln Ala Pro Thr Lys Gly Leu Glu Trp Val
        35                  40                  45

Ala Thr Ile Ser Tyr Asp Gly Asn Asp Thr Tyr Tyr Arg Asp Ser Val
    50                  55                  60

Lys Gly Arg Phe Thr Val Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Val Arg His Arg Leu Ile Tyr Thr Thr Asp Tyr Tyr Tyr Glu Val Met
            100                 105                 110

Asp Val Trp Gly Gln Gly Ala Ser Val Thr Val Ser Ser
        115                 120                 125

<210> SEQ ID NO 175
<211> LENGTH: 125
<212> TYPE: PRT
<213> ORGANISM: Artificial Sequence
<220> FEATURE:
<223> OTHER INFORMATION: 5826-8-R6A-B11 HCVR

<400> SEQUENCE: 175

Gln Val Gln Leu Lys Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Gly Met Ala Trp Val Arg Gln Ala Pro Thr Lys Gly Leu Glu Trp Val
        35                  40                  45

Ala Thr Thr Ser Tyr Asp Gly Asn Asp Thr Tyr Tyr Arg Asp Ser Val
    50                  55                  60

Lys Gly Arg Phe Thr Val Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Val Arg His Arg Leu Ile Tyr Thr Thr Asp Tyr Tyr Tyr Glu Val Met
            100                 105                 110

Asp Ala Trp Gly Gln Gly Ala Ser Val Thr Val Ser Ser
        115                 120                 125

<210> SEQ ID NO 176
<211> LENGTH: 119
<212> TYPE: PRT
<213> ORGANISM: Artificial Sequence
<220> FEATURE:
<223> OTHER INFORMATION: 5826-8-R6A-D12 HCVR & 5826-8-R6A-H11 HCVR

<400> SEQUENCE: 176

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asp Arg Cys Val Ser Trp Ile Arg Gln Pro Ser Gly Lys Gly Leu Glu
        35                  40                  45

Trp Leu Ala Thr Ile Cys Trp Asp Asp Ser Lys Gly Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Thr Ser Val Gly Thr Ala Asp Ile Ala Lys Tyr Tyr
                85                  90                  95

Cys Ala Arg Asn Ser Gly Asp Gly Arg Phe Ala Tyr Trp Gly Gln Gly
            100                 105                 110

Thr Leu Val Thr Val Ser Ser
        115

<210> SEQ ID NO 177
<211> LENGTH: 125
<212> TYPE: PRT
<213> ORGANISM: Artificial Sequence
<220> FEATURE:
<223> OTHER INFORMATION: 5826-8-R6A-E10 HCVR

<400> SEQUENCE: 177

Glu Val Gln Leu Glu Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Gly Met Ala Trp Val Arg Gln Ala Pro Thr Lys Gly Leu Glu Trp Val
        35                  40                  45

Ala Thr Ile Asn Tyr Asp Gly Arg Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Val Asp Ser Leu Gln Ser Glu Asp Thr Ala Thr Tyr Tyr Cys
                85                  90                  95

Thr Arg His Lys Leu Ile Tyr Thr Thr Asp Tyr Tyr Tyr Glu Val Met
            100                 105                 110

Asp Ala Trp Gly Gln Gly Ala Ser Val Thr Val Ser Ser
        115                 120                 125

<210> SEQ ID NO 178
<211> LENGTH: 125
<212> TYPE: PRT
<213> ORGANISM: Artificial Sequence
<220> FEATURE:
<223> OTHER INFORMATION: 5826-8-R5A-G6 HCVR

<400> SEQUENCE: 178

Glu Val Lys Leu Val Glu Ser Gly Gly Gly Leu Val Gln Pro Gly Arg
1               5                   10                  15

Ser Leu Lys Leu Ser Cys Ala Ala Ser Gly Phe Ser Phe Thr Asn Tyr
            20                  25                  30

Gly Met Ala Trp Val Arg Gln Ala Pro Thr Lys Gly Leu Glu Trp Val
        35                  40                  45

Ala Thr Ile Asn Tyr Asp Gly Ser Asn Thr Tyr Tyr Arg Asp Ser Val
    50                  55                  60

Lys Gly Arg Phe Thr Ile Ser Arg Asp Asn Ala Lys Arg Thr Leu Asp
65                  70                  75                  80

Leu Gln Met Asp Ser Leu Arg Ser Glu Asp Thr Ala Thr Tyr Tyr Cys
                85                  90                  95

Ala Arg His Arg Leu Met Tyr Thr Thr Asp Tyr Tyr Tyr Glu Val Met
            100                 105                 110

Asp Asp Trp Gly Gln Gly Ala Ser Val Thr Val Ser Ser
        115                 120                 125

<210> SEQ ID NO 179
<211> LENGTH: 125
<212> TYPE: PRT
<213> ORGANISM: Artificial Sequence
<220> FEATURE:
<223> OTHER INFORMATION: 5826-8-R5A-G8 HCVR

<400> SEQUENCE: 179

Glu Val Lys Leu Val Glu Ser Gly Gly Gly Leu Val Gln Pro Gly Arg
1               5                   10                  15

Ser Leu Lys Leu Ser Cys Ala Ala Ser Gly Phe Ser Phe Arg Asn Tyr
            20                  25                  30

Gly Met Ala Trp Val Arg Gln Ala Pro Thr Lys Gly Gln Glu Trp Val
        35                  40                  45

Ala Thr Ile Ser Tyr Asp Gly Asn Asp Thr Tyr Tyr Arg Asp Ser Val
    50                  55                  60

Lys Gly Arg Phe Thr Val Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Arg His Arg Leu Ile Tyr Thr Thr Asp Tyr Tyr Tyr Glu Val Leu
            100                 105                 110

Asp Ala Trp Gly Gln Gly Ala Ser Val Thr Val Ser Ser
        115                 120                 125

<210> SEQ ID NO 180
<211> LENGTH: 125
<212> TYPE: PRT
<213> ORGANISM: Artificial Sequence
<220> FEATURE:
<223> OTHER INFORMATION: 5826-8-R6A-H9 HCVR

<400> SEQUENCE: 180

Glu Val Lys Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser Asn Tyr
            20                  25                  30

Gly Met Ala Trp Val Arg Gln Ala Pro Thr Lys Gly Leu Glu Trp Val
        35                  40                  45

```
Ala Thr Ile Asn Tyr Asp Gly Arg Asn Thr Tyr Tyr Arg Asp Ser Val
            50                  55                  60

Lys Gly Arg Phe Thr Ile Ser Arg Asp Asn Ala Lys Ser Thr Leu Tyr
 65                  70                  75                  80

Leu Gln Val Asp Ser Leu Gln Ser Glu Asp Thr Ala Thr Tyr Tyr Cys
                 85                  90                  95

Thr Arg His Lys Leu Ile Tyr Thr Thr Asp Tyr Tyr Tyr Glu Val Met
            100                 105                 110

Asp Val Trp Gly Gln Gly Ala Ser Val Ala Val Ser Ser
            115                 120                 125

<210> SEQ ID NO 181
<211> LENGTH: 125
<212> TYPE: PRT
<213> ORGANISM: Artificial Sequence
<220> FEATURE:
<223> OTHER INFORMATION: 5826-8-R6A-H12 HCVR

<400> SEQUENCE: 181

Glu Val Lys Leu Val Glu Ser Gly Gly Ala Leu Val Gln Pro Gly Arg
 1               5                  10                  15

Ser Leu Lys Leu Ser Cys Ala Ala Ser Gly Phe Thr Phe Ser Asn Phe
                20                  25                  30

Gly Met Ala Trp Val Arg Gln Ala Pro Thr Lys Gly Leu Glu Trp Val
            35                  40                  45

Ala Thr Ile Asn Tyr Asp Gly Arg Asp Thr Tyr Tyr Arg Asp Ser Val
            50                  55                  60

Lys Gly Arg Phe Thr Val Ser Arg Asp Asn Ala Lys Ser Thr Leu Tyr
 65                  70                  75                  80

Leu Gln Met Asp Ser Leu Arg Ser Glu Asp Thr Ala Thr Tyr Tyr Cys
                 85                  90                  95

Thr Arg His Arg Leu Ile Tyr Thr Thr Asp Tyr Tyr Tyr Glu Val Met
            100                 105                 110

Asp Ala Trp Gly Arg Gly Ala Ser Val Thr Val Ser Ser
            115                 120                 125

<210> SEQ ID NO 182
<211> LENGTH: 117
<212> TYPE: PRT
<213> ORGANISM: Artificial Sequence
<220> FEATURE:
<223> OTHER INFORMATION: 5826-13-R3A-A10 HCVR

<400> SEQUENCE: 182

Glu Val Lys Leu Val Glu Ser Gly Pro Gly Leu Val Lys Pro Ser Gln
 1               5                  10                  15

Ser Leu Ser Leu Ala Cys Ser Ile Thr Asp Tyr Ser Ile Thr Asp Asn
                20                  25                  30

Tyr Trp Gly Trp Ile Arg Lys Phe Pro Gly Asn Lys Met Glu Trp Ile
            35                  40                  45

Gly His Ile Ser His Ser Gly Ser Thr Tyr Asn Pro Ser Leu Lys
 50                  55                  60

Ser Arg Ile Ser Phe Thr Arg Asp Thr Ser Lys Asn Gln Phe Phe Leu
 65                  70                  75                  80

Gln Leu Asn Ser Val Thr Pro Glu Asp Thr Ala Thr Tyr Phe Cys Ala
                 85                  90                  95

Arg Tyr Gly Ala Gly Ala Ser Phe Asp Tyr Trp Gly Gln Gly Val Met
            100                 105                 110
```

Val Thr Val Ser Ser
        115

<210> SEQ ID NO 183
<211> LENGTH: 117
<212> TYPE: PRT
<213> ORGANISM: Artificial Sequence
<220> FEATURE:
<223> OTHER INFORMATION: 5826-13-R3A-B1 HCVR

<400> SEQUENCE: 183

Glu Val Gln Leu Gln Gln Ser Gly Ala Glu Leu Thr Lys Pro Gly Ser
1               5                   10                  15

Ser Val Lys Ile Ser Cys Lys Ala Ser Gly Phe Thr Phe Thr Thr Tyr
            20                  25                  30

Asp Ile Gly Trp Leu Lys Gln Arg Pro Gly Gln Ala Leu Glu Trp Ile
        35                  40                  45

Gly Tyr Ile Asn Pro Gly Ser Gly Gly Ile Gly Tyr Asn Glu Lys Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Tyr Trp Gly Gln Gly Val Met
            100                 105                 110

Val Thr Val Ser Ser
        115

<210> SEQ ID NO 184
<211> LENGTH: 117
<212> TYPE: PRT
<213> ORGANISM: Artificial Sequence
<220> FEATURE:
<223> OTHER INFORMATION: 5826-13-R3A-B3 HCVR

<400> SEQUENCE: 184

Glu Val Gln Leu Gln Gln Ser Gly Ala Gly Leu Thr Lys Pro Gly Ala
1               5                   10                  15

Ser Val Lys Ile Ser Cys Lys Ala Ser Gly Tyr Thr Phe Thr Thr Tyr
            20                  25                  30

Asp Ile Gly Trp Ile Lys Gln Arg Pro Gly Gln Ala Leu Glu Trp Ile
        35                  40                  45

Gly Ser Ile Asn Pro Gly Ser Gly Gly Ile Ala Tyr Ser Glu Lys Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Tyr Trp Gly Gln Gly Val Leu
            100                 105                 110

Val Thr Val Ser Ser
        115

<210> SEQ ID NO 185
<211> LENGTH: 116
<212> TYPE: PRT
<213> ORGANISM: Artificial Sequence
<220> FEATURE:
<223> OTHER INFORMATION: 5826-13-R3A-D5 HCVR

<400> SEQUENCE: 185

Glu Val Lys Leu Val Glu Ser Gly Pro Gly Leu Val Lys Pro Ser Gln
1               5                   10                  15

Ser Leu Ser Leu Thr Cys Ser Val Thr Gly Tyr Phe Ile Thr Gly Asn
            20                  25                  30

Tyr Leu Ala Trp Ile Arg Lys Phe Pro Gly Asn Lys Met Glu Trp Ile
        35                  40                  45

Gly His Ile Lys Ser Ser Gly Thr Thr Thr Tyr Asn Pro Ser Leu Lys
    50                  55                  60

Ser Arg Val Ser Ile Thr Arg Asp Thr Ser Lys Asn Gln Phe Phe Leu
65                  70                  75                  80

Gln Leu Asn Ser Val Thr Ser Glu Asp Thr Ala Thr Tyr Tyr Cys Ala
                85                  90                  95

Arg His Gly His Tyr Val Met Asp Val Trp Gly Gln Gly Ala Ser Val
            100                 105                 110

Thr Val Ser Ser
        115

<210> SEQ ID NO 186
<211> LENGTH: 117
<212> TYPE: PRT
<213> ORGANISM: Artificial Sequence
<220> FEATURE:
<223> OTHER INFORMATION: 5826-13-R3A-D6 HCVR

<400> SEQUENCE: 186

Glu Val Gln Leu Gln Gln Ser Gly Ala Glu Leu Thr Lys Pro Gly Ser
1               5                   10                  15

Ser Val Lys Ile Ser Cys Lys Ala Ser Gly Tyr Thr Phe Thr Thr Tyr
            20                  25                  30

Asp Ile Gly Trp Ile Lys Gln Arg Pro Gly Gln Ala Leu Glu Trp Ile
        35                  40                  45

Gly Ser Ile Asn Pro Gly Ser Gly Ile Gly Tyr Asn Glu Arg Phe
    50                  55                  60

Lys Gly Lys Ala Thr Leu Thr Val Asp Lys Ser Ser Thr Ala Phe
65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Tyr Trp Gly Gln Gly Val Met
            100                 105                 110

Val Thr Val Ser Ser
        115

<210> SEQ ID NO 187
<211> LENGTH: 117
<212> TYPE: PRT
<213> ORGANISM: Artificial Sequence
<220> FEATURE:
<223> OTHER INFORMATION: 5826-13-R4A-E2 HCVR

<400> SEQUENCE: 187

Gln Val Gln Leu Lys Gln Ser Gly Ala Glu Leu Thr Lys Pro Gly Ser
1               5                   10                  15

Ser Val Lys Ile Ser Cys Lys Ala Ser Gly Tyr Thr Phe Thr Thr Tyr
            20                  25                  30

Asp Ile Gly Trp Leu Lys Gln Arg Pro Gly Gln Ala Leu Glu Trp Ile
        35                  40                  45

Gly Tyr Ile Asn Pro Gly Gly Gly Ile Gly Tyr Asn Glu Lys Phe
            50                  55                  60

Lys Gly Lys Ala Thr Leu Thr Val Asp Lys Ser Ser Thr Ala Phe
 65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Tyr Trp Gly Gln Gly Val Met
            100                 105                 110

Val Thr Val Ser Ser
            115

<210> SEQ ID NO 188
<211> LENGTH: 117
<212> TYPE: PRT
<213> ORGANISM: Artificial Sequence
<220> FEATURE:
<223> OTHER INFORMATION: 5826-13-R4A-E6 HCVR

<400> SEQUENCE: 188

Asp Val Lys Leu Gln Glu Ser Gly Pro Gly Leu Val Lys Pro Ser Gln
 1               5                  10                  15

Ser Leu Ser Leu Thr Cys Ser Val Thr Gly His Ser Ile Thr Ser Asn
            20                  25                  30

Tyr Trp Gly Trp Ile Arg Lys Phe Pro Gly Asn Lys Met Glu Trp Ile
        35                  40                  45

Gly Gln Ile Ser His Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
 65                  70                  75                  80

Gln Leu Asn Ser Val Thr Thr Glu Asp Thr Ala Thr Tyr Tyr Cys Gly
                85                  90                  95

Arg Tyr Gly Ala Gly Ser Ser Phe Asp Tyr Trp Gly Gln Gly Val Met
            100                 105                 110

Val Thr Val Ser Ser
            115

<210> SEQ ID NO 189
<211> LENGTH: 117
<212> TYPE: PRT
<213> ORGANISM: Artificial Sequence
<220> FEATURE:
<223> OTHER INFORMATION: 5826-13-R4A-E9 HCVR

<400> SEQUENCE: 189

Glu Val Gln Leu Gln Gln Ser Gly Ala Glu Leu Thr Lys Pro Gly Ser
 1               5                  10                  15

Ser Val Lys Ile Ser Cys Lys Ala Ser Gly Tyr Thr Phe Thr Thr Tyr
            20                  25                  30

Asp Ile Gly Trp Ile Lys Gln Arg Pro Gly Gln Ala Leu Glu Trp Ile
        35                  40                  45

Gly Ser Ile Asn Pro Gly Ser Gly Ile Gly Tyr Asn Glu Lys Phe
    50                  55                  60

Lys Gly Lys Ala Thr Leu Thr Val Asp Lys Ser Ser Ser Thr Val Phe
 65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Asn Trp Gly Gln Gly Val Leu

-continued

```
                100                 105                 110
Val Thr Val Ser Ser
        115

<210> SEQ ID NO 190
<211> LENGTH: 117
<212> TYPE: PRT
<213> ORGANISM: Artificial Sequence
<220> FEATURE:
<223> OTHER INFORMATION: 5826-13-R4A-F10 HCVR

<400> SEQUENCE: 190

Glu Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Thr Thr Tyr
            20                  25                  30

Asp Ile Gly Trp Ile Lys Gln Arg Pro Gly Gln Ala Leu Glu Trp Ile
        35                  40                  45

Gly Ser Ile Asn Pro Gly Ser Gly Gly Ile Gly Tyr Asn Glu Lys Phe
    50                  55                  60

Lys Gly Lys Ala Thr Leu Thr Val Asp Lys Ser Ser Arg Thr Val Phe
65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Tyr Trp Gly Gln Gly Val Met
            100                 105                 110

Val Thr Val Ser Ser
        115

<210> SEQ ID NO 191
<211> LENGTH: 117
<212> TYPE: PRT
<213> ORGANISM: Artificial Sequence
<220> FEATURE:
<223> OTHER INFORMATION: 5826-13-R4A-G11 HCVR

<400> SEQUENCE: 191

Glu Val Gln Leu Gln Gln Ser Gly Pro Glu Leu Ala Lys Pro Gly Ser
1               5                   10                  15

Ser Val Lys Ile Ser Cys Lys Ala Ser Gly Tyr Thr Phe Thr Thr Tyr
            20                  25                  30

Asp Ile Gly Trp Ile Lys Gln Arg Pro Gly Gln Ala Leu Glu Trp Ile
        35                  40                  45

Gly Ser Ile Asn Pro Gly Ser Gly Gly Ile Gly Tyr Asn Glu Lys Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Tyr Trp Gly Gln Gly Val Met
            100                 105                 110

Val Thr Val Ser Ser
        115

<210> SEQ ID NO 192
<211> LENGTH: 117
<212> TYPE: PRT
<213> ORGANISM: Artificial Sequence
<220> FEATURE:
```

<223> OTHER INFORMATION: 5826-13-R4A-G12 HCVR

<400> SEQUENCE: 192

Glu Val Gln Leu Gln Gln Ser Gly Ala Gly Leu Thr Lys Pro Gly Ala
1               5                   10                  15

Ser Val Lys Ile Ser Cys Thr Ala Ser Gly Tyr Thr Phe Thr Thr Tyr
                20                  25                  30

Asp Arg Gly Trp Leu Arg Gln Arg Pro Gly Gln Ala Leu Glu Trp Ile
            35                  40                  45

Gly Ser Ile Asn Pro Gly Gly Gly Thr Gly Tyr Asn Glu Lys Phe
        50                  55                  60

Lys Gly Asn Ala Thr Leu Thr Val Asp Lys Ser Ser Thr Ala Phe
65                  70                  75                  80

Met Gln Leu Ser Ser Leu Thr Pro Glu Asp Thr Ala Asp Tyr Tyr Cys
                85                  90                  95

Ala Arg Pro Leu Arg Arg Val Leu Asp Tyr Trp Gly Gln Gly Val Leu
            100                 105                 110

Val Thr Val Ser Ser
        115

<210> SEQ ID NO 193
<211> LENGTH: 116
<212> TYPE: PRT
<213> ORGANISM: Artificial Sequence
<220> FEATURE:
<223> OTHER INFORMATION: 5826-13-R4A-H1 HCVR

<400> SEQUENCE: 193

Asp Val Lys Leu Gln Glu Ser Gly Pro Gly Leu Val Lys Pro Ser Gln
1               5                   10                  15

Ser Leu Ser Leu Thr Cys Ser Val Thr Gly His Ser Ile Thr Ser Asn
                20                  25                  30

Tyr Trp Gly Trp Ile Arg Lys Leu Pro Gly Asn Lys Met Glu Trp Ile
            35                  40                  45

Gly Gln Ile Ser His Ser Gly Ser Thr Ser Tyr Asn Pro Ser Leu Ile
        50                  55                  60

Ser Arg Ile Ser Ile Thr Arg Asp Thr Ser Asn Gln Phe Phe Leu Gln
65                  70                  75                  80

Leu Asn Ser Val Thr Thr Glu Asp Thr Ala Thr Tyr Tyr Cys Gly Arg
                85                  90                  95

Tyr Gly Ala Gly Ser Ser Phe Asp Tyr Trp Gly Gln Gly Val Met Val
            100                 105                 110

Thr Val Ser Ser
        115

<210> SEQ ID NO 194
<211> LENGTH: 117
<212> TYPE: PRT
<213> ORGANISM: Artificial Sequence
<220> FEATURE:
<223> OTHER INFORMATION: 5826-13-R4A-H2 HCVR

<400> SEQUENCE: 194

Glu Val Gln Leu Gln Gln Ser Gly Ala Glu Leu Thr Lys Pro Gly Ser
1               5                   10                  15

Ser Val Lys Ile Ser Cys Lys Ala Ser Gly Tyr Thr Phe Thr Thr Tyr
                20                  25                  30

Asp Ile Gly Trp Ile Lys Gln Arg Pro Gly Gln Ala Leu Glu Trp Ile 35                  40                  45
Gly Ser Ile Asn Pro Gly Ser Gly Gly Ile Gly Tyr Asn Glu Lys Phe
        50                  55                  60
Lys Gly Lys Ala Thr Leu Thr Val Asp Arg Ser Ser Thr Ala Phe
65                  70                  75                  80
Met Gln Leu Ser Ser Leu Thr Pro Glu Asp Thr Ala Val Tyr Tyr Cys
                85                  90                  95
Ala Arg Pro Leu Arg Arg Val Leu Asp Asn Trp Gly Gln Gly Val Leu
            100                 105                 110
Val Thr Val Ser Ser
        115

<210> SEQ ID NO 195
<211> LENGTH: 117
<212> TYPE: PRT
<213> ORGANISM: Artificial Sequence
<220> FEATURE:
<223> OTHER INFORMATION: 5826-13-R4A-H3 HCVR

<400> SEQUENCE: 195

Glu Val Gln Leu Gln Gln Ser Gly Gly Glu Leu Thr Lys Pro Gly Ser
1               5                   10                  15
Ser Val Lys Ile Ser Cys Lys Ala Ser Gly Tyr Thr Phe Ser Thr Tyr
                20                  25                  30
Asp Ile Gly Trp Ile Lys Gln Arg Pro Gly Gln Ala Leu Glu Trp Ile
            35                  40                  45
Gly Ser Ile Asn Pro Gly Ser Gly Gly Ile Gly Tyr Asn Glu Lys Phe
        50                  55                  60
Lys Gly Lys Ala Thr Leu Thr Val Asp Lys Ser Ser Thr Ala Phe
65                  70                  75                  80
Met Gln Leu Ser Ser Leu Thr Pro Glu Asp Thr Ala Val Tyr Tyr Cys
                85                  90                  95
Ala Arg Pro Leu Arg Arg Val Leu Asp Tyr Trp Gly Gln Gly Val Met
            100                 105                 110
Val Thr Val Ser Ser
        115

<210> SEQ ID NO 196
<211> LENGTH: 117
<212> TYPE: PRT
<213> ORGANISM: Artificial Sequence
<220> FEATURE:
<223> OTHER INFORMATION: 5826-13-R4A-H4 HCVR

<400> SEQUENCE: 196

Asp Val Lys Leu Gln Glu Ser Gly Pro Gly Leu Val Lys Pro Ser Gln
1               5                   10                  15
Ser Leu Ser Leu Thr Cys Ser Val Thr Gly His Ser Ile Thr Gly Asn
                20                  25                  30
Tyr Trp Gly Trp Ile Arg Lys Phe Pro Gly Asn Lys Met Glu Trp Ile
            35                  40                  45
Gly Gln Ile Ser His Ser Gly Ser Thr Tyr Asn Pro Ser Leu Lys
        50                  55                  60
Ser Arg Ile Ser Ile Thr Arg Asp Thr Ser Lys Asn Gln Phe Phe Leu
65                  70                  75                  80
Gln Leu Asn Ser Val Thr Thr Glu Asp Thr Ala Thr Tyr Tyr Cys Gly
                85                  90                  95

Arg Tyr Gly Ala Gly Ser Ser Phe Asp Tyr Trp Gly Gln Gly Val Met
                100                 105                 110

Val Thr Val Ser Ser
        115

<210> SEQ ID NO 197
<211> LENGTH: 117
<212> TYPE: PRT
<213> ORGANISM: Artificial Sequence
<220> FEATURE:
<223> OTHER INFORMATION: 5826-13-R4A-H5 HCVR

<400> SEQUENCE: 197

Glu Val Gln Leu Gln Gln Ser Gly Ala Gly Leu Thr Lys Pro Gly Gly
1               5                   10                  15

Ser Val Lys Ile Ser Cys Lys Val Ser Gly Tyr Thr Phe Thr Thr Tyr
                20                  25                  30

Asp Ile Gly Trp Leu Lys Gln Arg Pro Gly Gln Ala Leu Glu Trp Ile
            35                  40                  45

Gly Ser Ile Asn Pro Gly Gly Gly Thr Gly Tyr Asn Glu Lys Phe
        50                  55                  60

Lys Gly Lys Ala Thr Leu Thr Val Asp Lys Ser Ser Thr Ala Phe
65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Tyr Trp Gly Gln Gly Val Leu
                100                 105                 110

Val Thr Val Ser Ser
        115

<210> SEQ ID NO 198
<211> LENGTH: 116
<212> TYPE: PRT
<213> ORGANISM: Artificial Sequence
<220> FEATURE:
<223> OTHER INFORMATION: 5826-13-R4A-H6 HCVR

<400> SEQUENCE: 198

Glu Val Gln Leu Gln Gln Ser Gly Ala Gly Leu Thr Lys Pro Gly Ala
1               5                   10                  15

Ser Val Lys Ile Ser Cys Lys Ala Ser Gly Tyr Thr Phe Thr Thr Tyr
                20                  25                  30

Asp Ile Gly Trp Leu Lys Gln Arg Pro Gly Gln Ala Leu Glu Trp Ile
            35                  40                  45

Gly Ser Ile Asn Pro Gly Gly Gly Thr Gly Tyr Asn Glu Lys Phe
        50                  55                  60

Lys Gly Lys Ala Thr Leu Thr Val Asp Lys Ser Ser Thr Ala Phe
65                  70                  75                  80

Met Gln Leu Ser Ser Leu Thr Pro Glu Asp Thr Ala Val Tyr Tyr Cys
                85                  90                  95

Ala Arg Pro Leu Arg Val Leu Asp Tyr Trp Gly Gln Gly Val Leu Val
                100                 105                 110

Thr Val Ser Ser
        115

<210> SEQ ID NO 199
<211> LENGTH: 117
<212> TYPE: PRT
<213> ORGANISM: Artificial Sequence

```
<220> FEATURE:
<223> OTHER INFORMATION: 5826-13-R4A-H9 HCVR

<400> SEQUENCE: 199

Glu Val Gln Leu Gln Gln Ser Gly Ala Glu Leu Thr Lys Pro Gly Ser
1               5                   10                  15

Ser Val Lys Ile Ser Cys Lys Ala Ser Gly Tyr Thr Phe Thr Thr Tyr
            20                  25                  30

Asp Ile Gly Trp Ile Lys Gln Arg Pro Gly Gln Ala Leu Glu Trp Ile
        35                  40                  45

Gly Ser Ile Asn Pro Gly Ser Gly Ile Gly Tyr Asn Glu Arg Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Glu Asp Thr Ala Val Tyr Tyr Cys
                85                  90                  95

Ala Arg Pro Leu Arg Arg Val Leu Asp Tyr Trp Gly Arg Gly Val Met
            100                 105                 110

Val Thr Val Ser Ser
        115

<210> SEQ ID NO 200
<211> LENGTH: 117
<212> TYPE: PRT
<213> ORGANISM: Artificial Sequence
<220> FEATURE:
<223> OTHER INFORMATION: 5826-13-R4A-H10 HCVR & 5826-13-R4A-H12 HCVR

<400> SEQUENCE: 200

Glu Val Gln Leu Glu Glu Ser Gly Pro Gly Leu Val Lys Pro Ser Gln
1               5                   10                  15

Ser Leu Ser Leu Thr Cys Ser Val Thr Gly His Ser Ile Thr Ser Asn
            20                  25                  30

Tyr Trp Gly Trp Ile Arg Lys Phe Pro Gly Asn Lys Met Glu Trp Ile
        35                  40                  45

Gly Gln Ile Ser His Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Gly
                85                  90                  95

Arg Tyr Gly Ala Gly Ser Ser Phe Asp Tyr Trp Gly Gln Gly Val Met
            100                 105                 110

Val Thr Val Ser Ser
        115

<210> SEQ ID NO 201
<211> LENGTH: 117
<212> TYPE: PRT
<213> ORGANISM: Artificial Sequence
<220> FEATURE:
<223> OTHER INFORMATION: 5826-13-R4A-H11 HCVR

<400> SEQUENCE: 201

Gln Val Gln Leu Lys Glu Ser Gly Pro Gly Leu Val Lys Pro Ser His
1               5                   10                  15

Ser Leu Ser Leu Thr Cys Ser Val Thr Gly His Ser Ile Thr Ser Asn
            20                  25                  30
```

Tyr Trp Gly Trp Ile Arg Lys Phe Pro Gly Asn Lys Met Glu Trp Ile
                35                  40                  45

Gly Gln Ile Ser His Thr Gly Ser Ser Thr Tyr Asn Pro Ser Leu Lys
 50                  55                  60

Ser Arg Ile Ser Phe Thr Arg Asp Thr Ser Lys Asn Gln Phe Phe Leu
 65                  70                  75                  80

Gln Leu Asn Ser Val Thr Thr Glu Asp Ser Ala Thr Tyr Tyr Cys Gly
                 85                  90                  95

Arg Tyr Gly Ala Gly Ser Ser Phe Asp Tyr Trp Gly Gln Gly Val Met
                100                 105                 110

Val Thr Val Ser Ser
            115

<210> SEQ ID NO 202
<211> LENGTH: 113
<212> TYPE: PRT
<213> ORGANISM: Artificial Sequence
<220> FEATURE:
<223> OTHER INFORMATION: 5826-8-R6A-A10 LCVR

<400> SEQUENCE: 202

Asp Val Leu Met Thr Gln Thr Pro Ser Ser Gln Ala Ala Ser Ala Gly
 1               5                  10                  15

Glu Lys Val Thr Met Ser Cys Lys Ser Ser Gln Ser Leu Leu Tyr Asn
                20                  25                  30

Glu Asn Lys Lys Asn Tyr Leu Ala Trp Phe Gln Gln Lys Pro Gly Gln
                35                  40                  45

Ser Pro Lys Leu Leu Ile Tyr Trp Ala Ser Thr Arg Glu Ser Gly Val
 50                  55                  60

Pro Asp Arg Phe Ile Gly Gly Gly Ser Gly Thr Asp Phe Thr Leu Thr
 65                  70                  75                  80

Ile Ser Ser Val Gln Ala Glu Asp Leu Ala Val Tyr Tyr Cys Gln Glu
                 85                  90                  95

Tyr Tyr Lys Phe Pro Trp Thr Phe Gly Gly Gly Thr Lys Leu Glu Leu
                100                 105                 110

Lys

<210> SEQ ID NO 203
<211> LENGTH: 113
<212> TYPE: PRT
<213> ORGANISM: Artificial Sequence
<220> FEATURE:
<223> OTHER INFORMATION: 5826-8-R6A-B11 LCVR & 5826-8-R5A-G6 LCVR

<400> SEQUENCE: 203

Asp Ile Val Met Thr Gln Ser Pro Ser Ser Gln Ala Val Ser Ala Gly
 1               5                  10                  15

Glu Lys Val Thr Met Ser Cys Lys Ser Ser Gln Ser Leu Leu Tyr Asn
                20                  25                  30

Glu Asn Lys Lys Asn Tyr Leu Ala Trp Phe Gln Gln Lys Pro Gly Gln
                35                  40                  45

Ser Pro Lys Leu Leu Ile Tyr Trp Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asp
                 85                  90                  95

```
Tyr Tyr His Phe Pro Trp Thr Phe Gly Gly Gly Thr Lys Leu Glu Leu
                100                 105                 110
Lys
```

<210> SEQ ID NO 204
<211> LENGTH: 112
<212> TYPE: PRT
<213> ORGANISM: Artificial Sequence
<220> FEATURE:
<223> OTHER INFORMATION: 5826-8-R6A-D12 LCVR

<400> SEQUENCE: 204

```
Asp Val Leu Met Thr Gln Thr Pro Pro Thr Leu Ser Ala Thr Ile Gly
1               5                   10                  15

Gln Ser Val Ser Ile Ser Cys Lys Ser Ser Gln Ser Leu Leu His Ser
                20                  25                  30

Asn Gly Asn Thr Tyr Leu Asn Trp Leu Leu Gln Arg Pro Gly Gln Ser
            35                  40                  45

Pro Gln Leu Leu Ile Tyr Ser Val Ser Lys Leu Glu Ser Gly Val Pro
        50                  55                  60

Asn Arg Phe Ser Gly Ser Gly Ser Gln Thr Asp Phe Thr Leu Lys Ile
65                  70                  75                  80

Ser Glu Val Glu Ala Glu Asp Met Gly Val Tyr Tyr Cys Met Gln Ala
                85                  90                  95

Thr His Ala Pro Phe Thr Phe Gly Ser Trp Thr Lys Leu Glu Ile Lys
                100                 105                 110
```

<210> SEQ ID NO 205
<211> LENGTH: 113
<212> TYPE: PRT
<213> ORGANISM: Artificial Sequence
<220> FEATURE:
<223> OTHER INFORMATION: 5826-8-R6A-E10 LCVR

<400> SEQUENCE: 205

```
Asp Ile Val Met Thr Gln Ala Pro Ser Ser Gln Ala Val Ser Pro Gly
1               5                   10                  15

Glu Lys Val Thr Met Ser Cys Lys Ser Ser Gln Ser Leu Leu Tyr Asn
                20                  25                  30

Glu Asn Lys Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ala Gly Val
        50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Tyr Tyr Lys Phe Pro Trp Pro Phe Gly Gly Gly Thr Lys Leu Glu Leu
                100                 105                 110
Lys
```

<210> SEQ ID NO 206
<211> LENGTH: 113
<212> TYPE: PRT
<213> ORGANISM: Artificial Sequence
<220> FEATURE:
<223> OTHER INFORMATION: 5826-8-R5A-G8 LCVR

<400> SEQUENCE: 206

-continued

Asp Ile Val Met Thr Gln Ala Pro Ser Ser Gln Ala Val Ser Ala Gly
1               5                   10                  15

Glu Lys Val Thr Met Ser Cys Lys Ser Ser Gln Ser Leu Leu Tyr Asn
            20                  25                  30

Glu Asn Lys Lys Asn Tyr Leu Ala Trp Phe Gln Gln Lys Pro Gly Gln
        35                  40                  45

Ser Pro Lys Leu Leu Ile Tyr Trp Ala Ser Thr Arg Lys Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Tyr Tyr Lys Phe Pro Trp Thr Phe Gly Gly Gly Thr Lys Leu Glu Leu
            100                 105                 110

Arg

<210> SEQ ID NO 207
<211> LENGTH: 113
<212> TYPE: PRT
<213> ORGANISM: Artificial Sequence
<220> FEATURE:
<223> OTHER INFORMATION: 5826-8-R6A-H9 LCVR

<400> SEQUENCE: 207

Asp Ile Val Met Thr Gln Ser Pro Ser Ser Gln Ala Val Ser Pro Gly
1               5                   10                  15

Glu Lys Val Thr Met Asn Cys Lys Ser Ser Gln Ser Leu Leu Tyr Asn
            20                  25                  30

Glu Asn Lys Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ala Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Tyr Tyr Lys Phe Pro Trp Pro Phe Gly Gly Gly Thr Lys Leu Glu Leu
            100                 105                 110

Lys

<210> SEQ ID NO 208
<211> LENGTH: 112
<212> TYPE: PRT
<213> ORGANISM: Artificial Sequence
<220> FEATURE:
<223> OTHER INFORMATION: 5826-8-R6A-H11 LCVR

<400> SEQUENCE: 208

Asp Val Leu Met Thr Gln Thr Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Asn Gly Asn Thr Tyr Leu Asn Trp Leu Leu Gln Arg Pro Gly Gln Ser
        35                  40                  45

Pro Gln Leu Leu Ile Tyr Ser Val Ser Asn Leu Glu Ser Gly Val Pro
    50                  55                  60

Asn Arg Phe Ser Gly Ser Gly Ser Glu Thr Asp Phe Thr Leu Lys Ile

```
                65                  70                  75                  80
Ser Gly Val Glu Ala Glu Asp Leu Gly Val Tyr Tyr Cys Met Gln Ala
                85                  90                  95

Thr His Ala Pro Phe Thr Phe Gly Ser Gly Thr Lys Leu Glu Ile Lys
            100                 105                 110

<210> SEQ ID NO 209
<211> LENGTH: 113
<212> TYPE: PRT
<213> ORGANISM: Artificial Sequence
<220> FEATURE:
<223> OTHER INFORMATION: 5826-8-R6A-H12 LCVR

<400> SEQUENCE: 209

Asp Ile Val Met Thr Gln Ser Pro Ser Ser Gln Ala Val Ser Pro Gly
1               5                  10                  15

Glu Lys Val Thr Met Asn Cys Lys Ser Ser Gln Ser Leu Leu Tyr Asn
                20                  25                  30

Glu Asn Lys Lys Asn Tyr Leu Ala Trp Tyr Gln Lys Pro Gly Gln
            35                  40                  45

Ser Pro Lys Leu Leu Ile Tyr Trp Ala Ser Thr Arg Glu Ala Gly Val
        50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Tyr Tyr Lys Phe Pro Tyr Thr Phe Gly Ala Gly Thr Lys Leu Glu Leu
            100                 105                 110

Lys

<210> SEQ ID NO 210
<211> LENGTH: 107
<212> TYPE: PRT
<213> ORGANISM: Artificial Sequence
<220> FEATURE:
<223> OTHER INFORMATION: 5826-13-R3A-A10 LCVR

<400> SEQUENCE: 210

Asp Ile Gln Leu Thr Gln Ser Pro His Ser Leu Ser Ala Ser Leu Gly
1               5                  10                  15

Glu Thr Val Ser Ile Glu Cys Leu Ala Ser Glu Gly Ile Ser Asn Tyr
                20                  25                  30

Leu Ala Trp Tyr Gln Gln Lys Pro Gly Lys Ser Pro Gln Leu Leu Ile
            35                  40                  45

Tyr Tyr Thr Ser Ser Leu Gln Asp Gly Val Pro Ser Arg Phe Ser Gly
        50                  55                  60

Ser Gly Ser Gly Thr Gln Tyr Ser Leu Lys Ile Ser Asn Met Gln Pro
65                  70                  75                  80

Glu Asp Glu Gly Val Tyr Tyr Cys Gln Gln Tyr Lys Tyr Pro Trp
                85                  90                  95

Thr Phe Gly Gly Gly Thr Lys Leu Glu Leu Lys
            100                 105

<210> SEQ ID NO 211
<211> LENGTH: 107
<212> TYPE: PRT
<213> ORGANISM: Artificial Sequence
<220> FEATURE:
<223> OTHER INFORMATION: 5826-13-R3A-B1 LCVR
```

<400> SEQUENCE: 211

Asp Ile Val Met Thr Gln Ser Pro Ser Leu Pro Ala Ser Leu Gly
1               5                   10                  15

Glu Arg Val Thr Ile Ser Cys Arg Ala Ser Gln Gly Ile Ser Asn Lys
            20                  25                  30

Leu Asn Trp Tyr Gln Gln Lys Pro Asp Gly Thr Ile Lys Pro Leu Ile
        35                  40                  45

Tyr Tyr Thr Ser Arg Leu Gln Ser Gly Val Pro Ser Arg Phe Ser Gly
50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Asp Ala Ser Phe Pro Pro
                85                  90                  95

Thr Phe Gly Ala Gly Thr Lys Val Glu Leu Lys
            100                 105

<210> SEQ ID NO 212
<211> LENGTH: 107
<212> TYPE: PRT
<213> ORGANISM: Artificial Sequence
<220> FEATURE:
<223> OTHER INFORMATION: 5826-13-R3A-B3 LCVR & 5826-13-R4A-H5 LCVR

<400> SEQUENCE: 212

Asp Ile Gln Leu Thr Gln Ser Pro Ser Ser Leu Pro Ala Ser Leu Gly
1               5                   10                  15

Glu Arg Val Thr Ile Ser Cys Arg Ala Ser Gln Gly Ile Ser Asn Lys
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Asp Ala Ser Phe Pro Pro
                85                  90                  95

Thr Phe Gly Gly Gly Thr Lys Leu Glu Leu Lys
            100                 105

<210> SEQ ID NO 213
<211> LENGTH: 110
<212> TYPE: PRT
<213> ORGANISM: Artificial Sequence
<220> FEATURE:
<223> OTHER INFORMATION: 5826-13-R3A-D5 LCVR

<400> SEQUENCE: 213

Asp Ile Val Leu Thr Gln Ser Pro Val Leu Ala Val Ser Leu Gly Gln
1               5                   10                  15

Arg Ala Thr Ile Ser Cys Arg Ala Ser Gln Ser Val Ser Thr Ser Thr
            20                  25                  30

Tyr Asn Phe Met His Trp Tyr Gln Gln Lys Pro Gly Gln Gln Pro Arg
        35                  40                  45

Leu Leu Ile Tyr Asp Ala Ser His Leu Ala Ser Ser Val Pro Ala Arg
    50                  55                  60

Phe Ser Gly Ser Gly Ser Gly Thr Asp Phe Thr Leu Thr Ile Asn Pro
65                  70                  75                  80

```
Val Gln Ala Asp Asp Ile Ala Thr Tyr Tyr Cys Gln Gln Ser Arg Glu
            85                  90                  95

Leu Pro Leu Thr Phe Gly Ser Gly Thr Lys Leu Glu Ile Lys
            100                 105                 110
```

<210> SEQ ID NO 214
<211> LENGTH: 107
<212> TYPE: PRT
<213> ORGANISM: Artificial Sequence
<220> FEATURE:
<223> OTHER INFORMATION: 5826-13-R3A-D6 LCVR

<400> SEQUENCE: 214

```
Asp Ile Leu Met Thr Gln Ser Pro Ser Ser Leu Ser Ala Ser Leu Gly
1               5                   10                  15

Glu Arg Val Thr Ile Ser Cys Arg Ala Ser Gln Gly Ile Gly Asn Lys
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65              70                  75                  80

Glu Asp Phe Ala Met Tyr Tyr Cys Gln Gln Asp Ala Ser Phe Pro Pro
                85                  90                  95

Thr Phe Gly Gly Gly Thr Lys Leu Glu Leu Lys
            100                 105
```

<210> SEQ ID NO 215
<211> LENGTH: 107
<212> TYPE: PRT
<213> ORGANISM: Artificial Sequence
<220> FEATURE:
<223> OTHER INFORMATION: 5826-13-R4A-E2 LCVR

<400> SEQUENCE: 215

```
Asp Ile Gln Leu Thr Gln Ser Pro Ser Ser Leu Pro Ala Ser Leu Gly
1               5                   10                  15

Glu Arg Val Thr Ile Ser Cys Arg Ala Ser Gln Gly Ile Ser Asn Lys
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65              70                  75                  80

Glu Asp Phe Ala Met Tyr Phe Cys Gln Gln Asp Ala Ser Phe Pro Pro
                85                  90                  95

Thr Phe Gly Gly Gly Thr Lys Leu Glu Leu Lys
            100                 105
```

<210> SEQ ID NO 216
<211> LENGTH: 107
<212> TYPE: PRT
<213> ORGANISM: Artificial Sequence
<220> FEATURE:
<223> OTHER INFORMATION: 5826-13-R4A-E6 LCVR

<400> SEQUENCE: 216

```
Asp Ile Gln Met Thr Gln Thr Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Tyr Gln Gln Lys Pro Gly Lys Ser Pro Gln Leu Leu Ile
        35                  40                  45

Tyr Tyr Thr Ser Ser Phe Gln Asp Gly Val Pro Ser Arg Phe Ser Gly
    50                  55                  60

Ser Gly Ser Gly Thr Gln Tyr Ser Leu Lys Ile Ser Asn Met Gln Pro
65                  70                  75                  80

Glu Asp Glu Gly Val Tyr Tyr Cys Gln Gln Gly Tyr Lys Tyr Pro Trp
                85                  90                  95

Thr Phe Gly Gly Gly Thr Lys Leu Glu Leu Lys
            100                 105
```

<210> SEQ ID NO 217
<211> LENGTH: 107
<212> TYPE: PRT
<213> ORGANISM: Artificial Sequence
<220> FEATURE:
<223> OTHER INFORMATION: 5826-13-R4A-E9 LCVR

<400> SEQUENCE: 217

```
Asp Ile Leu Met Thr Gln Ser Pro Ser Arg Pro Ala Ser Leu Gly
1               5                   10                  15

Glu Arg Val Thr Ile Ser Cys Arg Ala Ser Gln Gly Ile Gly Asn Lys
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Asp Ala Ser Phe Pro Pro
                85                  90                  95

Thr Phe Gly Gly Gly Thr Lys Leu Glu Leu Lys
            100                 105
```

<210> SEQ ID NO 218
<211> LENGTH: 107
<212> TYPE: PRT
<213> ORGANISM: Artificial Sequence
<220> FEATURE:
<223> OTHER INFORMATION: 5826-13-R4A-F10 LCVR

<400> SEQUENCE: 218

```
Asp Ile Gln Met Thr Gln Thr Pro Ser Ser Leu Pro Ala Ser Leu Gly
1               5                   10                  15

Glu Arg Val Thr Ile Ser Cys Arg Ala Ser Gln Gly Ile Ser Lys Lys
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65                  70                  75                  80

Glu Asp Phe Ala Ile Tyr Tyr Cys Gln Gln Asp Ala Ser Phe Pro Pro
                85                  90                  95
```

```
Thr Phe Gly Gly Gly Thr Lys Leu Glu Leu Lys
            100                 105

<210> SEQ ID NO 219
<211> LENGTH: 106
<212> TYPE: PRT
<213> ORGANISM: Artificial Sequence
<220> FEATURE:
<223> OTHER INFORMATION: 5826-13-R4A-G11 LCVR

<400> SEQUENCE: 219

Asp Ile Gln Leu Thr Gln Ser Pro Ser Ser Leu Pro Ala Ser Leu Gly
1               5                   10                  15

Glu Arg Val Thr Ile Ser Cys Arg Ala Ser Gln Gly Ile Ser Lys Lys
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Ser Gly Thr Asp Tyr Ser Leu Thr Ile Ser Ser Leu Glu Pro Glu
65                  70                  75                  80

Asp Phe Ala Met Tyr Tyr Cys Gln Gln Asp Ala Ser Phe Pro Pro Thr
                85                  90                  95

Phe Gly Gly Gly Thr Lys Leu Glu Leu Lys
            100                 105

<210> SEQ ID NO 220
<211> LENGTH: 107
<212> TYPE: PRT
<213> ORGANISM: Artificial Sequence
<220> FEATURE:
<223> OTHER INFORMATION: 5826-13-R4A-G12 LCVR

<400> SEQUENCE: 220

Asp Ile Leu Met Thr Gln Ser Pro Ser Ser Leu Pro Ala Ser Leu Gly
1               5                   10                  15

Glu Arg Val Thr Ile Ser Cys Gly Ala Ser Gln Gly Ile Gly Asn Lys
            20                  25                  30

Val Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Thr Gly Thr Asp Tyr Ser Leu Thr Ile Ser Ser Leu Glu Pro
65                  70                  75                  80

Glu Asp Phe Ala Met Tyr Tyr Cys Gln Gln Asp Ala Ser Phe Pro Pro
                85                  90                  95

Thr Phe Gly Gly Gly Thr Lys Leu Glu Leu Lys
            100                 105

<210> SEQ ID NO 221
<211> LENGTH: 107
<212> TYPE: PRT
<213> ORGANISM: Artificial Sequence
<220> FEATURE:
<223> OTHER INFORMATION: 5826-13-R4A-H1 LCVR

<400> SEQUENCE: 221

Asp Ile Gln Met Thr Gln Thr Pro His Ser Leu Ser Ala Ser Leu Gly
1               5                   10                  15
```

```
Glu Thr Val Ser Ile Glu Cys Leu Ala Ser Glu Gly Ile Ser Asn Tyr
            20                  25                  30

Leu Ala Trp Tyr Gln Arg Lys Pro Gly Lys Ser Pro Gln Leu Leu Ile
        35                  40                  45

Tyr Tyr Thr Ile Ser Leu Gln Asp Gly Val Pro Ser Arg Phe Ser Gly
50                  55                  60

Ser Gly Ser Gly Thr Gln Tyr Ser Leu Lys Ile Ser Asn Met Gln Pro
65                  70                  75                  80

Glu Asp Glu Gly Val Phe Tyr Cys Gln Gln Gly Tyr Lys Tyr Pro Trp
                85                  90                  95

Thr Phe Gly Gly Gly Thr Lys Leu Glu Leu Lys
            100                 105

<210> SEQ ID NO 222
<211> LENGTH: 107
<212> TYPE: PRT
<213> ORGANISM: Artificial Sequence
<220> FEATURE:
<223> OTHER INFORMATION: 5826-13-R4A-H2 LCVR

<400> SEQUENCE: 222

Asp Ile Gln Leu Thr Gln Ser Pro Ser Ser Leu Pro Ala Ser Leu Gly
1               5                   10                  15

Glu Arg Val Thr Ile Ser Cys Arg Ala Ser Gln Gly Ile Gly Asn Lys
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Asp Ala Ser Phe Pro Pro
                85                  90                  95

Thr Phe Gly Gly Gly Thr Lys Leu Glu Leu Lys
            100                 105

<210> SEQ ID NO 223
<211> LENGTH: 107
<212> TYPE: PRT
<213> ORGANISM: Artificial Sequence
<220> FEATURE:
<223> OTHER INFORMATION: 5826-13-R4A-H3 LCVR

<400> SEQUENCE: 223

Asp Ile Leu Met Thr Gln Ser Pro Ser Ser Leu Ser Ala Ser Leu Gly
1               5                   10                  15

Glu Arg Val Thr Ile Ser Cys Arg Ala Ser Gln Gly Ile Gly Asn Lys
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Asp Thr Ser Phe Pro Pro
                85                  90                  95

Thr Phe Gly Ala Gly Thr Lys Leu Glu Leu Lys
            100                 105
```

<210> SEQ ID NO 224
<211> LENGTH: 107
<212> TYPE: PRT
<213> ORGANISM: Artificial Sequence
<220> FEATURE:
<223> OTHER INFORMATION: 5826-13-R4A-H4 LCVR & 5826-13-R4A-H10 LCVR & 5826-13-R4A-H11 LCVR

<400> SEQUENCE: 224

Asp Ile Gln Met Thr Gln Thr Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Tyr Gln Gln Lys Pro Gly Lys Ser Pro Gln Leu Leu Ile
        35                  40                  45

Tyr Tyr Thr Ile Ser Leu Gln Asp Gly Val Pro Ser Arg Phe Ser Gly
    50                  55                  60

Ser Gly Ser Gly Thr Gln Tyr Ser Leu Lys Ile Ser Asn Met Gln Pro
65                  70                  75                  80

Glu Asp Glu Gly Val Phe Tyr Cys Gln Gln Gly Tyr Lys Tyr Pro Trp
                85                  90                  95

Thr Phe Gly Gly Gly Thr Lys Leu Glu Leu Lys
            100                 105

<210> SEQ ID NO 225
<211> LENGTH: 106
<212> TYPE: PRT
<213> ORGANISM: Artificial Sequence
<220> FEATURE:
<223> OTHER INFORMATION: 5826-13-R4A-H6 LCVR

<400> SEQUENCE: 225

Asp Ile Gln Met Thr Gln Thr Pro Ser Ser Leu Pro Ala Ser Leu Glu
1               5                   10                  15

Arg Val Thr Ile Ser Cys Arg Ala Ser Gln Gly Ile Ser Asn Lys Leu
            20                  25                  30

Asn Trp Tyr Gln Lys Lys Pro Asp Gly Thr Ile Lys Pro Leu Ile Tyr
        35                  40                  45

Tyr Thr Ser Asn Leu Gln Ser Gly Val Pro Ser Arg Phe Ser Gly Ser
    50                  55                  60

Gly Ser Gly Thr Asp Tyr Ser Leu Thr Ile Ser Ser Leu Glu Pro Glu
65                  70                  75                  80

Asp Phe Ala Met Tyr Phe Cys Gln Gln Asp Ala Ser Phe Pro Pro Thr
                85                  90                  95

Phe Gly Gly Gly Thr Gln Leu Glu Leu Lys
            100                 105

<210> SEQ ID NO 226
<211> LENGTH: 107
<212> TYPE: PRT
<213> ORGANISM: Artificial Sequence
<220> FEATURE:
<223> OTHER INFORMATION: 5826-13-R4A-H9 LCVR

<400> SEQUENCE: 226

Asp Ile Gln Leu Thr Gln Ser Pro Ser Ser Arg Pro Ala Ser Leu Gly
1               5                   10                  15

Glu Arg Val Thr Ile Ser Cys Arg Ala Ser Gln Gly Ile Gly Asn Lys
            20                  25                  30

```
Leu Asn Trp Tyr Gln Gln Lys Pro Asp Gly Thr Ile Lys Pro Leu Ile
            35                  40                  45

Tyr Tyr Thr Ser Asn Leu Gln Ser Gly Val Pro Ser Arg Phe Ser Gly
        50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Asp Ala Ser Phe Pro Pro
                85                  90                  95

Thr Phe Gly Gly Gly Thr Lys Leu Glu Leu Lys
                100                 105

<210> SEQ ID NO 227
<211> LENGTH: 107
<212> TYPE: PRT
<213> ORGANISM: Artificial Sequence
<220> FEATURE:
<223> OTHER INFORMATION: 5826-13-R4A-H12 LCVR

<400> SEQUENCE: 227

Asp Ile Gln Met Thr Gln Thr Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Tyr Gln Gln Lys Pro Gly Lys Ser Pro Gln Leu Leu Ile
            35                  40                  45

Tyr Tyr Ala Ser Ser Leu Gln Asp Gly Val Pro Ser Arg Phe Ser Gly
        50                  55                  60

Ser Gly Ser Gly Thr Gln Tyr Ser Leu Lys Ile Ser Asn Met Gln Pro
65                  70                  75                  80

Glu Asp Glu Gly Val Tyr Tyr Cys Gln Gln Gly Tyr Lys Tyr Pro Trp
                85                  90                  95

Thr Phe Gly Gly Gly Thr Lys Leu Glu Leu Lys
                100                 105
```